United States Patent
Kaiser

(10) Patent No.: US 12,286,433 B1
(45) Date of Patent: Apr. 29, 2025

(54) AZAINDOLE ROCK INHIBITORS

(71) Applicant: Avicenna Biosciences, Inc., Durham, NC (US)

(72) Inventor: Thomas Maxwell Kaiser, Durham, NC (US)

(73) Assignee: Avicenna Biosciences, Inc., Durham, NC (US)

( * ) Notice: Subject to any disclaimer, the term of this patent is extended or adjusted under 35 U.S.C. 154(b) by 0 days.

(21) Appl. No.: 18/915,221

(22) Filed: Oct. 14, 2024

Related U.S. Application Data

(63) Continuation of application No. 18/610,051, filed on Mar. 19, 2024, which is a continuation of application No. PCT/US2023/086402, filed on Dec. 29, 2023.

(60) Provisional application No. 63/436,408, filed on Dec. 30, 2022.

(51) Int. Cl.
  *C07D 471/04* (2006.01)
  *A61K 31/437* (2006.01)
  *A61K 9/00* (2006.01)
  *A61K 9/08* (2006.01)
  *A61K 47/20* (2006.01)
  *A61K 47/38* (2006.01)

(52) U.S. Cl.
  CPC .......... *C07D 471/04* (2013.01); *A61K 31/437* (2013.01); *A61K 9/0019* (2013.01); *A61K 9/08* (2013.01); *A61K 47/20* (2013.01); *A61K 47/38* (2013.01)

(58) Field of Classification Search
  CPC .......................... C07D 471/04; A61K 31/437
  See application file for complete search history.

(56) References Cited

U.S. PATENT DOCUMENTS

| | | |
|---|---|---|
| 6,858,638 B2 | 2/2005 | Damour et al. |
| 10,717,735 B2 | 7/2020 | Ibrahim et al. |
| 2009/0029970 A1 | 1/2009 | Takeshita |
| 2019/0002442 A1 | 1/2019 | Zhao et al. |
| 2019/0010143 A1 | 1/2019 | Zhao et al. |
| 2019/0031654 A1 | 1/2019 | Ibrahim et al. |
| 2022/0002266 A1 | 1/2022 | Zhao et al. |
| 2022/0273662 A1 | 9/2022 | Oh et al. |
| 2023/0257376 A1 | 8/2023 | Li et al. |
| 2023/0312530 A1 | 10/2023 | Zhao et al. |

FOREIGN PATENT DOCUMENTS

| | | |
|---|---|---|
| WO | WO 2009023179 A2 | 2/2009 |
| WO | WO 2009155209 A1 | 12/2009 |
| WO | WO 2011050245 A1 | 4/2011 |
| WO | WO 2021214200 A1 | 4/2021 |
| WO | WO 2023139379 A1 | 7/2023 |
| WO | WO 2023209692 A1 | 11/2023 |

OTHER PUBLICATIONS

Bye, Nicole et al. "Rho kinase inhibition following traumatic brain injury in mice promotes functional improvement and acute neuron survival but has little effect on neurogenesis, glial responses or neuroinflammation", Experimental Neurology 279, 86-95, 2016.

Chowdhury, Sarwat et al. "Discovery and optimization of indoles and 7-azaindoles as Rho kinase (ROCK) inhibitors (part-I)." *Bioorganic & medicinal chemistry letters* 21.23, 7107-7112, 2011.

Defert, Olivier and Sandro Boland "Rho kinase inhibitors: a patent review (2014-2016)." *Expert opinion on therapeutic patents* 27.4, 507-515, 2017.

Duffy, Philip et al. "Rho-associated kinase II (ROCKII) limits axonal growth after trauma within the adult mouse spinal cord." *Journal of Neuroscience* 29.48, 15266-15276, 2009.

Feng, Yangbo et al. "Discovery of substituted 4-(pyrazol-4-yl)-phenylbenzodioxane-2-carboxamides as potent and highly selective Rho kinase (ROCK-II) inhibitors." *Journal of medicinal chemistry* 51.21, 6642-6645, 2008.

Feng, Yangbo and Philip V. LoGrasso "Rho kinase inhibitors: a patent review (2012-2013)." *Expert opinion on therapeutic patents* 24.3, 295-307, 2014.

Feng, Yangbo et al. "Rho kinase (ROCK) inhibitors and their therapeutic potential." *Journal of medicinal chemistry* 59.6, 2269-2300, 2016.

Glyn, Richard J. and Graham Pattison. "The effects on lipophilicity of replacing oxygenated functionality with their fluorinated bioisosteres", 2021.

International search report and written opinion for PCT/US23/86402, 10 pages, mailed on May 23, 2024.

Koch, Jan Christoph et al. "ROCK inhibition in models of neurodegeneration and its potential for clinical translation." *Pharmacology & Therapeutics* 189, 1-21, 2018.

Koch, Jan C. et al. "Compassionate use of the ROCK inhibitor fasudil in three patients with amyotrophic lateral sclerosis." *Frontiers in Neurology* 11, 479836, 2020.

Li, Xiaohong et al. "PRKX critically regulates endothelial cell proliferation, migration, and vascular-like structure formation." *Developmental biology* 356.2, 475-485, 2011.

Lingor, Paul et al. "ROCK-ALS: protocol for a randomized, placebo-controlled, double-blind phase IIa trial of safety, tolerability and efficacy of the rho kinase (ROCK) inhibitor fasudil in amyotrophic lateral sclerosis." *Frontiers in Neurology* 10, 447797, 2019.

Lograsso, Philip V. and Yangbo Feng "Rho kinase (ROCK) inhibitors and their application to inflammatory disorders." *Current topics in medicinal chemistry* 9.8, 704-723, 2009.

Moskal, Natalia et al. "ROCK inhibitors upregulate the neuroprotective Parkin-mediated mitophagy pathway." *Nature communications* 11.1, 88, 2020.

Naseer, Shahmir et al. "Traumatic brain injury leads to alterations in contusional cortical miRNAs involved in dementia", Biomolecules 12.10, 1457, 2022.

(Continued)

Primary Examiner — Amanda L. Aguirre
Assistant Examiner — Chris E Simmons
(74) Attorney, Agent, or Firm — Knowles Intellectual Property Strategies, LLC

(57) ABSTRACT

This invention provides rho-associated protein kinase (ROCK) inhibiting compounds for therapeutic applications as described further herein.

1 Claim, No Drawings

(56) References Cited

OTHER PUBLICATIONS

Rikitake, Yoshiyuki and James K. Liao "ROCKs as therapeutic targets in cardiovascular diseases." *Expert review of cardiovascular therapy* 3.3, 441-451, 2005.

Roser, Anna-Elisa, Lars Tönges and Paul Lingor "Modulation of microglial activity by Rho-kinase (ROCK) inhibition as therapeutic strategy in Parkinson's disease and amyotrophic lateral sclerosis." *Frontiers in aging neuroscience* 9, 94, 2017.

Sessions, E. Hampton et al. "Discovery and optimization of indole and 7-azaindoles as Rho kinase (ROCK) inhibitors (part-II)." *Bioorganic & medicinal chemistry letters* 21.23, 7113-7118, 2011.

Staiger, B. "Pharmaceutical Dosage Forms: A Review", 2017 first published; 2018 last updated, https://walrus.com/articles/pharmaceutical-dosage-forms-a-review, 2017.

Sun, Shaoyi, and Jianmin Fu "Methyl-containing pharmaceuticals: Methylation in drug design", Bioorganic & medicinal chemistry letters 28.20, 3283-3289, 2018.

Tatenhorst, Lars et al. "Fasudil attenuates aggregation of α-synuclein in models of Parkinson's disease." *Acta neuropathologica communications* 4, 1-17, 2016.

Wang, Qing et al. "Advantages of Rho-associated kinases and their inhibitor fasudil for the treatment of neurodegenerative diseases." *Neural regeneration research* 17.12, 2623-2631, 2022.

Weber, Audrey J. and Jeremy H. Herskowitz "Perspectives on ROCK2 as a Therapeutic Target for Alzheimer's Disease." *Frontiers in Cellular Neuroscience* 15, 636017, 2021.

Yin, Yan et al. "Benzothiazoles as Rho-associated kinase (ROCK-II) inhibitors." *Bioorganic & medicinal chemistry letters* 19.23, 6686-6690, 2009.

US, 2024/0246972 A1, U.S. Appl. No. 18/610,041, Thomas Maxwell Kaiser, filed Jul. 25, 2024.

US, 2024/0254124 A1, U.S. Appl. No. 18/610,051, Thomas Maxwell Kaiser, filed Aug. 1, 2024.

AZAINDOLE ROCK INHIBITORS

CROSS REFERENCE TO RELATED APPLICATIONS

This application is a continuation of U.S. patent application Ser. No. 18/610,051, filed on Mar. 19, 2024, which is a continuation of International Patent Application No. PCT/US2023/086402, filed in the U.S. Receiving Office on Dec. 29, 2023, which claims the benefit of U.S. Provisional Application 63/436,408, filed Dec. 30, 2022. The entirety of each of these applications is hereby incorporated by reference for all purposes.

FIELD OF THE INVENTION

This invention provides rho-associated protein kinase (ROCK) inhibiting compounds for therapeutic applications as described further herein.

BACKGROUND

ROCK (Rho-associated protein kinase) is a kinase belonging to the AGC (cAMP-dependent protein kinase (PKA)/protein kinase G (PKG)/protein kinase C (PKC)) family of serine-threonine kinases and is activated by the GTP-bound form of RhoA. Two isoforms of mammalian Rho kinase, ROCK1 and ROCK2, have been described. They are approximately 160-kDa in weight proteins consisting of 1354 and 1388 amino acids, respectively, and contain an N-terminally located kinase domain, followed by a coiled-coil region containing the Rho-binding domain (RBD), a Pleckstrin homology domain (PH), and a cysteine-rich region at the C-terminus. The RBD binds exclusively to GTP-bound active RhoA and RhoC. The two ROCK isoforms share approximately 60% overall amino acid identity and approximately 90% identity within the N-terminal kinase domain. The carboxyl-terminal region comprises two cysteine-rich zinc finger-like motif domains and a split pleckstrin homology domain, which plays a role in the stabilization of the membrane binding of ROCK. (See, S. Hartmann, A. J. Ridley, and S. Lutz. "The Function of Rho-Associated Kinases ROCK1 and ROCK2 in the Pathogenesis of Cardiovascular Disease", *Frontiers in Pharmacology*, November 2015, Vol. 6, Art. 276; J. C. Koch, L. Tatenhorst, A.-E. Roser, K.-A. Saal, L. Tonges, P. Lingor. "ROCK inhibition in models of neurodegeneration and its potential for clinical translation", *Pharmacology & Therapeutics* 189 (2018) 1-21; Y. Feng, P. V. LoGrasso, O. Defert, and R. Li. "Rho Kinase (ROCK) Inhibitors and Their Therapeutic Potential", *J. Med. Chem.* 2016, 59, 2269-2300.)

In its native form, ROCK is enzymatically inactive. This is caused by an auto-inhibition of the ROCK kinase domain by the carboxyl-terminal region of ROCK. The best-characterized upstream activators of ROCK are Rho-GTPase proteins RhoA and RhoC. In activated GTP-bound state, they interact with the Rho-binding domain of ROCK and induce conformational changes that disrupt the autoinhibitory function of the carboxyl-terminal region. (J. C. Koch, L. Tatenhorst, A.-E. Roser, K.-A. Saal, L. Tonges, P. Lingor. "ROCK inhibition in models of neurodegeneration and its potential for clinical translation", *Pharmacology & Therapeutics* 189 (2018) 1-21.) There are a large number of downstream targets that are phosphorylated by ROCK.

Activation of ROCK leads to the phosphorylation of several central regulator proteins resulting in diverse cellular responses like autophagy, cell survival and apoptosis, vesicle dynamics, cytoskeleton regulation, cell growth and regeneration, as well as cell shape and motility. In response to activators of Rho, which stimulate Rho-guanine nucleotide exchange factor (GEF) and lead to the formation of active GTP-bound Rho, ROCKs mediate a broad range of cellular responses that involve the actin cytoskeleton. For example, they control assembly of the actin cytoskeleton and cell contractility by phosphorylating a variety of proteins, such as myosin light chain (MLC) phosphatase, LIM-kinases, adducin and Ezrin/Radixin/Moesin (ERM) proteins. ROCK2 can alter the sensitivity of smooth muscle cell contraction to $Ca^{2+}$, since MLCK is $Ca^{2+}$ sensitive. ROCKs are important regulators of cellular growth, migration, metabolism and apoptosis, through control of the actin cytoskeletal assembly and cell contraction. ROCK1 expression tends to be more ubiquitous (ROCK1 messenger RNA and protein are highly expressed in the lung, liver, spleen, kidney, and testis), while ROCK2 is most highly expressed in cardiac and brain tissues. ROCKs regulate cell polarity and migration, predominantly through enhancing actomyosin contraction and focal adhesions. Increased ROCK activity is observed in tumor metastasis and overexpression of constitutively activated ROCK promotes tumor invasion. (Y. Rikitake et al., "ROCKs as therapeutic targets in cardiovascular diseases", *Expert. Rev. Cardiovasc. Ther.,* 2005 May; 3(3): 441-451. doi:10.1586/14779072.3.3.441; A. V. Schofield and O. Bernard, "Rho-associated coiled-coil kinase (ROCK) signaling and disease", *Crit. Rev. Biochem. Mol. Biol.* 2013 July-August; 48(4): 301-16.

Pharmacologic inhibitors of ROCKs, such as Y-27632, Fasudil (HA1077) and hydroxyfasudil, which target their ATP-dependent kinase domains, can inhibit both ROCK1 and ROCK2. ROCK inhibitors have been investigated for the treatment of a variety of pathological conditions including asthma, cancer, erectile dysfunction, glaucoma, insulin resistance, kidney failure, neuronal degeneration and osteoporosis. To date, two ROCK inhibitors are approved for clinical use: Fasudil for the treatment of cerebral vasospasm and Ripasudil for the treatment of glaucoma.

Fasudil (an isoquinoline derivative) was shown to effectively inhibit ROCK and other kinases like PKA, PKG, PKC, and MLCK (J. C. Koch et al., "Compassionate use of the ROCK inhibitor Fasudil in three patients with myotrophic lateral sclerosis" *Front. Neurol*. March 2020, Volume 11, Article 173). A randomized, placebo-controlled, double-blind phase IIa clinical study of ROCK inhibitor Fasudil in amyotrophic lateral sclerosis (ALS) was started Feb. 20, 2019, and is currently ongoing (Clinical Trials Identifier: NCT03792490; Eudra-CT-Nr.: 2017-003676-31).

Several synthetic ROCK inhibitors identified by researchers at Scripps Research Institute based on indole, 5-azaindole, and 7-azaindole heterocyclic systems have been described in literature (S. Chowdhury et al., "Discovery and optimization of indoles and 7-azaindoles as Rho kinase (ROCK) inhibitors (part-I)", *Bioorg. Med. Chem. Lett*. 21 (2011) 7107-7112; E. H. Sessions et al., "Discovery and optimization of indole and 7-azaindoles as Rho kinase (ROCK) inhibitors (Part-II)", *Bioorg. Med. Chem. Lett*. 21 (2011) 7113-7118.) Synthesis and inhibitory activity of some benzothiazole derivatives against ROCK have also been previously disclosed (Y. Yin et al., "Benzothiazoles as Rho-associated kinase (ROCK-II) inhibitors", *Bioorg. Med. Chem. Lett*. 19 (2009) 6686-6690.). Additional ROCK inhibitors are described in WO 2011/050245 which was filed by researchers at Scripps Research Institute. The ROCK inhibitory activity of these indole, azaindole and benzothiazole compounds varies significantly depending on substituents attached to the heterocyclic ring.

Patent applications describing ROCK inhibitors and their uses include WO 2023/209692, WO 2023/139379, WO 2022/020381, WO 2022/150676, WO 2022/042712, WO 2022/012409, WO 2021/214200, WO 2021/095945, WO 2020/177292, WO 2020/094111, WO 2019/000683, WO 2019/000682, WO 2018/130178, WO 2018/108156, WO 2014/177699, WO 2011/050245, WO 2010/065907, WO 2010/065907, WO 2010/032875, WO 2009/155209, WO 2007/026920, and WO 2006/088088.

Despite these efforts, there remains a need for new ROCK inhibiting compounds to treat disorders mediated by ROCK1 and/or ROCK2 in a subject in need thereof for example a human.

SUMMARY OF THE INVENTION

Azaindole compounds of Formula I, Formula II, and Formula III and their pharmaceutically acceptable salts, uses, and manufacture are provided that inhibit a rho-associated protein kinase (ROCK). These compounds exhibit advantageous ADME properties (absorption, distribution, metabolism, and/or excretion) and higher potency in enzyme inhibition assays than close analogues (see Example 24 and Example 25). It has also been surprisingly discovered that these compounds also have activity against protein kinase X (PRKX, see Table 2A and Table 2B). Both ROCK and PRKX activity drive neurodegeneration in amyotrophic lateral sclerosis (ALS). Therefore by inhibiting both enzymes certain compounds of the present invention are expected to exert advantageous therapeutic efficacy against this disease in humans.

In certain aspects the compound of the present invention is Compound 1:

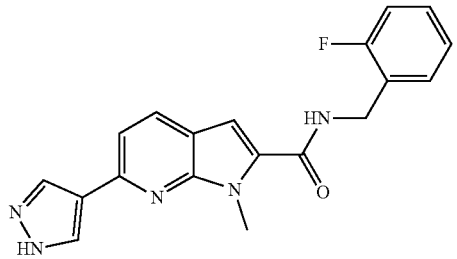

or a pharmaceutically acceptable salt thereof.

In other aspects the compound of the present invention is Compound 2:

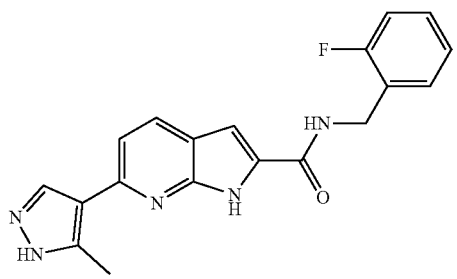

or a pharmaceutically acceptable salt thereof.

Compound 1 and Compound 2 are highly potent inhibitors of ROCK1, ROCK2, and PRKX (see Table 2A and Table 2B). These two compounds have superior efflux ratios when compared to the eight tested comparator compounds (see Table 3A and Table 3B). These properties are important for the treatment of a ROCK1 or ROCK2 mediated disorder, for example for the treatment of ALS.

An effective amount of a compound of the present invention provided herein or its pharmaceutically acceptable salt and/or its pharmaceutically acceptable composition can be used to treat a disorder which is mediated by ROCK1 and/or ROCK2. In some embodiments, a method to treat a subject with a disorder mediated by ROCK1 and/or ROCK2 is provided that includes administering an effective amount of one or more compounds as described herein, or a pharmaceutically acceptable salt thereof, to the subject, typically a human, optionally in a pharmaceutically acceptable composition. In certain embodiments the disorder is mediated by ROCK1. In additional embodiments the disorder is mediated by ROCK2. In other embodiments the disorder is mediated by PRKX. In certain embodiments, the disorder is mediated by ROCK1 and PRKX.

In certain aspects a compound of Formula I, Formula II, or Formula III is provided:

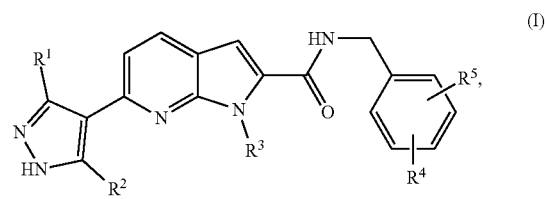

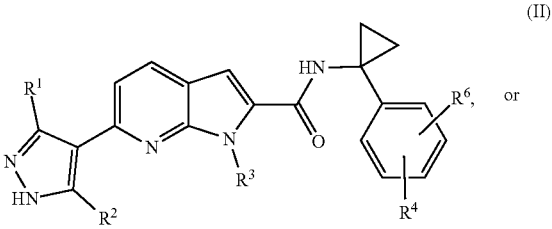

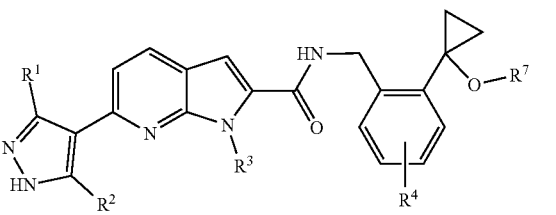

or a pharmaceutically acceptable salt thereof;
wherein:
$R^1$ and $R^2$ are independently selected from hydrogen, $C_1$-$C_4$ alkyl, $C_1$-$C_4$ haloalkyl, and halogen;
in certain embodiments $R^1$ and $R^2$ are hydrogen;
$R^3$ is selected from hydrogen, $C_1$-$C_4$ alkyl, and $C_1$-$C_4$ haloalkyl;
in certain embodiments $R^3$ is H or $CH_3$;
$R^4$ and $R^5$ are independently selected from hydrogen, $C_1$-$C_4$ alkyl, $C_1$-$C_4$ haloalkyl, and halogen;
$R^6$ is selected from hydrogen, $C_1$-$C_4$ alkyl, $C_1$-$C_4$ haloalkyl, halogen, $C_1$-$C_4$ alkyl-$OR^7$, and $OR^7$; and
$R^7$ is selected from hydrogen, $C_1$-$C_4$ alkyl, and $C_1$-$C_4$ haloalkyl.

Every combination of variables, substituents, embodiments, and the compounds that result from these combinations, is deemed specifically and individually disclosed, as such depiction is for convenience of space only and not intended to describe only a genus or even a subgenus of compounds.

In certain aspects a compound of the present invention is used to treat a ROCK1 or ROCK2 mediated disorder in the central nervous system (CNS). In other aspects a compound of the present invention is used to treat a peripheral disorder that is mediated by ROCK1 or ROCK2.

In certain aspects the compound of Formula I is of Formula:

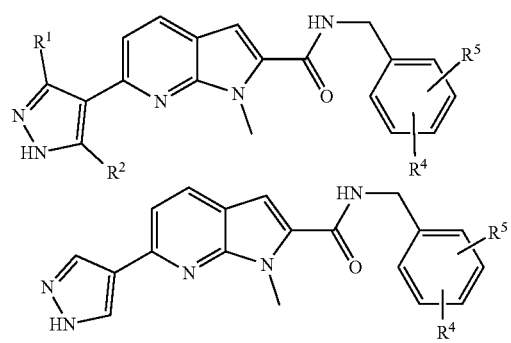

or

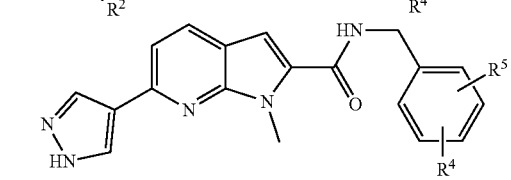

or a pharmaceutically acceptable salt thereof.

In other aspects the compound of Formula I is of Formula:

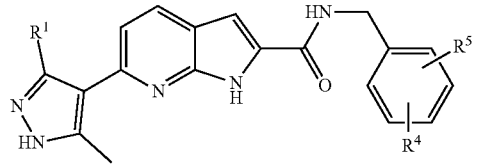

or a pharmaceutically acceptable salt thereof.

In certain embodiments the compound of Formula I is selected from:

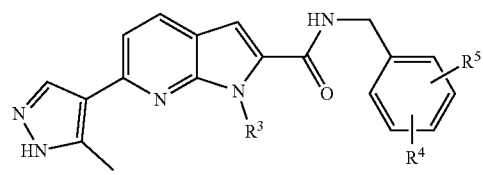
(I-A)

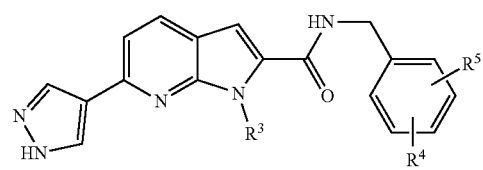
(I-B)

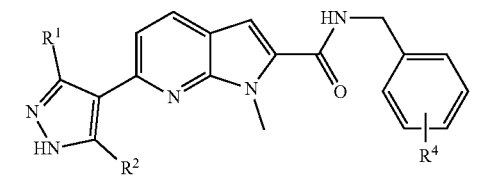
(I-C)

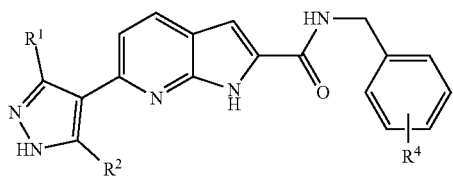
(I-D)

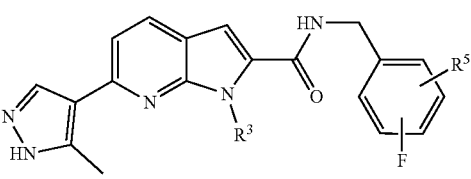
(I-E)

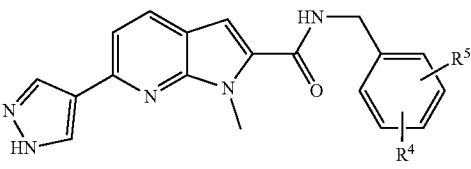
(I-F)

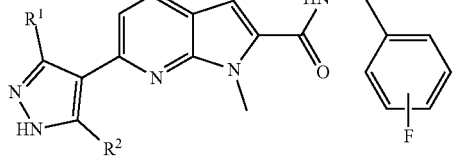
(I-G)

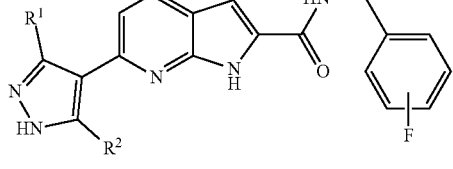
(I-H)

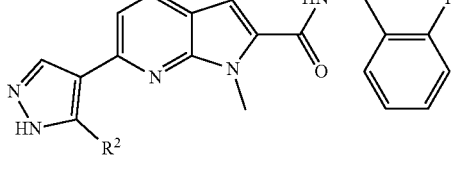
(I-I)

and

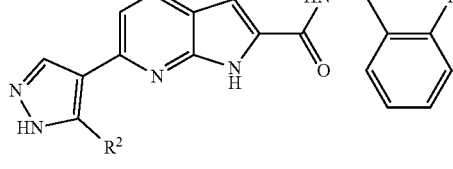
(I-J)

or a pharmaceutically acceptable salt thereof.

Non-limiting examples of compounds of Formula I include:

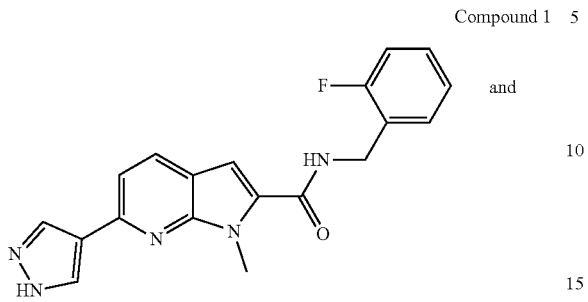

Compound 1

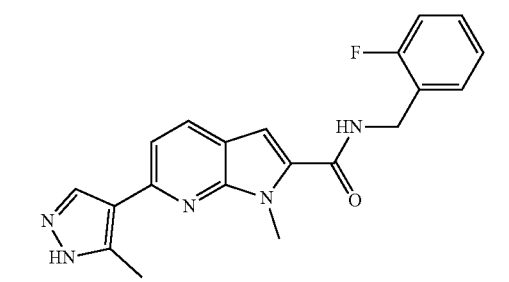

Compound 2 or a pharmaceutically acceptable salt thereof.

Additional non-limiting examples of compounds of Formula I include:

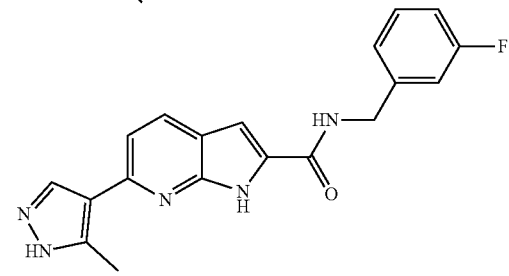

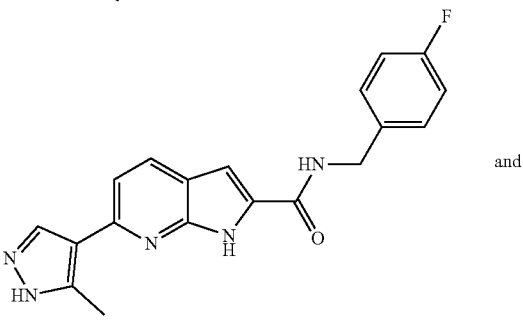

and

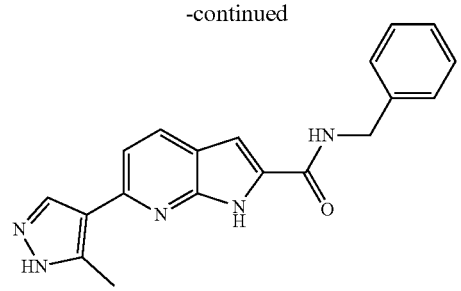

or a pharmaceutically acceptable salt thereof.

In other embodiments, the compound of Formula I is selected from:

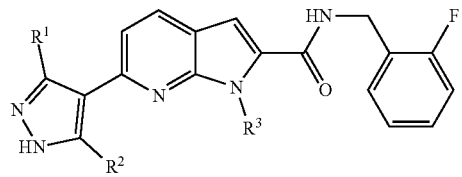

(I-K)

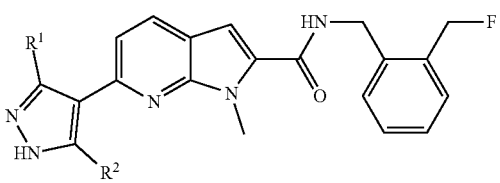

(I-L)

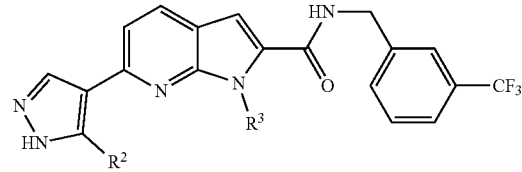

(I-M)

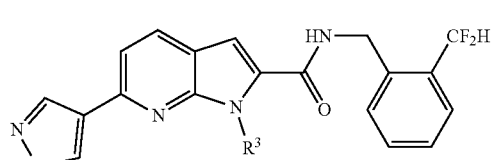

(I-N)

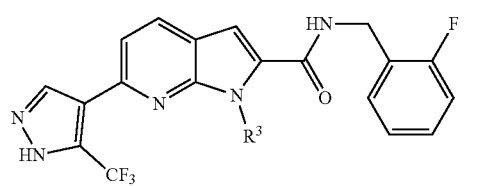

(I-O)

and (I-P)

or a pharmaceutically acceptable salt thereof.

In other embodiments, the compound of Formula I is selected from:
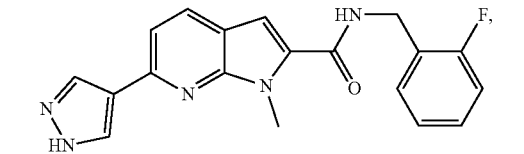
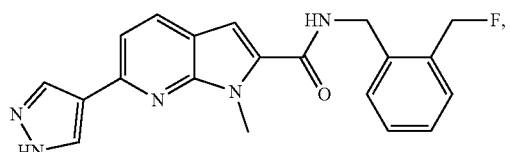
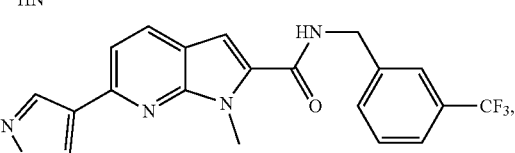
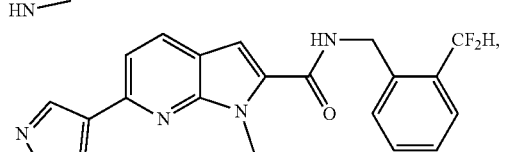
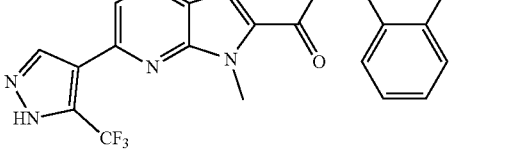
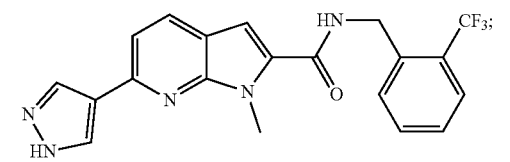
or a pharmaceutically acceptable salt thereof.
In certain embodiments the compound of Formula II is selected from:
(II-A)
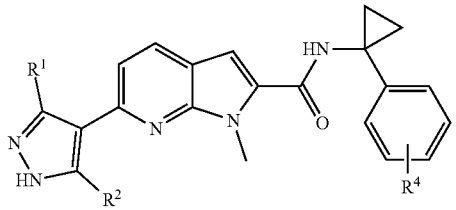
(II-B)
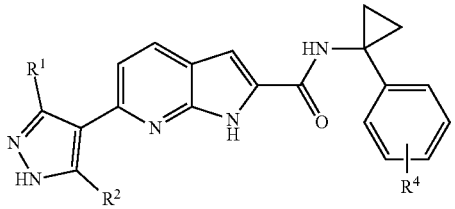
(II-C)
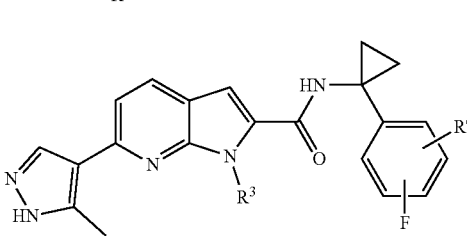
(II-D)
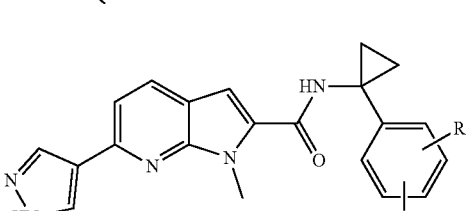
(II-E)
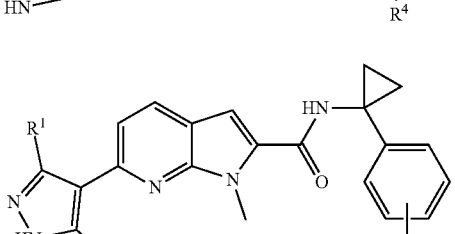
(II-F)
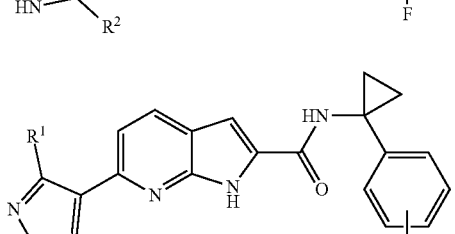
(II-G)
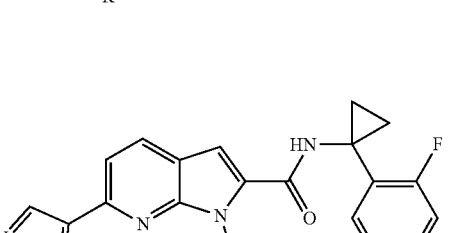
(II-H)
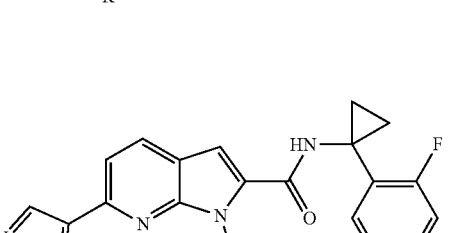
(II-I)
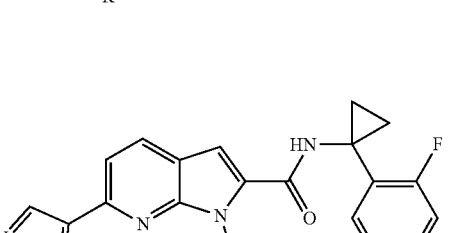
and

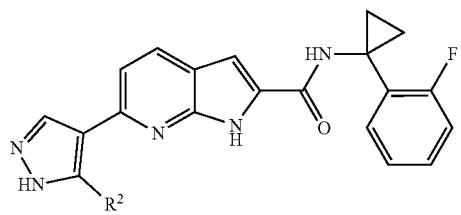

(II-J)

or a pharmaceutically acceptable salt thereof.

In other embodiments, the compound of Formula II is selected from

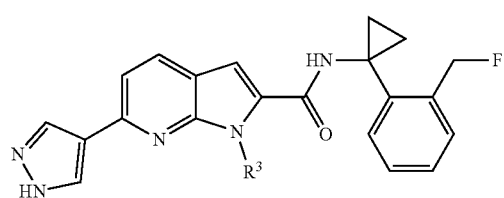

(II-K)

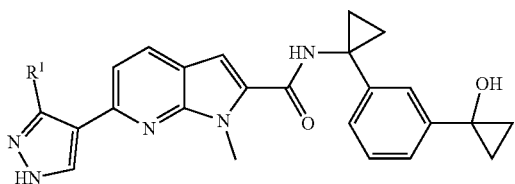

(II-L)

and

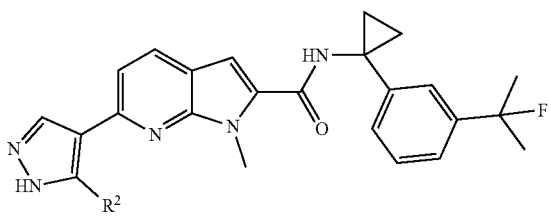

(II-M)

or a pharmaceutically acceptable salt thereof.

Non-limiting examples of compounds of Formula II include:

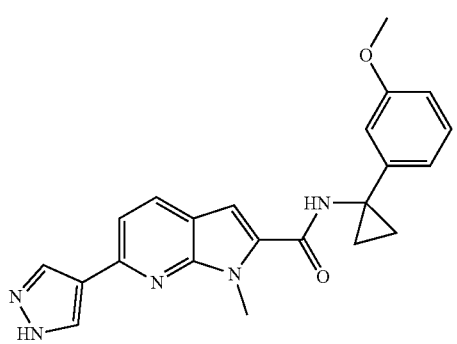

Compound 3

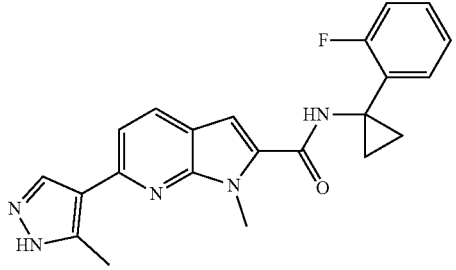

Compound 4 and

Compound 5

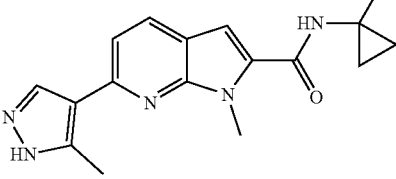

or a pharmaceutically acceptable salt thereof.

Additional non-limiting examples of compounds of Formula II include:

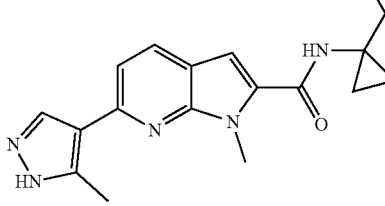

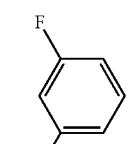

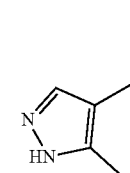

and

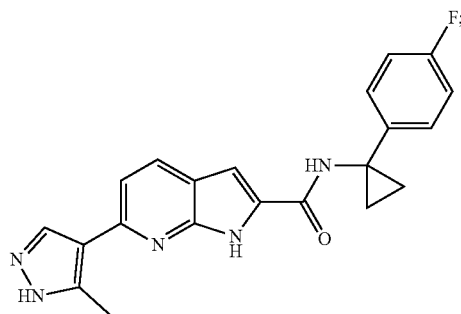
or a pharmaceutically acceptable salt thereof.
Additional examples of compounds of Formula II include:
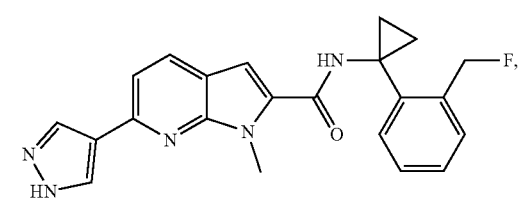
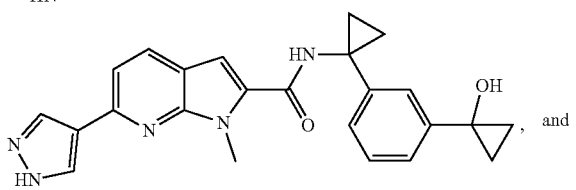, and
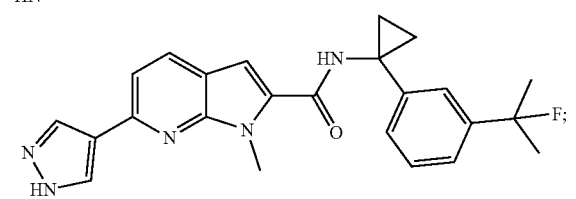
or a pharmaceutically acceptable salt thereof.
In certain embodiments the compound of Formula III is selected from:
(III-A)
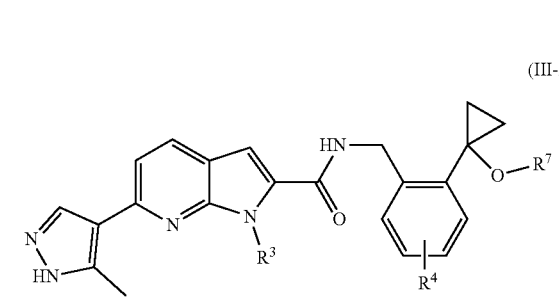
(III-B)
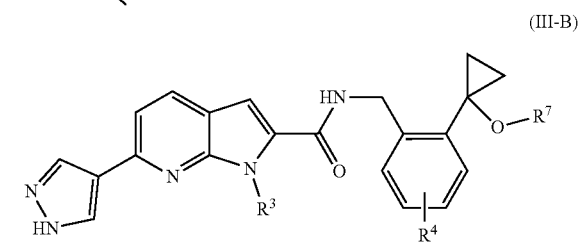
(III-C)
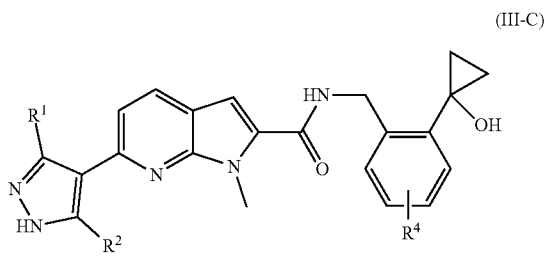
(III-D)
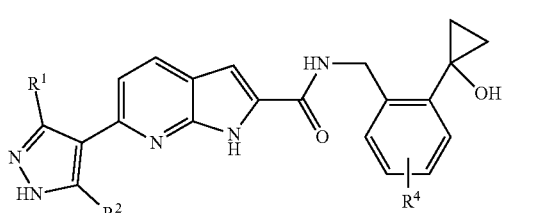
(III-E)
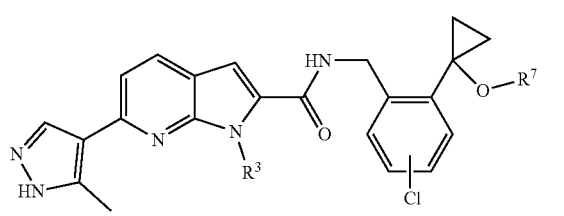
(III-F)
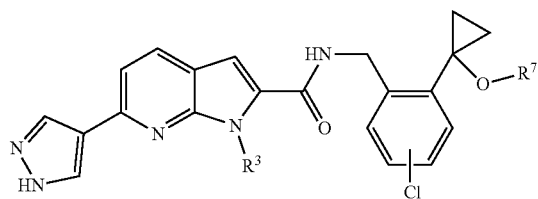
(III-G)
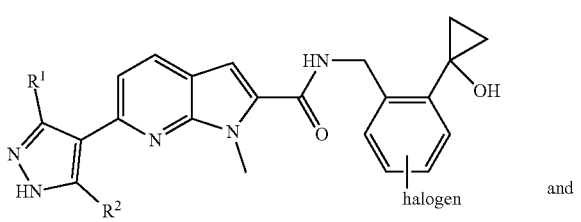 and
(III-H)
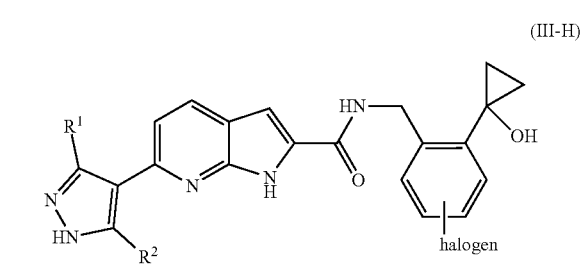
or a pharmaceutically acceptable salt thereof.

Non-limiting examples of compounds of Formula III include:

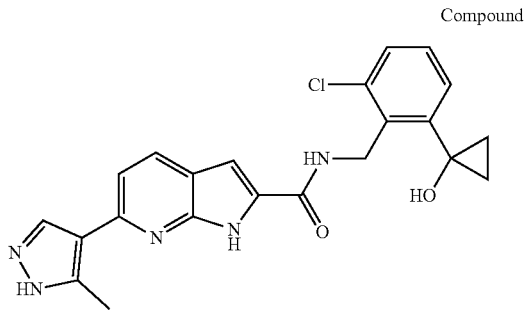

Compound 6 or a pharmaceutically acceptable salt thereof.

In certain embodiments, a compound of the present invention has sufficient ADME properties to penetrate the blood brain barrier. Adequate levels of blood penetration are important for the treatment of neurodegenerative disorders. For example, blood penetration is required to treat amyotrophic lateral sclerosis because this disease primarily affects nerve cells in the brain. In other embodiments a compound of the present invention is used to treat stroke, spinal cord injury, Alzheimer's or Parkinson's disease.

In certain embodiments, a method of treatment is provided comprising administering an effective amount of a compound of Formula I, Formula II, or Formula III, or a pharmaceutically acceptable salt thereof to a subject in need thereof, for example, a human, optionally in a pharmaceutically acceptable composition. For example, in certain embodiments, a compound of Formula I, Formula II, or Formula III or a pharmaceutically acceptable salt thereof is administered to a human to treat a neurodegenerative disorder, for example amyotrophic lateral sclerosis (ALS) or Parkinson's disease (PD).

In certain embodiments, a compound of the present invention is used to treat ALS. For example, in certain embodiments, a compound of the present invention is used to treat bulbar, respiratory, flail arm, classical, pyramidal, or flail leg ALS. In certain embodiments, a compound of the present invention is used to treat Parkinson's disease. For example, in certain embodiments, a compound of the present invention is used to treat motor-cognitive, cognitive dominant or motor dominant Parkinson's disease.

In other embodiments a compound of the present invention is used to treat a disorder selected from cerebral vasospasm, pulmonary hypertension, acute lung injury exfoliation syndrome, ocular hypertension, or glaucoma (for example exfoliative glaucoma). Alternatively, a compound of the present invention can be used to treat an edema (for example pulmonary edema), inflammatory bowel disease, or inflammation.

In certain embodiments, the compound of the present invention provides one or more advantages over close analogues thereof. For example, a selected compound of Formula I, Formula II, or Formula III can demonstrate a) advantageous potency against ROCK1, ROCK2, and/or PRKX; b) advantageous permeability; c) a lower efflux ratio; d) less hERG activity; e) advantageous blood brain barrier penetration; and/or f) advantageous bioavailability as compared to a close analogue thereof. As a result of these advantageous properties, in certain embodiments a compound of the present invention can be taken orally to treat a disorder mediated by ROCK1 and/or ROCK2, including for example, a neurodegenerative disorder such as amyotrophic lateral sclerosis or Parkinson's disease.

Select compounds of the present invention also have advantageous properties when compared to Fasudil. For example Compound 1, Compound 2, Compound 3, Compound 4, and Compound 5 when tested in head-to-head studies against Fasudil, had superior ROCK1 and ROCK2 inhibiting activity and exhibited a lower efflux ratio (see Example 24 and Example 25). The concentration of Compound 1 required to inhibit half of ROCK2's activity was more than 50-fold lower than the concentration required for Fasudil (Example 24). Similarly, the concentration of Compound 2, Compound 3, Compound 4, and Compound 5 required to inhibit half of ROCK2's activity was more than an order of magnitude lower than the concentration required for Fasudil (Example 24).

In certain embodiments, the selected compound of Formula I, Formula II, or Formula III or a pharmaceutically acceptable salt thereof, has at least one desired isotopic substitution of an atom, at an amount above the natural abundance of the isotope, i.e., enriched. In certain embodiments, the compound of Formula I, Formula II, or Formula III, or its pharmaceutically acceptable salt thereof, includes a deuterium atom or multiple deuterium atoms. For example, in certain embodiments a compound of Formula I, Formula II, or Formula III or a pharmaceutically acceptable salt thereof has one or more deuterium substitutions at a site of metabolism. In other embodiments a compound of Formula I, Formula II, or Formula III or a pharmaceutically acceptable salt thereof has one or more deuterium substitutions next to the site of metabolism.

Other features and advantages of the present application will be apparent from the following detailed description.

The present invention thus includes at least the following features:

(a) A compound of Formula I, Formula II, or Formula III as described herein, or a pharmaceutically acceptable salt or isotopic derivative (including a deuterated derivative) thereof, (b) A method to treat a ROCK1 and/or ROCK2 mediated disorder, such as a neurodegenerative disorder, including for example ALS or Parkinson's disease, comprising administering an effective amount of a compound of Formula I, Formula II, or Formula III or pharmaceutically acceptable salt thereof, to a subject in need thereof, (c) A compound of Formula I, Formula II, or Formula III or a pharmaceutically acceptable salt thereof for use in the treatment of a disorder that is mediated by ROCK1 and/or ROCK2, for example a neurodegenerative disorder, including for example ALS or Parkinson's disease;

(d) Use of a compound of Formula I, Formula II, or Formula III, or a pharmaceutically acceptable salt thereof, in an effective amount in the treatment of a subjecting need thereof, typically a human, with a ROCK1 and/or ROCK2 mediated disorder, for example a neurodegenerative disorder, including for example ALS or Parkinson's disease;

(e) Use of a compound of Formula I, Formula II, or Formula III, or a pharmaceutically acceptable salt thereof, in the manufacture of a medicament for the treatment of a ROCK1 and/or ROCK2 mediated disorder, for example a neurodegenerative disorder, including for example ALS or Parkinson's disease;

(f) A pharmaceutical composition comprising an effective subject-treating amount of a compound of Formula I, Formula II, or Formula III, or a pharmaceutically acceptable salt, and a pharmaceutically acceptable excipient;

(g) Any of (a)-(f) above wherein the compound is of Formula I.

(h) Any of (a)-(f) above wherein the compound is Compound 1.

(i) Any of (a)-(f) above wherein the compound is Compound 2.

(j) Any of (a)-(f) above wherein the compound is Compound 10.

(k) Any of (a)-(f) above wherein the compound is Compound 11.

(l) Any of (a)-(f) above wherein the compound is Compound 12.

(m) Any of (a)-(f) above wherein the compound is Compound 13.

(n) Any of (a)-(f) above wherein the compound is Compound 14.

(o) Any of (a)-(f) above wherein the compound is of Formula II.

(p) Any of (a)-(f) above wherein the compound is Compound 3.

(q) Any of (a)-(f) above wherein the compound is Compound 4.

(r) Any of (a)-(f) above wherein the compound is Compound 5.

(s) Any of (a)-(f) above wherein the compound is Compound 7.

(t) Any of (a)-(f) above wherein the compound is Compound 8.

(u) Any of (a)-(f) above wherein the compound is Compound 9.

(v) Any of (a)-(f) above wherein the compound is of Formula III.

(w) Any of (a)-(f) above wherein the compound is Compound 6.

DETAILED DESCRIPTION OF THE INVENTION

I. Definitions

Compounds are described using standard nomenclature. Unless defined otherwise, all technical and scientific terms used herein have the same meaning as is commonly understood by one of skill in the art to which this invention belongs.

The terms "a" and "an" do not denote a limitation of quantity, but rather denote the presence of at least one of the referenced item. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of examples, or exemplary language (e.g., "such as"), is intended merely to better illustrate the invention and does not pose a limitation on the scope of the invention unless otherwise claimed.

The present invention includes a compound of Formula I, Formula II, or Formula III or its pharmaceutically acceptable salt thereof, with at least one desired isotopic substitution of an atom, at an amount above the natural abundance of the isotope, i.e., enriched. Isotopes are atoms having the same atomic number but different mass numbers, i.e., the same number of protons but a different number of neutrons.

Examples of isotopes that can be incorporated into compounds of the invention include isotopes of hydrogen, carbon, nitrogen, oxygen, fluorine, chlorine and iodine such as $^{2}H$, $^{3}H$, $^{11}C$, $^{13}C$ $^{14}C$, $^{15}N$, $^{17}O$, $^{18}O$, $^{18}F$, $^{36}Cl$, and $^{125}I$ respectively. In one non-limiting embodiment, isotopically labelled compounds can be used in metabolic studies (with, for example $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Isotopic substitutions, for example deuterium substitutions, can be partial or complete. Partial deuterium substitution means that at least one hydrogen is substituted with deuterium. In certain embodiments, the isotope is 90, 95 or 99% or more enriched in an isotope at any location of interest. In one non-limiting embodiment, deuterium is 90, 95 or 99% enriched at a desired location.

In one non-limiting embodiment, the substitution of a hydrogen atom for a deuterium atom can be provided in a compound of Formula I, Formula II, or Formula III, or a pharmaceutically acceptable salt thereof optionally in a metabolically labile position, or a position in close proximity to a metabolically labile position. In one non-limiting embodiment, the substitution of a hydrogen atom for a deuterium atom occurs within one or more groups selected from any of R's or variables described herein. For example, when any of the groups are, or contain for example through substitution, methyl, ethyl, or methoxy, the alkyl residue may be deuterated (in non-limiting embodiments, $CDH_2$, $CD_2H$, $CD_3$, $CH_2CD_3$, $CD_2CD_3$, $CHDCH_2D$, $CH_2CD_3$, $CHDCHD_2$, $OCDH_2$, $OCD_2H$, or $OCD_3$ etc.).

In certain aspects a compound of the present invention may form a solvate with a solvent (including for example water). Therefore, in one non-limiting embodiment, the invention includes a solvated form of the compound. The term "solvate" refers to a molecular complex of a compound of the present invention (including a salt thereof) with one or more solvent molecules. Non-limiting examples of solvents are water, ethanol, isopropanol, dimethyl sulfoxide, acetone and other common organic solvents. The term "hydrate" refers to a molecular complex comprising a compound of the invention and water. Pharmaceutically acceptable solvates in accordance with the invention include those wherein the solvent may be isotopically substituted, e.g. $D_2O$, $d_6$-acetone, $d_6$-DMSO (dimethyl sulfoxide). A solvate can be in a liquid or solid form.

A dash ("-") that is not between two letters or symbols is used to indicate a point of attachment for a substituent. For example, —(C=O)NH$_2$ is attached through carbon of the carbonyl (C=O) group.

"Alkyl" is a straight, branched, or cyclic saturated aliphatic hydrocarbon group. In certain embodiments, the alkyl is $C_1$-$C_2$, $C_1$-$C_3$, or $C_1$-$C_4$, and where the alkyl is cyclic, it may be, for example a $C_3$-$C_4$ moiety. The specified ranges as used herein indicate an alkyl group having each member of the range described as an independent species. For example, the term $C_1$-$C_4$ alkyl as used herein indicates a straight or branched alkyl group having from 1, 2, 3, or 4 carbon atoms and is intended to mean that each of these is described as an independent species and therefore each subset is considered separately disclosed. Examples of alkyl include, but are not limited to, methyl, ethyl, n-propyl, isopropyl, n-butyl, isobutyl, sec-butyl, and t-butyl. The term "alkyl" also encompasses cycloalkyl or carbocyclic groups. For example, when a term is used that includes "alk" then "cycloalkyl" or "carbocyclic" can be considered part of the definition, unless unambiguously excluded by the context. For example, and without limitation, the terms alkyl, alkoxy, haloalkyl, etc., can all be considered to include the cyclic forms of alkyl, unless unambiguously excluded by context.

In certain embodiments "alkyl" is a $C_1$-$C_4$alkyl, $C_1$-$C_3$alkyl, or $C_1$-$C_2$alkyl.

In certain embodiments "alkyl" has one carbon.

In certain embodiments "alkyl" has two carbons.

In certain embodiments "alkyl" has three carbons.

In certain embodiments "alkyl" has four carbons.

Non-limiting examples of "alkyl" include: methyl, ethyl, propyl, and butyl.

Additional non-limiting examples of "alkyl" include: isopropyl and isobutyl.

Additional non-limiting examples of "alkyl" include: sec-butyl and tert-butyl.

In certain embodiments "cycloalkyl" is a $C_3$-$C_4$cycloalkyl.

In certain embodiments "cycloalkyl" has three carbons.

In certain embodiments "cycloalkyl" has four carbons.

Non-limiting examples of "cycloalkyl" include: cyclopropyl and cyclobutyl.

"Halo" and "Halogen" refers independently to fluorine, chlorine, bromine or iodine.

"Haloalkyl" is a straight, branched or cyclic alkyl groups substituted with 1 or more halo atoms described above, up to the maximum allowable number of halogen atoms. Examples of haloalkyl groups include, but are not limited to, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perhaloalkyl" means an alkyl group having all hydrogen atoms replaced with halogen atoms. Examples include but are not limited to, trifluoromethyl and pentafluoroethyl.

In certain embodiments "haloalkyl" is a $C_1$-$C_4$haloalkyl, $C_1$-$C_3$haloalkyl, or $C_1$-$C_2$haloalkyl.

In certain embodiments "haloalkyl" has one carbon.

In certain embodiments "haloalkyl" has one carbon and one halogen.

In certain embodiments "haloalkyl" has one carbon and two halogens.

In certain embodiments "haloalkyl" has one carbon and three halogens.

In certain embodiments "haloalkyl" has two carbons.

In certain embodiments "haloalkyl" has three carbons.

In certain embodiments "haloalkyl" has four carbons.

In certain embodiments "haloalkyl" is perhaloalkyl.

Non-limiting examples of "haloalkyl" include:

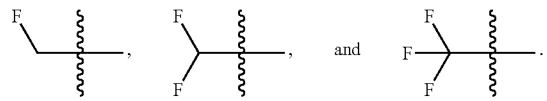

Additional non-limiting examples of "haloalkyl" include:

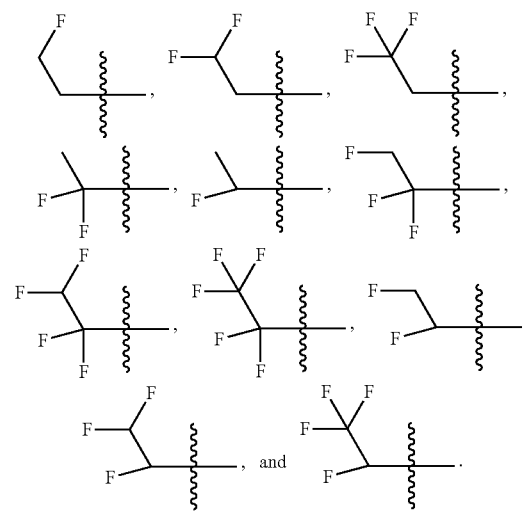

Additional non-limiting examples of "haloalkyl" include:

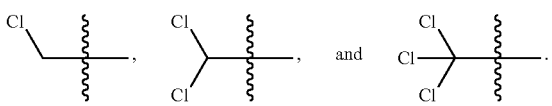

Additional non-limiting examples of "haloalkyl" include:

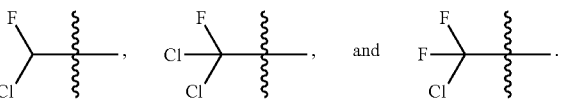

A "dosage form" means a unit of administration of an active agent. Examples of dosage forms include tablets, capsules, injections, suspensions, liquids, emulsions, implants, particles, spheres, creams, ointments, suppositories, inhalable forms, transdermal forms, buccal, sublingual, topical, gel, mucosal, and the like. A "dosage form" can also include an implant, for example an optical implant.

An "effective amount" as used herein, means an amount which provides a therapeutic benefit.

"Parenteral" administration of a pharmaceutical composition includes, e.g., subcutaneous (s.c.), intravenous (i.v.), intramuscular (i.m.), intrasternal injection, or infusion techniques.

To "treat" a disease as the term is used herein, means to reduce the frequency or severity of at least one sign or symptom of a disease or disorder experienced by a subject (i.e. palliative treatment) or to decrease a cause or effect of the disease or disorder (i.e. disease-modifying treatment).

As used herein, "pharmaceutical compositions" are compositions comprising at least one active agent, and at least one other substance, such as a carrier. "Pharmaceutical combinations" are combinations of at least two active agents which may be combined in a single dosage form or provided together in separate dosage forms with instructions that the active agents are to be used together to treat any disorder described herein.

As used herein, "pharmaceutically acceptable salt" is a form of the disclosed compound in which the parent compound is modified by making inorganic and organic, non-toxic, acid or base addition salts thereof. The salts of the present compounds can be synthesized from a parent compound that contains a basic or acidic moiety by conventional chemical methods. Generally, such salts can be prepared by reacting the free base forms of these compounds with a stoichiometric amount of the appropriate acid, or a free acid form of the compound with a stoichiometric amount of the appropriate base (such as Na, Ca, Mg, or K hydroxide, carbonate, bicarbonate, or the like), Such reactions are typically carried out in water or in an organic solvent, or in a mixture of the two. Generally, non-aqueous media like ether, ethyl acetate, ethanol, isopropanol, or acetonitrile are typical, where practicable.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—(CH$_2$)$_n$—COOH where n is 0-4, and the like, or using a different acid that produces the same counterion. Lists of additional suitable salts may be found, e.g., in *Remington's Pharmaceutical Sciences*, 17th ed., Mack Publishing Company, Easton, Pa., p. 1418 (1985).

The term "carrier" applied to pharmaceutical compositions/combinations of the invention refers to a diluent, excipient, or vehicle with which an active compound is provided.

A "pharmaceutically acceptable carrier" or "pharmaceutically acceptable excipient" means a carrier or excipient that is useful in preparing a pharmaceutical composition/combination that is generally safe, suitably non-toxic and neither biologically nor otherwise inappropriate for administration to a subject, typically a human.

A "patient" or "subject" is a human or domesticated animal in need of treatment for any of the disorders as specifically described herein. Non-limiting examples of domesticated animals include dogs, cats, horses, and livestock. As described further herein, the words patient or subject typically refers to a human patient or subject, and unless otherwise indicated by the text is assumed to refer to a human. In an alternative embodiment, the patient or subject is a domesticated animal in need of such therapy and responsive thereto. "Livestock" refers to animals that are generally kept for agricultural purposes, including, for example, cows, sheep, goats, pigs, and poultry.

A "therapeutically effective amount" of a pharmaceutical composition/combination of this invention means an amount effective, when administered to a subject, to provide a therapeutic benefit such as an amelioration of symptoms or reduction or diminution of the disease itself.

Unless otherwise defined, all technical and scientific terms used herein have the same meaning as commonly understood by one of ordinary skill in the art to which this application belongs. In the specification, singular forms also include the plural unless the context clearly dictates otherwise. Although methods and materials similar or equivalent to those described herein can be used in the practice or testing of the present application, suitable methods and materials are described below. All publications, patent applications, patents, and other references mentioned herein are incorporated by reference. The references cited herein are not admitted to be prior art to the claimed application. In the case of conflict, the present specification, including definitions, will control. In addition, the materials, methods, and examples are illustrative only and are not intended to be limiting.

II. Compounds of Formula I, Formula II, and Formula III

In certain aspects, the present invention provides a compound of Formula I, Formula II, or Formula III or a pharmaceutically acceptable salt thereof.

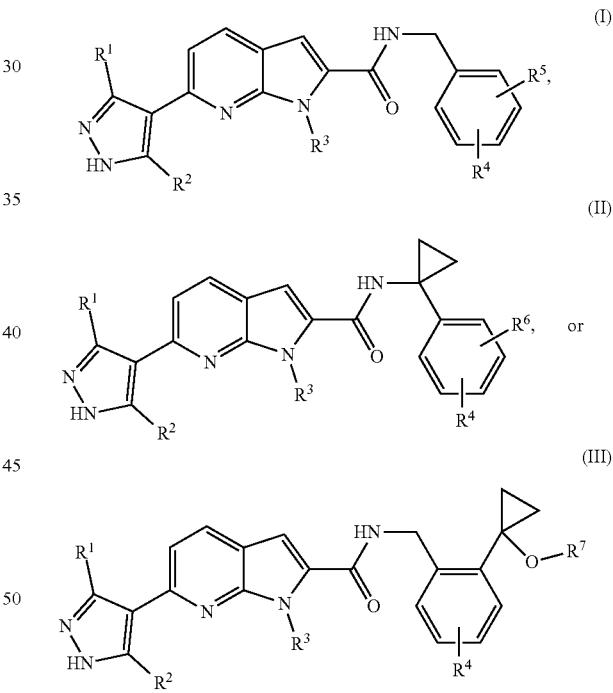

wherein all variables are defined herein.

In certain embodiments, the compound of Formula I is selected from:

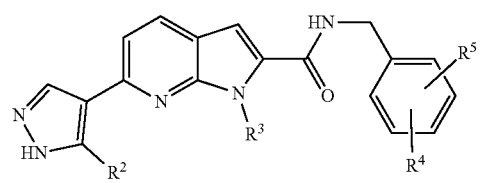

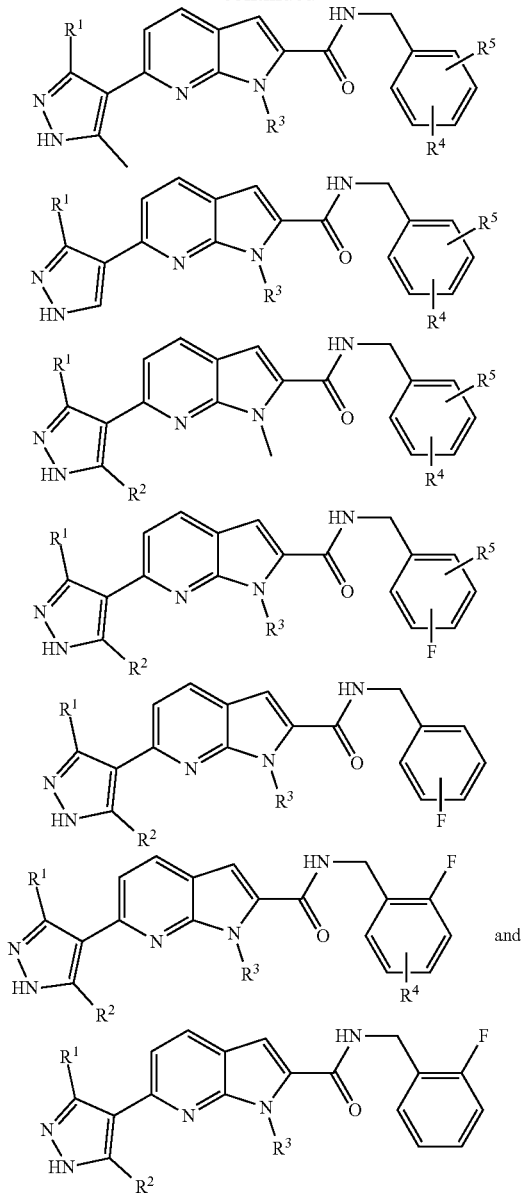
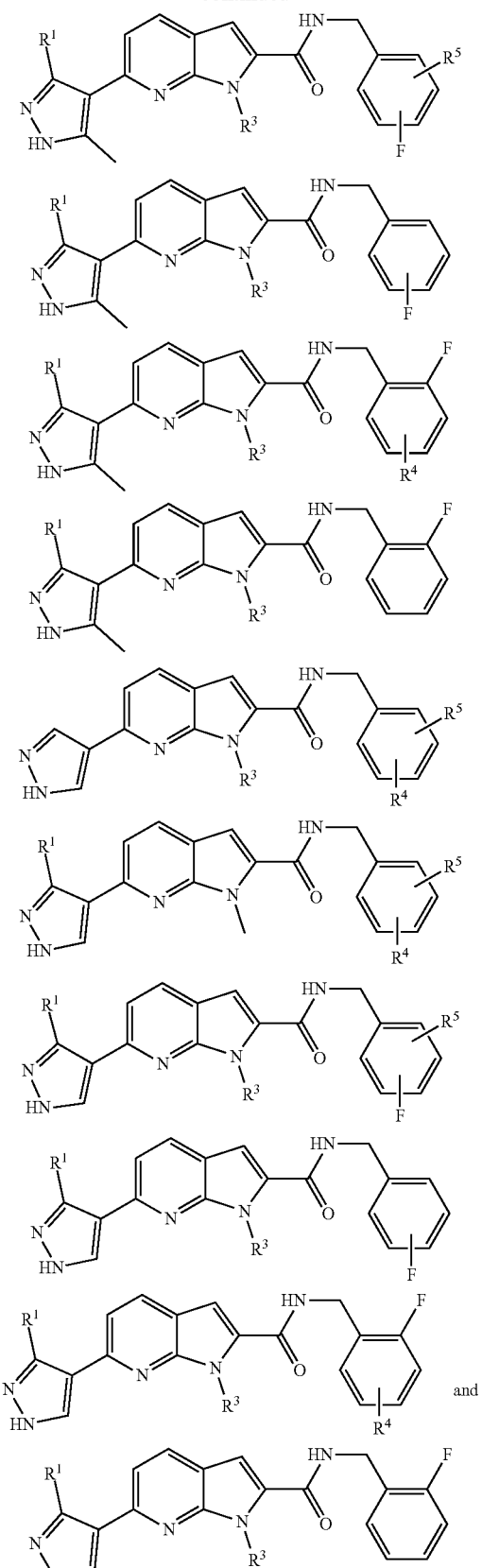
or a pharmaceutically acceptable salt thereof.
In certain embodiments, the compound of Formula I is selected from:
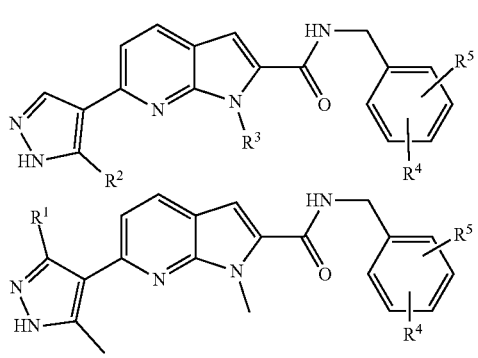
or a pharmaceutically acceptable salt thereof.

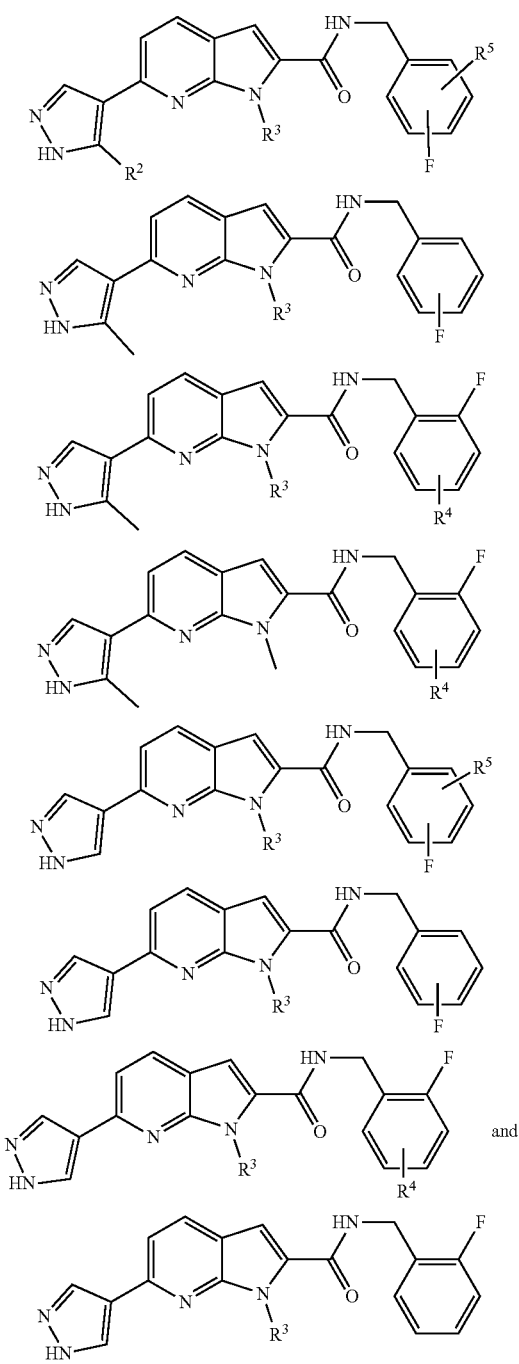
or a pharmaceutically acceptable salt thereof.
In other embodiments the compound of Formula I is selected from:
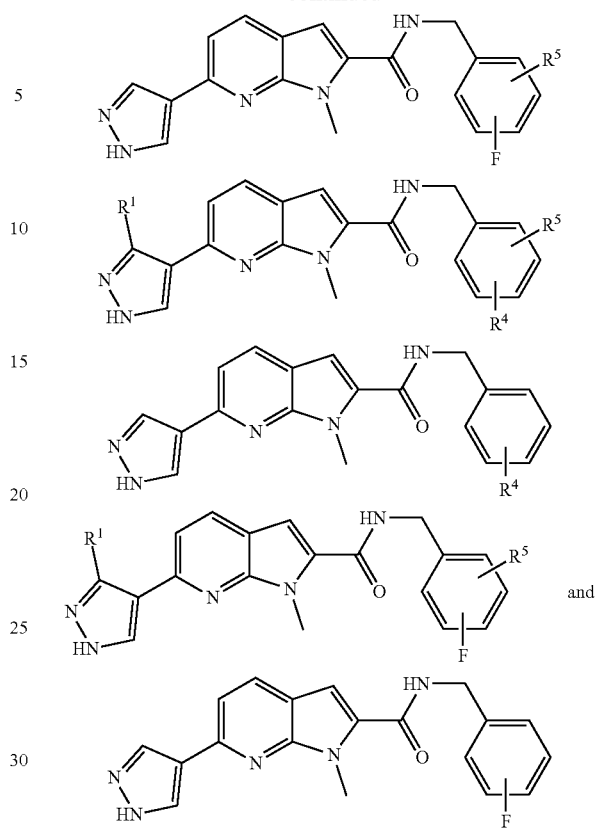
or a pharmaceutically acceptable salt thereof.
In other embodiments the compound of Formula I is selected from:
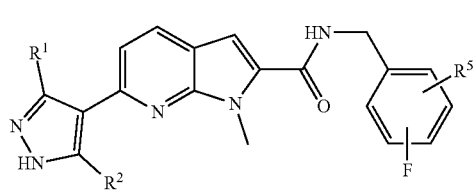
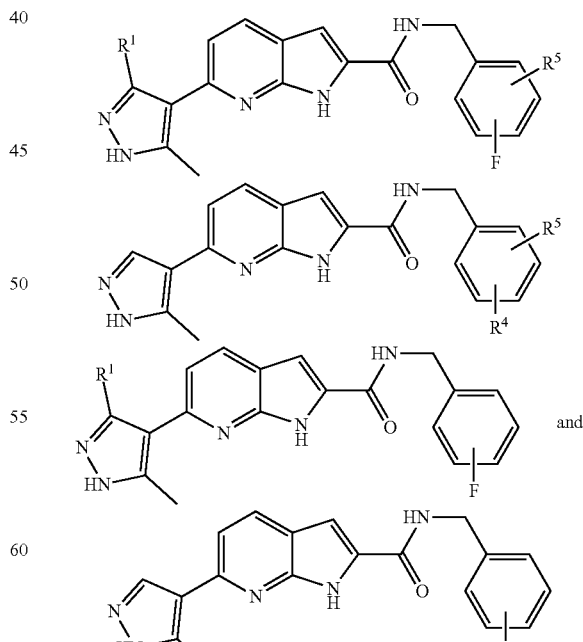
or a pharmaceutically acceptable salt thereof.

In certain embodiments, the compound of Formula I is selected from:
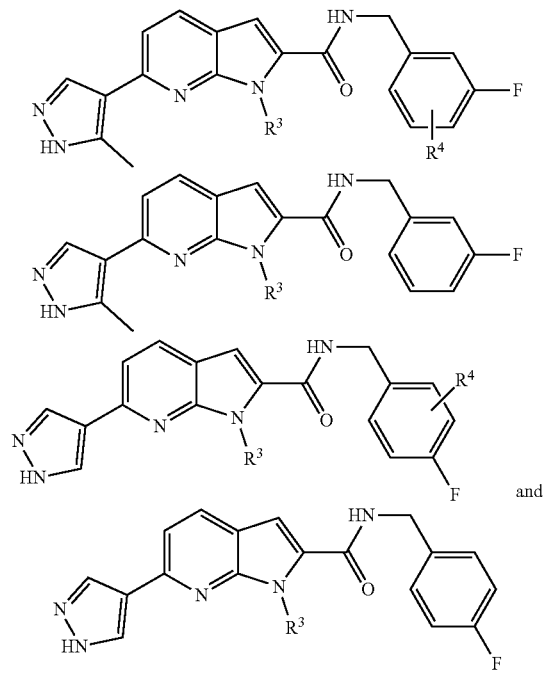
or a pharmaceutically acceptable salt thereof.
Non-limiting examples of compounds of Formula I include:
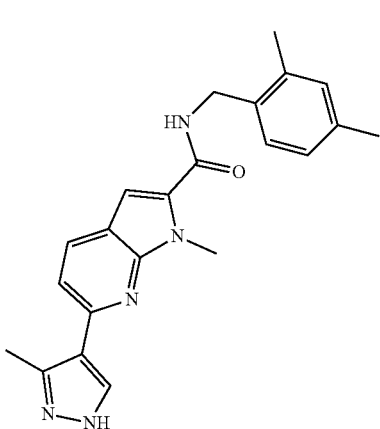
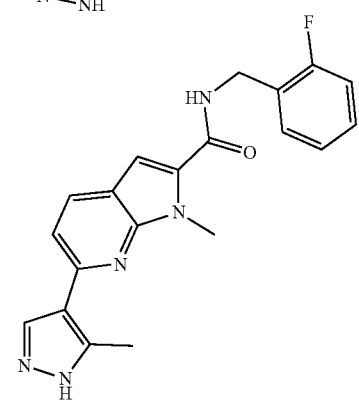
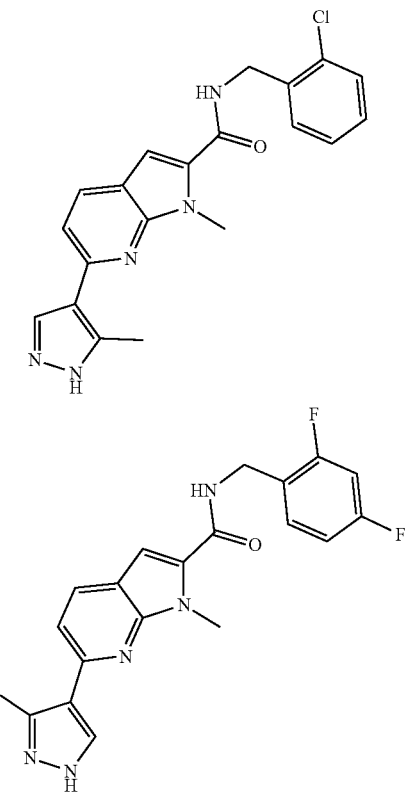
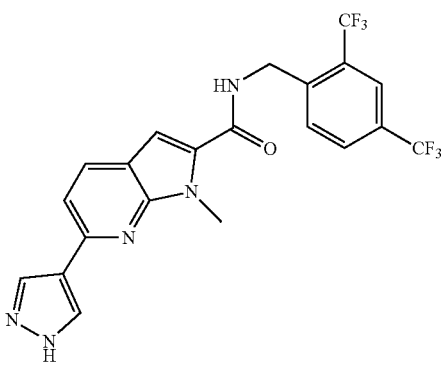
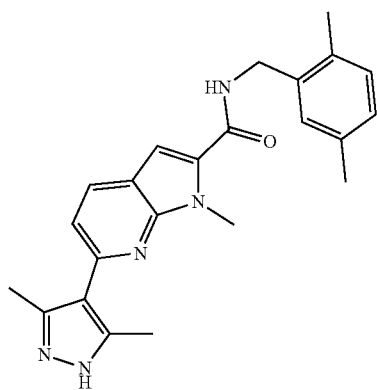

29
-continued
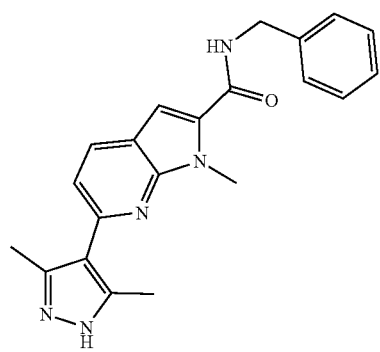
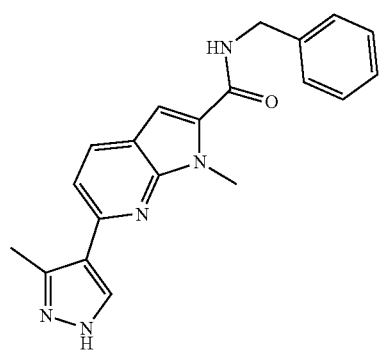
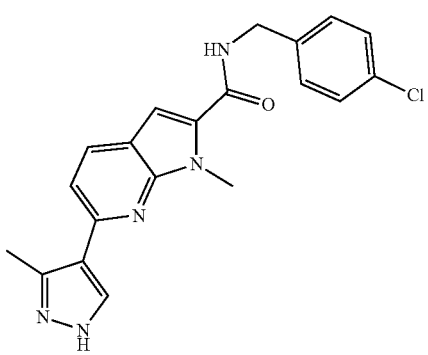
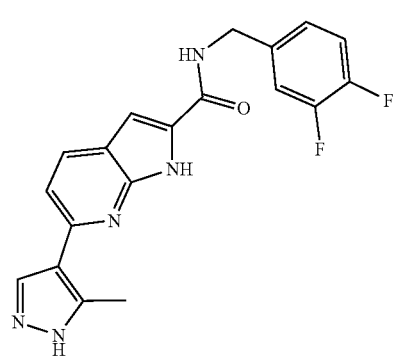
30
-continued
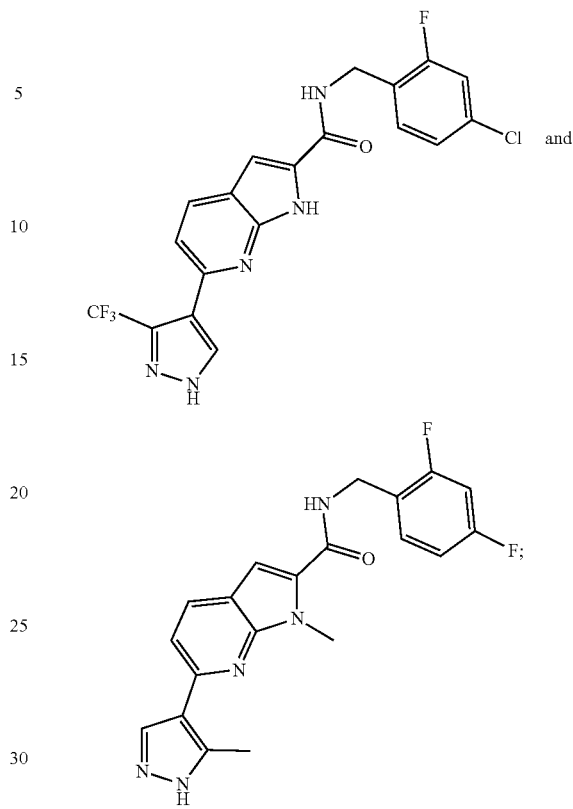
or a pharmaceutically acceptable salt thereof.
In alternative embodiments, the compound of Formula I is selected from:
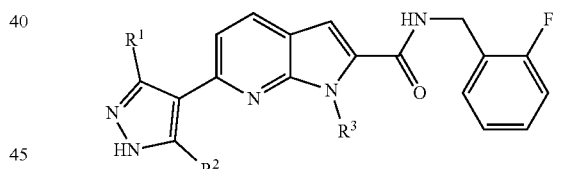
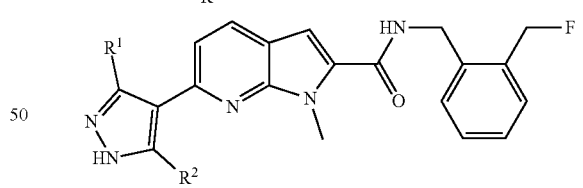
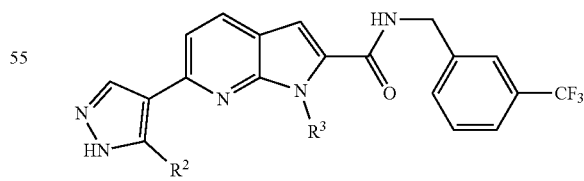
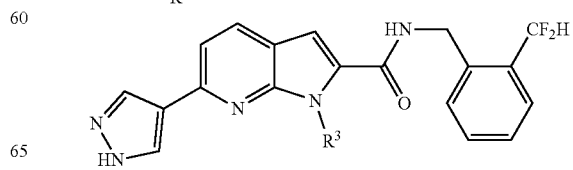

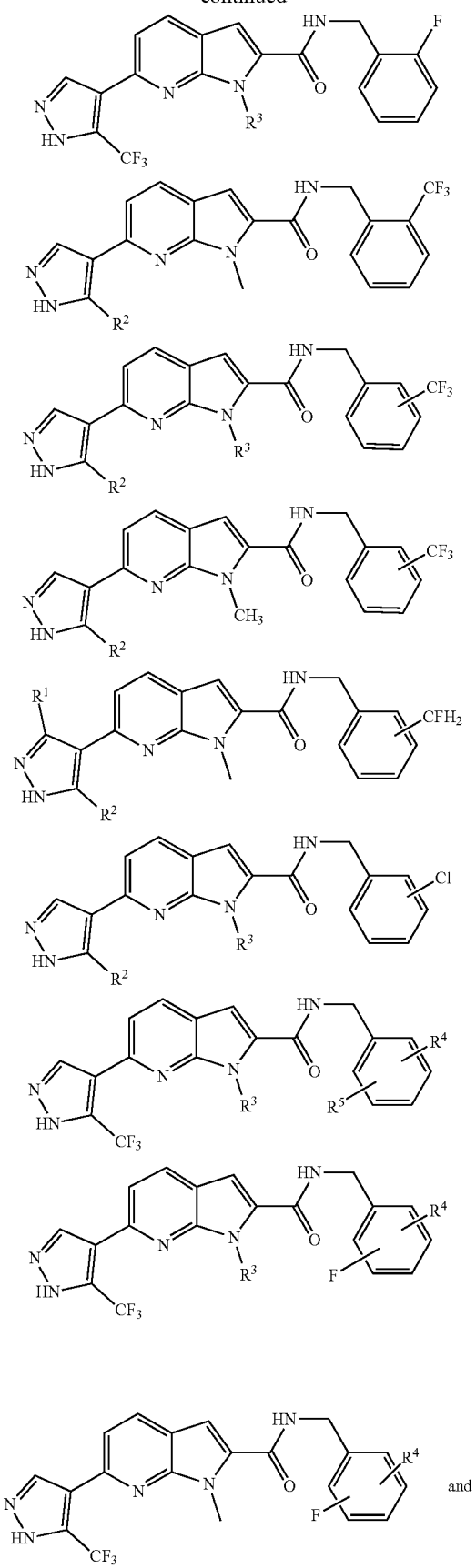
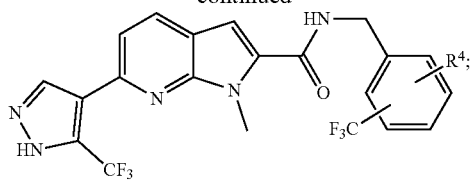
or a pharmaceutically acceptable salt thereof.
Alternative examples of a compound of Formula I include:
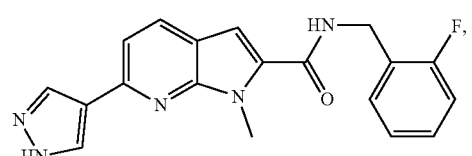
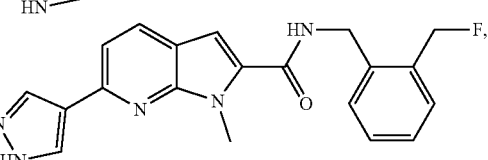
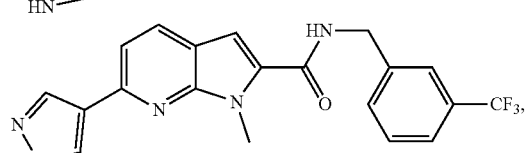
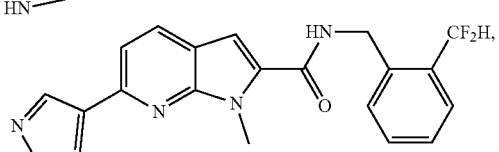
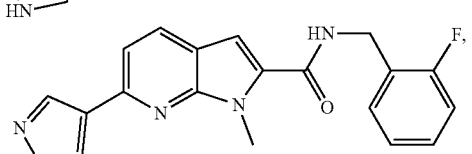
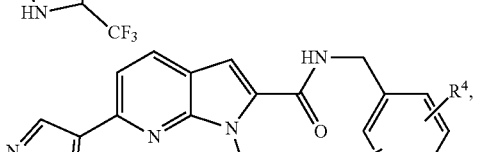
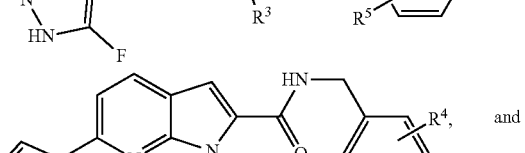
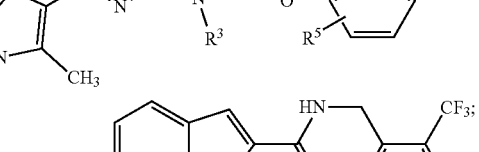
or a pharmaceutically acceptable salt thereof.

In certain embodiments, the compound of Formula II is selected from:
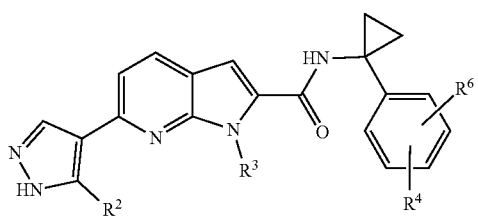
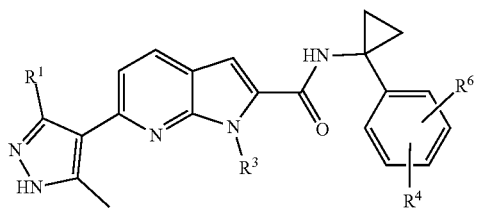
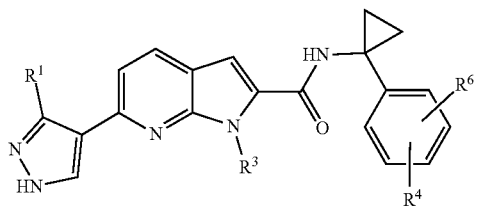
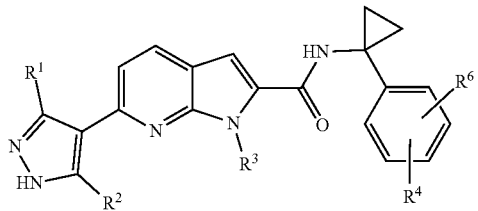
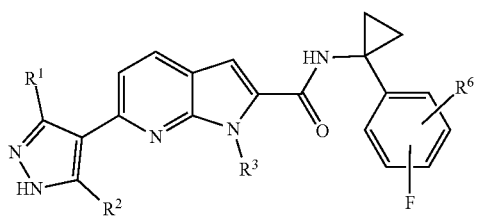
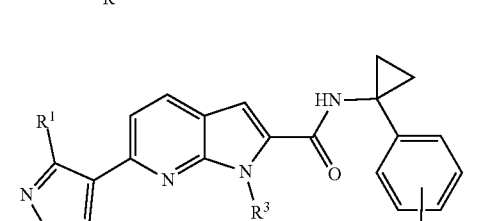
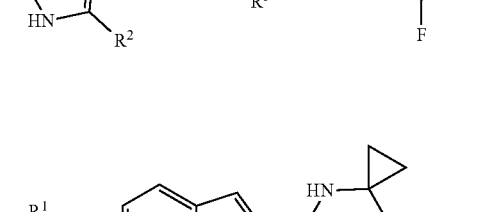
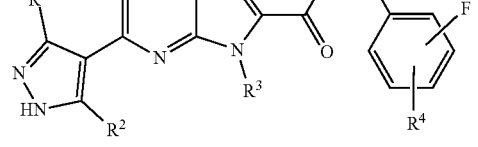
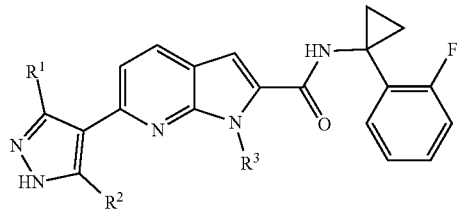
or a pharmaceutically acceptable salt thereof.
In certain embodiments, the compound of Formula II is selected from:
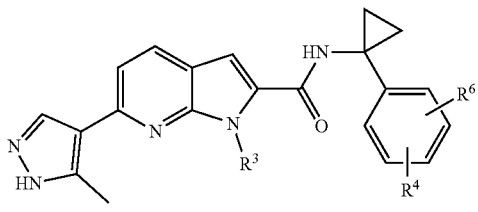
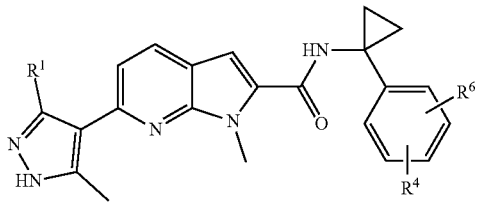
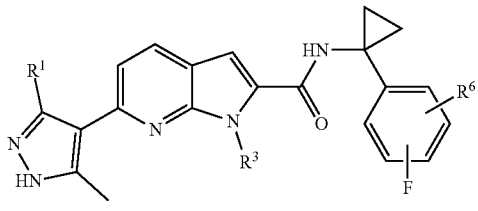
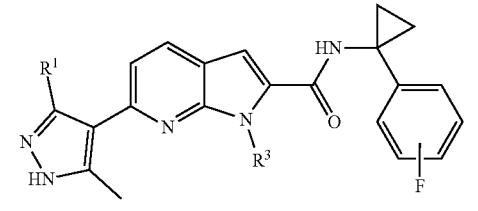
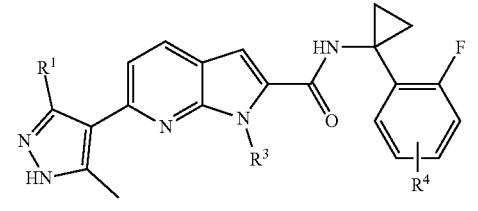
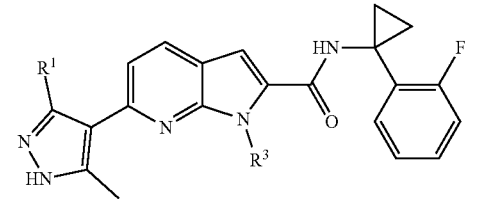

-continued
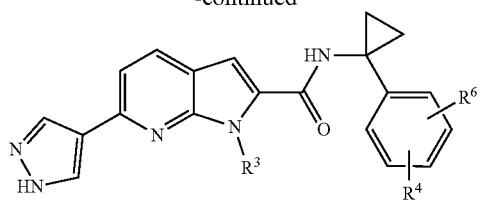
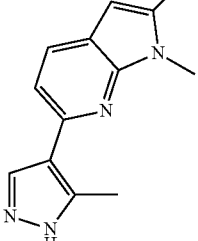
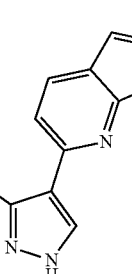
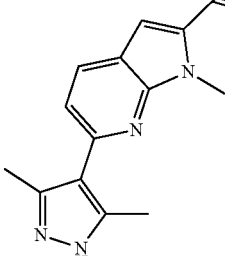
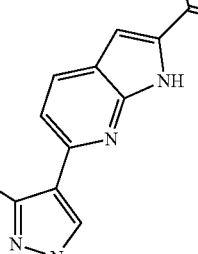
or a pharmaceutically acceptable salt thereof.
Non-limiting examples of compounds of Formula II include:
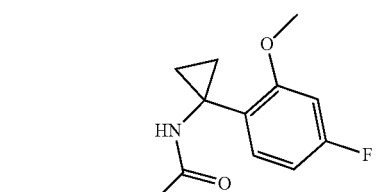
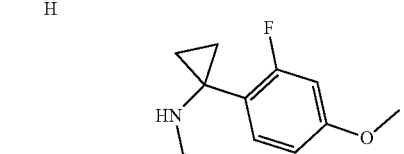
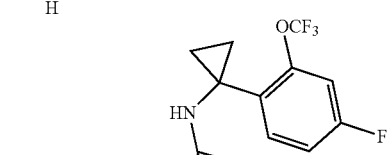
and
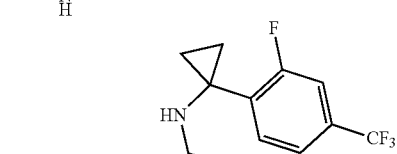

-continued
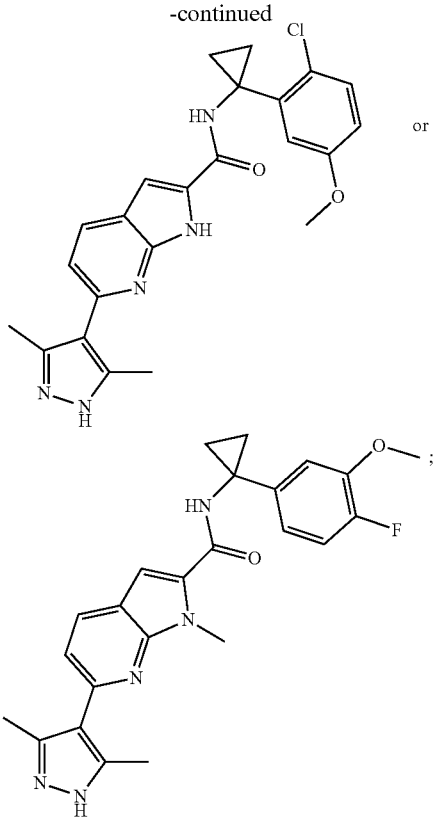
or
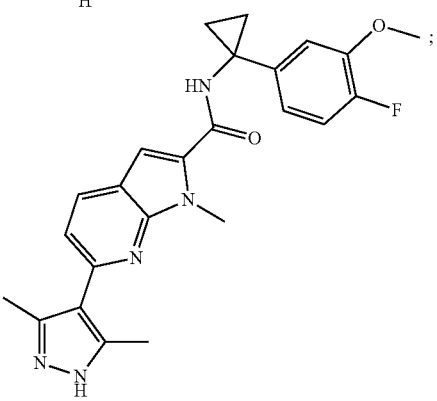
or a pharmaceutically acceptable salt thereof.
In alternative embodiments, a compound of Formula II is selected from:
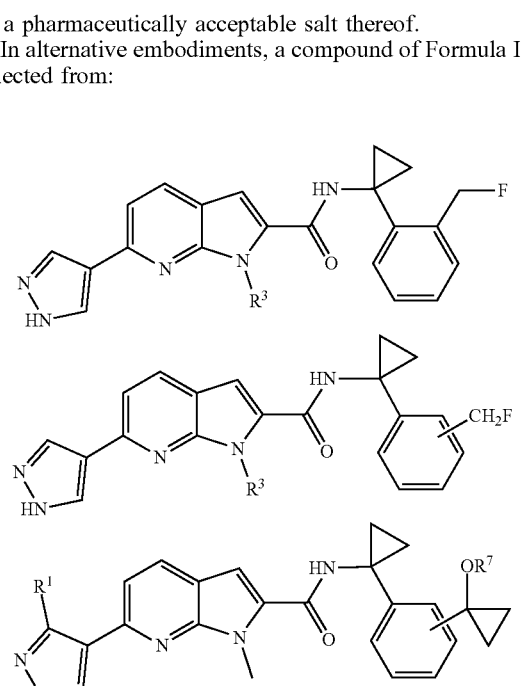
-continued
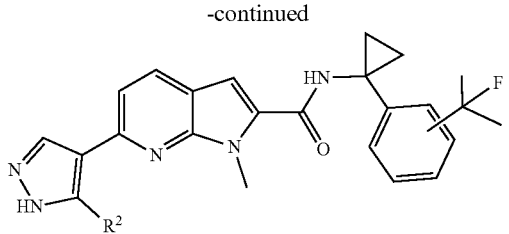
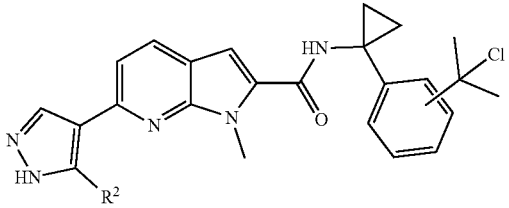
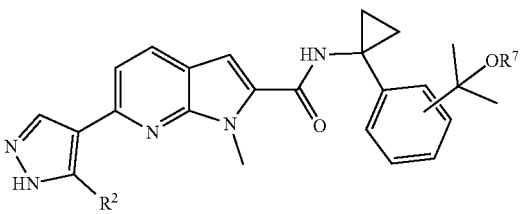
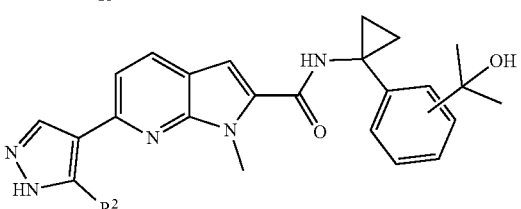
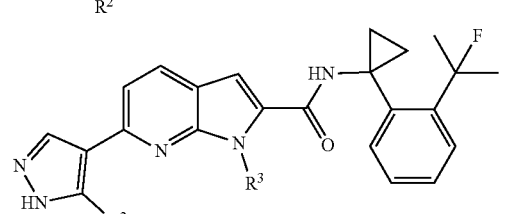
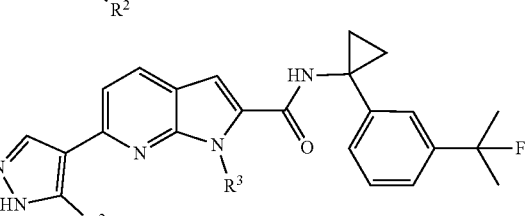
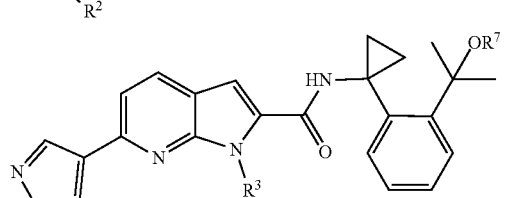
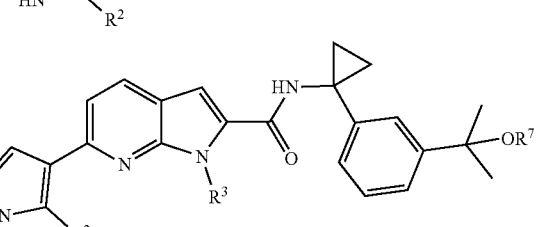

-continued or a pharmaceutically acceptable salt thereof.

Additional non-limiting examples of compounds of the present invention include:

or a pharmaceutically acceptable salt thereof.

Embodiments of $R^1$

In certain embodiments $R^1$ is hydrogen.
In certain embodiments $R^1$ is $CH_3$.
In certain embodiments $R^1$ is $C_2H$.
In certain embodiments $R^2$ is $CH_2CH_2CH_3$.
In certain embodiments $R^1$ is iso-$C_3H_7$.
In certain embodiments $R^1$ is F.
In certain embodiments $R^1$ is $C_1$.
In certain embodiments $R^1$ is Br.
In certain embodiments $R^1$ is $CF_3$.
In certain embodiments $R^1$ is $CH_2F$.
In certain embodiments $R^1$ is $CH_2CF_3$.

Embodiments of $R^2$

In certain embodiments $R^2$ is hydrogen.
In certain embodiments $R^2$ is $CH_3$.
In certain embodiments $R^2$ is $C_2H$.
In certain embodiments $R^2$ is $CH_2CH_2CH_3$.
In certain embodiments $R^2$ is iso-$C_3H_7$.
In certain embodiments $R^2$ is F.
In certain embodiments $R^2$ is $C_1$.
In certain embodiments $R^2$ is Br.
In certain embodiments $R^2$ is $CF_3$.
In certain embodiments $R^2$ is $CH_2F$.
In certain embodiments $R^2$ is $CH_2CF_3$.

Embodiments of $R^3$

In certain embodiments $R^3$ is hydrogen.
In certain embodiments $R^3$ is $CH_3$.
In certain embodiments $R^3$ is $C_2H_5$.
In certain embodiments $R^3$ is $CH_2CH_2CH_3$.
In certain embodiments $R^3$ is iso-$C_3H_7$.
In certain embodiments $R^3$ is $CF_3$.
In certain embodiments $R^3$ is $CH_2F$.
In certain embodiments $R^3$ is $CH_2CF_3$.

Embodiments of $R^4$

In certain embodiments $R^4$ is hydrogen.
In certain embodiments $R^4$ is $CH_3$.

In certain embodiments $R^4$ is $C_2H$.
In certain embodiments $R^4$ is $CH_2CH_2CH_3$.
In certain embodiments $R^4$ is iso-$C_3H_7$.
In certain embodiments $R^4$ is F.
In certain embodiments $R^4$ is $C_1$.
In certain embodiments $R^4$ is Br.
In certain embodiments $R^4$ is $CF_3$.
In certain embodiments $R^4$ is $CH_2F$.
In certain embodiments $R^4$ is $CH_2CF_3$.

Embodiments of $R^5$

In certain embodiments $R^5$ is hydrogen.
In certain embodiments $R^5$ is $CH_3$.
In certain embodiments $R^5$ is $C_2H$.
In certain embodiments $R^5$ is $CH_2CH_2CH_3$.
In certain embodiments $R^5$ is iso-$C_3H_7$.
In certain embodiments $R^5$ is F.
In certain embodiments $R^5$ is $C_1$.
In certain embodiments $R^5$ is Br.
In certain embodiments $R^5$ is $CF_3$.
In certain embodiments $R^5$ is $CH_2F$.
In certain embodiments $R^5$ is $CH_2CF_3$.

Embodiments of $R^6$

In certain embodiments $R^6$ is hydrogen.
In certain embodiments $R^6$ is $CH_3$.
In certain embodiments $R^6$ is $C_2H$.
In certain embodiments $R^6$ is $CH_2CH_2CH_3$.
In certain embodiments $R^6$ is iso-$C_3H_7$.
In certain embodiments $R^6$ is F.
In certain embodiments $R^6$ is $C_1$.
In certain embodiments $R^6$ is Br.
In certain embodiments $R^6$ is $CF_3$.
In certain embodiments $R^6$ is $CH_2F$.
In certain embodiments $R^6$ is $CH_2CF_3$.
In certain embodiments $R^6$ is OH.
In certain embodiments $R^6$ is $OCH_3$.
In certain embodiments $R^6$ is $OC_2H_5$.
In certain embodiments $R^6$ is $OCH_2CH_2CH_3$.
In certain embodiments $R^6$ is $OC_3H_7$-iso.
In certain embodiments $R^6$ is $OCF_3$.
In certain embodiments $R^6$ is $OCH_2CF_3$.

Embodiments of $R^7$

In certain embodiments $R^7$ is hydrogen.
In certain embodiments $R^7$ is $CH_3$.
In certain embodiments $R^7$ is $C_2H$.
In certain embodiments $R^7$ is $CH_2CH_2CH_3$.
In certain embodiments $R^7$ is iso-$C_3H_7$.
In certain embodiments $R^7$ is $CF_3$.
In certain embodiments $R^7$ is $CH_2F$.
In certain embodiments $R^7$ is $CH_2CF_3$.
In certain embodiments,

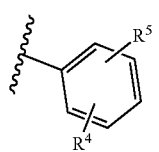

is of structure:

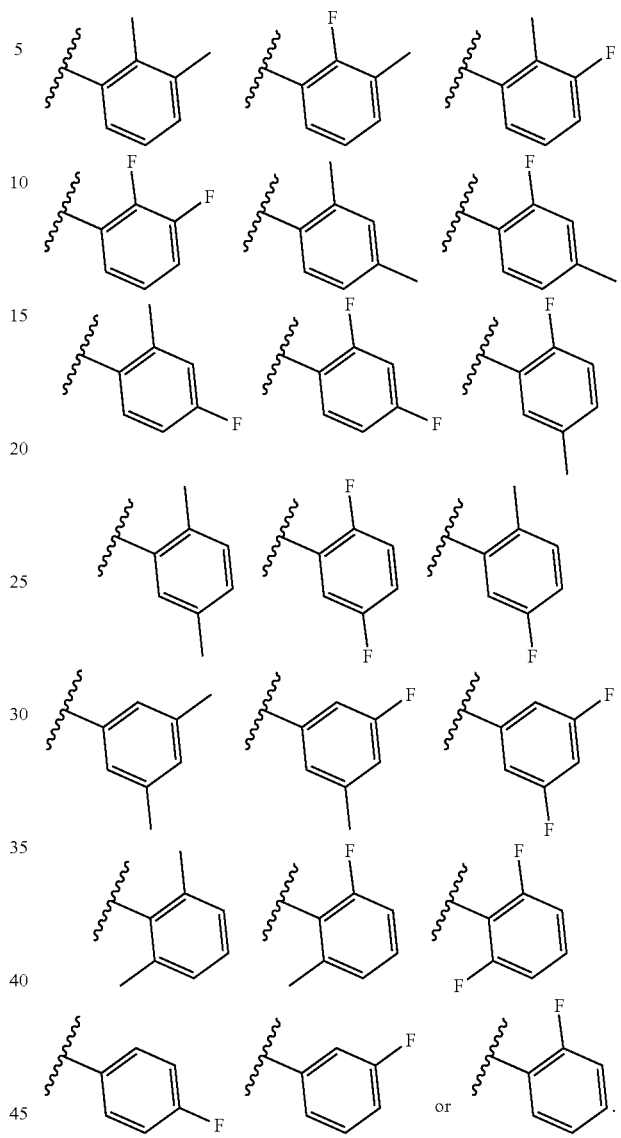

In certain embodiments,

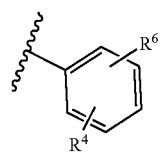

is of structure:

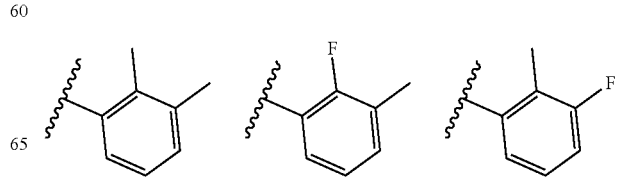

-continued

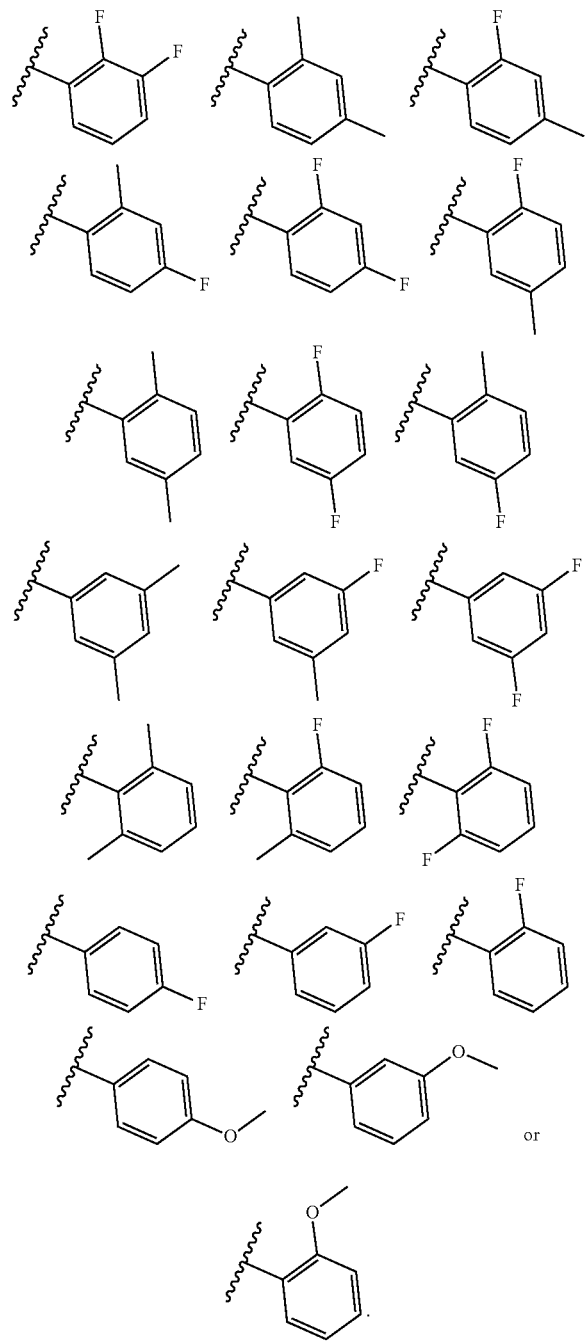

In certain embodiments,

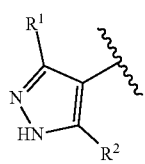

is of structure:

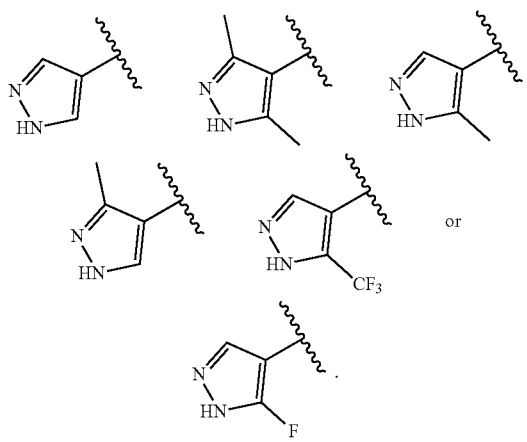

The structure of the compounds of the present invention are typically selected such that they are sufficiently stable to sustain a shelf life of at least two, three, four, or five months under ambient conditions. To accomplish this, each of the variables described herein is selected such that the resulting compound achieves a desired shelf life of at least two, three, four, or five months under ambient conditions. One of ordinary skill in the art is well aware of the stability of chemical moieties and can avoid those that are not stable or are too reactive under appropriate conditions.

Additional Embodiments

1. A compound of Formula:

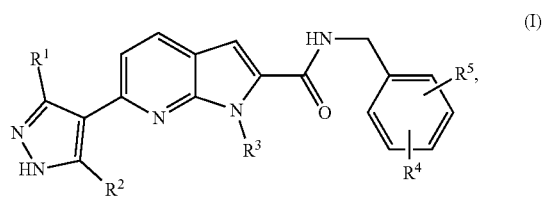

(I)

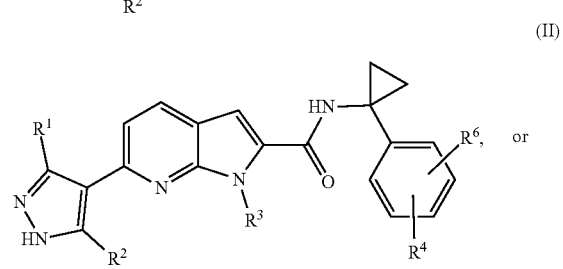

(II)

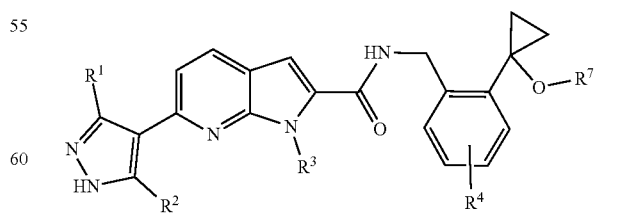

(III)

or a pharmaceutically acceptable salt thereof;
wherein:
 $R^1$ and $R^2$ are independently selected from hydrogen, $C_1$-$C_4$ alkyl, $C_1$-$C_4$ haloalkyl, and halogen;

R[3] is selected from hydrogen, $C_1$-$C_4$ alkyl, and $C_1$-$C_4$ haloalkyl;

R[4] and R[5] are independently selected from hydrogen, $C_1$-$C_4$ alkyl, $C_1$-$C_4$ haloalkyl, and halogen;

R[6] is selected from hydrogen, $C_1$-$C_4$ alkyl, $C_1$-$C_4$ haloalkyl, halogen, $C_1$-$C_4$ alkyl-OR[7], and OR[7]; and R[7] is selected from hydrogen, $C_1$-$C_4$ alkyl, and $C_1$-$C_4$ haloalkyl.

2. The compound of embodiment 1, wherein the compound is of Formula:

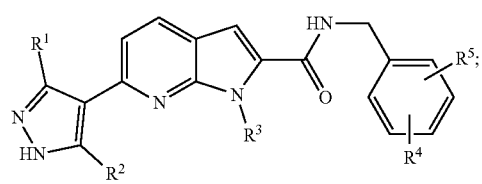
(I)

or a pharmaceutically acceptable salt thereof

3. The compound of embodiment 2, wherein the compound is of Formula:

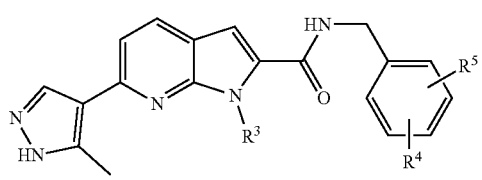
(I-A)

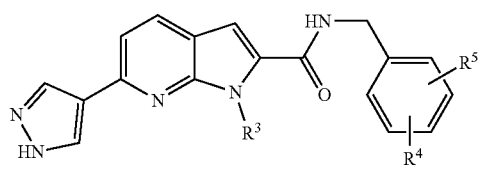
(I-B)

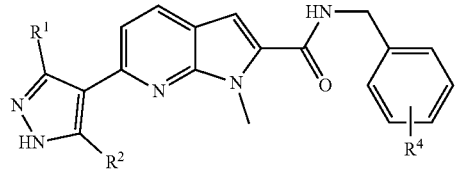
(I-C)

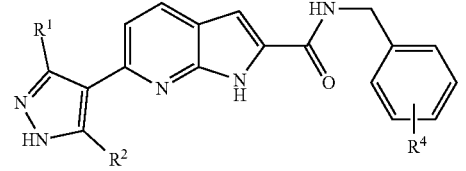
(I-D)

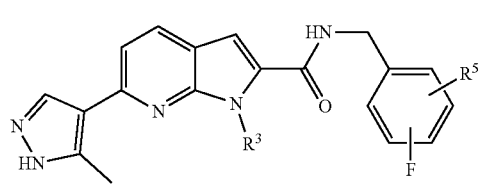
(I-E)

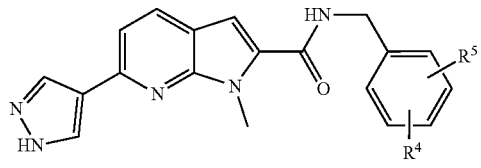
(I-F)

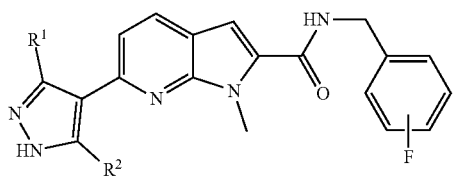
(I-G)

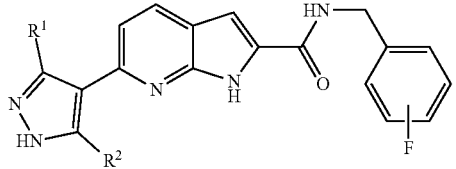
(I-H)

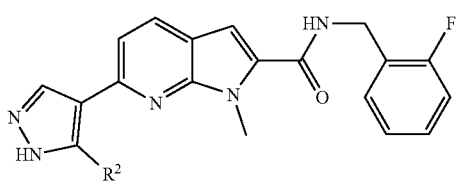
(I-I)

or

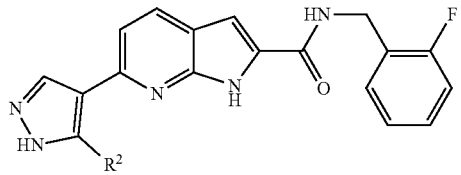
(I-J)

or a pharmaceutically acceptable salt thereof.

4. The compound of any one of embodiments 1-3, wherein R[5] is hydrogen.

5. The compound of any one of embodiments 1-3, wherein R[5] is halogen.

6. The compound of any one of embodiments 1-3, wherein R[5] is fluoro.

7. The compound of any one of embodiments 1-3, wherein R[5] is chloro.

8. The compound of any one of embodiments 1-3, wherein R[5] is methyl.

9. The compound of any one of embodiments 1-3, wherein R[5] is ethyl.

10. The compound of embodiment 1, wherein the compound is of Formula:

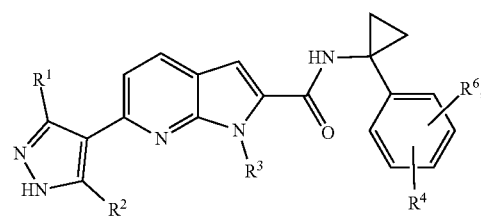
(II)

or a pharmaceutically acceptable salt thereof.

11. The compound of embodiment 10, wherein the compound is of Formula:

(II-A), (II-B), (II-C), (II-D), (II-E), (II-F), (II-G), (II-H), (II-I), (II-J)

or a pharmaceutically acceptable salt thereof.

12. The compound of embodiment 10 or embodiment 11, wherein $R^6$ is hydrogen.

13. The compound of embodiment 10 or embodiment 11, wherein $R^6$ is OMe.

14. The compound of embodiment 10 or embodiment 11, wherein $R^6$ is halogen.

15. The compound of embodiment 10 or embodiment 11, wherein $R^6$ is fluoro.

16. The compound of embodiment 10 or embodiment 11, wherein $R^6$ is chloro.

17. The compound of embodiment 10 or embodiment 11, wherein $R^6$ is methyl.

18. The compound of embodiment 10 or embodiment 11, wherein $R^6$ is ethyl.

19. The compound of embodiment 1, wherein the compound is of Formula:

(III)

or a pharmaceutically acceptable salt thereof.

20. The compound of embodiment 19, wherein the compound is of Formula:

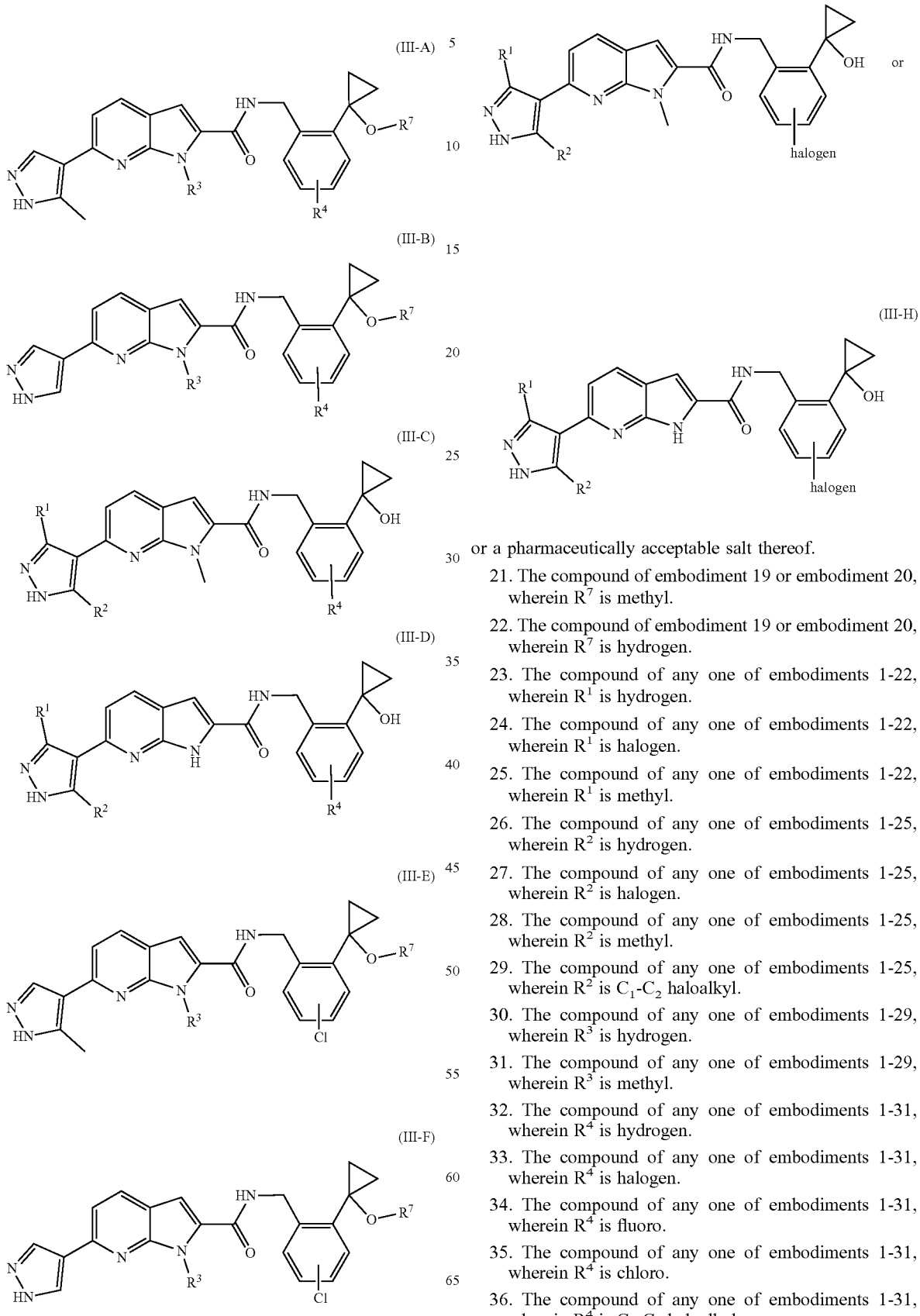

or a pharmaceutically acceptable salt thereof.

21. The compound of embodiment 19 or embodiment 20, wherein $R^7$ is methyl.

22. The compound of embodiment 19 or embodiment 20, wherein $R^7$ is hydrogen.

23. The compound of any one of embodiments 1-22, wherein $R^1$ is hydrogen.

24. The compound of any one of embodiments 1-22, wherein $R^1$ is halogen.

25. The compound of any one of embodiments 1-22, wherein $R^1$ is methyl.

26. The compound of any one of embodiments 1-25, wherein $R^2$ is hydrogen.

27. The compound of any one of embodiments 1-25, wherein $R^2$ is halogen.

28. The compound of any one of embodiments 1-25, wherein $R^2$ is methyl.

29. The compound of any one of embodiments 1-25, wherein $R^2$ is $C_1$-$C_2$ haloalkyl.

30. The compound of any one of embodiments 1-29, wherein $R^3$ is hydrogen.

31. The compound of any one of embodiments 1-29, wherein $R^3$ is methyl.

32. The compound of any one of embodiments 1-31, wherein $R^4$ is hydrogen.

33. The compound of any one of embodiments 1-31, wherein $R^4$ is halogen.

34. The compound of any one of embodiments 1-31, wherein $R^4$ is fluoro.

35. The compound of any one of embodiments 1-31, wherein $R^4$ is chloro.

36. The compound of any one of embodiments 1-31, wherein $R^4$ is $C_1$-$C_2$ haloalkyl.

37. A compound of structure:

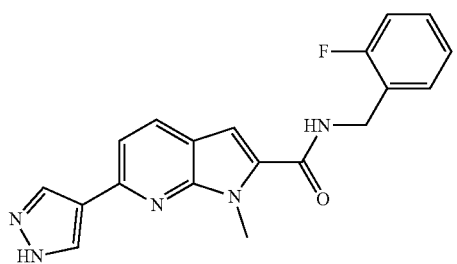

or a pharmaceutically acceptable salt thereof.

38. A compound of structure:

or a pharmaceutically acceptable salt thereof.

39. A compound of structure:

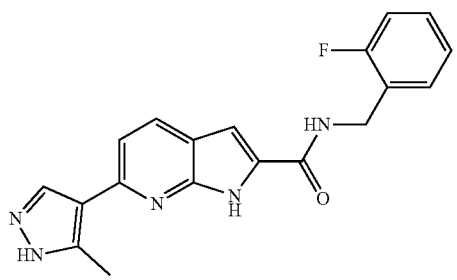

or a pharmaceutically acceptable salt thereof.

40. A compound of structure:

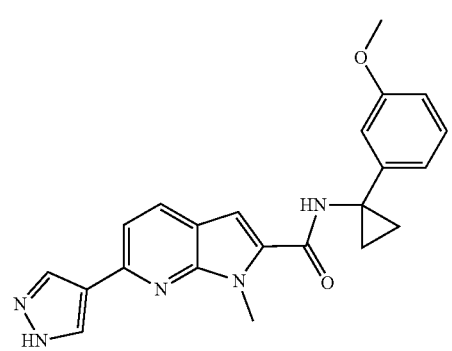 [SMILES: COc1cccc(C2(NC(=O)c3cc4ccc(-c5cn[nH]c5)nc4n3C)CC2)c1]

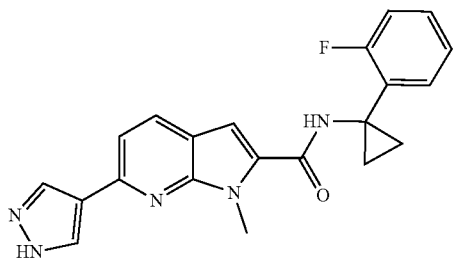

or a pharmaceutically acceptable salt thereof

41. A compound of structure:

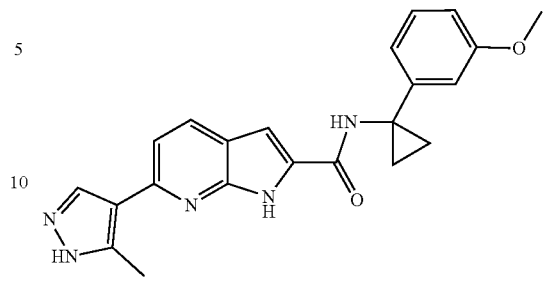

or a pharmaceutically acceptable salt thereof.

42. A compound of structure:

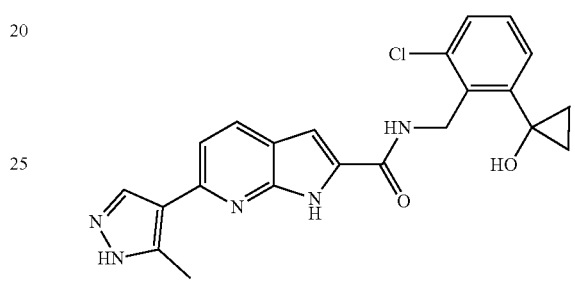

or a pharmaceutically acceptable salt thereof

43. A compound of structure:

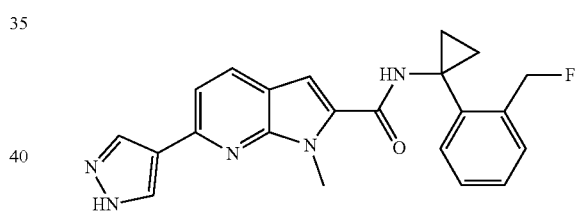

or a pharmaceutically acceptable salt thereof.

44. A compound of structure:

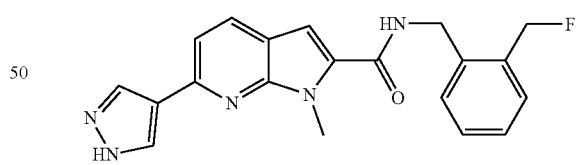

or a pharmaceutically acceptable salt thereof.

45. A compound of structure:

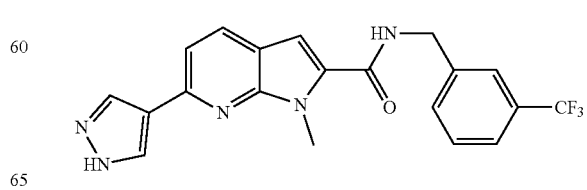

or a pharmaceutically acceptable salt thereof

46. A compound of structure:

or a pharmaceutically acceptable salt thereof.

47. A compound of structure:

or a pharmaceutically acceptable salt thereof.

48. A compound of structure:

or a pharmaceutically acceptable salt thereof.

49. A compound of structure:

or a pharmaceutically acceptable salt thereof.

50. A compound of structure:

or a pharmaceutically acceptable salt thereof.

51. A compound of Formula:

or a pharmaceutically acceptable salt thereof,
wherein:
$R^1$ and $R^2$ are independently selected from hydrogen, $C_1$-$C_4$ alkyl, $C_1$-$C_4$ haloalkyl, and halogen; and
$R^4$ and $R^5$ are independently selected from hydrogen, $C_1$-$C_4$ alkyl, $C_1$-$C_4$ haloalkyl, and halogen.

52. The compound of embodiment 51, wherein $R^2$ is hydrogen.
53. The compound of embodiment 51, wherein $R^2$ is F.
54. The compound of embodiment 51, wherein $R^2$ is Cl.
55. The compound of embodiment 51, wherein $R^2$ is methyl.
56. The compound of embodiment 51, wherein $R^2$ is $C_1$-$C_2$ haloalkyl.
57. A compound of Formula:

or a pharmaceutically acceptable salt thereof;
wherein:
$R^1$ is selected from hydrogen, $C_1$-$C_4$ alkyl, $C_1$-$C_4$ haloalkyl, and halogen; and
$R^4$ and $R^5$ are independently selected from hydrogen, $C_1$-$C_4$ alkyl, $C_1$-$C_4$ haloalkyl, and halogen.

58. The compound of any one of embodiments 51-57, wherein $R^1$ is hydrogen.
59. The compound of any one of embodiments 51-57, wherein $R^1$ is F.
60. The compound of any one of embodiments 51-57, wherein $R^1$ is Cl.
61. The compound of any one of embodiments 51-57, wherein $R^1$ is methyl.
62. The compound of any one of embodiments 51-57, wherein $R^1$ is $C_1$-$C_2$ haloalkyl.
63. The compound of any one of embodiments 51-62, wherein $R^4$ is hydrogen.
64. The compound of any one of embodiments 51-62, wherein $R^4$ is halogen.
65. The compound of any one of embodiments 51-62, wherein $R^4$ is fluoro.
66. The compound of any one of embodiments 51-62, wherein $R^4$ is chloro.
67. The compound of any one of embodiments 51-62, wherein $R^4$ is $C_1$-$C_2$ haloalkyl.
68. The compound of any one of embodiments 51-67, wherein $R^5$ is hydrogen.
69. The compound of any one of embodiments 51-67, wherein $R^5$ is halogen.
70. The compound of any one of embodiments 51-67, wherein $R^5$ is fluoro.

71. The compound of any one of embodiments 51-67, wherein $R^5$ is chloro.
72. The compound of any one of embodiments 51-67, wherein $R^5$ is $C_1$-$C_2$ haloalkyl.
73. A pharmaceutical composition comprising a compound of any one of embodiments 1-72 or a pharmaceutically acceptable salt thereof, and a pharmaceutically acceptable excipient.
74. The pharmaceutical composition of embodiment 73, wherein the pharmaceutical composition is suitable for oral administration.
75. The pharmaceutical composition of embodiment 73, wherein the pharmaceutical composition is suitable for parenteral administration.
76. The pharmaceutical composition of embodiment 73, wherein the pharmaceutical composition is suitable for intravenous administration.
77. A method of treating a ROCK1 or ROCK2 mediated disorder comprising administering an effective amount of a compound of any one of embodiments 1-72 or a pharmaceutically acceptable salt thereof, optionally in a pharmaceutical composition, to a subject in need thereof.
78. The method of embodiment 77, wherein the subject is a human.
79. The method of embodiment 78, wherein the disorder is a neurodegenerative disorder.
80. The method of embodiment 79, wherein the neurodegenerative disorder is amyotrophic lateral sclerosis.
81. The method of embodiment 78, wherein the neurodegenerative disorder is Parkinson's disease.
82. Use of a compound of any one of embodiments 1-72 or a pharmaceutically acceptable salt thereof, optionally in a pharmaceutical composition, in the manufacture of a medicament for the treatment of a ROCK1 or ROCK2 mediated disorder.
83. Use of a compound of any one of embodiments 1-72 or a pharmaceutically acceptable salt thereof, optionally in a pharmaceutical composition, in the treatment of a ROCK1 or ROCK2 mediated disorder.
84. The use of embodiment 82 or 83, wherein the disorder is a neurodegenerative disorder.
85. The use of embodiment 84, wherein the neurodegenerative disorder is amyotrophic lateral sclerosis.
86. The use of embodiment 82 or 83, wherein the neurodegenerative disorder is Parkinson's disease.

III. Methods of Treatment

Rho-associated coiled-coil kinase (ROCK) isoforms 1 and 2 are downstream targets of GTP-bound and activated Rho GTPase proteins that phosphorylate a number of substrates involved in myosin-actin-cytoskeletal architecture, actin-filament dynamics, neurofilament, and actin-binding proteins. ROCK1 is expressed in a variety of human tissues including the heart, pancreas, lung, liver, skeletal muscle, and kidney, but is not substantially expressed in the brain (Fujisawa, K. et al. Identification of the rho-binding domain of p160ROCK, a rho-associated coiled-coil containing protein kinase. J Biol Chem. 271:23022-8(1996)). ROCK2 is preferentially expressed in the brain and skeletal muscle (Nakagawa, O. et al. ROCK-I and ROCK-II, two isoforms of rho-associated coiled-coil forming protein serine/threonine kinase in mice. FEBS Lett. 395:189-93(1996)). Increased activity of ROCK2 is implicated in defects on dendritic spine structure and function in several model systems (Swanger, S. A. et al. ROCK1 and ROCK2 inhibition alters dendritic spine morphology in hippocampal neurons. Cell Logist. 5:e1133266(2015); Sellers, K. J. et al. Amyloid R synaptotoxicity is Wnt-PCP dependent and blocked by fasudil. Alzheimers Dement. 14:306-17(2018); Henderson et al. Pharmacologic inhibition of LIMK1 provides dendritic spine resilience against beta-amyloid. Sci Signal. 12:eaaw9318(2019)). Indeed, ROCK2 is implicated in a number of neurodegenerative and neurological disorders including Parkinson disease (PD), amyotrophic lateral sclerosis (ALS), Alzheimer disease (AD), spinal cord injury, stroke, and neuroinflammation (Weber, A. J. et al. Perspectives on ROCK2 as a Therapeutic Target for Alzheimer's Disease. Front in Cell Neurosci. 15:636017(2021)).

ROCK2 is shown to regulate several complex neuronal processes associated with neurodegenerative disorders. For example, AAV.shRNA-mediated downregulation of ROCK2 rescued dopaminergic neurons in the substantia nigra (SN) and preserves motor behavior in a 6-hydroxydopamine (6-OHDA)-induced Parkinson mouse model (Saal, K. et al. Neurobiol Dis. 73:150-62(2015)). ROCK inhibition can be used to modulate these neuronal processes. For example, in a study in mice ROCK inhibition led to decreased midbrain alpha-synuclein pathology and improved motor and cognitive function in a mouse model expressing human mutant alpha-synuclein ($aSyn^{A53T}$) (Tatenhorst et al. Fasudil attenuates aggregation of α-synuclein in models of Parkinson's disease. Acta Neuropathol Commun. 4:39(2016)).

ROCK proteins are present in many types of nerve cells in the CNS. Excess activity of ROCK proteins in the CNS leads to oxidative stress, uncontrolled inflammation, immune abnormality, energy metabolism disorders, neuronal cell loss, reactive gliosis, and/or impaired synaptic transmission, thus promoting the development of neurodegenerative diseases. ROCK protein overexpression has been detected in the lesions of Alzheimer's disease (AD), Parkinson's disease (PD), and multiple sclerosis (MS), revealing that ROCK proteins are involved in the pathology of these diseases and might be important initiators of pathogenesis. Inhibition of ROCK proteins has been shown to cause several biological events, such as increased neurite outgrowth, axonal regeneration, and activation of prosurvival protein kinase B (AKT). (Q. Wang et al. "Advantages of Rho-associated kinases and their inhibitor Fasudil for the treatment of neurodegenerative diseases", *Neural Regen. Res.* 2022, 17(12):2623-2631.)

Because of ROCK's role in neuronal processes its over activity or increased concentration is associated with various neurological defects. For example, increased levels of ROCK2 protein are observed in progressive stages of AD (Herskowitz et al. 2013). While increased ROCK activity is observed in $SOD1^{G93A}$ ALS mutant model mice (Gunther, R. et al. Rho Kinase Inhibition with Fasudil in the $SOD1^{G93A}$ Mouse Model of Amyotrophic Lateral Sclerosis—Symptomatic Treatment Potential After Disease Onset. Front Pharmacol. 8:17(2017)). Thus, a compound of the present invention or a pharmaceutically acceptable salt thereof can be administered in an effective amount to treat a neurological disease. Non-limiting examples of neurological diseases include amyotrophic lateral sclerosis (ALS), Parkinson's disease (PD), Alzheimer's disease (AD), and neurological deficiencies caused by spinal cord injuries.

Based on the above-described roles of ROCK1 and ROCK2 in central nervous system disorders, methods and uses to treat subjects such as humans afflicted with such disorders are provided herein. In certain embodiments a method of treating a subject with a ROCK1 and/or ROCK2 mediated disorder is provided comprising administering an effective amount of a compound of Formula I, Formula II, or Formula III or a pharmaceutically acceptable salt thereof to the subject. Non-limiting examples of disorders mediated by ROCK1 and/or ROCK2 are provided below.

In certain aspects Compound 1 or a pharmaceutically acceptable salt thereof is used to treat a ROCK1 mediated disorder.

In other aspects Compound 2 or a pharmaceutically acceptable salt thereof is used to treat a ROCK1 mediated disorder. Alternatively, Compound 3, Compound 4, Compound 5, or Compound 6 or a pharmaceutically acceptable salt thereof can be used treat a ROCK1 mediated disorder. In other embodiments, Compound 7, Compound 8, Compound 9, Compound 10, Compound 11, Compound 12, Compound 13, or Compound 14 or a pharmaceutically acceptable salt thereof can be used treat a ROCK1 mediated disorder.

In certain aspects Compound 1 or a pharmaceutically acceptable salt thereof is used to treat a ROCK2 mediated disorder.

In other aspects Compound 2 or a pharmaceutically acceptable salt thereof is used to treat a ROCK2 mediated disorder. Alternatively, Compound 3, Compound 4, Compound 5, or Compound 6 or a pharmaceutically acceptable salt thereof can be used treat a ROCK2 mediated disorder. In other embodiments, Compound 7, Compound 8, Compound 9, Compound 10, Compound 11, Compound 12, Compound 13, or Compound 14 or a pharmaceutically acceptable salt thereof can be used treat a ROCK2 mediated disorder.

In certain aspects Compound 1 or a pharmaceutically acceptable salt thereof is used to treat a disorder mediated by both ROCK1 and ROCK2.

In other aspects Compound 2 or a pharmaceutically acceptable salt thereof is used to treat a disorder mediated by both ROCK1 and ROCK2. Alternatively, Compound 3, Compound 4, Compound 5, or Compound 6 or a pharmaceutically acceptable salt thereof can be used treat a disorder mediated by both ROCK1 and ROCK2. In other embodiments, Compound 7, Compound 8, Compound 9, Compound 10, Compound 11, Compound 12, Compound 13, or Compound 14 or a pharmaceutically acceptable salt thereof can be used treat a disorder mediated by ROCK1 and ROCK2.

Specific examples of disorders that can be treated with the compounds described herein or their pharmaceutically acceptable salts are described below.

Amyotrophic Lateral Sclerosis (ALS)

Amyotrophic lateral sclerosis (ALS) is a relatively rare neurodegenerative disease that affects an estimated million individuals (Hardiman, O. et al. Amyotrophic lateral sclerosis. Nat Rev Dis Primers. 3(17071):1-19(2017)), with different risk levels geographically. ALS is characterized by degeneration of upper motor neurons and lower motor neurons that contribute to both motor and non-motor symptoms. Several subtypes of ALS have been identified including bulbar, respiratory, flail arm, classical, pyramidal, and flail leg ALS.

In certain embodiments, a compound of the present invention is used to treat ALS. For example, in certain embodiments, a compound of the present invention is used to treat bulbar, respiratory, flail arm, classical, pyramidal, or flail leg ALS.

The present invention includes the use of an effective amount of a compound of Formula I, Formula II, or Formula III or a pharmaceutically acceptable salt thereof to treat a subject such as a human with ALS or a secondary condition associated with ALS.

In certain aspects Compound 1 or a pharmaceutically acceptable salt thereof is used to treat ALS.

In other aspects Compound 2 or a pharmaceutically acceptable salt thereof is used to treat ALS. Alternatively, Compound 3, Compound 4, Compound 5, or Compound 6 or a pharmaceutically acceptable salt thereof can be used treat ALS. In other embodiments, Compound 7, Compound 8, Compound 9, Compound 10, Compound 11, Compound 12, Compound 13, or Compound 14 or a pharmaceutically acceptable salt thereof can be used treat ALS.

Parkinson Disease (PD)

Parkinson disease (PD) is the second-most common neurodegenerative disorder following Alzheimer disease, with an estimated 2 to 3 cases per 100,000 individuals worldwide (Parkinson's Foundation. Statistics. 2022). PD is characterized by several dysregulated mechanisms and pathways which contribute to neuronal loss in the substantia nigra (SN), including alpha-synuclein proteostasis, mitochondrial function, oxidative stress, calcium homeostasis, axonal transport, and neuroinflammation (Poewe, W. et al. Parkinson disease. Nat Rev Dis Primers. 3(17013):1-21(2017)). Intracellular alpha-synuclein aggregates are a hallmark of PD, as well as SN neuronal loss and striatal dopamine deficiency. Subjects are diagnosed with PD based on the presence of bradykinesia and other motor defects, as well as non-motor symptoms. Several subtypes of PD have been identified including motor-cognitive, cognitive dominant and motor dominant PD. There is presently no cure for PD and treatments focus on slowing the progression and/or decreasing the symptoms of PD.

In certain embodiments, a compound of the present invention is used to treat PD. For example, in certain embodiments, a compound of the present invention is used to treat motor-cognitive, cognitive dominant or motor dominant PD.

The present invention includes the use of an effective amount of a compound of Formula I, Formula II, or Formula III or a pharmaceutically acceptable salt thereof to treat a subject such as a human with PD or a secondary condition associated with PD.

In certain aspects Compound 1 or a pharmaceutically acceptable salt thereof is used to treat PD.

In other aspects Compound 2 or a pharmaceutically acceptable salt thereof is used to treat PD. Alternatively, Compound 3, Compound 4, Compound 5, or Compound 6 or a pharmaceutically acceptable salt thereof can be used treat PD. In other embodiments, Compound 7, Compound 8, Compound 9, Compound 10, Compound 11, Compound 12, Compound 13, or Compound 14 or a pharmaceutically acceptable salt thereof can be used treat PD.

Alzheimer Disease (AD)

Alzheimer disease (AD) is the most common cause of dementia affecting over 40 million people in 2016 (GBD 2016 Dementia Collaborators. Global, regional, and national burden of Alzheimer's disease and other dementias, 1990-2016: a systematic analysis for the Global Burden of Disease Study 2016. Lancet Neurol. 18(1):88-106(2019)) and is expected to increase to 150 million by 2050 worldwide. Estimation of the global prevalence of dementia in 2019 and forecasted prevalence in 2050: an analysis for the Global Burden of Disease Study 2019. Lancet Public Health. 7(2): e105-e125(2022)). AD is a neurodegenerative disorder characterized by extracellular plaques comprising amyloid beta and intracellular neurofibrillary tangles comprising tau leading to neuronal loss (Knopman, D. S. et al. Alzheimer disease. Nat Rev Dis Primers. 7(33):1-21(2021)). Subjects with AD present with cognitive impairment and dementia. Symptoms of cognitive impairment include loss in short-term memory, expressive speech, visuospatial processing, and executive functioning. AD risk factors include rare, dominantly inherited mutations in APP (encoding amyloid precursor protein), PSEN1 (encoding presenilin 1), and PSEN2 (encoding presenilin 2) causing autosomal dominant forms of AD. Much more common is the development of sporadic late-onset AD which is influenced by more common but incompletely penetrant genetic polymorphisms in genes such as APOE.

In certain embodiments, a compound of the present invention is used to treat AD. AD treatments can be beneficial at several stages in the progression of the disease. For example, in certain embodiments, a compound of the present invention is used to treat a subject with no cognitive impairment but high levels of amyloid beta and/or tau biomarkers, subjective cognitive decline in the absence of impaired cognitive testing scoring, mild cognitive impairment, clinically confirmed AD, or autosomal dominant AD.

The present invention includes the use of an effective amount of a compound of Formula I, Formula II, or Formula III or a pharmaceutically acceptable salt thereof to treat a subject such as a human with AD or a secondary condition associated with AD.

In certain aspects Compound 1 or a pharmaceutically acceptable salt thereof is used to treat AD.

In other aspects Compound 2 or a pharmaceutically acceptable salt thereof is used to treat AD. Alternatively, Compound 3, Compound 4, Compound 5, or Compound 6 or a pharmaceutically acceptable salt thereof can be used treat AD. In other embodiments, Compound 7, Compound 8, Compound 9, Compound 10, Compound 11, Compound 12, Compound 13, or Compound 14 or a pharmaceutically acceptable salt thereof can be used treat AD.

Spinal Cord Injury

Spinal cord injuries can trigger complex and varied neurological effects including axon degeneration and mild to severe loss of cognitive function.

In certain embodiments a compound described herein is used to treat a spinal cord injury. For example, a compound of the present invention may be used to promote axon regeneration and functional recovery in a subject who has had a spinal cord injury.

The present invention includes the use of an effective amount of a compound of Formula I, Formula II, or Formula III or a pharmaceutically acceptable salt thereof to treat a subject such as a human with a spinal cord injury or a secondary condition associated with a spinal cord injury.

In certain aspects Compound 1 or a pharmaceutically acceptable salt thereof is used to treat a spinal cord injury.

In other aspects Compound 2 or a pharmaceutically acceptable salt thereof is used to treat spinal cord injury. Alternatively, Compound 3, Compound 4, Compound 5, or Compound 6 or a pharmaceutically acceptable salt thereof can be used treat spinal cord injury. In other embodiments, Compound 7, Compound 8, Compound 9, Compound 10, Compound 11, Compound 12, Compound 13, or Compound 14 or a pharmaceutically acceptable salt thereof can be used treat a spinal cord injury.

Stroke

Stroke is a neurological disorder that occurs when one or more blood vessels that supply blood to the brain are blocked or rupture. The depletion of blood in the brain causes damage to the brain tissue in the area where the blood vessel previously delivered blood. There are two common categories of stroke: ischemic stroke and hemorrhagic stroke. Ischemic stroke occurs when the brain tissue is ischemic due to a decrease in the supply of blood caused by a blockage. Hemorrhagic stroke instead occurs due to hemorrhage when a blood vessel ruptures. Ischemic stroke is the most common form of stroke. When an ischemic stroke occurs, cells cannot obtain sufficient oxygen and nutrients due to the interruption of blood flow.

In certain embodiments a compound described herein is used to treat a stroke. Non-limiting examples of strokes include ischemic stroke, acute ischemic stroke, thrombosis, embolism, transient ischemic attack, leukoplakia, and infarction.

The present invention includes the use of an effective amount of a compound of Formula I, Formula II, or Formula III or a pharmaceutically acceptable salt thereof to treat a subject such as a human who has had a stroke or a secondary condition associated with a stroke.

In certain aspects Compound 1 or a pharmaceutically acceptable salt thereof is used to treat a stroke.

In other aspects Compound 2 or a pharmaceutically acceptable salt thereof is used to treat a stroke. Alternatively, Compound 3, Compound 4, Compound 5, or Compound 6 or a pharmaceutically acceptable salt thereof can be used treat a stroke. In other embodiments, Compound 7, Compound 8, Compound 9, Compound 10, Compound 11, Compound 12, Compound 13, or Compound 14 or a pharmaceutically acceptable salt thereof can be used treat a stroke.

Other Neurodegenerative Disorders

In addition to ROCKs important role in the regulation of several complex neuronal processes research has identified ROCK as a regulator of reactive oxygen species (ROS). This biological function allows ROCK inhibition to modulate additional neurodegenerative disorders (Kang H. et al. Chemical Screening Identifies ROCK as a Target for Recovering Mitochondrial Function in Hutchinson-Gilford Progeria Syndrome. Aging Cell 16:541-50(2017) and Sheng W. et al. Reactive Oxygen Species from Human Astrocytes Induce Functional Impairment and Oxidative Damage. Neurochem. Res. 38:2148-59(2013)).

Non-limiting examples of neurodegenerative diseases including ataxia, Huntington's disease, motor neuron disease, multiple system atrophy, Creutzfeldt-Jakob disease, dementia, non-dementia cognitive impairment, and progressive supranuclear palsy. Non-limiting examples of dementia include senile dementia, cerebrovascular dementia, post-traumatic dementia, dementia caused by brain tumors, and dementia caused by chronic subdural hematoma.

In other embodiments a compound herein is used to prevent a stroke or provide neuroprotection for example acute neuroprotection.

In certain aspects a compound of the present invention is used to reduce inflammation. For example, a compound of the present invention can be administered to a subject in need thereof to reduce inflammation in the brain.

The present invention thus includes the use of an effective amount of a compound of Formula I, Formula II, or Formula III or a pharmaceutically acceptable salt thereof to treat a subject such as a human with a neurodegenerative disorder such as one of those listed above or a secondary condition associated with the neurodegenerative disorder.

In certain aspects Compound 1 or a pharmaceutically acceptable salt thereof is used to treat the neurodegenerative disorder.

In other aspects Compound 2 or a pharmaceutically acceptable salt thereof is used to treat a neurodegenerative. Alternatively, Compound 3, Compound 4, Compound 5, or Compound 6 or a pharmaceutically acceptable salt thereof can be used treat a neurodegenerative disorder. In other embodiments, Compound 7, Compound 8, Compound 9, Compound 10, Compound 11, Compound 12, Compound 13, or Compound 14 or a pharmaceutically acceptable salt thereof can be used treat a neurodegenerative disorder.

Pain Disorders

Pain is a subjective sensation reflecting an tissue damage and exhibits various forms. Pain is classified into somatic pain and psychogenic pain, and somatic pain is further classified into nociceptive pain and neuropathic pain. Nociceptive pain is caused by external stimulation or visceral pathology. Nociceptive pain is mainly acute, which disappears following cure of underlying disease, and plays a role as a biological signal generated by a disorder. Neuropathic pain is chronic pain caused by dysfunction of the peripheral or central nervous system and includes pain from various sources including pain due to diabetes, nerve compression and spinal cord injury. Psychogenic pain is chronic pain, which is due to mental disorder rather than physical disorder and cannot be explained by organic disorder, and includes chronic headache, abdominal pain of unknown cause and the like. Chronic pain can impart large distress to patients and thus, is an important target of treatment. Non-limiting examples of chronic pain include chronic pain associated with arthritis, diabetes, cancer and the like which requires pain treatment in addition to treatment of underlying disease.

ROCK inhibitors have been shown to exert an analgesic effect on pain. In certain embodiments a compound described herein is used to treat a pain disorder. In certain aspects a compound of the present invention may be used to treat somatic pain. For example a compound of the present invention may be used to treat nociceptive pain or neuropathic pain. In certain embodiments a compound of the present invention is used to treat nociceptive pain. Non-limiting examples of nociceptive pain include acute pain arising from an underlying disease. In certain embodiments a compound of the present invention is used to treat neuropathic pain. Non-limiting examples of neuropathic pain include chronic pain caused by diabetes, nerve compression, or a spinal cord injury. In certain aspects a compound of the present invention or a pharmaceutically acceptable salt thereof is used to treat pain arising from arthritis, for example, osteoarthritis or rheumatoid arthritis.

The present invention thus includes the use of an effective amount of a compound of Formula I, Formula II, or Formula III or a pharmaceutically acceptable salt thereof to treat a subject such as a human with a pain disorder such as one of those listed above or a secondary condition associated with the pain disorder.

In certain aspects Compound 1 or a pharmaceutically acceptable salt thereof is used to treat a pain disorder.

In other aspects Compound 2 or a pharmaceutically acceptable salt thereof is used to treat a pain disorder. Alternatively, Compound 3, Compound 4, Compound 5, or Compound 6 or a pharmaceutically acceptable salt thereof can be used treat a pain disorder. In other embodiments, Compound 7, Compound 8, Compound 9, Compound 10, Compound 11, Compound 12, Compound 13, or Compound 14 or a pharmaceutically acceptable salt thereof can be used treat a pain disorder.

Cardiovascular Diseases

Studies have demonstrated that the Rho/ROCK pathway is increased in hypertensive patients. For example, increased ROCK-dependent smooth muscle contraction is observed in the aorta in the early stage of atherosclerosis. During atherosclerosis lesion formation, ROCK activity, is increased in certain areas and cell types including endothelium, periadventitial adipocytes and macrophage foam cells, supporting a role of ROCK in the ERM phosphorylation-mediated macrophage infiltration and foam cell formation. ROCK has a role in cardiac ischemia/reperfusion injuries, where blood flow is restricted or cut off and then is reintroduced into the area. A deleterious role of RhoA/ROCK signaling in ischemia/reperfusion injury has been demonstrated in several in vivo models including mouse, rat and swine. (M. Surma et al., "Rho kinase as a therapeutic target in cardiovascular disease", Future Cardiol. 2011 September; 7(5): 657-671. doi:10.2217/fca.11.51).

In certain embodiments a compound described herein is used to treat a cardiovascular disorder. Non-limiting examples of cardiovascular disorders include coronary heart disease, stroke, peripheral arterial disease, and aortic disease.

The present invention thus includes the use of an effective amount of a compound of Formula I, Formula II, or Formula III or a pharmaceutically acceptable salt thereof to treat a subject such as a human with a cardiovascular disorder such as one of those listed above or a secondary condition associated with the cardiovascular disorder.

In certain aspects Compound 1 or a pharmaceutically acceptable salt thereof is used to treat a cardiovascular disorder.

In other aspects Compound 2 or a pharmaceutically acceptable salt thereof is used to treat a cardiovascular disorder. Alternatively, Compound 3, Compound 4, Compound 5, or Compound 6 or a pharmaceutically acceptable salt thereof can be used treat a cardiovascular disorder. In other embodiments, Compound 7, Compound 8, Compound 9, Compound 10, Compound 11, Compound 12, Compound 13, or Compound 14 or a pharmaceutically acceptable salt thereof can be used treat a cardiovascular disorder.

Ocular Disorders

The ability of ROCK proteins to mediate smooth muscle contractions in the eye has made ROCK a target for the treatment of ocular disorders. ROCK mediates calcium sensitization and smooth muscle contraction. The $Ca^{2+}$-sensitizing effect of smooth muscle constricting agents has been ascribed to ROCK-mediated phosphorylation of MYPT-I, the regulatory subunit of myosin light chain phosphatase (MLCP). MYPT-1 is used by the body to inhibit the activity of MLCP. By inhibiting MLCP ROCK activated phosphorylation of MYPT-1 results in enhanced phosphorylation of the myosin light chain and smooth muscle contraction (WO 2005/003101 and WO 2005/034866). Glaucoma is an ophthalmic disease that leads to irreversible visual impairment. Glaucoma is characterized by a progressive optic neuropathy caused in part by deleterious effects resulting from increased intraocular pressure. In healthy individuals, intraocular pressures ranges from 12 to 20 mm Hg, averaging approximately 16 mm Hg. However, in individuals suffering from primary open angle glaucoma, intraocular pressures generally rise above 22 to 30 mm Hg. In angle closure or acute glaucoma intraocular pressure can reach as high as 70 mm Hg leading to blindness within only a few days. The loss of vision can also result from statistically normal intraocular pressures in individuals with unusually pressure-sensitive eyes; a condition known as normotensive glaucoma (See, e.g., P. L. Kaufman and T. W. Mittag, "Medical Therapy Of Glaucoma," Ch. 9, Sec. II (pp. 9.7-9.30) In P. L. Kaufman and T. W. Mittag (eds.): Glaucoma (Vol. 7 of S. M. Podos and M. Yanoff (eds): Textbook of Ophthalmology Series). London, Mosby-Year Book Europe Ltd. (1994); A. C. Guyton, Textbook of Medical Physiology (W. B. Saunders Co., Sixth Ed.), pp. 386-89 (1981)). Open-angle glaucoma constitutes the majority of all primary glaucomas and is characterized by abnormally high resistance to fluid (aqueous humor) drainage from the eye. In the glaucomatous eye, the rate of aqueous humor production remains constant, while it is the increased resistance to outflow that is responsible for the elevated intraocular pressure.

In certain embodiments a compound of the present invention or a pharmaceutically acceptable salt thereof is used to treat an ocular disorder. Non-limiting examples of ocular disorders include glaucoma (for example open angle glaucoma, angle closure glaucoma, acute glaucoma, and normotensive glaucoma) or intraocular pressure.

The present invention thus includes the use of an effective amount of a compound of Formula I, Formula II, or Formula III or a pharmaceutically acceptable salt thereof to treat a subject such as a human with an ocular disorder such as one of those listed above or a secondary condition associated with the ocular disorder.

In certain aspects Compound 1 or a pharmaceutically acceptable salt thereof is used to treat an ocular disorder.

In other aspects Compound 2 or a pharmaceutically acceptable salt thereof is used to treat an ocular disorder. Alternatively, Compound 3, Compound 4, Compound 5, or Compound 6 or a pharmaceutically acceptable salt thereof can be used treat an ocular disorder. In other embodiments, Compound 7, Compound 8, Compound 9, Compound 10, Compound 11, Compound 12, Compound 13, or Compound 14 or a pharmaceutically acceptable salt thereof can be used treat an ocular disorder.

ROCK has recently emerged as a novel therapeutic target for neurodegenerative disorders (J. C. Koch, L. Tatenhorst, A.-E. Roser, K.-A. Saal, L. Tonges, P. Lingor. "ROCK inhibition in models of neurodegeneration and its potential for clinical translation", *Pharmacology & Therapeutics* 189 (2018) 1-21). While ROCK1 is expressed preferentially in peripheral tissue, ROCK2 is highly expressed in the central nervous system (CNS). Axonal growth inhibitory molecules (e.g., Nogo, MAG, OMgp, ephrins, semaphorins) bind to specific extracellular receptors and signal via ROCK to trigger axonal degeneration, growth cone collapse, and impaired axonal regeneration. In non-neuronal structures, regulation of the actin cytoskeleton plasticity by ROCK also mediates vasoconstriction and vascular remodeling. Levels of ROCK increase with age and tissue of ALS patients shows increased levels of ROCK2 as well as its downstream targets LIMK1 and cofilin. Increased ROCK activity results in higher levels of phosphorylated adducin as well as activation of phosphatase and tensin homolog (PTEN) and decreased Akt activity. PTEN activation by ROCK exerts negative effects on cell growth, proliferation and metabolism. Inhibition of ROCK counteracts neuronal apoptosis and axonal degeneration and on the other hand fosters axonal regeneration and modulates microglia activation. (J. C. Koch et al., "Compassionate use of the ROCK inhibitor Fasudil in three patients with amyotrophic lateral sclerosis" *Front. Neurol.* March 2020, Volume 11, Article 173, doi: 10.3389/fneur.2020.00173.)

Protein Kinase X (PRKX)

PRKX, human protein kinase X, is an X chromosome encoded cAMP-dependent serine/threonine kinase. The cAMP-dependent protein kinases (cAPKs) play a key role in many signal transduction processes, mediating the majority of the known effects of cAMP in the eukaryotic cell. These multisubstrate enzymes regulate the activity of proteins involved in signal transduction, energy metabolism, cell proliferation, or differentiation by phosphorylation of Ser or Thr residues, which alters the biological properties of the target proteins. The human protein kinase PRKX is related to the catalytic subunit of cAMP-dependent protein kinases but is distinct from the isoforms Cα, Cβ, and Cγ. PRKX has 53.2% identity to the human Cα subunit of cAPK (PKA-Cα) in the catalytic core region. This degree of homology is much lower than the similarity of the two human isoforms Cα and Cβ (90.5% identity). PRKX mRNA is present in a variety of tissues, with the highest levels of expression in fetal and adult brain, kidney, and lung. (B. Zimmermann et al., "PRKX Is a Novel Catalytic Subunit of the cAMP-dependent Protein Kinase Regulated by the Regulatory Subunit Type I", *Journal of Biological Chemistry*, Vol. 274, No. 9, Issue of February 26, pp. 5370-5378, 1999.) In contrast to the ubiquitously expressed Ca subunit, PRKX is mainly active during embryonic organ development and cellular differentiation in hematopoietic lineages. It was found to be crucial for macrophage and granulocyte maturation. PRKX was shown to be involved in renal development, regulating epithelial cell migration, ureteric bud branching, and induction of glomeruli formation (M. Diskar et al., "Regulation of cAMP-dependent protein kinases: the human protein kinase X (PrKX) reveals the role of the catalytic subunit αH-αI loop", *Journal of Biological Chemistry*, Vol. 285, No. 46, pp. 35910-35918, Nov. 12, 2010).

The role of PRKX in disease pathology is not well understood. However, a recent study identified the dysregulation of PRKX expression as a possible molecular cause for Mayer-Rokitansky-Küster-Hauser (MRKH) syndrome (P. Pontecorvi et al., "Altered Expression of Candidate Genes in Mayer-Rokitansky-Küster-Hauser Syndrome May Influence Vaginal Keratinocytes Biology: A Focus on Protein Kinase X", *Biology*, 2021, 10, 450.). PRKX has also been indicated in the pathology of amyotrophic lateral sclerosis (ALS) (Oliverira G. et al., Early Gene Expression Changes in Sketal Muscle from SOD1(G93A) Amyotrophic Lateral Sclerosis Animal Model).

In certain embodiments a method of treating a subject with a PRKX mediated disorder is provided comprising administering an effective amount of a compound of Formula I, Formula II, or Formula III or a pharmaceutically acceptable salt thereof to the subject. Non-limiting examples of disorders mediated by PRKX are provided herein.

Mayer-Rokitansky-Küster-Hauser (MRKH) Syndrome

PRKX has been implicated in the development of Mayer-Rokitansky-Küster-Hauser (MRKH) syndrome (P. Pontecorvi et al., "Altered Expression of Candidate Genes in Mayer-Rokitansky-Küster-Hauser Syndrome May Influence Vaginal Keratinocytes Biology: A Focus on Protein Kinase X", Biology, 2021, 10, 450.). Thus, in certain embodiments a compound of the present invention or a pharmaceutically acceptable salt thereof is used to treat MRKH syndrome.

The present invention thus includes the use of an effective amount of a compound of Formula I, Formula II, or Formula III or a pharmaceutically acceptable salt thereof to treat a subject such as a human with Mayer-Rokitansky-Küster-Hauser (MRKH) syndrome or a secondary condition associated with Mayer-Rokitansky-Küster-Hauser (MRKH) syndrome.

In certain aspects Compound 1 or a pharmaceutically acceptable salt thereof is used to treat MRKH.

In other aspects Compound 2 or a pharmaceutically acceptable salt thereof is used to treat MRKH. Alternatively, Compound 3, Compound 4, Compound 5, or Compound 6 or a pharmaceutically acceptable salt thereof can be used treat a pain disorder. In other embodiments, Compound 7, Compound 8, Compound 9, Compound 10, Compound 11, Compound 12, Compound 13, or Compound 14 or a pharmaceutically acceptable salt thereof can be used treat MRKH.

IV. Pharmaceutical Compositions

A compound of Formula I, Formula II, or Formula III or its pharmaceutically acceptable salt thereof, as described herein can be administered as the neat chemical, but is more typically administered as a pharmaceutical composition, that includes an effective amount for a subject, typically a human, in need of such treatment for a disorder described herein. Accordingly, the disclosure provides pharmaceutical compositions comprising an effective amount of compound or pharmaceutically acceptable salt thereof together with at least one pharmaceutically acceptable excipient for a use described herein. The pharmaceutical composition may contain the compound as the only active agent, or, in an alternative embodiment, the compound and at least one additional therapeutic agent.

In general, the compositions of the disclosure will be administered in a therapeutically effective amount by any of the accepted modes of administration. Suitable dosage ranges depend upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this application, to ascertain a therapeutically effective amount of the compositions of the disclosure for a given disease.

In certain embodiments, the pharmaceutical composition is in a dosage form that contains from about 1 mg to about 1000 mg, from about 10 mg to about 1000 mg, from about 100 mg to about 800 mg, or from about 200 mg to about 600 mg of the active compound and optionally from about 1 mg to about 2000 mg, from about 10 mg to about 1000 mg, from about 100 mg to about 800 mg, or from about 200 mg to about 600 mg of an additional therapeutic agent in a unit dosage form. Examples are dosage forms with at least about 1, 5, 10, 25, 50, 100, 200, 250, 300, 400, 500, 600, 700, or 750 mg of active compound, or its salt.

A pharmaceutically or therapeutically effective amount of the composition will be delivered to the subject. The precise effective amount will vary from subject to subject, and will depend upon the species, age, the subject's size and health, the nature and extent of the condition being treated, recommendations of the treating physician, and the therapeutics or combination of therapeutics selected for administration. The effective amount for a given situation can be determined by routine experimentation. The subject can be administered as many doses as is required to reduce and/or alleviate the signs, symptoms, or causes of the disorder in question, or bring about any other desired alteration of a biological system. When desired, formulations can be prepared with enteric coatings adapted for sustained or controlled release administration of the active ingredient.

In some embodiments, a compound or its pharmaceutically acceptable salt as disclosed herein or used as described is administered once a day (QD), twice a day (BID), or three times a day (TID). In some embodiments, compounds disclosed herein or used as described are administered QD, BID, or TID for at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 26 days, at least 27 days, at least 28 days, at least 29 days, at least 30 days, at least 31 days, at least 35 days, at least 45 days, at least 60 days, at least 75 days, at least 90 days, at least 120 days, at least 150 days, at least 180 days, or longer, including indefinitely.

In certain embodiments, the compound of the present invention is administered once a day, twice a day, three times a day, or four times a day.

In certain embodiments, the compound of the present invention is administered orally once a day. In certain embodiments, the compound of the present invention is administered orally twice a day. In certain embodiments, the compound of the present invention is administered orally three times a day. In certain embodiments, the compound of the present invention is administered orally four times a day.

In certain embodiments, the compound of the present invention is administered intravenously once a day. In certain embodiments, the compound of the present invention is administered intravenously twice a day. In certain embodiments, the compound of the present invention is administered intravenously three times a day. In certain embodiments, the compound of the present invention is administered intravenously four times a day.

In some embodiments the compound of the present invention is administered with a treatment holiday in between treatment cycles. For example, the compound may have a treatment holiday of 1 day, 2 days, 3 days, 4 days, 5 days, 6 days, 7 days, 8 days, 9 days, 10 days, 11 days, 12 days, 13 days, or 14 days per treatment cycle.

The pharmaceutical composition may also include a molar ratio of the active compound and an additional active agent. As non-limiting illustrative examples, the pharmaceutical composition may contain a molar ratio of about 0.5:1, about 1:1, about 2:1, about 3:1 or from about 1.5:1 to about 4:1 of an anti-inflammatory or immunosuppressing agent.

These compositions can contain any amount of active compound that achieves the desired result, for example between 0.1 and 99 weight % (wt. %) of the compound and usually at least about 5 wt. % of the compound. Some embodiments contain from about 25 wt. % to about 50 wt. % or from about 5 wt. % to about 75 wt. % of the compound.

In certain embodiments, the compound is administered as a pharmaceutically acceptable salt. Non-limiting examples of pharmaceutically acceptable salts include: acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, and valerate salts.

Thus, the selected compound of the present invention or pharmaceutically acceptable salt thereof can be administered as a pharmaceutical composition which is suitable for generally for systemic, parenteral or topical administration. Non-limiting examples include or oral (including buccal and sub-lingual), rectal, nasal, topical, transdermal, pulmonary, parenteral injection (including intramuscular, intra-arterial, intrathecal, subcutaneous and intravenous), inhalation or spray, intra-aortal, intracranial, subdermal, intraperitoneal, subcutaneous, or by other means of administration. A typical manner of administration is oral or intravenous, using a convenient daily dosage regimen which can be adjusted according to the degree of affliction.

Depending on the intended mode of administration, the pharmaceutical compositions can be in the form of solid, semi-solid or liquid dosage forms, such as, for example, tablets, suppositories, pills, capsules, powders, liquids, syrup, suspensions, creams, ointments, lotions, paste, gel, spray, aerosol, foam, or oil, injection or infusion solution, a transdermal patch, a subcutaneous patch, an inhalation formulation, in a medical device, suppository, buccal, or sub-lingual formulation, parenteral formulation, or an ophthalmic solution, or the like, preferably in unit dosage form suitable for single administration of a precise dosage.

Some dosage forms, such as tablets and capsules, are subdivided into suitably sized unit doses containing appropriate quantities of the active components, e.g., an effective amount to achieve the desired purpose. Oral pharmaceutical compositions include an effective amount of the selected drug in combination with a pharmaceutically acceptable carrier or excipient and, in addition, can include other pharmaceutical agents, adjuvants, diluents, buffers, and the like.

Pharmaceutically acceptable excipients must be of sufficiently high purity and sufficiently low toxicity to render them suitable for administration to the subject being treated. The pharmaceutically acceptable excipient can be inert or it can possess pharmaceutical benefits of its own. The amount of excipient employed in conjunction with the compound is sufficient to provide a practical quantity of material for administration per unit dose of the compound.

Classes of excipients include, but are not limited to adjuvants, binders, buffering agents, coloring agents, diluents, disintegrants, emulsifiers, flavorants, gels, glidants, lubricants, preservatives, stabilizers, surfactants, solubilizer, tableting agents, wetting agents or solidifying material.

Some excipients may be listed in more than one class, for example vegetable oil may be used as a lubricant in some formulations and a diluent in others.

Exemplary pharmaceutically acceptable excipients include sugars, starches, celluloses, powdered tragacanth, malt, gelatin; talc, petroleum jelly, lanoline, polyethylene glycols, alcohols, transdermal enhancers and vegetable oils. Optional active agents may be included in a pharmaceutical composition, which do not substantially interfere with the activity of the compound of the present invention.

Some excipients include, but are not limited, to liquids such as water, saline, glycerol, polyethylene glycol, hyaluronic acid, ethanol, and the like. The compound can be provided, for example, in the form of a solid, a liquid, spray dried material, a microparticle, nanoparticle, controlled release system, etc., as desired according to the goal of the therapy. Suitable excipients for non-liquid formulations are also known to those of skill in the art. A thorough discussion of pharmaceutically acceptable excipients and salts is available in Remington's Pharmaceutical Sciences, 18th Edition (Easton, Pennsylvania: Mack Publishing Company, 1990).

Additionally, auxiliary substances, such as wetting or emulsifying agents, biological buffering substances, surfactants, and the like, can be present in the pharmaceutical composition. A biological buffer can be any solution which is pharmacologically acceptable, and which provides the formulation with the desired pH, i.e., a pH in the physiologically acceptable range. Examples of buffer solutions include saline, phosphate buffered saline, Tris buffered saline, Hank's buffered saline, and the like.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, and the like, an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered can also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, and the like. Actual methods of preparing such dosage forms are known, or will be apparent, to those skilled in this art; for example, see Remington's Pharmaceutical Sciences, referenced above.

In yet another embodiment provided is the use of permeation enhancer excipients including polymers such as: polycations (chitosan and its quaternary ammonium derivatives, poly-L-arginine, aminated gelatin); polyanions (N-carboxymethyl chitosan, poly-acrylic acid); and, thiolated polymers (carboxymethyl cellulose-cysteine, polycarbophil-cysteine, chitosan-thiobutylamidine, chitosan-thioglycolic acid, chitosan-glutathione conjugates).

Tablets and capsules for oral use can include one or more commonly used carriers such as lactose and corn starch. Lubricating agents, such as magnesium stearate, are also typically added. Typically, the compositions of the disclosure can be combined with an oral, non-toxic, pharmaceutically acceptable inert excipient such as lactose, starch, sucrose, glucose, methyl cellulose, magnesium stearate, dicalcium phosphate, calcium sulfate, mannitol, sorbitol and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

When liquid suspensions are used, the active agent can be combined with any oral, non-toxic, pharmaceutically acceptable inert excipient such as ethanol, glycerol, water, and the like and with emulsifying and suspending agents. If desired, flavoring, coloring and/or sweetening agents can be added as well. Other optional components for incorporation into an oral formulation herein include, but are not limited to, preservatives, suspending agents, thickening agents, and the like.

For ocular delivery, the compound can be administered, as desired, for example, via intravitreal, intrastromal, intracameral, sub-tenon, sub-retinal, retro-bulbar, peribulbar, suprachoroidal, conjunctival, subconjunctival, episcleral, periocular, transscleral, retrobulbar, posterior juxtascleral, circumcorneal, or tear duct injections, or through a mucus, mucin, or a mucosal barrier, in an immediate or controlled release fashion or via an ocular device.

Parenteral formulations can be prepared in conventional forms, either as liquid solutions or suspensions, solid forms suitable for solubilization or suspension in liquid prior to injection, or as emulsions. Typically, sterile injectable suspensions are formulated according to techniques known in the art using suitable excipients, dispersing or wetting agents and suspending agents. The sterile injectable formulation can also be a sterile injectable solution or a suspension in an acceptably nontoxic parenterally acceptable diluent or solvent. Among the acceptable vehicles and solvents that can be employed are water, Ringer's solution and isotonic sodium chloride solution. In addition, sterile, fixed oils, fatty esters or polyols are conventionally employed as solvents or suspending media. In addition, parenteral administration can involve the use of a slow release or sustained release system such that a constant level of dosage is maintained.

Parenteral administration includes intraarticular, intravenous, intramuscular, intradermal, intraperitoneal, and subcutaneous routes, and include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Administration via certain parenteral routes can involve introducing the formulations of the disclosure into the body of a subject through a needle or a catheter, propelled by a sterile syringe or some other mechanical device such as a continuous infusion system. A formulation provided by the disclosure can be administered using a syringe, injector, pump, or any other device recognized in the art for parenteral administration.

Preparations according to the disclosure for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms can also contain adjuvants such as preserving, wetting, emulsifying, and dispersing agents. They can be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

Sterile injectable solutions are prepared by incorporating one or more of the compounds of the disclosure in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, typical methods of preparation are vacuum-drying and freeze-drying techniques which yield a powder of the active ingredient plus any additional desired ingredient from a previously sterile-filtered solution thereof. Thus, for example, a parenteral composition suitable for administration by injection is prepared by stirring 1.5% by weight of active ingredient in 10% by volume propylene glycol and water. The solution is made isotonic with sodium chloride and sterilized.

Alternatively, the pharmaceutical compositions of the disclosure can be administered in the form of suppositories for rectal administration. These can be prepared by mixing the agent with a suitable nonirritating excipient which is solid at room temperature but liquid at the rectal temperature and therefore will melt in the rectum to release the drug. Such materials include cocoa butter, beeswax and polyethylene glycols.

The pharmaceutical compositions of the disclosure can also be administered by nasal aerosol or inhalation. Such compositions are prepared according to techniques well-known in the art of pharmaceutical formulation and can be prepared as solutions in saline, employing benzyl alcohol or other suitable preservatives, absorption promoters to enhance bioavailability, propellants such as fluorocarbons or nitrogen, and/or other conventional solubilizing or dispersing agents.

Formulations for buccal administration include tablets, lozenges, gels and the like. Alternatively, buccal administration can be affected using a transmucosal delivery system as known to those skilled in the art. The compounds of the disclosure can also be delivered through the skin or mucosal tissue using conventional transdermal drug delivery systems, i.e., transdermal "patches" wherein the agent is typically contained within a laminated structure that serves as a drug delivery device to be affixed to the body surface. In such a structure, the drug composition is typically contained in a layer, or "reservoir," underlying an upper backing layer. The laminated device can contain a single reservoir, or it can contain multiple reservoirs. In certain embodiments, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like.

V. Combination Therapy

A compound of Formula I, Formula II, or Formula III, or a pharmaceutically acceptable salt thereof can be used in an effective amount, either alone or in combination with a second therapeutic agent, to treat a subject such as a human with a ROCK1 and/or ROCK2 mediated disorder.

The term "second therapeutic agent" is used to describe an agent, other than the selected compound according to the present invention, which can be used in combination or alternation with a compound of the present invention to achieve a desired result of therapy. In certain embodiments, the compound of the present invention and the second therapeutic agent are administered in a manner that they are active in vivo during overlapping time periods, for example, have time-period overlapping Cmax, Tmax, AUC or another pharmacokinetic parameter. In another embodiment, the compound of the present invention and the second therapeutic agent are administered to a subject in need thereof and they do not have overlapping pharmacokinetic parameters, however, one has a therapeutic impact on the therapeutic efficacy of the other.

Non-limiting examples of second therapeutic agents include riluzole, edaravone, sodium phenyl butyrate, taururrsodiol, levodopa, selegiline, rasagiline, safinamide, pramipexole, rotigotine, apomorphine, tolcapone, entacapone, trihexyphenidyl, benztropine, orphenadrine, procyclidine, biperiden, amantadine, and istradefylline.

In certain embodiments a compound of Formula I, II or III of the present invention or a pharmaceutically acceptable salt thereof is used in combination or alternation with tiluzole, edaravone, or taurusodiol to treat ALS.

In certain aspects Compound 1 or a pharmaceutically acceptable salt thereof is used to treat ALS in combination with tiluzole, edaravone, or taurusodiol.

In other aspects Compound 2 or a pharmaceutically acceptable salt thereof is used to treat ALS in combination with tiluzole, edaravone, or taurusodiol. Alternatively, Compound 3, Compound 4, Compound 5, or Compound 6 or a pharmaceutically acceptable salt thereof can be used treat ALS in combination with tiluzole, edaravone, or taurusodiol. In certain embodiments, Compound 7, Compound 8, Compound 9, Compound 10, Compound 11, Compound 12, Compound 13, or Compound 14 or a pharmaceutically acceptable salt thereof can be used treat ALS in combination with tiluzole, edaravone, or taurusodiol.

In certain embodiments a compound of the present invention of a pharmaceutically acceptable salt thereof is used in combination or alternation with levodopa, selegiline, rasagiline, safinamide, pramipexole, rotigotine, apomorphine, tolcapone, entacapone, trihexyphenidyl, benztropine, orphenadrine, procyclidine, biperiden, amantadine, and istradefylline to treat PD.

In certain aspects Compound 1 or a pharmaceutically acceptable salt thereof is used to treat PD in combination with levodopa, selegiline, rasagiline, safinamide, pramipexole, rotigotine, apomorphine, tolcapone, entacapone, trihexyphenidyl, benztropine, orphenadrine, procyclidine, biperiden, amantadine, or istradefylline.

In other aspects Compound 2 or a pharmaceutically acceptable salt thereof is used to treat PD in combination with levodopa, selegiline, rasagiline, safinamide, pramipexole, rotigotine, apomorphine, tolcapone, entacapone, trihexyphenidyl, benztropine, orphenadrine, procyclidine, biperiden, amantadine, or istradefylline. Alternatively, Compound 3, Compound 4, Compound 5, or Compound 6 or a pharmaceutically acceptable salt thereof can be used treat PD in combination with levodopa, selegiline, rasagiline, safinamide, pramipexole, rotigotine, apomorphine, tolcapone, entacapone, trihexyphenidyl, benztropine, orphenadrine, procyclidine, biperiden, amantadine, or istradefylline. In certain embodiments, Compound 7, Compound 8, Compound 9, Compound 10, Compound 11, Compound 12, Compound 13, or Compound 14 or a pharmaceutically acceptable salt thereof can be used treat PD in combination with levodopa, selegiline, rasagiline, safinamide, pramipexole, rotigotine, apomorphine, tolcapone, entacapone, trihexyphenidyl, benztropine, orphenadrine, procyclidine, biperiden, amantadine, or istradefylline.

In certain aspects a compound of the present invention or a pharmaceutically acceptable salt thereof is used in combination with another ROCK inhibitor. Non-limiting examples of ROCK inhibitors include fasudil, netarsudil, and ripasudil.

In certain embodiments a compound of the present invention of a pharmaceutically acceptable salt thereof is used in combination or alternation with fasudil to treat ALS or PD.

In certain aspects Compound 1 or a pharmaceutically acceptable salt thereof is used to treat PD or ALS in combination with fasudil.

In other aspects Compound 2 or a pharmaceutically acceptable salt thereof is used to treat PD or ALS in combination with fasudil. Alternatively, Compound 3, Compound 4, Compound 5, or Compound 6 or a pharmaceutically acceptable salt thereof can be used treat PD or ALS in combination with fasudil. In certain embodiments, Compound 7, Compound 8, Compound 9, Compound 10, Compound 11, Compound 12, Compound 13, or Compound 14 or a pharmaceutically acceptable salt thereof is used to treat PD or ALS in combination with fasudil.

In certain embodiments a compound of the present invention of a pharmaceutically acceptable salt thereof is used in combination or alternation with netarsudil or ripasudil to treat an ocular disorder.

In certain aspects Compound 1 or a pharmaceutically acceptable salt thereof is used to treat an ocular disorder in combination with netarsudil or ripasudil.

In other aspects Compound 2 or a pharmaceutically acceptable salt thereof is used to treat an ocular disorder in combination with netarsudil or ripasudil. Alternatively, Compound 3, Compound 4, Compound 5, or Compound 6 or a pharmaceutically acceptable salt thereof can be used treat an ocular disorder in combination with netarsudil or ripasudil. In certain embodiments, Compound 7, Compound 8, Compound 9, Compound 10, Compound 11, Compound 12, Compound 13, or Compound 14 or a pharmaceutically acceptable salt thereof can be used treat an ocular disorder in combination with netarsudil or ripasudil.

VI. General Synthesis

The compounds described herein can be prepared by methods known by those skilled in the art. In one non-limiting example, the disclosed compounds can be made using the schemes below. The abbreviations used in the synthetic procedures have the following definitions.

| Abbreviation | Definition |
| --- | --- |
| dichloromethane | Methylene dichloride/Dichloromethane |
| DIPEA | N,N-diisopropylethylamine |
| N,N-Dimethylformamide | N,N-dimethylformamide |
| DMSO | Dimethylsulfoxide |
| ES+/ESI | Electrospray positive ionization |
| ethyl acetate | Ethyl Acetate |
| EtOH | Ethanol |
| HATU | (1-[Bis(dimethylamino)methylene]-1H-1,2,3-triazolo[4,5-b]pyridinium 3-oxide hexafluorophosphate/Hexafluorophosphate Azabenzotriazole Tetramethyl Uronium |
| HCl | Hydrochloric acid/Hydrochloride |
| HPLC | High Performance Liquid Chromatography/High Pressure Liquid Chromatography |
| LCMS | Liquid Chromatography Mass Spectrometry |
| MeOH | Methanol |
| NMR | nuclear magnetic resonance |
| r.t. | Room temperature |
| t-Bu | tert-Butyl |
| THF | tetrahydrofuran |

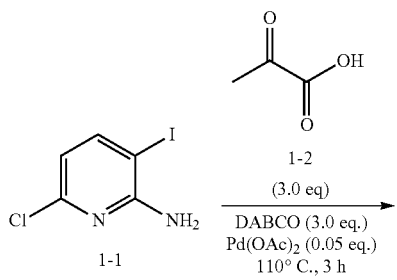

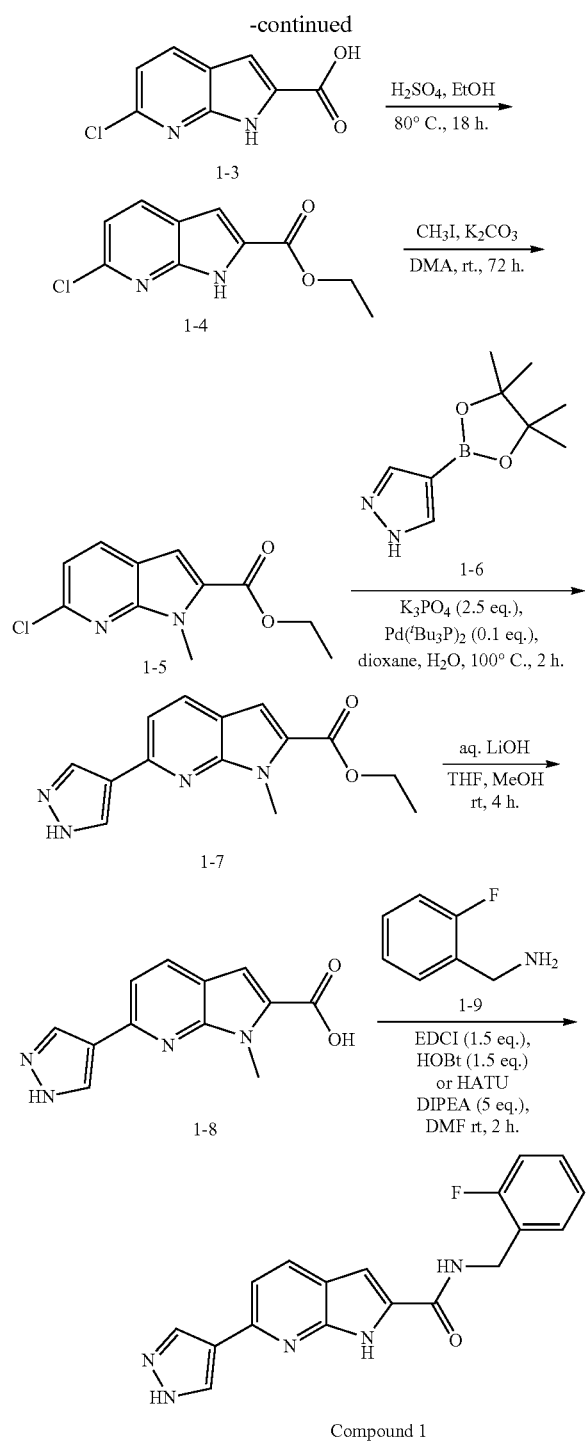

To a solution of 6-chloro-3-iodopyridin-2-amine (1-1) (9.00 g, 35.4 mmol), 2-oxopropanoic acid (1-2) (9.34 g, 106 mmol) and DABCO (11.9 g, 106 mmol) in N,N-dimethylformamide (255 mL) was added palladium(II) acetate (0.397 g, 1.77 mmol), and the reaction mixture was degassed three times and stirred under nitrogen atmosphere at 110° C. for three hours until the reaction was completed, which was monitored by LCMS. The resulting mixture was concentrated in vacuo. The residue was diluted with ethyl acetate (500 mL) and extracted with aq. sodium hydroxide (2 M, 500 mL×3). The combined aqueous layer was concentrated to c.a. 500 mL and acidified with aq. HCl (1 M) to pH 3. The mixture was filtered, and the filter-cake was collected, washed with water and dried to afford 1-3 (5.49 g, 74% yield) as a yellow solid. ESI m/z: 196.9 (M+H)$^+$, retention time 1.23 min, 93.9% @254 nm. $^1$H NMR (500 MHz, DMSOd$_6$) δ 12.41 (s, 1H), 8.12 (d, J=8.0 Hz, 1H), 7.18 (d, J=8.0 Hz, 1H), 7.06 (s, 1H) ppm.

Ethyl 6-chloro-1H-pyrrolo[2,3-b]pyridine-2-carboxylate (1-4)

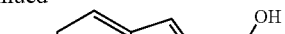

To a solution of 1-3 (5.70 g, 35.4 mmol) in ethanol (170 mL) was added 98% sulfuric acid (14.5 g, 145 mmol) at 0° C., and the reaction mixture was stirred at 80° C. for eighteen hours, which was monitored by LCMS. The resulting mixture was neutralized with sat. aq. sodium bicarbonate to pH 7-8 and then concentrated to remove ethanol. The residual aqueous mixture was diluted with water (300 mL) and extracted with ethyl acetate (500 mL×3). The combined organic solution was washed with brine, dried over anhydrous sodium sulfate, and concentrated in vacuo. The crude product was purified by silica gel column chromatography (petroleum ether/ethyl acetate, v/v=2) to give 1-4 (4.29 g, 66% yield) as a yellow solid. ESI m/z: 224.9 (M+H)$^+$, retention time 1.82 min, 98.6% @254 nm. $^1$H NMR (500 MHz, DMSOd$_6$) δ 12.75 (s, 1H), 8.17 (d, J=8.0 Hz, 1H), 7.23 (d, J=8.0 Hz, 1H), 7.21 (d, J=2.0 Hz, 1H), 4.35 (q, J=7.0 Hz, 2H), 1.34 (t, J=7.0 Hz, 3H) ppm.

Ethyl 6-chloro-1-methyl-1H-pyrrolo[2,3-b]pyridine-2-carboxylate (1-5)

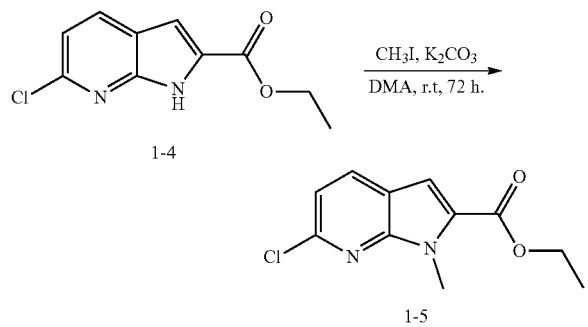

To a suspension of 1-4 (1.03 g, 4.60 mmol) and potassium carbonate (2.54 g, 18.4 mmol) in N,N-dimethylacetamide (DMA, 21.0 mL) was added iodomethane (1.96 g, 13.8 mmol). The reaction mixture was stirred at room temperature for 72 hours, which was monitored by LCMS. The resulting mixture was poured into water (63 mL). The precipitate was filtered to collect, washed with water (5 mL×2) and dried. The crude product was purified by silica gel column chromatography (petroleum ether/ethyl acetate, v/v=2) to give 1-5 (766 mg, 70% yield) as a yellow solid. ESI m/z: 238.9 (M+H)$^+$, retention time 2.02 min, 97.5% @214 nm. $^1$H NMR (500 MHz, DMSOd$_6$) δ 8.20 (d, J=8.5 Hz, 1H), 7.31 (s, 1H), 7.28 (d, J=8.0 Hz, 1H), 4.35 (q, J=7.0 Hz, 2H), 4.01 (s, 3H), 1.35 (t, J=7.0 Hz, 3H) ppm.

Ethyl 1-methyl-6-(1H-pyrazol-4-yl)-1H-pyrrolo[2,3-b]pyridine-2-carboxylate (1-7)

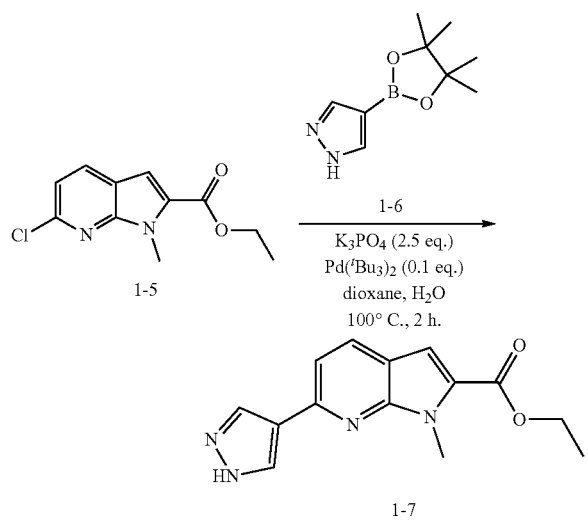

To a solution of 1-5 (766 mg, 3.22 mmol) in 1,4-dioxane (28.0 mL) and water (7.0 mL) was added 4-(4,4,5,5-tetramethyl-1,3,2-dioxaborolan-2-yl)-1H-pyrazole 1-6 (1.25 g, 6.44 mol), potassium phosphate (2.05 g, 9.66 mmol) and bis(tri-tert-butylphosphine)palladium (0.164 g, 0.322 mmol) under nitrogen gas. The reaction mixture was stirred under argon atmosphere at 100° C. for two hours and the reaction progress was monitored by LCMS. The resulting mixture was diluted with water (20 mL) and extracted with ethyl acetate (100 mL×3). The combined organic phase was washed with saturated sodium chloride solution (50 mL), dried over anhydrous sodium sulfate, and concentrated in vacuo. The residue was purified by silica gel column chromatography (dichloromethane/methanol, v/v=20) to give 1-7 (653 mg, 75.1% yield) as a light-yellow solid. ESI m/z: 271.0 (M+H)$^+$, retention time 1.69 min, 98.3% @214 nm. $^1$H NMR (500 MHz, DMSOd$_6$) δ 13.03 (s, 1H), 8.29 (s, 2H), 8.08 (d, J=8.0 Hz, 1H), 7.56 (d, J=8.5 Hz, 1H), 7.22 (s, 1H), 4.34 (q, J=7.0 Hz, 2H), 4.08 (s, 3H), 1.35 (t, J=7.0 Hz, 3H) ppm.

1-Methyl-6-(1H-pyrazol-4-yl)-1H-pyrrolo[2,3-b]pyridine-2-carboxylic acid (1-8)

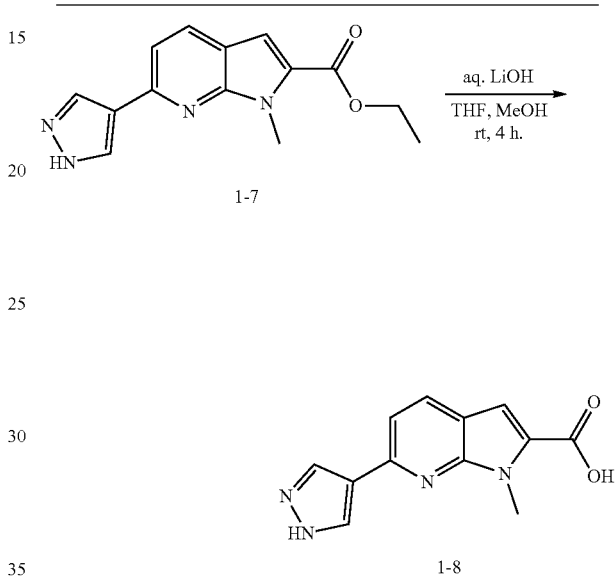

To a solution of compound 1-7 (400 mg, 1.48 mmol) in water (2.6 mL), tetrahydrofuran (THF, 7.8 mL) and methanol (2.6 mL) was added lithium hydroxide monohydrate (0.311 g, 7.41 mmol). The reaction mixture was stirred at 20° C. for three hours and the reaction progress was monitored by LCMS. The reaction mixture was concentrated in vacuo and diluted with water (2 mL). The aqueous mixture was acidified with conc. aq. hydrochloride to pH 1 and then filtered. The filter-cake was dried in vacuo to give 1-8 (357 mg, 99.4% yield). ESI m/z: 243.1 (M+H)$^+$, retention time 1.07 min, purity >99.9% @254 nm. $^1$H NMR (400 MHz, DMSOd$_6$) δ 8.30 (s, 2H), 8.07 (d, J=8.4 Hz, 1H), 7.56 (d, J=8.4 Hz, 1H), 7.18 (s, 1H), 4.08 (s, 3H) ppm.

N-(2-fluorobenzyl)-1-methyl-6-(1H-pyrazol-4-yl)-1H-pyrrolo[2,3-b]pyridine-2-carboxamide (Compound 1)

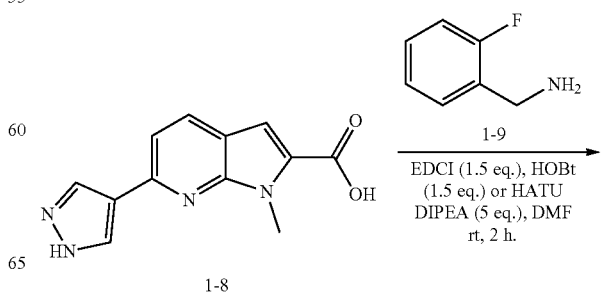

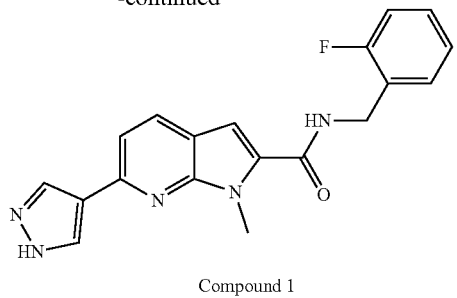

Compound 1

To a solution of 1-8 (5.9 g, 24.4 mmol) in N,N-dimethylformamide (236 mL) was added (2-fluorophenyl)methanamine 1-9 (3.66 g, 29.3 mmol, CAS: 89-99-6), EDCI (7.01 g, 36.6 mmol), HOBt (4.94 g, 36.6 mmol) and DIPEA (15.7 g, 122 mmol). The reaction was monitored by LCMS. After stirring at 25° C. for eighteen hours, the reaction mixture was quenched with water (600 mL) and was then extracted with ethyl acetate (600 mL×3). The combined organic phase was washed with saturated sodium chloride solution (500 mL), dried over anhydrous sodium sulfate, and concentrated. The residue was purified by prep-HPLC (5-95% acetonitrile in aq. ammonium bicarbonate (10 mM)) to give desired product Compound 1 (1.96 g, 23% yield) as a white solid. ESI m/z: 349.9 (M+H)$^+$, retention time 1.59 min, purity >99.9% @254 nm. $^1$H NMR (400 MHz, DMSOd$_6$) δ 13.06 (s, 1H), 9.10 (t, J=5.5 Hz, 1H), 8.26 (s, 2H), 8.05 (d, J=8.5 Hz, 1H), 7.53 (d, J=8.5 Hz, 1H), 7.43 (t, J=8.0 Hz, 1H), 7.36-7.29 (m, 1H), 7.24-7.13 (m, 3H), 4.54 (d, J=5.5 Hz, 2H), 4.06 (s, 3H) ppm. $^{19}$F NMR (376 MHz, DMSOd$_6$) 6-118.97 ppm.

Example 2: Synthesis of N-(2-fluorobenzyl)-6-(5-methyl-1H-pyrazol-4-yl)-1H-pyrrolo[2,3-b]pyridine-2-carboxamide (Compound 2)

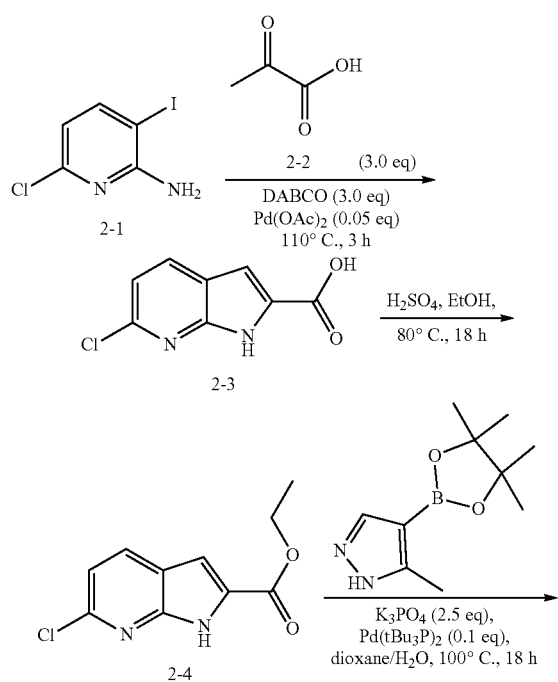

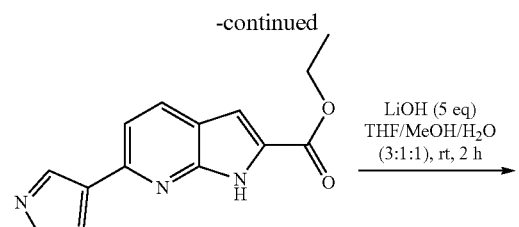

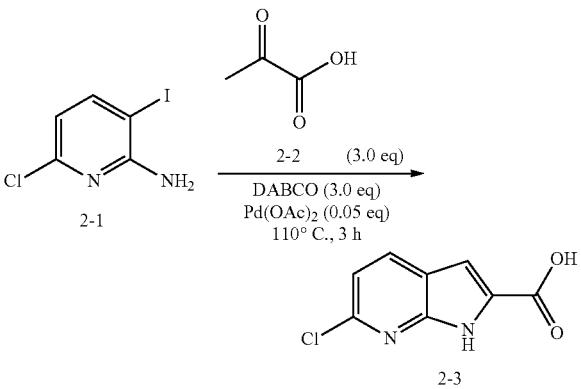

Compound 2

6-Chloro-1H-pyrrolo[2,3-b]pyridine-2-carboxylic acid (2-3)

To a solution of 6-chloro-3-iodopyridin-2-amine (2-1) (9.00 g, 35.4 mmol), 2-oxopropanoic acid (2-2) (9.34 g, 106 mmol) and DABCO (11.9 g, 106 mmol) in N,N-dimethylformamide (255 mL) was added palladium(II) acetate (0.397 g, 1.77 mmol). The reaction mixture was degassed three times and stirred under N$_2$ atmosphere at 110° C. for three hours. LCMS showed the reaction was completed. Then the mixture was concentrated under vacuum to remove the solvent. To the residue, ethyl acetate (500 mL) was added, and the mixture was extracted with 2M aq. sodium hydroxide (500 mL×3). The aqueous layer was concentrated under vacuum to 500 mL. Then the aqueous solution was acidified with HCl to pH=3. And the mixture was filtered. The filter-cake was washed and dried to afford 6-chloro-1H-pyrrolo[2,3-b]pyridine-2-carboxylic acid (5.49 g, 74.1%) as yellow solid. LCMS: ESI [M+H]$^+$ 196.9 was found, retention time 1.23 min, purity 93.9% at 254 nm. $^1$H NMR (500 MHz, DMSOd$_6$) δ 12.41 (s, 1H), 8.12 (d, J=8.0 Hz, 1H), 7.18 (d, J=8.0 Hz, 1H), 7.06 (s, 1H) ppm.

Ethyl 6-chloro-1H-pyrrolo[2,3-b]pyridine-2-carboxylate (2-4)

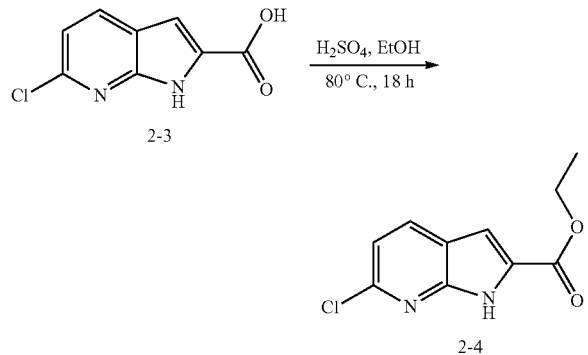

To a solution of 2-3 (5.70 g, 35.4 mmol) in ethanol (170 mL) was added 98% sulfuric acid (14.5 g, 145 mmol). The reaction mixture was stirred at 80° C. for eighteen hours. LCMS showed the reaction was completed. Then the mixture was alkalified with sodium bicarbonate and concentrated under vacuum to remove the ethanol. To the mixture, water (300 mL) was added, and the mixture was extracted with ethyl acetate (500 mL×3). The organic phase was washed with saturated sodium chloride solution, dried with sodium sulfate and concentrated under vacuum. The residue was purified with silica column (petroleum ether:ethyl acetate=2:1) to afford ethyl 6-chloro-1H-pyrrolo [2,3-b] pyridine-2-carboxylate (2-4) (4.29 g, 65.9%) as yellow solid. LCMS: ESI: 224.9 [M+H]+, retention time 1.82 min, purity 98.6% at 254 nm. $^1$H NMR (500 MHz, DMSOd$_6$) δ 12.75 (s, 1H), 8.17 (d, J=8.0 Hz, 1H), 7.23 (d, J=8.0 Hz, 1H), 7.21 (d, J=2.0 Hz, 1H), 4.35 (q, J=7.0 Hz, 2H), 1.34 (t, J=7.0 Hz, 3H) ppm.

Ethyl 6-(5-methyl-1H-pyrazol-4-yl)-1H-pyrrolo[2,3-b]pyridine-2-carboxylate (2-5)

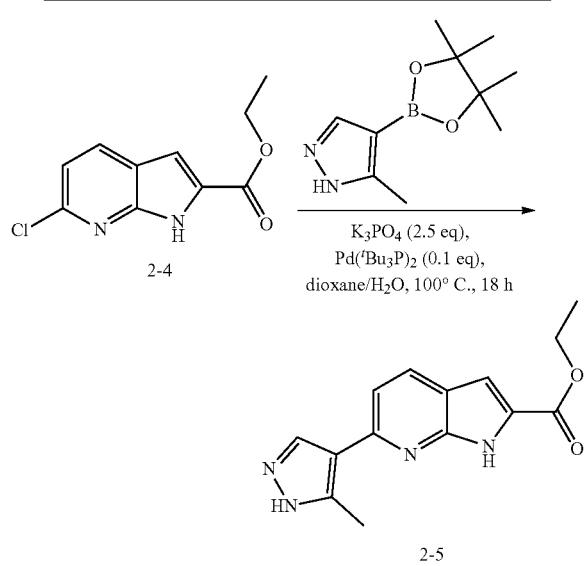

To a solution of 2-4 (3.50 g, 15.6 mmol), 5-methyl-4-(4, 4,5,5-tetramethyl-1,3,2-dioxaborolan-2-yl)-1H-pyrazole (6.5 g, 31.3 mol) and potassium phosphate (8.29 g 39.1 mmol) in 1,4-dioxane (70.0 mL) and water (17.5 mL) was added bis(tri-tert-butylphosphine)palladium (0.799 g, 1.56 mmol). The reaction mixture was stirred under argon atmosphere at 100° C. for eighteen hours. And the desired product was found by LCMS. Then water (100 mL) was added to the reaction mixture at 25° C. And the reaction mixture was extracted with ethyl acetate (200 mL×3), the organic phase was combined and washed with saturated sodium chloride solution (200 mL), then dried with sodium sulfate, and filtered. The filtrate was concentrated. The residue was purified with silica column (dichloromethane:methanol=20:1) to give ethyl 6-(5-methyl-1H-pyrazol-4-yl)-1H-pyrrolo[2, 3-b]pyridine-2-carboxylate (2-5) (1.14 g, 27.0%). LCMS: ESI [M+H]$^+$ 271.0, retention time 1.65 min, purity 96.0% at 214 nm. $^1$H NMR (500 MHz, DMSOd$_6$) δ 12.73 (s, 1H), 12.26 (s, 1H), 8.04 (d, J=8.5 Hz, 2H), 7.43 (d, J=8.5 Hz, 1H), 7.12 (d, J=2.0 Hz, 1H), 4.33 (q, J=7.0 Hz, 2H), 2.61 (s, 3H), 1.34 (t, J=7.0 Hz, 3H) ppm.

6-(5-Methyl-1H-pyrazol-4-yl)-1H-pyrrolo[2,3-b]pyridine-2-carboxylic acid (2-6)

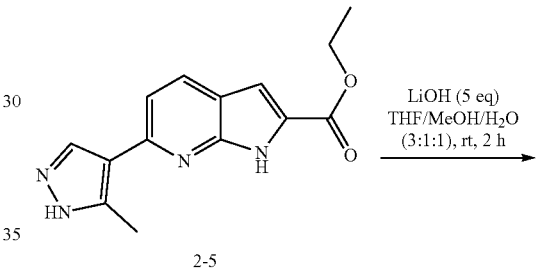

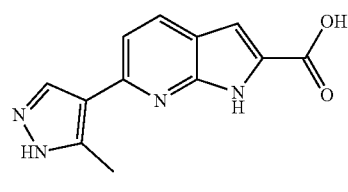

To a solution of 2-5 (1.14 g, 4.22 mmol) in water (3 mL), tetrahydrofuran (9 mL) and methanol (3 mL), lithium hydroxide monohydrate (0.886 g, 21.1 mmol) was added. The reaction mixture was stirred at 20° C. for two hours. LCMS showed that the reaction was completed. The reaction mixture was concentrated under vacuum to remove tetrahydrofuran and methanol. Water (3 mL) was added and then 36.5% hydrochloric acid solution was added to adjust pH to 1, and then filtered. The filter-cake was dried under vacuum to give 6-(5-methyl-1H-pyrazol-4-yl)-1H-pyrrolo [2,3-b]pyridine-2-carboxylic acid (2-6) (0.956 g, 93.7%). LCMS: ESI [M+H]$^+$ 243.1, retention time 1.12 min, purity 100% at 254 nm. $^1$H NMR (500 MHz, DMSOd$_6$) δ 12.15 (s, 1H), 8.15 (s, 1H), 8.06 (d, J=8.5 Hz, 1H), 7.44 (d, J=8.5 Hz, 1H), 7.07 (d, J=2.0 Hz, 1H), 2.63 (s, 3H) ppm.

N-(2-fluorobenzyl)-6-(5-methyl-1H-pyrazol-4-yl)-1H-pyrrolo[2,3-b]pyridine-2-carboxamide Compound 2)

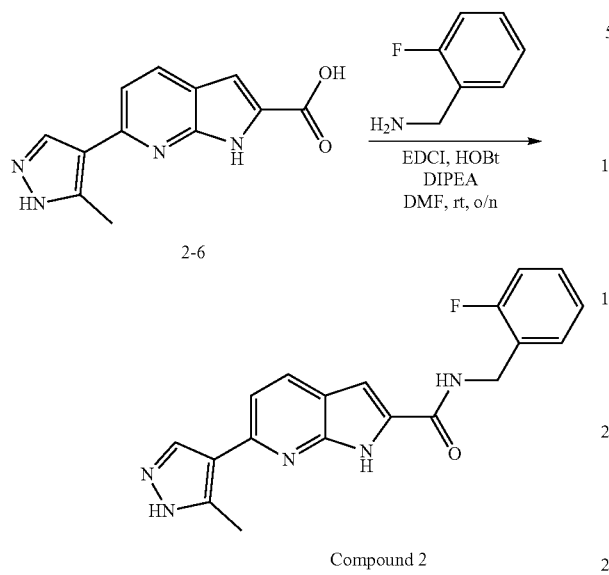

To a solution of 2-6 (70.0 mg, 0.289 mmol) in N,N-dimethylformamide (3.00 mL), (2-fluorophenyl)methanamine (43.4 mg, 0.347 mmol), N-(3-(dimethylamino)propyl)propionamide dihydrochloride (83.2 mg, 0.434 mmol), 1-hydroxybenzotriazole (58.6 mg, 0.434 mmol) and N,N-diisopropylethylamine (187 mg, 1.45 mmol) were added. The reaction mixture was stirred at 25° C. for eighteen hours. Then water (6 mL) was added to the reaction mixture. And then the reaction mixture was extracted with ethyl acetate (30 mL×3), the organic phase was combined and washed with saturated sodium chloride solution (10 mL), and then dried with sodium sulfate and filtered. The filtrate was concentrated. The residue was purified with prep-HPLC to give N-(2-fluorobenzyl)-6-(5-methyl-1H-pyrazol-4-yl)-1H-pyrrolo[2,3-b]pyridine-2-carboxamide (Compound 2) as white solid. (29.9 mg, 29.6%) LCMS: ESI [M+H]+ 350.2, retention time 1.64 min, purity 100% at 254 nm. $^1$H NMR (500 MHz, DMSOd$_6$) δ 12.68 (s, 1H), 11.88 (s, 1H), 8.94 (t, J=5.5 Hz, 1H), 8.02 (d, J=8.0 Hz, 2H), 7.45-7.41 (m, 1H), 7.39 (d, J=8.0 Hz, 1H), 7.37-7.30 (m, 1H), 7.24-7.17 (m, 2H), 7.13 (d, J=2.0 Hz, 1H), 4.56 (d, J=5.5 Hz, 2H), 2.60 (s, 3H) ppm.

Example 3: Synthesis of N-(1-(3-methoxyphenyl)cyclopropyl)-1-methyl-6-(1H-pyrazol-4-yl)-1H-pyrrolo[2,3-b]pyridine-2-carboxamide (Compound 3)

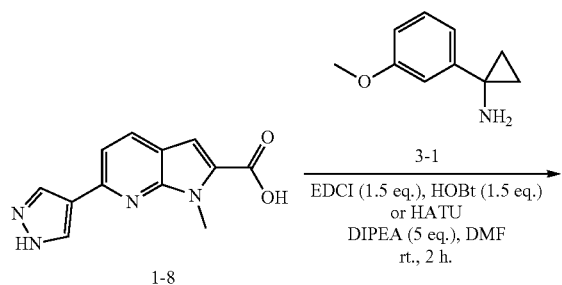

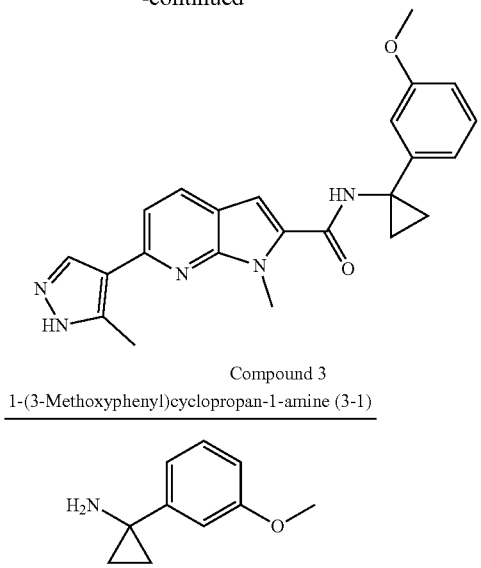

Compound 3
1-(3-Methoxyphenyl)cyclopropan-1-amine (3-1)

To a solution of 3-methoxybenzonitrile (2.2 g, 16.5 mmol) and Ti(O$^i$Pr)$_4$ (5.17 g, 18.2 mmol) in anhydrous tetrahydrofuran (50 mL) was added ethylmagnesium bromide (2 M in THF, 18.2 mL) at −78° C. The yellow solution was stirred for ten minutes at this temperature and then was allowed to warm to room temperature slowly for an hour. To the solution was added boron trifluoride diethyl etherate (1 M in THF, 33 mL), and the reaction mixture was stirred at room temperature for an hour, which was monitored by LCMS. The reaction was quenched with aq. HCl (1 N, 60 mL) and diluted with ethyl acetate (100 mL). The resulting mixture was then basified with aq. sodium hydroxide (10%, 200 mL) and extracted with ethyl acetate. The organic layer was dried over anhydrous sodium sulfate and concentrated. The crude product was purified by prep-HPLC to give compound 3-1 (900 mg, 33% yield) as colorless oil. ESI m/z: 164.1 [M+H]+, retention time 1.525 min, 96% @254 nm. $^1$HNMR (500 MHz, DMSOd$_6$) δ 7.18-7.15 (m, 1H), 6.92-6.91 (m, 1H), 6.81-6.79 (m, 1H), 6.70-6.68 (m, 1H), 3.74 (s, 3H), 0.95-0.91 (m, 2H), 0.90-0.87 (m, 2H) ppm.

N-(1-(3-methoxyphenyl)cyclopropyl)-1-methyl-6-(1H-pyrazol-4-yl)-1H-pyrrolo[2,3-b]pyridine-2-carboxamide (Compound 3)

To a solution of 1-8 (400 mg, 1.65 mmol) in N,N-dimethylformamide (100 mL) were added 1-(3-methoxyphenyl)cyclopropan-1-amine 3-1 (323 mg, 1.98 mmol), HATU (940 mg, 2.5 mmol) and DIPEA (639 mg, 4.95 mmol). The reaction mixture was stirred at room temperature for fifteen minutes. The reaction was then quenched with water (300 mL). The resulting mixture was extracted with ethyl acetate (200 mL×3) and the combined organic solution was washed with saturated sodium chloride solution (300 mL), dried over anhydrous sodium sulfate, and concentrated in vacuo. The residue was purified directly by reserved phase flash chromatography (0-100% methanol in aq. ammonium bicarbonate (0.05%)) to give Compound 3 (180 mg, 28% yield) as a light-yellow solid. ESI m/z: 388 [M+H]$^+$. Retention time: 1.78 min, >99.9% @214 & 254 nm. $^1$H NMR (400 MHz, DMSOd$_6$) δ 13.1 (s, 1H), 9.25 (s, 1H), 8.34-8.22 (m, 2H), 8.06 (d, J=8.0 Hz, 1H), 7.53 (d, J=8.0 Hz, 1H), 7.22-7.19 (m, 2H), 6.82-6.75 (m, 3H), 4.03 (s, 3H), 3.72 (s, 3H), 1.30 (s, 4H) ppm.

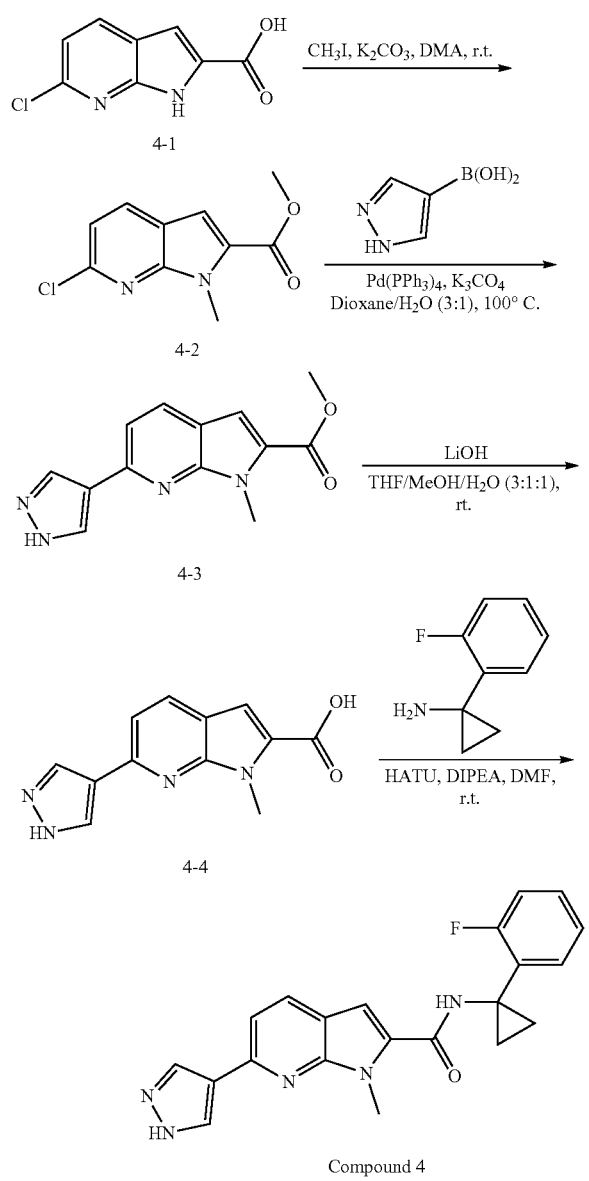

Compound 4

Methyl 6-chloro-1-methyl-1H-pyrrolo[2,3-b]pyridine-2-carboxylate

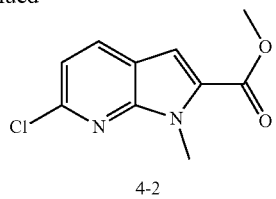

4-2

To a stirred mixture of 6-chloro-1H-pyrrolo[2,3-b]pyridine-2-carboxylic acid (4-1) (14 g, 71.214 mmol, 1.0 equiv) and K$_2$CO$_3$ (49.21 g, 356.070 mmol, 5.0 equiv) in N,N-dimethylacetamide (150 mL) was added CH$_3$I (21.23 g, 149.549 mmol, 2.1 equiv) dropwise at 0° C. The resulting mixture was stirred overnight at room temperature. The reaction was monitored by LCMS. After completion, the reaction was quenched with water at room temperature. The aqueous layer was extracted with ethyl acetate (2×500 mL). The organic layer was concentrated under reduced pressure. The residue was purified by silica gel column chromatography, eluted with petroleum ether and ethyl acetate (3:1) to afford methyl 6-chloro-1-methyl-1H-pyrrolo[2,3-b]pyridine-2-carboxylate (4-2) (10.5 g, 65.6%) as a yellow solid. MS (ESI) m/z: 225 [M+H]$^+$.

Methyl 1-methyl-6-(1H-pyrazol-4-yl)-1H-pyrrolo[2,3-b]pyridine-2-carboxylate

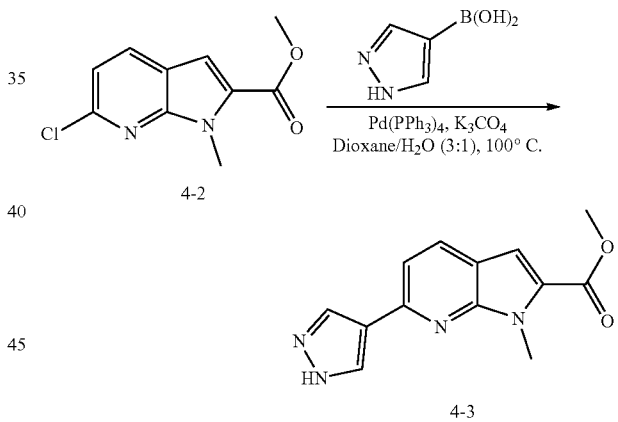

4-3

A mixture of methyl 6-chloro-1-methylpyrrolo[2,3-b]pyridine-2-carboxylate (4-2) (10 g, 44.516 mmol, 1.0 equiv), 1H-pyrazol-4-yl-boronic acid (7.47 g, 66.774 mmol, 1.5 equiv), Pd(PPh$_3$)$_4$ (5.14 g, 4.452 mmol, 0.1 equiv) and K$_2$CO$_3$ (24.61 g, 178.064 mmol, 4.0 equiv) in 1,4-dioxane (90 mL) and H$_2$O (30 mL) was stirred overnight at 100° C. under nitrogen atmosphere. The reaction was monitored by LCMS. The reaction was quenched with water at room temperature. The resulting mixture was extracted with ethyl acetate (3×300 mL). The combined organic layers were dried over anhydrous Na$_2$SO$_4$. After filtration, the filtrate was concentrated under reduced pressure. The residue was purified by silica gel column chromatography, eluted with petroleum ether and ethyl acetate (1:1), to afford methyl 1-methyl-6-(1H-pyrazol-4-yl)pyrrolo[2,3-b]pyridine-2-carboxylate (4-3) (4.4 g, 38.6%) as a yellow solid. MS (ESI) m/z: 257 [M+H]$^+$.

1-Methyl-6-(1H-pyrazol-4-yl)-1H-pyrrolo[2,3-b]pyridine-2-carboxylic acid

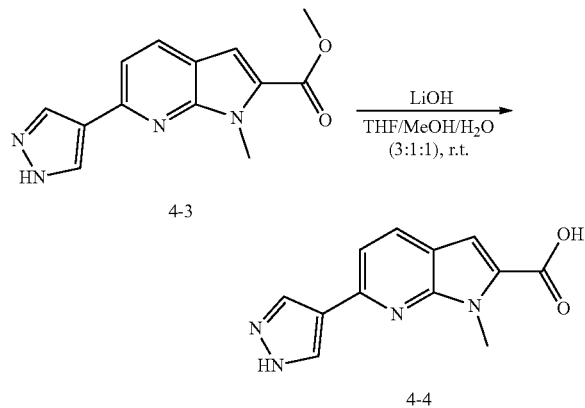

4-3

4-4

A mixture of methyl 1-methyl-6-(1H-pyrazol-4-yl)pyrrolo[2,3-b]pyridine-2-carboxylate (4-3) (4.3 g, 16.78 mmol, 1.0 equiv) and LiOH (2.01 g, 83.9 mmol, 5.0 equiv) in tetrahydrofuran (30 mL), methanol (10 mL) and H$_2$O (10 mL) was stirred for two hours at room temperature. The reaction was monitored by LCMS. The resulting mixture was concentrated under reduced pressure. The residue was purified by silica gel column chromatography, eluted with ethyl acetate and methanol (5:1), to afford 1-methyl-6-(1H-pyrazol-4-yl)pyrrolo[2,3-b]pyridine-2-carboxylic acid (4-4) (3.5 g, 86.1%) as a white solid. MS (ESI) m/z: 243 [M+H]$^+$.

N-[1-(2-fluorophenyl)cyclopropyl]-1-methyl-6-(1H-pyrazol-4-yl)pyrrolo[2,3-b]pyridine-2-carboxamide (Compound 4)

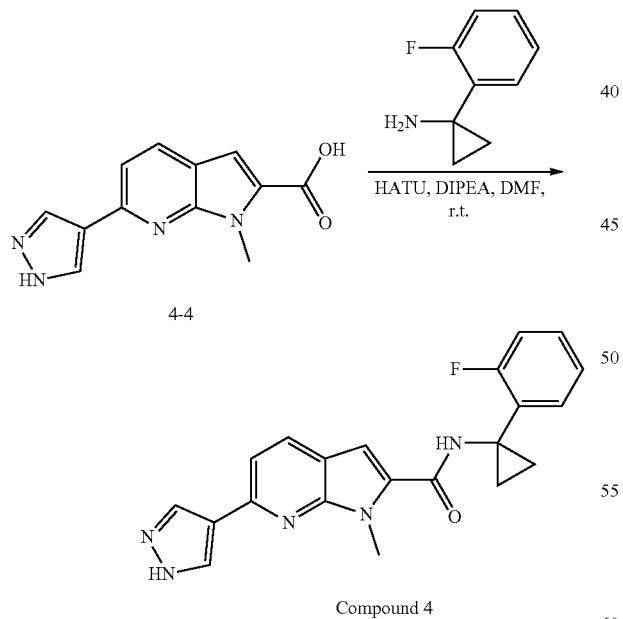

Compound 4

A mixture of 1-methyl-6-(1H-pyrazol-4-yl)pyrrolo[2,3-b]pyridine-2-carboxylic acid (4-4) (3.4 g, 14.036 mmol, 1.0 equiv), DIPEA (9.07 g, 70.180 mmol, 5.0 equiv) and 1-(2-fluorophenyl)cyclopropan-1-amine (3.18 g, 21.054 mmol, 1.5 equiv) in N,N-dimethylformamide (25 mL) was stirred for ten minutes at 0° C. To the above mixture was added HATU (8.01 g, 21.054 mmol, 1.5 equiv) in portions at 0° C. The resulting mixture was stirred for an additional two hours at room temperature. The reaction was monitored by LCMS. The reaction was quenched with water at room temperature. The resulting mixture was extracted with ethyl acetate (2×200 mL). The combined organic layers were dried over anhydrous Na$_2$SO$_4$ and filtered. After filtration, the filtrate was concentrated under reduced pressure. The residue was purified by reversed-phase flash chromatography with the following conditions: column, C18 silica gel; mobile phase, acetonitrile in water (0.1% FA), 10% to 50% gradient in 40 min; detector, UV 254 nm. This resulted in N-[1-(2-fluorophenyl)cyclopropyl]-1-methyl-6-(1H-pyrazol-4-yl)pyrrolo[2,3-b]pyridine-2-carboxamide (Compound 4) (2.8914 g, 52.7%) as a dark yellow solid. MS (ESI) m/z: 376.30 [M+H]$^+$. $^1$H-NMR (CD$_3$OD) δ: 8.26 (s, 2H), 8.00 (d, J=8.4 Hz, 1H), 7.66 (td, J=8.0, 1.6 Hz, 1H), 7.47 (d, J=8.2 Hz, 1H), 7.32-7.21 (m, 1H), 7.17-6.96 (m, 3H), 4.02 (s, 3H), 1.31 (s, 4H) ppm.

Example 5: Synthesis of N-(1-(3-methoxyphenyl)cyclopropyl)-6-(5-methyl-1H-pyrazol-4-yl)-1H-pyrrolo[2,3-b]pyridine-2-carboxamide (Compound 5)

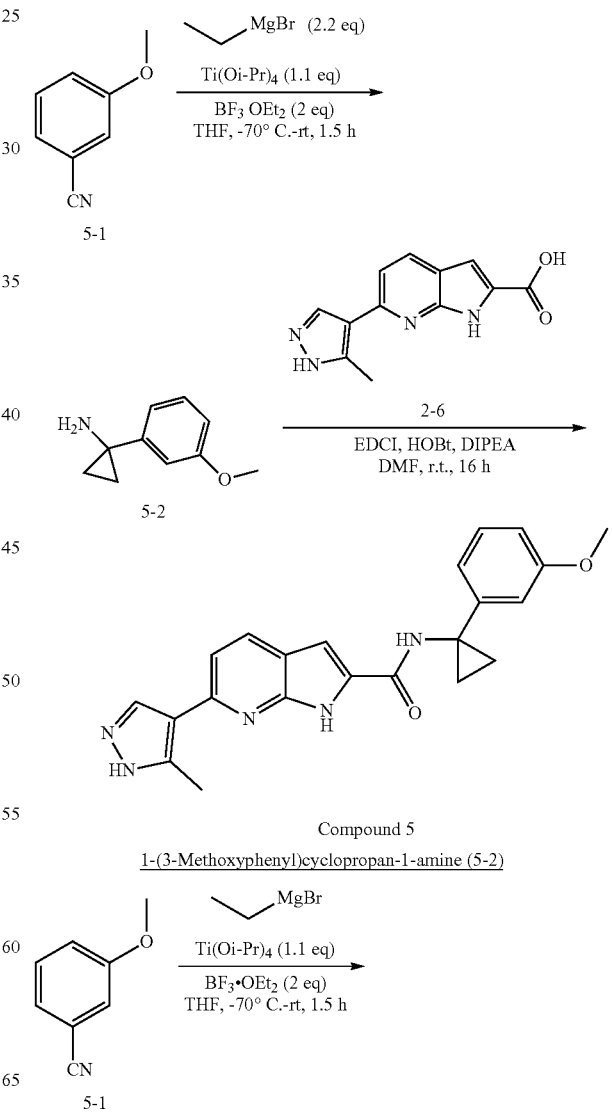

Compound 5

1-(3-Methoxyphenyl)cyclopropan-1-amine (5-2)

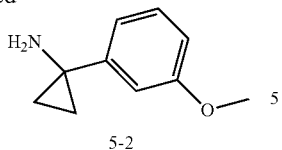

5-2

To a solution of 3-methoxybenzonitrile (5-1) (2.2 g, 16.54 mol) and Ti(Oi-Pr)₄ (5.17 g, 18.2 mmol) in 50 mL of tetrahydrofuran was added ethylmagnesium bromide (2M in THF, 18.2 mL) at −78° C. The resulting yellow solution was stirred for ten minutes. After the reaction mixture was warmed to room temperature (1 hour), BF₃·Et₂O (1M in THF, 33 mL) was added to. the reaction mixture, and the mixture was stirred at room temperature for one hour. To the resulting mixture, 1N HCl (60 mL) and ethyl acetate (100 mL) was added, and then NaOH (10% aq, 200 mL) was added. The reaction mixture was extracted with ethyl acetate, concentrated, and purified by prep-HPLC to afford 1-(3-methoxyphenyl) cyclopropan-1-amine (4-2) (900 mg, 33%) as colorless oil. LCMS: LC retention time 1.525 min. MS (ESI) m/z: 164.1 [M+H]⁺, purity: 98% at 214 nm; 96% at 254 nm. ¹H NMR (500 MHz, DMSOd₆): δ 7.18-7.15 (m, 1H), 6.92-6.91 (m, 1H), 6.81-6.79 (m, 1H), 6.70-6.68 (m, 1H), 3.74 (s, 3H), 0.95-0.91 (m, 2H), 0.90-0.87 (m, 2H) ppm.

N-(1-(3-methoxyphenyl)cyclopropyl)-6-(5-methyl-1H-pyrazol-4-yl)-1H-pyrrolo[2,3-b]pyridine-2-carboxamide (Compound 5)

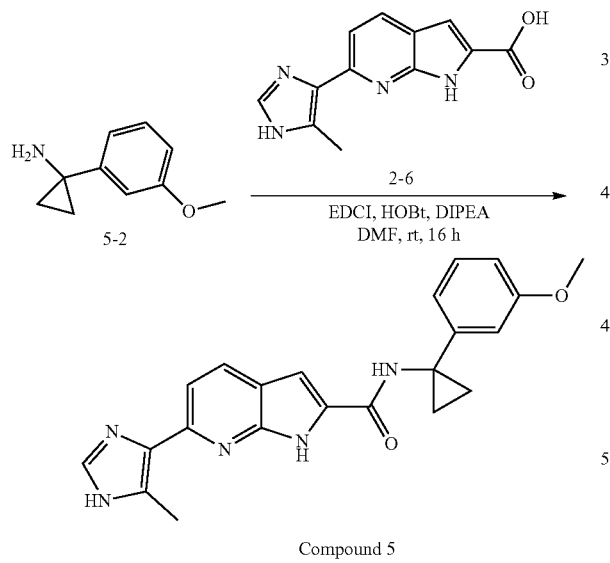

Compound 5

A mixture of 1-(3-methoxyphenyl)cyclopropan-1-amine (5-2) (47 mg, 0.29 mmol), 6-(5-methyl-1H-pyrazol-4-yl)-1H-pyrrolo[2,3-b]pyridine-2-carboxylic acid (2-6) (70 mg, 0.29 mmol), EDCI (84 mg, 0.44 mmol), HOBt (54 mg, 0.44 mmol), DIPEA (187 mg, 1.5 mmol) in N,N-dimethylformamide (2 mL) was stirred at room temperature for twelve hours. LCMS showed the reaction was completed, the mixture was purified by prep-HPLC to give the target product (Compound 5) as a white solid (26 mg, 23%). LCMS: LC retention time 1.643 min. MS (ESI) m/z 388 [M+H]⁺. Purity: 98% (214 nm). ¹H NMR (500 MHz, DMSOd₆) δ 12.68 (s, 1H), 11.80 (s, 1H), 9.11 (s, 1H), 8.03 (d, J=8.5 Hz, 2H), 7.40 (d, J=8.5 Hz, 1H), 7.26 (d, J=8.0 Hz, 1H), 7.15 (d, J=2.0 Hz, 1H), 6.81 (d, J=7.5 Hz, 1H), 6.74 (m, 2H), 3.71 (s, 3H), 2.59 (s, 3H), 1.27 (s, 4H) ppm.

Example 6: Synthesis of N-(2-chloro-6-(1-hydroxycyclopropyl)benzyl)-6-(5-methyl-1H-pyrazol-4-yl)-1H-pyrrolo[2,3-b]pyridine-2-carboxamide (Compound 6)

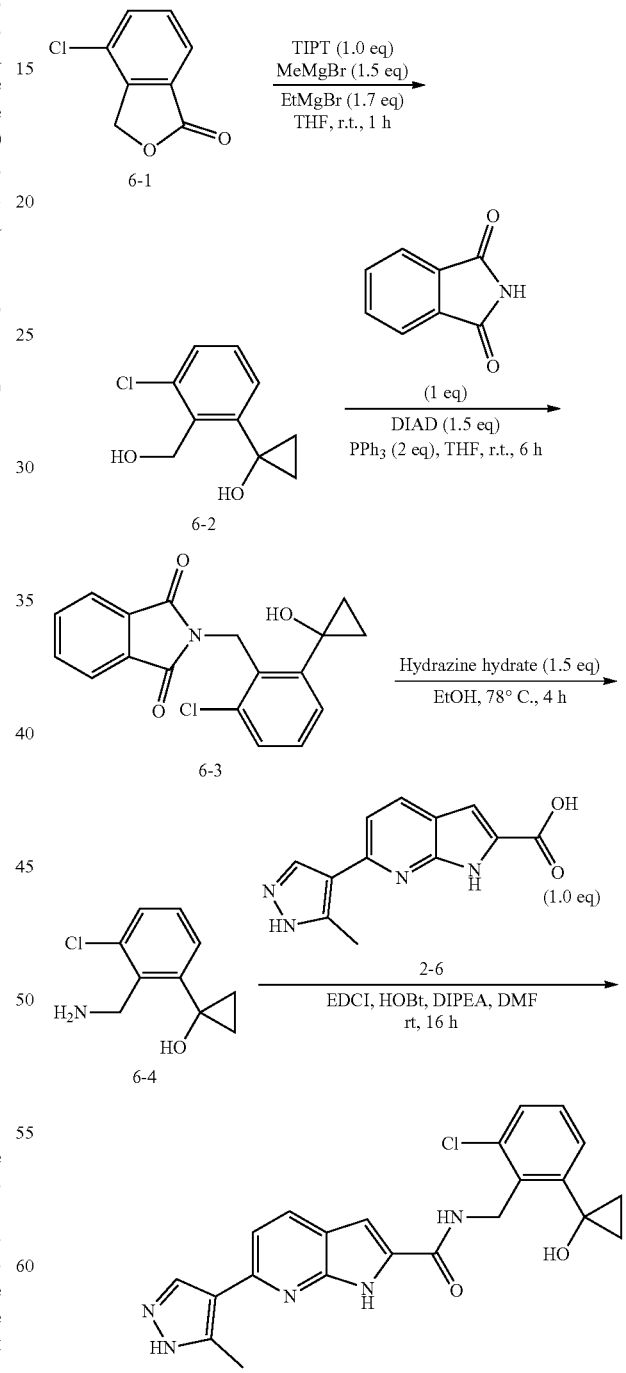

Compound 6

1-(3-Chloro-2-(hydroxymethyl)phenyl)cyclopropan-1-ol (6-2)

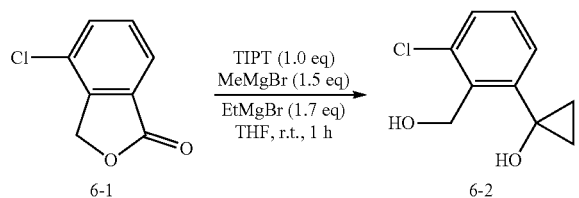

To a solution of titanium tetraisopropanolate (1.69 g, 5.93 mmol) in tetrahydrofuran (20 mL) was added MeMgBr (8.90 mL, 1.0 mol/L), the solution was stirred for ten minutes then cooled to 0° C. Then 4-chloroisobenzofuran-1(3H)-one (6-1) (1.00 g, 5.93 mmol) was added, and EtMgBr (3.36 mL, 3.0 mol/L) was added dropwise to the reaction mixture. The solution was stirred at room temperature for one hour under nitrogen. The organic phase was quenched by 10% $H_2SO_4$ (7.00 mL), partitioned between water (30.0 mL) and ethyl acetate (30.0 mL×3), washed with saturated sodium chloride solution (30.0 mL), dried over anhydrous sodium sulfate, and filtered. After filtration, the filtrate was concentrated under the reduced pressure and the crude residue was purified by flash column chromatography to afford 1-(3-chloro-2-(hydroxymethyl)phenyl)cyclopropan-1-ol (6-2) (600 mg, 2.87 mmol, yield: 48.7%) as light oil. LCMS: LC retention time 1.49 min. MS (ESI) m/z: 181.0 [M+H−17]$^+$, 100% at UV 254 nm. $^1$H NMR (500 MHz, DMSO-d$_6$) δ, 7.40-7.38 (m, 1H), 7.35-7.33 (m, 1H), 7.29-7.26 (m, 1H), 5.97 (s, 1H), 4.94-4.93 (m, 1H), 4.90-4.89 (d, J=5 Hz, 2H), 1.01-0.98 (m, 2H), 0.93-0.91 (m, 2H) ppm.

2-(2-Chloro-6-(1-hydroxycyclopropyl)benzyl)isoindoline-1,3-dione (6-3)

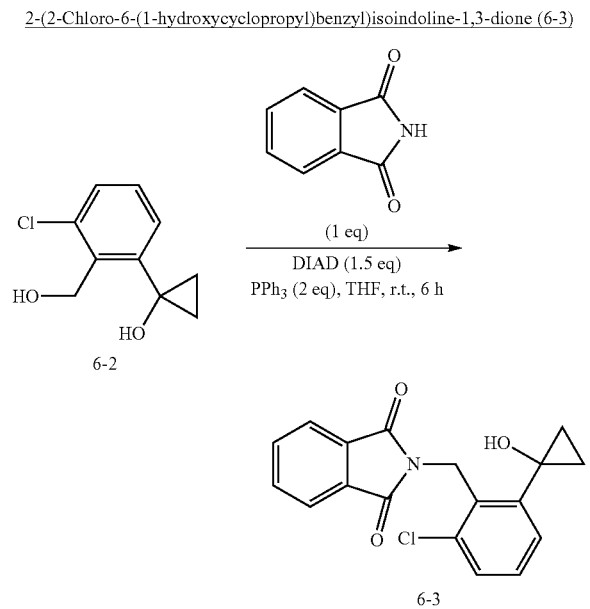

To a stirred solution of 6-2 (500 mg, 2.52 mmol) in tetrahydrofuran (10.0 mL) was added isoindoline-1,3-dione (370 mg, 5.25 mmol) and triphenylphosphine (1.98 g, 7.55 mmol). The solution was cooled to 0° C. and diisopropyl azodicarboxylate (0.763 g, 0.00378 mol) was added dropwise under nitrogen. The solution was stirred at room temperature for six hours. The reaction mixture was partitioned between water (10.0 mL) and dichloromethane (10.0 mL×3). The organic phase was washed with saturated sodium chloride solution (10.0 mL), dried over anhydrous sodium sulfate, and filtered. After filtration, the solvent was concentrated under the reduced pressure and the crude residue was purified by flash column chromatography to afford 2-(2-chloro-6-(1-hydroxycyclopropyl)benzyl)isoindoline-1,3-dione (6-3) (700 mg, 76.4%) as a light oil. LCMS: LC retention time 1.80 min. MS (ESI) m/z: 327.9 [M+H]$^+$, purity: 86.9% at UV 254 nm. $^1$H NMR (500 MHz, DMSO) δ, 7.83 (s, 4H), 7.39-7.37 (m, 1H), 7.35-7.33 (m, 1H), 7.30-7.27 (t, J=15.5 Hz, 1H), 5.85 (s, 1H), 5.21 (s, 2H), 1.08-1.06 (m, 2H), 0.99-0.91 (m, 2H) ppm.

1-(2-(Aminomethyl)-3-chlorophenyl)cyclopropan-1-ol (6-4)

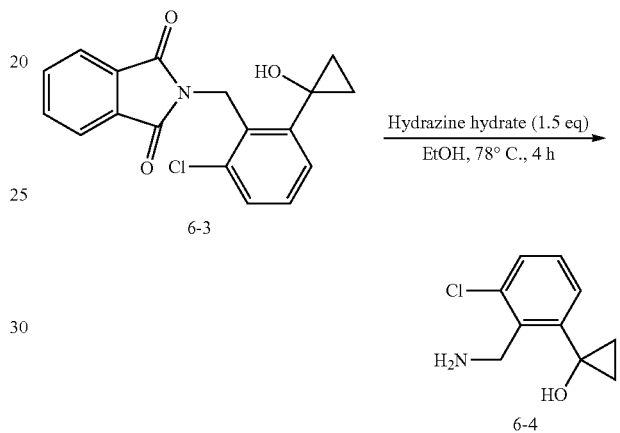

To a mixture of 6-3 (700 mg, 2.14 mmol) in ethanol (10.0 mL) was added hydrazine hydrate (160 mg, 3.20 mmol). The reaction mixture was stirred at 78° C. for four hours. The reaction mixture was partitioned between water (10.0 mL) and dichloromethane (10.0 mL×3), washed with saturated sodium chloride solution (10.0 mL), dried over anhydrous sodium sulfate, and filtered. After filtration, the solvent was concentrated under the reduced pressure and. the crude residue was purified by reverse phase column chromatography to give 1-(2-(aminomethyl)-3-chlorophenyl) cyclopropan-1-ol (6-4) (350 mg, 78.8%) as a pink solid. LCMS: LC retention time 1.46 min. MS (ESI) m/z: 198.0 [M+H]$^+$, purity: 100% at UV 254 nm.

N-(2-chloro-6-(1-hydroxycyclopropyl)benzyl)-6-(5-methyl-1H-pyrazol-4-yl)-1H-pyrrolo[2,3-b]pyridine-2-carboxamide (Compound 6)

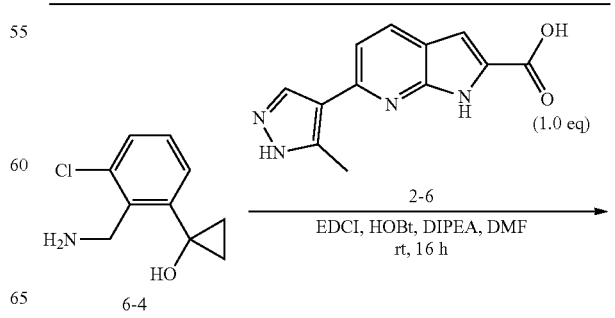

-continued

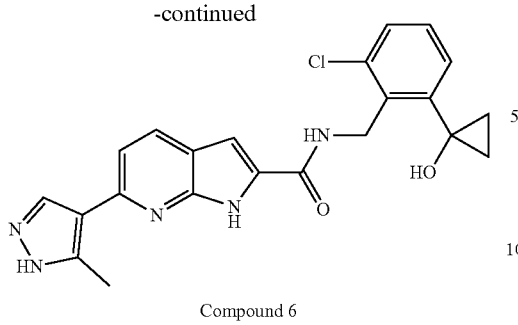

Compound 6

To a stirred solution of 2-6 (70.0 mg, 0.289 mmol) in N,N-dimethylformamide (4.00 mL) was added 6-4 (5.71 mg, 0.289 mmol), EDCI (83.1 mg, 0.433 mmol), HOBt (58.6 mg, 0.433 mmol) and DIPEA (112 mg, 0.867 mmol). The reaction mixture was stirred at room temperature for six hours. The reaction mixture was partitioned between water (10.0 mL) and dichloromethane (10.0 mL×3). The organic phase was washed with saturated sodium chloride solution (10.0 mL), dried over anhydrous sodium sulfate, and filtered. After filtration, the solvent was concentrated under the reduced pressure and the crude residue was purified by prep-HPLC to give N-(2-chloro-6-(1-hydroxycyclopropyl)benzyl)-6-(5-methyl-1H-pyrazol-4-yl)-1H-pyrrolo[2,3-b]pyridine-2-carboxamide (Compound 6) (29.0 mg, yield: 23.8%) as a white solid. LCMS: LC retention time 1.93 min. MS (ESI) m/z 422.1 [M+H]$^+$, purity: 98% at UV 254 nm. $^1$H NMR (500 MHz, DMSO) δ 11.86 (s, 1H), 8.40-8.39 (m, 1H), 7.99-7.98 (m, 2H), 7.46-7.33 (m, 4H), 7.07-7.06 (d, J=2 Hz, 1H), 6.21 (s, 1H), 4.93-4.92 (d, J=4 Hz, 1H), 2.58 (s, 3H), 1.03-1.01 (m, 2H), 0.98-0.96 (m, 2H).

Example 7: Synthesis of N-(1-(3-(1-hydroxycyclopropyl)phenyl)cyclopropyl)-1-methyl-6-(1H-pyrazol-4-yl)-1H-pyrrolo[2,3-b]pyridine-2-carboxamide (Compound 7)

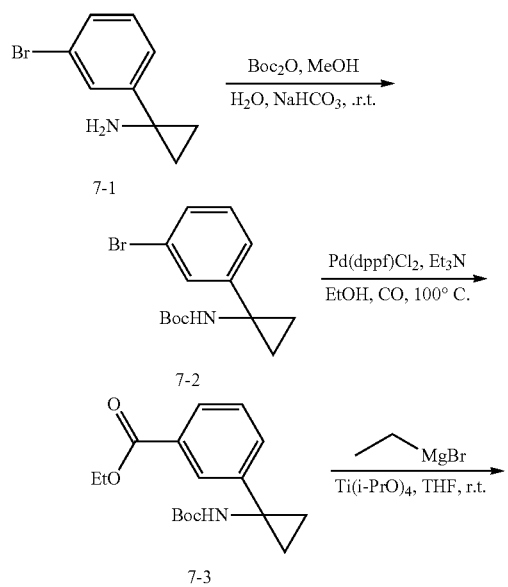

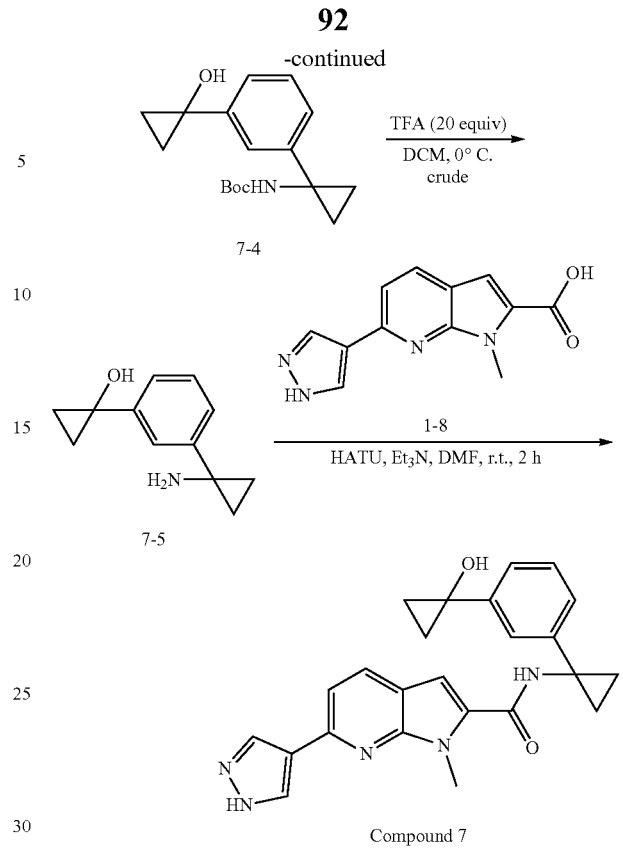

Compound 7

Tert-Butyl N-[1-(3-bromophenyl)cyclopropyl]carbamate (7-2)

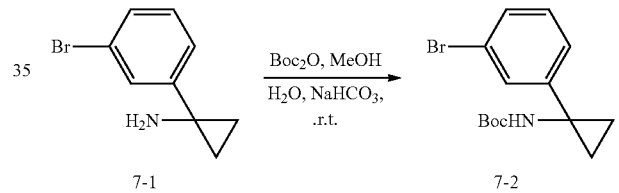

A solution of 1-(3-bromophenyl)cyclopropan-1-amine (5.0 g, 23.58 mmol, 1.0 equiv), di-tert-butyl dicarbonate, and NaHCO$_3$ (0.99 g, 11.79 mmol, 0.5 equiv) in H$_2$O (10 mL) and methanol (40 mL) was stirred for one hour at room temperature. The reaction was monitored by LCMS. The resulting mixture was concentrated under reduced pressure. The residue was purified by silica gel column chromatography, eluted with petroleum ether/ethyl acetate (5:1) to afford tert-butyl N-[1-(3-bromophenyl)cyclopropyl]carbamate (7-2) (7.1 g, 96.46%) as a light yellow solid. MS (ESI) m/z: 312.2 [M+H]$^+$.

Ethyl 3-{1-[(tert-butoxycarbonyl)amino]cyclopropyl}benzoate (7-3)

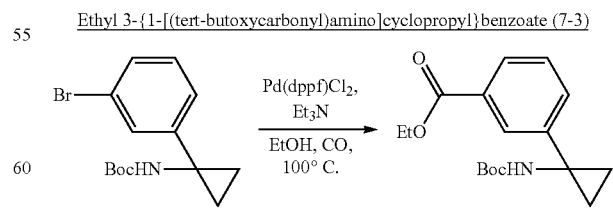

A solution of tert-butyl N-[1-(3-bromophenyl)cyclopropyl]carbamate (7-2) (10.0 g, 32.03 mmol, 1.0 equiv) and Pd(dppf)Cl$_2$ (2.34 g, 3.20 mmol, 0.1 equiv) in ethanol (20 mL) was stirred for 4 hours at 100° C. under carbon monoxide atmosphere. Desired product could be detected by LCMS. The mixture was allowed to cool down to room temperature. The resulting mixture was concentrated under reduced pressure. The residue was purified by silica gel column chromatography, eluted with petroleum ether/ethyl acetate (6:1) to afford ethyl 3-{1-[(tert-butoxycarbonyl) amino]cyclopropyl}benzoate (7-3) (8.7 g, 88.95%) as a colorless oil. MS (ESI) m/z: 306.2 [M+H]$^+$.

Tert-Butyl N-{1-[3-(1-hydroxycyclopropyl)phenyl]cyclopropyl}carbamate (7-4)

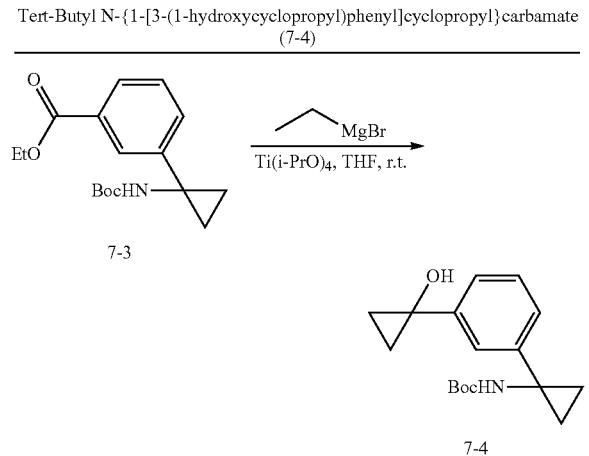

To a stirred solution of ethyl 3-{1-[(tert-butoxycarbonyl) amino]cyclopropyl}benzoate (7-3) (1.0 g, 3.28 mmol, 1.0 equiv) and Ti(Oi-Pr)$_4$ (1.40 g, 4.91 mmol, 1.5 equiv) in tetrahydrofuran (50 mL) was added ethylmagnesium bromide (2.62 g, 19.65 mmol, 6.0 equiv) in portions at 0° C. under nitrogen atmosphere. The resulting mixture was stirred for one and half hours at room temperature under nitrogen atmosphere. After completion, the reaction was quenched with water at room temperature. The resulting mixture was extracted with ethyl acetate (3×50 mL). The combined organic layers were washed with saturated sodium chloride solution (3×15 mL), dried over anhydrous Na$_2$SO$_4$, and filtered. After filtration, the filtrate was concentrated under reduced pressure. The residue was purified by silica gel column chromatography, eluted with petroleum ether/ethyl acetate (9:1) to afford tert-butyl N-{1-[3-(1-hydroxycyclopropyl)phenyl]cyclopropyl}carbamate (7-4) (467 mg, 49.28%) as a yellow oil. MS (ESI) m/z: 290.3 [M+H]$^+$.

1-(3-(1-Aminocyclopropyl)phenyl)cyclopropan-1-ol (7-5)

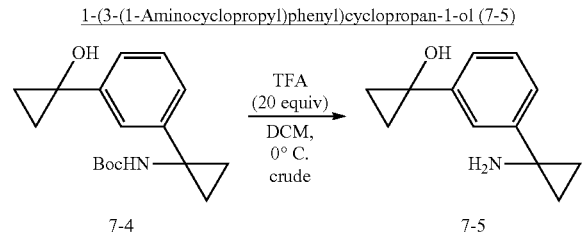 [SMILES: CC(C)(C)OC(=O)NC1(c2cccc(C3(O)CC3)c2)CC1 ; NC1(c2cccc(C3(O)CC3)c2)CC1]

A solution of tert-butyl N-{1-[3-(1-hydroxycyclopropyl) phenyl]cyclopropyl}carbamate (7-4) (476 mg, 1.65 mmol, 1.0 equiv) and TFA (2.44 mL, 32.90 mmol, 20 equiv) in dichloromethane (4 mL) was stirred for 30 minutes at 0° C. The reaction was monitored by LCMS. The resulting mixture was neutralized with NaHCO$_3$ powder at 0° C. and successively concentrated under reduced pressure after filtration. The crude product (7-5) was used in the next step directly without further purification. MS (ESI) m/z: 190.2 [M+H]$^+$.

N-(1-(3-(1-hydroxycyclopropyl)phenyl)cyclopropyl)-1-methyl-6-(1H-pyrazol-4-yl)-1H-pyrrolo[2,3-b]pyridine-2-carboxamide (Compound 7)

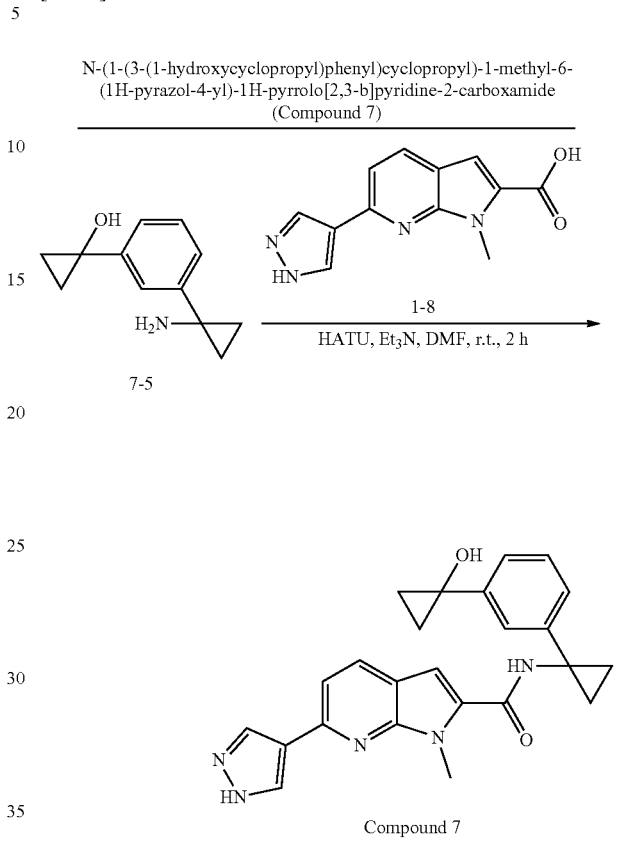

A solution of 1-methyl-6-(1H-pyrazol-4-yl)pyrrolo[2,3-b] pyridine-2-carboxylic acid (1-8) (200 mg, 0.826 mmol, 1.0 equiv), 1-[3-(1-aminocyclopropyl)phenyl]cyclopropan-1-ol (7-5) (234 mg, 1.24 mmol, 1.5 equiv), Et$_3$N (230 µL, 1.65 mmol, 2.0 equiv) and HATU (471 mg, 1.24 mmol, 1.5 equiv) in N,N-dimethylformamide (6 mL) was stirred for two hours at room temperature. The reaction was monitored by LCMS. After completion, the reaction was quenched with water, neutralized to pH 7 with HCl (1 M. aq.) at 0° C. The resulting mixture was extracted with ethyl acetate (2×30 mL). The combined organic layers were washed with water (2×30 mL), dried over anhydrous Na$_2$SO$_4$, and filtered. After filtration, the filtrate was concentrated under reduced pressure. The crude product was purified by Prep-HPLC with the following conditions (Column: XBridge Prep OBD C18 Column, 30*150 mm, 5 m; Mobile Phase A: Water (10 mmol/L NH$_4$HCO$_3$), Mobile Phase B: MeOH-Preparative; Flow rate: 60 mL/min; Gradient: 40% B to 56% B in 10 min, 56% B; Wave Length: 220/254 nm; RT1 (min): 10.48; Number Of Runs: 0) to afford N-{1-[3-(1-hydroxycyclopropyl)phenyl]cyclopropyl}-1-methyl-6-(1H-pyrazol-4-yl)pyrrolo[2,3-b]pyridine-2-carboxamide (Compound 7) (24 mg, purity 97.7%, yield 9.73%) as a white solid. MS (ESI) m/z: 414.00 [M+H]$^+$. $^1$H NMR (400 MHz, DMSO-d$_6$) δ: 13.05 (s, 1H), 9.23 (s, 1H), 8.38 (s, 1H), 8.13 (s, 1H), 8.05 (d, J=8.4 Hz, 1H), 7.52 (d, J=8.0 Hz, 1H), 7.23-7.16 (m, 3H), 7.05 (d, J=8.0 Hz, 1H), 6.98 (d, J=7.6 Hz, 1H), 5.82 (s, 1H), 4.01 (s, 3H), 1.33-1.22 (m, 4H), 1.09-1.04 (m, 2H), 0.92-0.86 (m, 2H) ppm.

Example 8: Synthesis of N-{1-[2-(fluoromethyl)phenyl]cyclopropyl}-1-methyl-6-(1H-pyrazol-4-yl)pyrrolo[2,3-b]pyridine-2-carboxamide (Compound 8)

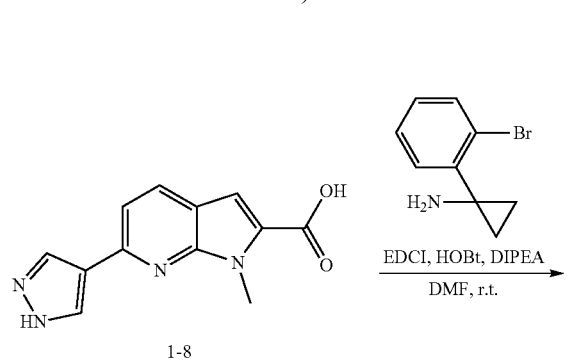

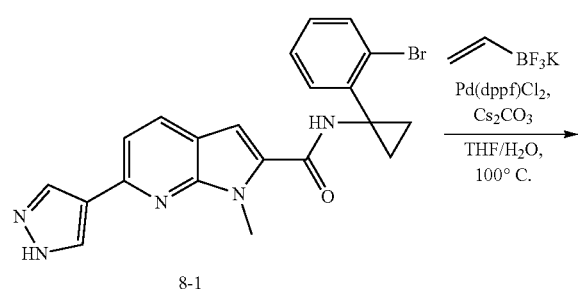

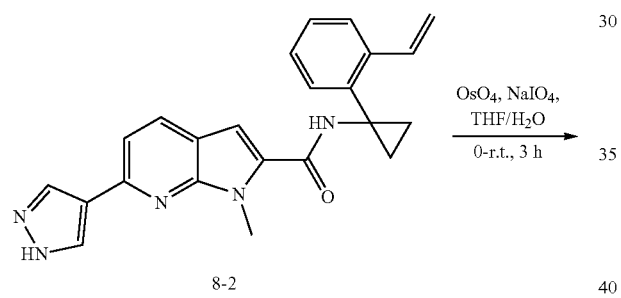

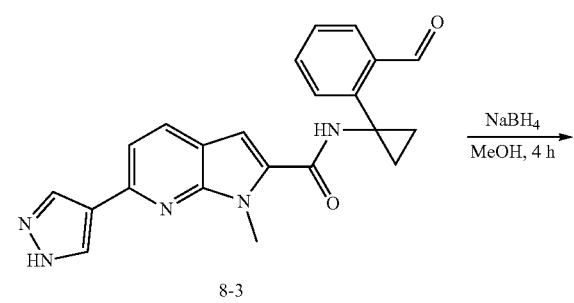

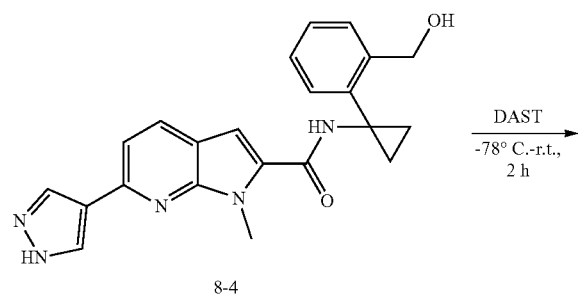

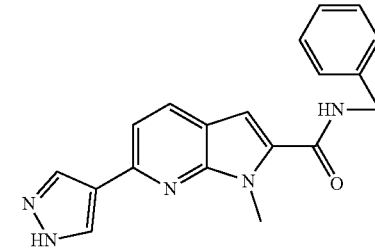

Compound 8
N-[1-(2-bromophenyl)cyclopropyl]-1-methyl-6-(1H-pyrazol-4-yl)pyrrolo[2,3-b]pyridine-2-carboxamide (8-1)

A solution of 1-methyl-6-(1H-pyrazol-4-yl)pyrrolo[2,3-b]pyridine-2-carboxylic acid (1-8) (1.0 g, 4.13 mmol, 1.0 equiv) in N,N-dimethylformamide (10 mL) was treated with 1-(2-bromophenyl)cyclopropan-1-amine (0.96 g, 4.54 mmol, 1.1 equiv), HOBt (558 mg, 4.13 mmol, 1.0 equiv), EDCI (791 mg, 4.13 mmol, 1.0 equiv) and DIPEA (2.16 mL, 12.38 mmol, 3.0 equiv) for two hours at room temperature. The reaction was monitored by LCMS. After completion, the reaction was quenched with water (10 mL) then extracted with ethyl acetate (3×20 mL). The combined organic layers were washed with saturated sodium chloride solution (20 mL), dried over anhydrous $Na_2SO_4$, and filtered. After filtration, the filtrate was concentrated under reduced pressure. The residue was purified by reversed-phase flash chromatography with the following conditions: column, C18 silica gel; mobile phase, acetonitrile in water (0.1% FA), 10% to 50% gradient in 10 minutes; detector, UV 254 nm. The resulting mixture was concentrated under reduced pressure. This resulted in N-[1-(2-bromophenyl)cyclopropyl]-1-methyl-6-(1H-pyrazol-4-yl)pyrrolo[2,3-b]pyridine-2-carboxamide (8-1) (1.14 g, 63.29%) as a light yellow powder. MS (ESI) m/z: 436.20 [M+H]$^+$.

N-[1-(2-ethenylphenyl)cyclopropyl]-1-methyl-6-(1H-pyrazol-4-yl)pyrrolo[2,3-b]pyridine-2-carboxamide (8-2)

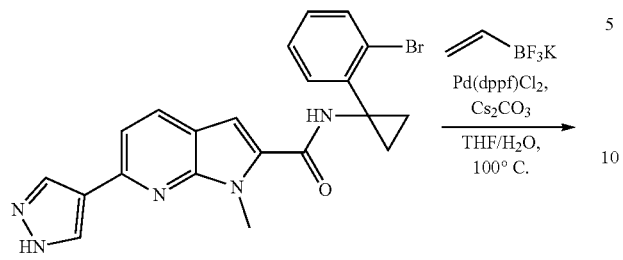

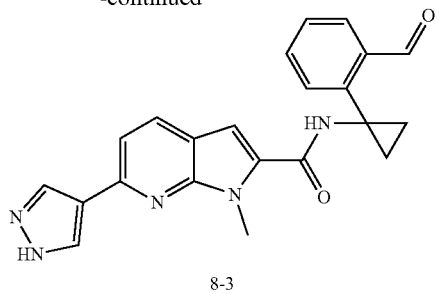

8-2

A solution of N-[1-(2-bromophenyl)cyclopropyl]-1-methyl-6-(1H-pyrazol-4-yl)pyrrolo[2,3-b]pyridine-2-carboxamide (8-1) (1.59 g, 3.66 mmol, 1.0 equiv), ethenyltrifluoroborate potassium (976 mg, 7.29 mmol, 2.0 equiv), $Cs_2CO_3$ (3.57 g, 10.94 mmol, 3.0 equiv) and Pd(dppf)$Cl_2 \cdot CH_2Cl_2$ (594 mg, 0.73 mmol, 0.2 equiv) in tetrahydrofuran (36 mL) and $H_2O$ (3.6 mL) was stirred for six hours at 100° C. under nitrogen atmosphere. The reaction was monitored by LCMS. After completion, the reaction was quenched with water (100 mL) then extracted with ethyl acetate (3×200 mL). The combined organic layers were washed with saturated sodium chloride solution (100 mL), dried over anhydrous $Na_2SO_4$, and filtered. After filtration, the filtrate was concentrated under reduced pressure. The residue was purified by silica gel column chromatography, eluted with petroleum ether/ethyl acetate (1:1) to afford N-[1-(2-ethenylphenyl)cyclopropyl]-1-methyl-6-(1H-pyrazol-4-yl)pyrrolo[2,3-b]pyridine-2-carboxamide (8-2) (480 mg, 34.35%) as a yellow solid. MS (ESI) m/z: 384.45 [M+H]$^+$.

N-[1-(2-formylphenyl)cyclopropyl]-1-methyl-6-(1H-pyrazol-4-yl)pyrrolo[2,3-b]pyridine-2-carboxamide (8-3)

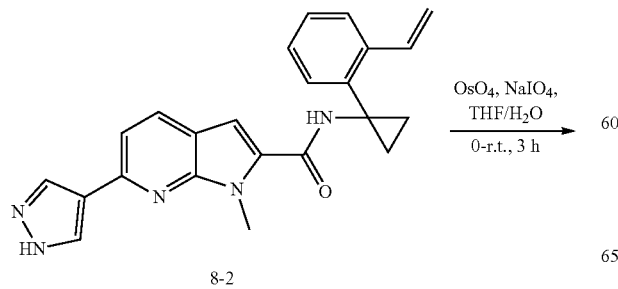

8-2

A solution of N-[1-(2-ethenylphenyl)cyclopropyl]-1-methyl-6-(1H-pyrazol-4-yl)pyrrolo[2,3-b]pyridine-2-carboxamide (8-2) (450 mg, 1.17 mmol, 1.0 equiv), $OsO_4$ (30.5 mg, 0.12 mmol, 0.1 equiv) and $NaIO_4$ (753 mg, 3.52 mmol, 3.0 equiv) in tetrahydrofuran (2 mL) and $H_2O$ (2 mL) was stirred for 40 minutes at 0° C. The resulting mixture was successively stirred for an additional two hours at room temperature. The reaction was monitored by LCMS. The reaction was quenched by the addition of saturated $Na_2S_2O_3$ (aq.) (3 mL) at room temperature. The resulting mixture was extracted with ethyl acetate (2×20 mL). The combined organic layers were washed with saturated sodium chloride solution (2×20 mL), dried over anhydrous $Na_2SO_4$, and filtered. After filtration, the filtrate was concentrated under reduced pressure. The residue was purified by silica gel column chromatography, eluted with petroleum ether/ethyl acetate (1:1) to afford N-[1-(2-formylphenyl)cyclopropyl]-1-methyl-6-(1H-pyrazol-4-yl)pyrrolo[2,3-b]pyridine-2-carboxamide (8-3) (160 mg, 35.37%) as an orange solid. MS (ESI) m/z: 386.40 [M+H]$^+$.

N-{1-[(2-hydroxymethyl)phenyl]cyclopropyl}-1-methyl-6-(1H-pyrazol-4-yl)pyrrolo[2,3-b]pyridine-2-carboxamide (8-4)

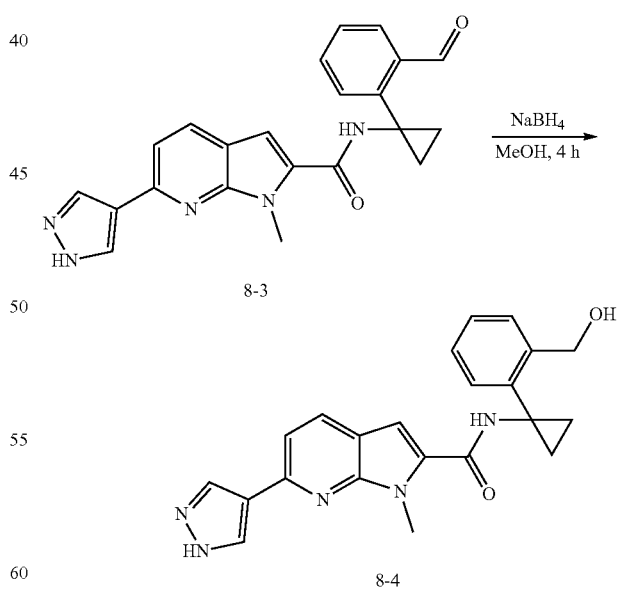

A solution of N-[1-(2-formylphenyl)cyclopropyl]-1-methyl-6-(1H-pyrazol-4-yl)pyrrolo[2,3-b]pyridine-2-carboxamide (8-3) (160 mg, 0.42 mmol, 1.0 equiv) and $NaBH_4$ (63 mg, 1.66 mmol, 4.0 equiv) in methanol (2 mL) was stirred for three hours at room temperature. The reaction was monitored by LCMS. After completion, the reaction was quenched by the addition of water (1 mL) at room temperature and concentrated under reduced pressure. The residue was purified by silica gel column chromatography, eluted with dichloromethane/methanol (10:1) to afford N-{1-[2-(hydroxymethyl)phenyl]cyclopropyl}-1-methyl-6-(1H-pyrazol-4-yl)pyrrolo[2,3-b]pyridine-2-carboxamide (8-4) (116 mg, 72.12%) as a light yellow solid. MS (ESI) m/z: 388.15 [M+H]$^+$.

N-{1-[2-fluoromethyl)phenyl]cyclopropyl}-1-methyl-6-(1H-pyrazol-4-yl)pyrrolo[2,3-b]pyridine-2-carboxamide (Compound 8)

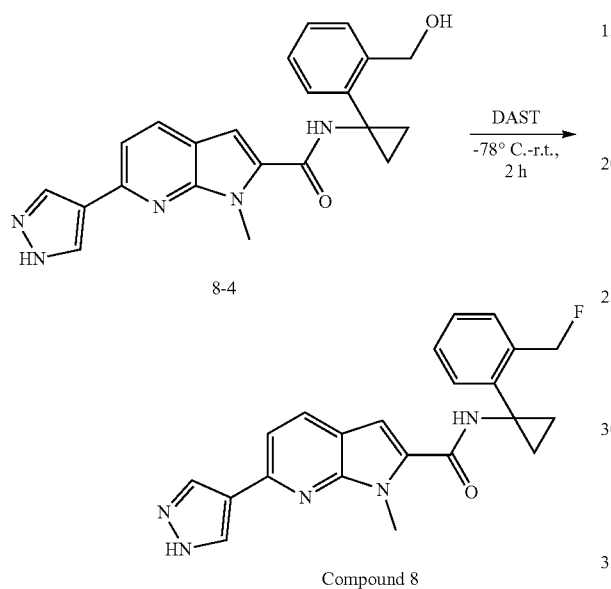

Compound 8

A solution of N-{1-[2-(hydroxymethyl)phenyl]cyclopropyl}-1-methyl-6-(1H-pyrazol-4-yl)pyrrolo[2,3-b]pyridine-2-carboxamide (8-4) (110 mg, 0.28 mmol, 1.0 equiv) and DAST (187 μL, 1.42 mmol, 5.0 equiv) in dichloromethane (5 mL) was stirred for 30 minutes at −78° C. under nitrogen atmosphere. The resulting mixture was stirred for an additional one hour at room temperature. The reaction was monitored by LCMS. After completion, the reaction was quenched by the addition of water (3 mL) at room temperature. The resulting mixture was extracted with ethyl acetate (2×20 mL). The combined organic layers were washed with saturated sodium chloride solution (2×20 mL), dried over anhydrous Na$_2$SO$_4$, and filtered. After filtration, the filtrate was concentrated under reduced pressure. The crude product was purified by Prep-HPLC with the following conditions (Column: Sunfire prep C18 column, 30*150 mm, 5 μm; Mobile Phase A: Water (0.1% FA), Mobile Phase B: Acetonitrile; Flow rate: 60 mL/min; Gradient: 30% B to 50% B in 10 min, 50% B; Wave Length: 254/220 nm; RT1 (min): 10.78; Number Of Runs: 0) to afford N-{1-[2-(fluoromethyl)phenyl]cyclopropyl}-1-methyl-6-(1H-pyrazol-4-yl)pyrrolo[2,3-b]pyridine-2-carboxamide (Compound 8) (1.7 mg, purity 98.6%, yield 1.52%) as a white solid. MS (ESI) m/z: 390.20 [M+H]$^+$. $^1$H NMR (400 MHz, MeOH-d$_4$) δ: 8.44 (s, 1H), 8.19 (s, 2H), 7.94 (d, J=8.0 Hz, 1H), 7.82-7.78 (m, 1H), 7.46-7.41 (m, 2H), 7.38-7.29 (m, 2H), 6.91 (s, 1H), 5.84 (d, J=47.6 Hz, 2H), 3.99 (s, 3H), 1.38-1.32 (m, 2H), 1.29-1.23 (m, 2H) ppm.

Example 9: Synthesis of N-{1-[3-(2-fluoropropan-2-yl)phenyl]cyclopropyl}-1-methyl-6-(1H-pyrazol-4-yl)pyrrolo[2,3-b]pyridine-2-carboxamide (Compound 9)

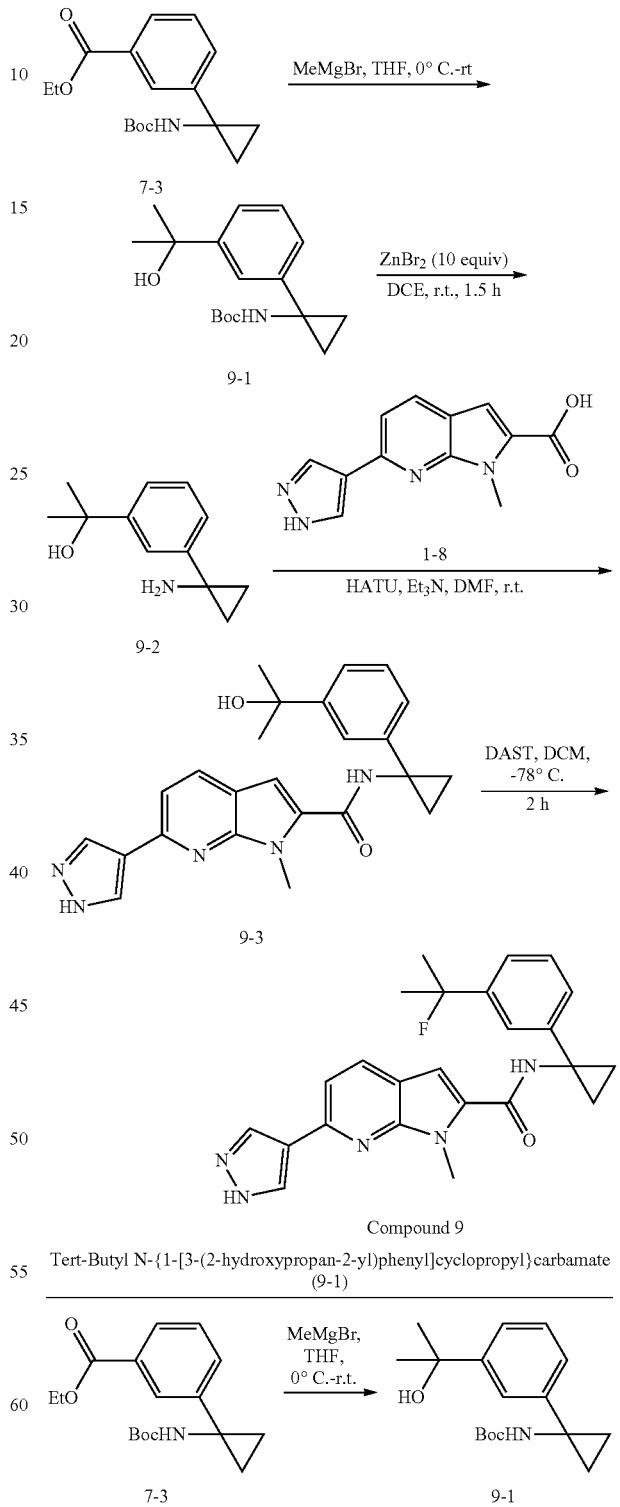

Compound 9

Tert-Butyl N-{1-[3-(2-hydroxypropan-2-yl)phenyl]cyclopropyl}carbamate (9-1)

A solution of ethyl 3-{1-[(tert-butoxycarbonyl)amino]cyclopropyl}benzoate (7-3) (2 g, 6.549 mmol, 1.0 equiv)

and MeMgBr (1.51 mL, 13.098 mmol, 2.0 equiv) in tetrahydrofuran (10 mL) was stirred for four hours at 0° C. under nitrogen atmosphere. Desired product could be detected by LCMS. After completion, the reaction was quenched by the addition 20 mL of saturated NH$_4$Cl (aq.) at 0° C. The resulting mixture was extracted with ethyl acetate (3×20 mL). The combined organic layers were washed with saturated sodium chloride solution (20 mL), dried over anhydrous Na$_2$SO$_4$, and filtered. After filtration, the filtrate was concentrated under reduced pressure. The residue was purified by reversed-phase flash chromatography with the following conditions: column, C18 silica gel; mobile phase, acetonitrile in water (10 mmol/L NH$_4$HCO$_3$), 10% to 60% gradient in 30 minutes; detector, UV 220 nm. This resulted in tert-butyl N-{1-[3-(2-hydroxypropan-2-yl)phenyl]cyclopropyl}carbamate (9-1) (1.6 g, 83.84%) as a white solid. MS (ESI) m/z: 292.2 [M+H]$^+$.

2-[3-(1-Aminocyclopropyl)phenyl]propan-2-ol (9-2)

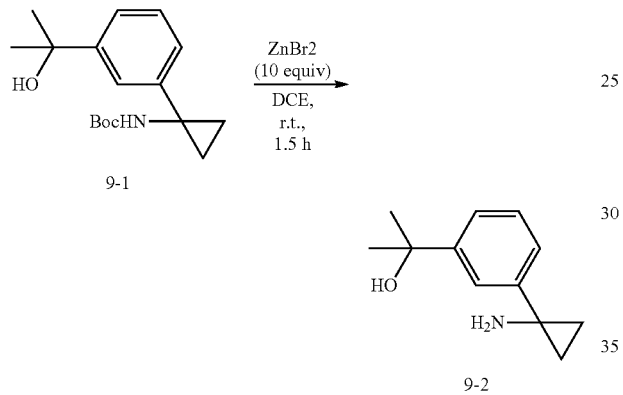

A solution of tert-butyl N-{1-[3-(2-hydroxypropan-2-yl)phenyl]cyclopropyl}carbamate (9-1) (1.5 g, 5.15 mmol, 1.0 equiv) and ZnBr$_2$ (11.60 g, 51.50 mmol, 10 equiv) in 1,2-dichloroethane (20 mL) was stirred for one and half hours at room temperature. The reaction was monitored by LCMS. The resulting mixture was concentrated under reduced pressure. The residue was purified by silica gel column chromatography, eluted with petroleum ether/ethyl acetate (1:1) to afford 2-[3-(1-aminocyclopropyl)phenyl]propan-2-ol (9-2) (330 mg, 33.52%) as a light grey solid. MS (ESI) m/z: 192.1 [M+H]$^+$.

N-{1-[3-(2-hydroxypropan-2-yl)phenyl]cyclopropyl}-1-methyl-6-(1H-pyrazol-4-yl)pyrrolo[2,3-b]pyridine-2-carboxamide (9-3)

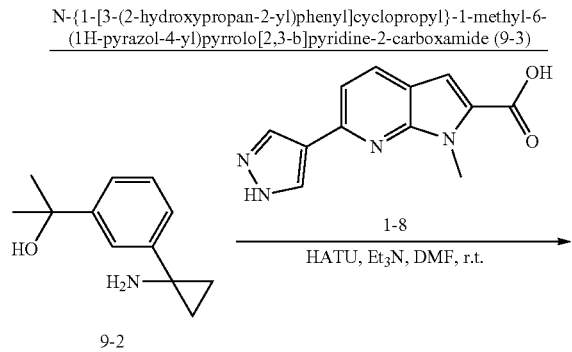

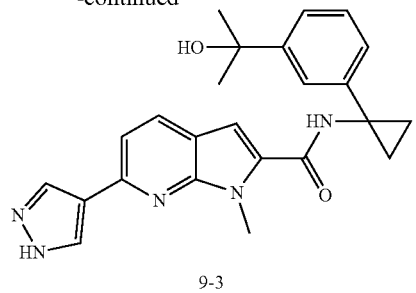

A solution of 1-methyl-6-(1H-pyrazol-4-yl)pyrrolo[2,3-b]pyridine-2-carboxylic acid (1-8) (300 mg, 1.24 mmol, 1.0 equiv) and 2-[3-(1-aminocyclopropyl)phenyl]propan-2-ol (9-2) (355 mg, 1.86 mmol, 1.5 equiv) in N,N-dimethylformamide (0.5 mL) was stirred for 3 minutes at 0° C. To the above mixture was added HATU (942 mg, 2.48 mmol, 2.0 equiv) in portions at 0° C. The resulting mixture was stirred for an additional one hour at room temperature. The reaction was monitored by LCMS. The residue was purified by reversed-phase flash chromatography with the following conditions: column, C18 silica gel; mobile phase, acetonitrile in water (10 mmol/L NH$_4$HCO$_3$), 20% to 70% gradient in 30 minutes; detector, UV 220 nm. This resulted in N-{1-[3-(2-hydroxypropan-2-yl)phenyl]cyclopropyl}-1-methyl-6-(1H-pyrazol-4-yl)pyrrolo[2,3-b]pyridine-2-carboxamide (9-3) (46 mg, 8.94%) as a light yellow solid. MS (ESI) m/z: 416.2 [M+H]$^+$.

N-{1-[3-(2-fluoropropan-2-yl)phenyl]cyclopropyl}-1-methyl-6-(1H-pyrazol-4-yl)pyrrolo[2,3-b]pyridine-2-carboxamide (Compound 9)

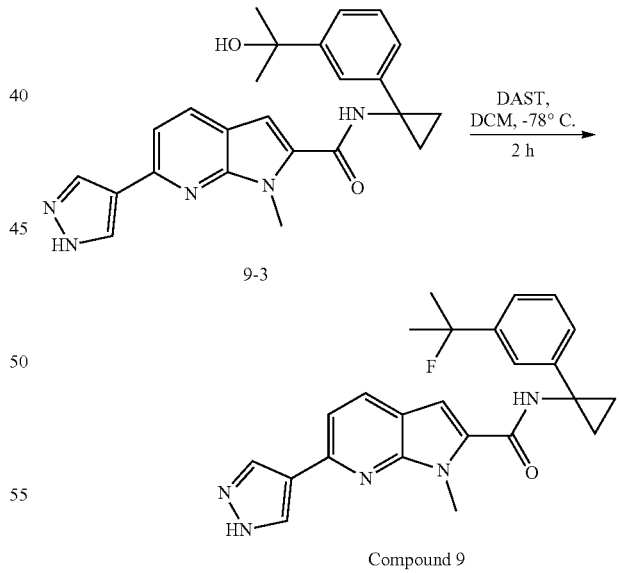

A solution of N-{1-[3-(2-hydroxypropan-2-yl)phenyl]cyclopropyl}-1-methyl-6-(1H-pyrazol-4-yl)pyrrolo [2,3-b]pyridine-2-carboxamide (9-3) (46 mg, 0.11 mmol, 1.0 equiv) and DAST (29 μL, 0.22 mmol, 2.0 equiv) in dichloromethane (0.5 mL) was stirred for 2 minutes at −78° C. under nitrogen atmosphere. The reaction was monitored by LCMS. The reaction was quenched by the addition of saturated NaHCO$_3$ (aq.) (1.0 mL) at 0° C. The resulting mixture was concentrated under reduced pressure. The crude product was purified by Prep-HPLC with the following conditions: Column: YMC-Actus Triart C18 ExRS, 30*150 mm, 5 μm; Mobile Phase A: Water (10 mmol/L NH$_4$HCO$_3$), Mobile Phase B: acetonitrile; Flow rate: 60 mL/min; Gradient: 36% B to 55% B in 9 minutes, 55% B; Wave Length: 254/220 nm; RT1 (min): 9.53; Number Of Runs: 0) to afford N-{1-[3-(2-fluoropropan-2-yl)phenyl]cyclopropyl}-1-methyl-6-(1H-pyrazol-4-yl)pyrrolo[2,3-b]pyridine-2-carboxamide (Compound 9) (23.2 mg, 46.73%) as a white solid. MS (ESI) m/z: 418.25 [M+H]$^+$. $^1$H NMR (400 MHz, MeOH-d$_4$) δ: 8.28-8.16 (m, 2H), 7.99 (d, J=8.4 Hz, 1H), 7.47 (d, J=8.0 Hz, 1H), 7.39 (s, 1H), 7.30-7.26 (m, 1H), 7.24-7.20 (m, 2H), 7.07 (s, 1H), 4.07 (s, 3H), 1.66 (s, 3H), 1.61 (s, 3H), 1.40-1.32 (m, 4H) ppm.

Example 10: Synthesis of N-{[2-(fluoromethyl)phenyl]methyl}-1-methyl-6-(1H-pyrazol-4-yl)pyrrolo[2,3-b]pyridine-2-carboxamide (Compound 10)

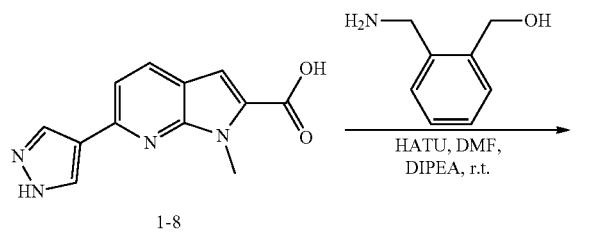

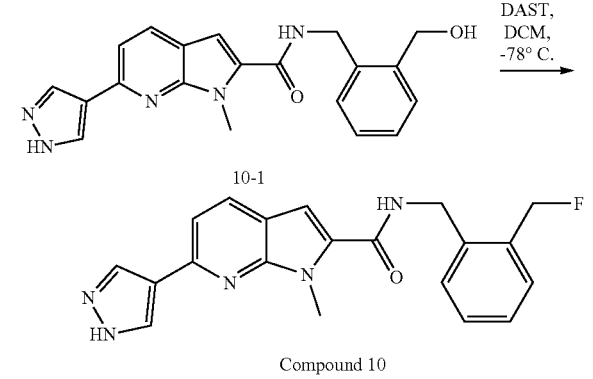

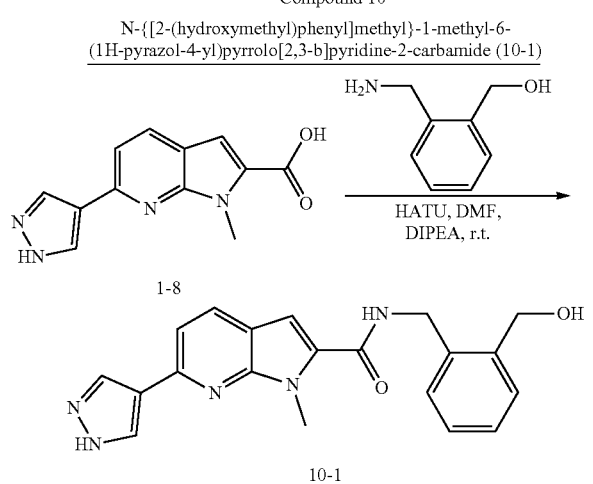

A solution of 1-methyl-6-(1H-pyrazol-4-yl)pyrrolo[2,3-b]pyridine-2-carboxylic acid (1-8) (150 mg, 0.619 mmol, 1.0 equiv), [2-(aminomethyl)phenyl]methanol (127 mg, 0.928 mmol, 1.5 equiv) in N,N-dimethylformamide (4 mL) was treated with DIPEA (400 mg, 3.095 mmol, 5.0 equiv) for 10 minutes at 0° C. under nitrogen atmosphere followed by the addition of HATU (471 mg, 1.238 mmol, 2.0 equiv) in portions at 0° C. The resulting mixture was stirred overnight at room temperature. The reaction was monitored by LCMS. After completion, the reaction was quenched with water (15 mL) at 0° C. The resulting mixture was extracted with ethyl acetate (3×20 mL). The combined organic layers were washed with saturated sodium chloride solution (20 mL) and dried over anhydrous Na$_2$SO$_4$ and filtered. After filtration, the filtrate was concentrated under reduced pressure. The residue was purified by reversed-phase flash chromatography with the following conditions: column, C18 silica gel; mobile phase, acetonitrile in water (0.1% TFA), 3% to 50% gradient in 30 minutes; detector, UV 254 nm, 220 nm. This resulted in N-{[2-(hydroxymethyl)phenyl]methyl}-1-methyl-6-(1H-pyrazol-4-yl)pyrrolo[2,3-b]pyridine-2-carboxamide (10-1) (110.0 mg, 49.1%) as a white solid. MS (ESI) m/z: 362.1 [M+H]$^+$.

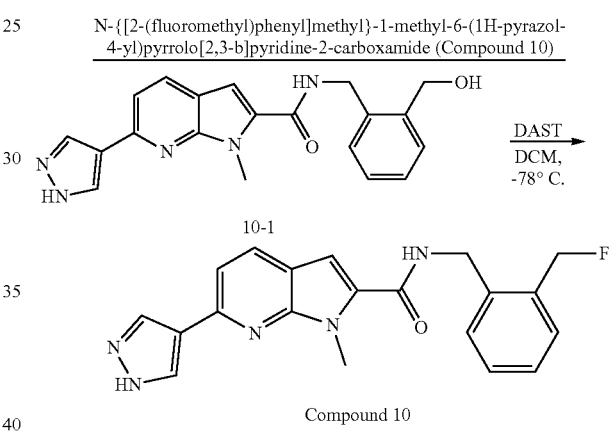

To a stirred solution of N-{[2-(hydroxymethyl)phenyl]methyl}-1-methyl-6-(1H-pyrazol-4-yl)pyrrolo[2,3-b]pyridine-2-carboxamide (10-1) (210 mg, 0.581 mmol, 1.0 equiv) in dichloromethane (14 mL) was added DAST (280.9 mg, 1.743 mmol, 3.0 equiv) dropwise at −78° C. under nitrogen atmosphere. The resulting mixture was stirred overnight at room temperature under nitrogen atmosphere. The reaction was monitored by LCMS. After completion, the reaction was quenched with NaHCO$_3$ (aq. sat.) at room temperature. The precipitated solids were collected by filtration and washed with H$_2$O (2×30 mL). The crude product was purified by Prep-HPLC with the following conditions (Column: XBridge Shield RP18 OBD Column, 30*150 mm, 5 μm; Mobile Phase A: Water (10 mmol/L NH$_4$HCO$_3$), Mobile Phase B: Acetonitrile; Flow rate: 50 mL/min; Gradient: 4% B to 15% B in 8 minutes, 15% B; Wave Length: 254/220 nm; RT1 (min): 7.17; Number Of Runs: 0) to afford N-{[2-(fluoromethyl)phenyl]methyl}-1-methyl-6-(1H-pyrazol-4-yl)pyrrolo[2,3-b]pyridine-2-carboxamide (Compound 10) (40.7 mg, 18.5%) as a white solid. MS (ESI) m/z: 364.00 [M+H]$^+$. $^1$H NMR (400 MHz, DMSO-d$_6$) δ: 13.04 (s, 1H), 9.07 (t, J=6.0 Hz, 1H), 8.37 (s, 1H), 8.14 (s, 1H), 8.05 (d, J=8.4 Hz, 1H), 7.52 (d, J=8.0 Hz, 1H), 7.47-7.37 (m, 3H), 7.36-7.28 (m, 1H), 7.16 (s, 1H), 5.64 (d, J=47.6 Hz, 2H), 4.57 (d, J=5.6 Hz, 2H), 4.05 (s, 3H) ppm.

Example 11: Synthesis of N-[(2-Fluorophenyl)methyl]-6-[3-(trifluoromethyl)-2H-pyrazol-4-yl]-1H-pyrrolo[2,3-b]pyridine-2-carboxamide (Compound 11)

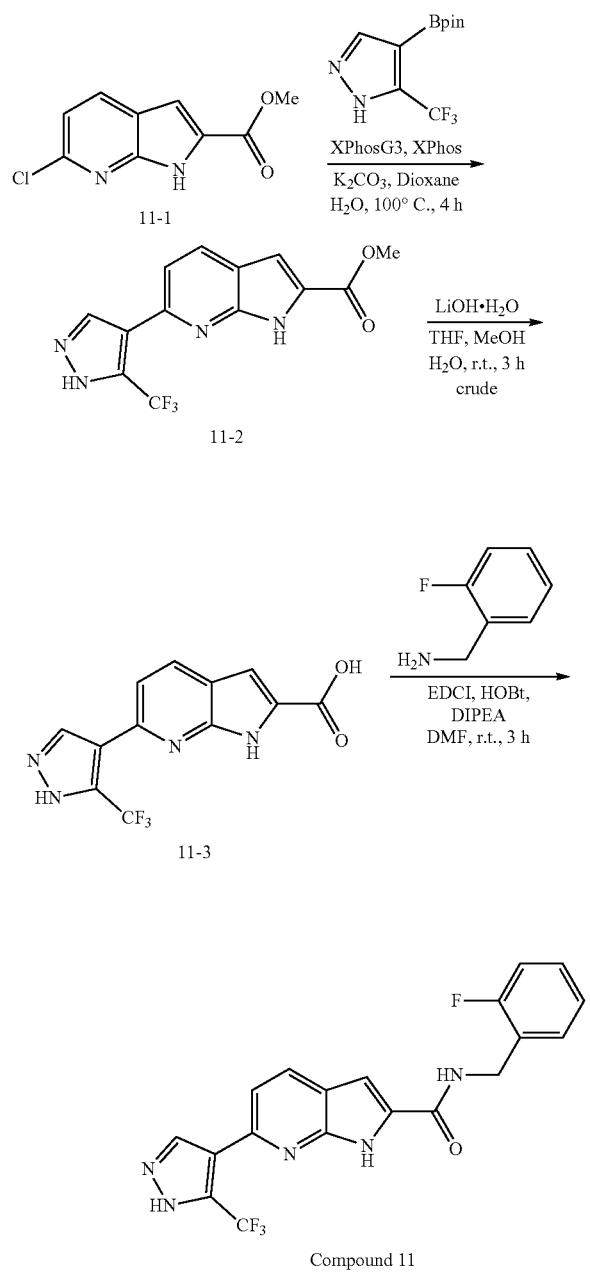

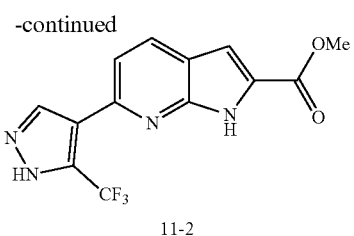

A solution of methyl 6-chloro-1H-pyrrolo[2,3-b]pyridine-2-carboxylate (11-1) (1.2 g, 5.697 mmol, 1.0 equiv), 4-(4,4,5,5-tetramethyl-1,3,2-dioxaborolan-2-yl)-3-(trifluoromethyl)-2H-pyrazole (2.24 g, 8.546 mmol, 1.5 equiv), $K_2CO_3$ (1.57 g, 11.394 mmol, 2.0 equiv), XPhos Pd G3 (482.2 mg, 0.570 mmol, 0.1 equiv) and XPhos (271.6 mg, 0.570 mmol, 0.1 equiv) in dioxane (75 mL) and $H_2O$ (15 mL) was stirred for four hours at 100° C. under nitrogen atmosphere. The reaction was monitored by LCMS. The resulting mixture was diluted with water (150 mL) and extracted with ethyl acetate (3×150 mL). The combined organic layers were washed with saturated sodium chloride solution (2×100 mL), dried over anhydrous $Na_2SO_4$, and filtered. After filtration, the filtrate was concentrated under reduced pressure. The residue was purified by silica gel column chromatography, eluted with dichloromethane/methanol (5:1) to afford methyl 6-[3-(trifluoromethyl)-2H-pyrazol-4-yl]-1H-pyrrolo[2,3-b]pyridine-2-carboxylate (11-2) (1.1 g, 62.2%) as a yellow solid. MS (ESI) m/z: 311.1 [M+H]$^+$.

6-[3-(Trifluoromethyl)-2H-pyrazol-4-yl]-1H-pyrrolo[2,3-b]pyridine-2-carboxylic acid (11-3)

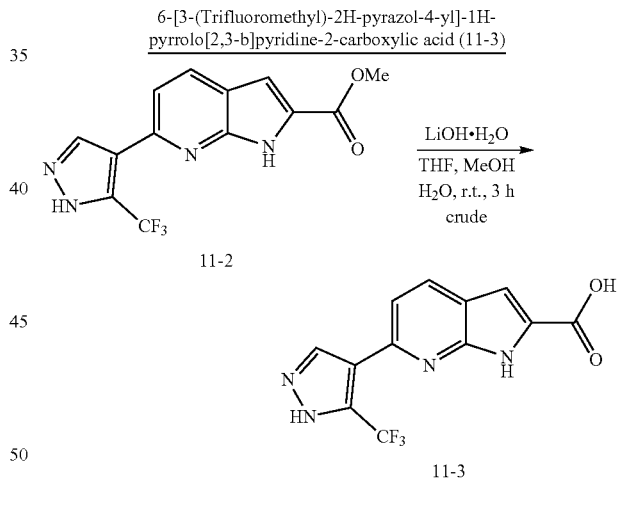

A solution of methyl 6-[3-(trifluoromethyl)-2H-pyrazol-4-yl]-1H-pyrrolo[2,3-b]pyridine-2-carboxylate (11-2) (1.2 g, 3.548 mmol, 1.0 equiv) and LiOH·$H_2O$ (811.5 mg, 19.340 mmol, 5.0 equiv) in tetrahydrofuran (27 mL), methanol (9 mL), and $H_2O$ (9 mL) was stirred for three hours at room temperature. The reaction was monitored by LCMS. The resulting mixture was concentrated under reduced pressure. The resulting mixture was diluted with water (30 mL) and acidified to pH 5 with HCl (aq.). The precipitated solids were collected by filtration and washed with diethyl ether (3×50 mL). This resulted in 6-[3-(trifluoromethyl)-2H-pyrazol-4-yl]-1H-pyrrolo[2,3-b]pyridine-2-carboxylic acid (11-3) (720.0 mg, crude) as a white solid. MS (ESI) m/z: 297.2 [M+H]$^+$ N-[(2-Fluorophenyl)methyl]-6-[3-(trifluoromethyl)-2H-pyrazol-4-yl]-1H-pyrrolo[2,3-b]pyridine-2-carboxamide (Compound 11)

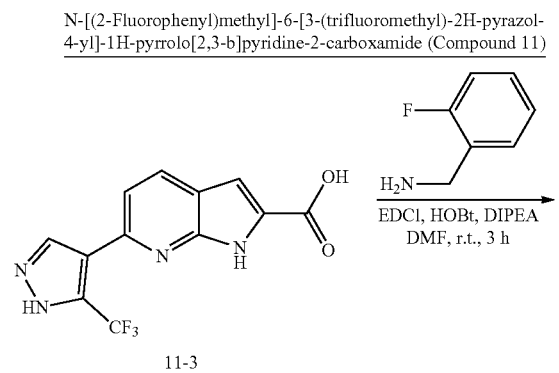

11-3

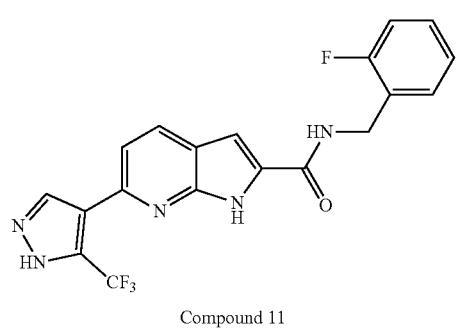

Compound 11

A solution of 6-[3-(trifluoromethyl)-2H-pyrazol-4-yl]-1H-pyrrolo[2,3-b]pyridine-2-carboxylic acid (11-3) (300 mg, 1.013 mmol, 1.0 equiv), HOBt (205.2 mg, 1.519 mmol, 1.5 equiv), DIEA (529.2 µL, 3.039 mmol, 3.0 equiv) and 1-(2-fluorophenyl)methanamine (190.1 mg, 1.519 mmol, 1.5 equiv) in N,N-dimethylformamide (10 mL) was stirred for three hours at room temperature. The reaction was monitored by LCMS. The resulting mixture was diluted with water (60 mL) and extracted with ethyl acetate (3×100 mL). The combined organic layers were washed with saturated sodium chloride solution (2×100 mL), dried over anhydrous Na$_2$SO$_4$ and filtered. After filtration, the filtrate was concentrated under reduced pressure. The crude product (300 mg) was purified by Prep-HPLC with the following conditions (Column: Sunfire prep C18 column, 30*150 mm, 5 µm; Mobile Phase A: Water (0.1% FA), Mobile Phase B: Acetonitrile; Flow rate: 60 mL/min; Gradient: 30% B to 48% B in 10 min; Wave Length: 254 nm/220 nm; RT1(min): 11.73) to afford N-[(2-fluorophenyl)methyl]-6-[3-(trifluoromethyl)-2H-pyrazol-4-yl]-1H-pyrrolo[2,3-b]pyridine-2-carboxamide (Compound 11) (58.0 mg, 14.0%) as a white solid. MS (ESI) m/z: 403.95 [M+H]$^+$. $^1$H NMR (300 MHz, DMSO-d$_6$) δ 13.77 (s, 1H), 12.03 (s, 1H), 8.99 (t, J=5.8 Hz, 1H), 8.49-8.34 (m, 1H), 8.12 (d, J=8.3 Hz, 1H), 7.51-7.28 (m, 3H), 7.28-7.10 (m, 3H), 4.57 (d, J=5.7 Hz, 2H) ppm. $^{19}$F NMR (282 MHz, DMSO-d$_6$) d −58.32 (s), −118.83 (s) ppm.

Example 12: Synthesis of N-{[2-(difluoromethyl)phenyl]methyl}-1-methyl-6-1H-pyrazol-4-yl)pyrrolo[2,3-b]pyridine-2-carboxamide (Compound 12)

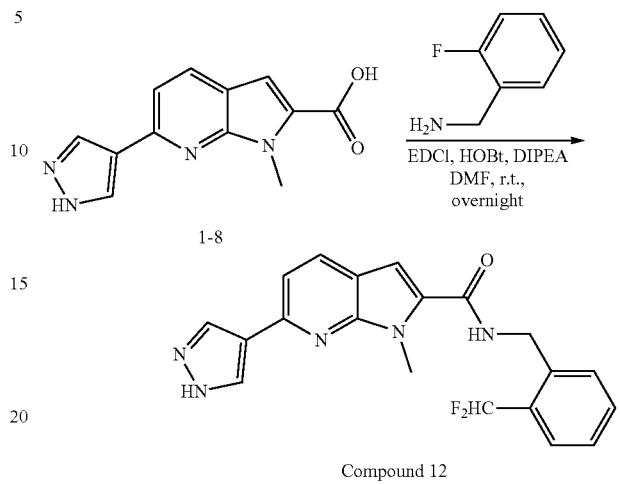

1-8

Compound 12

A solution of 1-methyl-6-(1H-pyrazol-4-yl)pyrrolo[2,3-b]pyridine-2-carboxylic acid (1-8) (325.0 mg, 1.342 mmol, 1.0 equiv), 1-[2-(difluoromethyl)phenyl]methanamine (253.03 mg, 1.610 mmol, 1.2 equiv), EDCI (385.79 mg, 2.013 mmol, 1.5 equiv), HOBt (271.94 mg, 2.013 mmol, 1.5 equiv) and DIPEA (701.10 µL, 4.026 mmol, 3.0 equiv) in N,N-dimethylformamide (10 mL) was stirred for three hours at room temperature. The reaction was monitored by LCMS. The resulting mixture was diluted with water (70 mL) and extracted with ethyl acetate (3×100 mL). The combined organic layers were washed with saturated sodium chloride solution (2×100 mL), dried over anhydrous Na$_2$SO$_4$, and filtered. After filtration, the filtrate was concentrated under reduced pressure. The crude product (300.0 mg) was purified by Prep-HPLC with the following conditions (Column: Sunfire prep C18 column, 30*150 mm, 5 µm; Mobile Phase A: Water (0.05% TFA), Mobile Phase B: Acetonitrile; Flow rate: 60 mL/minute; Gradient: isocratic 28% B to 48% B in 10 minutes; Wave Length: 254 nm/220 nm; RT1(min): 11.4) to afford N-{[2-(difluoromethyl)phenyl]methyl}-1-methyl-6-(1H-pyrazol-4-yl)pyrrolo[2,3-b]pyridine-2-carboxamide (Compound 12) (59.7 mg, 11.4%) as a white solid. MS (ESI) m/z: 382.05 [M+H]$^+$. $^1$H NMR (400 MHz, DMSO-d$_6$) δ 9.13 (t, J=6.0 Hz, 1H), 8.27 (s, 2H), 8.06 (d, J=8.2 Hz, 1H), 7.61 (d, J=7.7 Hz, 1H), 7.58-7.48 (m, 3H), 7.47-7.40 (m, 1H), 7.37 (t, J=54.8 Hz, 1H), 7.18 (s, 1H), 4.65 (d, J=5.9 Hz, 2H), 4.06 (s, 3H) ppm. $^{19}$F NMR (376 MHz, DMSO-d$_6$) δ −74.88 (s), −111.20 (s) ppm.

Example 13: Synthesis of 1-Methyl-6-(1H-pyrazol-4-yl)-N-{[3-(trifluoromethyl)phenyl]methyl}pyrrolo[2,3-b]pyridine-2-carboxamide (Compound 13)

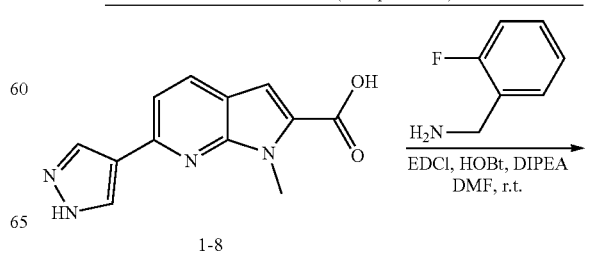

1-8

-continued

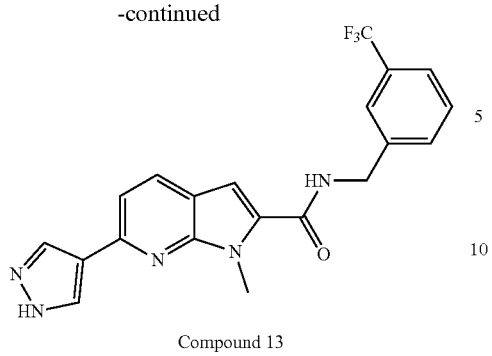

Compound 13

A solution of 1-methyl-6-(1H-pyrazol-4-yl)pyrrolo[2,3-b]pyridine-2-carboxylic acid (400 mg, 1.651 mmol, 1.0 equiv), EDCI (475 mg, 2.477 mmol, 1.5 equiv), HOBt (335 mg, 2.477 mmol, 1.5 equiv) in N,N-dimethylformamide (16 mL) was treated with DIPEA (320 mg, 2.477 mmol, 1.5 equiv) for 3 minutes at room temperature under nitrogen atmosphere followed by the addition of 1-[3-(trifluoromethyl)phenyl]methanamine (434 mg, 2.477 mmol, 1.5 equiv) dropwise at room temperature. The resulting mixture was stirred for two hours at room temperature under nitrogen atmosphere. The reaction was monitored by LCMS. The resulting mixture was diluted with water (40 mL) and extracted with ethyl acetate (3×50 mL). The combined organic layers were washed with saturated sodium chloride solution (3×20 mL), dried over anhydrous $Na_2SO_4$, and filtered. After filtration, the filtrate was concentrated under reduced pressure. The crude product (250 mg) was purified by Prep-HPLC with the following conditions (Column: XBridge Prep OBD C18 Column 30*150 mm, 5 µm; Mobile Phase A: Water (10 mmol/L $NH_4HCO_3$+0.1% $NH_3 \cdot H_2O$), Mobile Phase B: Acetonitrile; Flow rate: 60 mL/minute; Gradient: 32% B to 50% B in 10 minutes; Wave Length: 254 nm/220 nm; RT1 (min): 1) to afford 1-methyl-6-(1H-pyrazol-4-yl)-N-{[3-(trifluoromethyl)phenyl]methyl}pyrrolo[2,3-b]pyridine-2-carboxamide (Compound 13) (63.4 mg, 9.49%) as a white solid, MS (ESI) m/z: 400.20 [M+H]+. $^1$H NMR (300 MHz, DMSO-$d_6$) δ 13.06 (s, 1H), 9.20 (t, J=6.1 Hz, 1H), 8.39 (s, 1H), 8.14 (s, 1H), 8.06 (d, J=8.2 Hz, 1H), 7.73-7.56 (m, 4H), 7.53 (d, J=8.2 Hz, 1H), 7.16 (s, 1H), 4.58 (d, J=6.0 Hz, 2H), 4.06 (s, 3H) ppm. $^{19}$F NMR (282 MHZ, DMSO-$d_6$) δ −61.03 (s) ppm.

Example 14: Synthesis of 1-Methyl-6-(1H-pyrazol-4-yl)-N-{[2-(trifluoromethyl)phenyl]methyl}pyrrolo[2,3-b]pyridine-2-carboxamide (Compound 14)

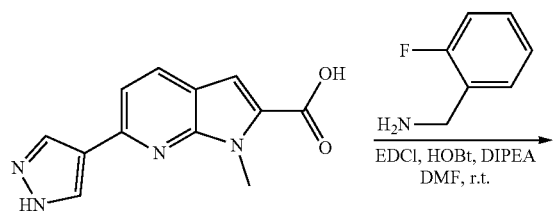

-continued

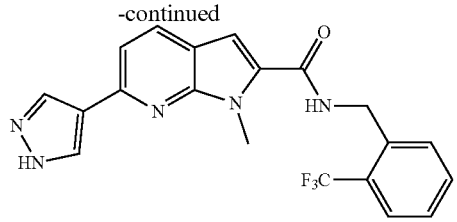

Compound 14

A solution of 1-methyl-6-(1H-pyrazol-4-yl)pyrrolo[2,3-b]pyridine-2-carboxylic acid (1-8) (414 mg, 1.71 mmol, 1.0 equiv), HATU (651 mg, 1.71 mmol, 1.0 equiv) and DIPEA (897 µL, 5.14 mmol, 3.0 equiv) in N,N-dimethylformamide (5 mL) was stirred for 10 minutes at room temperature followed by the addition of 1-[2-(trifluoromethyl)phenyl]methanamine (300 mg, 1.71 mmol, 1.0 equiv) at room temperature. The resulting mixture was stirred for an additional two hours at room temperature. The reaction was monitored by LCMS. The resulting mixture was extracted with ethyl acetate (2×50 mL). The combined organic layers were washed with water (2×50 mL), dried over anhydrous $Na_2SO_4$, and filtered. After filtration, the filtrate was concentrated under reduced pressure. The crude product was purified by Prep-HPLC with the following conditions (Column: XBridge Prep OBD C18 Column 30*150 mm, 5 µm; Mobile Phase A: Water (10 mmol/L $NH_4HCO_3$+0.1% $NH_3 \cdot H_2O$), Mobile Phase B: Acetonitrile; Flow rate: 60 mL/minute; Gradient: 23% B to 36% B in 10 minutes; Wave Length: 254 nm/220 nm; $RT_1$(min): 3) to afford 1-methyl-6-(1H-pyrazol-4-yl)-N-{[2-(trifluoromethyl)phenyl]methyl}pyrrolo[2,3-b]pyridine-2-carboxamide (59.2 mg, 8.60%) (Compound 14) as a white solid. MS (ESI) m/z: 400.20 [M+H]+. $^1$H NMR (400 MHz, Methanol-$d_4$) δ: 8.33-8.11 (m, 2H), 8.00 (d, J=10.8 Hz, 1H), 7.80-7.70 (m, 1H), 7.69-7.59 (m, 2H), 7.52-7.42 (m, 2H), 7.09 (s, 1H), 4.80 (s, 2H), 4.12 (s, 3H) ppm. $^{19}$F NMR (376 MHz, Methanol-$d_4$) δ −61.57 (s) ppm.

Example 15: Synthesis of N-(2,6-dimethoxybenzyl)-6-(5-methyl-1H-pyrazol-4-yl)-1H-pyrrolo[2,3-b]pyridine-2-carboxamide (Comparator 1, see generally WO 2011/050245

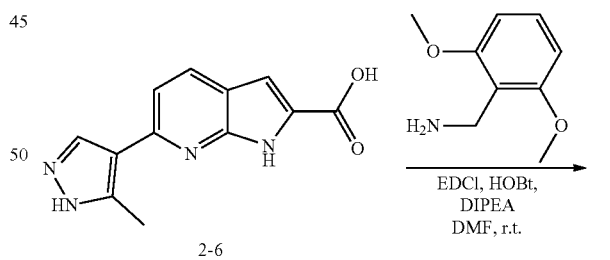

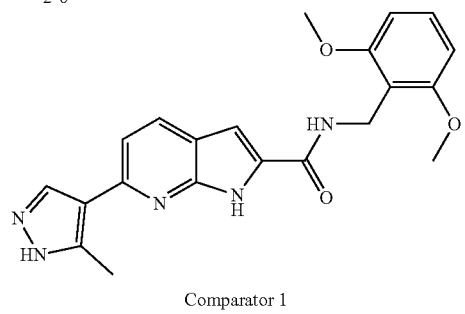

Comparator 1

To a stirred solution of 2-6 (70.0 mg, 0.000298 mol) in N,N-dimethylformamide (4 mL) was added (2,6-dimethoxyphenyl)methanamine (48.3 mg, 0.289 mmol), N-(3-(dimethylamino)propyl) propionamide dihydrochloride (83.1 mg, 0.433 mmol), 1-hydroxybenzotriazole (58.6 mg, 0.433 mmol) and N,N-diisopropylethylamine (112 mg, 0.867 mmol). The reaction mixture was stirred at room temperature for 16 hours. The reaction mixture was then partitioned between water (10.0 mL) and dichloromethane (10.0 mL three times). The organic phase was washed with saturated sodium chloride solution (10.0 mL), dried over anhydrous sodium sulfate, filtered, and concentrated. The crude residue was purified by prep-HPLC to give N-(2,6-dimethoxybenzyl)-6-(5-methyl-1H-pyrazol-4-yl)-1H-pyrrolo[2,3-b]pyridine-2-carboxamide (Comparator 1) (30.0 mg, 26%) as a white solid. LCMS: LC retention time 1.55 min. MS (ESI) m/z: 391.9 [M+H]$^+$, purity: 98.85% at 214 nm. $^1$H NMR (500 MHz, DMSO) δ 12.63 (s, 1H), 11.08 (s, 1H), 8.02-8.00 (m, 1H), 7.97 (d, J=8.5 Hz, 1H), 7.38 (d, J=9 Hz, 1H), 7.32-7.28 (m, 1H), 7.06 (s, 1H), 6.72 (d, J=8 Hz, 2H), 4.48 (s, 2H), 3.83 (s, 6H), 2.88 (s, 3H) ppm.

1H), 8.39 (t, J=5.0 Hz, 1H), 8.16-7.89 (m, 2H), 7.45-7.23 (m, 2H), 7.08 (d, J=2.0 Hz, 1H), 6.91 (d, J=8.5 Hz, 1H), 6.84 (t, J=8.5 Hz, 1H), 4.51 (d, J=5.0 Hz, 2H), 3.86 (s, 3H), 2.59 (s, 3H).

Example 17: Synthesis of N-(2-chloro-6-(oxetan-3-yloxy)benzyl)-6-(5-methyl-1H-pyrazol-4-yl)-1H-pyrrolo[2,3-b]pyridine-2-carboxamide (Comparator 3, see generally WO 2011/050245)

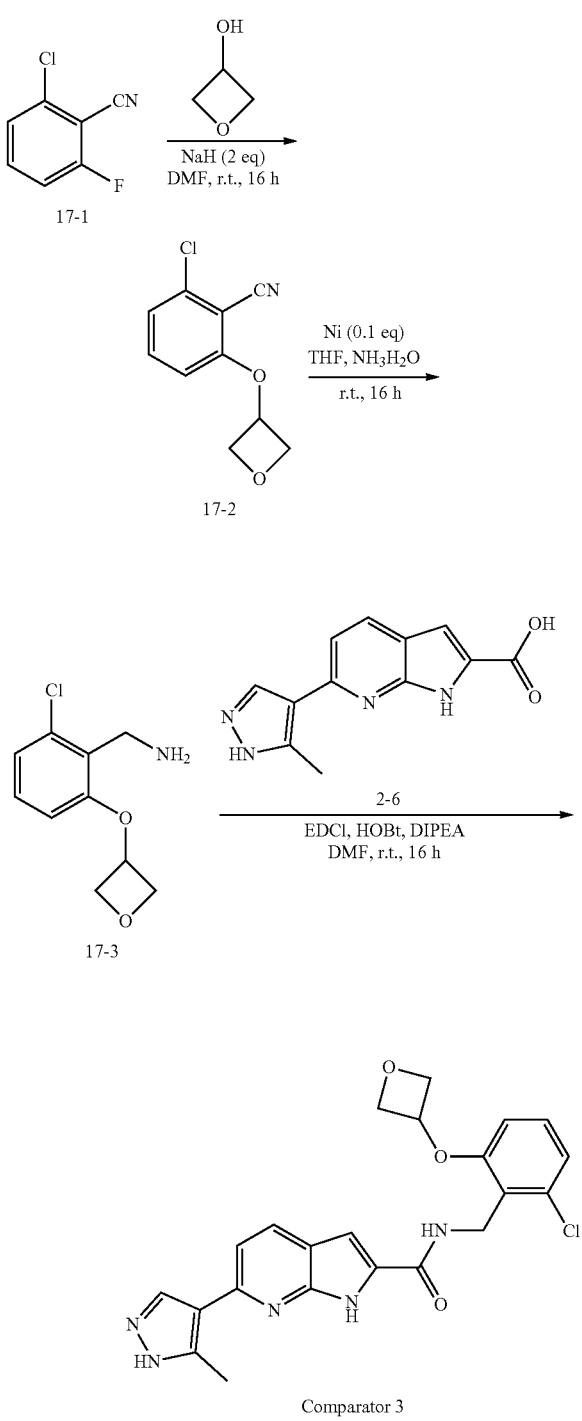

Comparator 3

Example 16: Synthesis of N-(2,fluoro-6-methoxybenzyl)-6-(5-methyl-1H-pyrazol-4-yl)-1H-pyrrolo[2,3-b]pyridine-2-carboxamide (Comparator 2, see generally WO 2011/050245

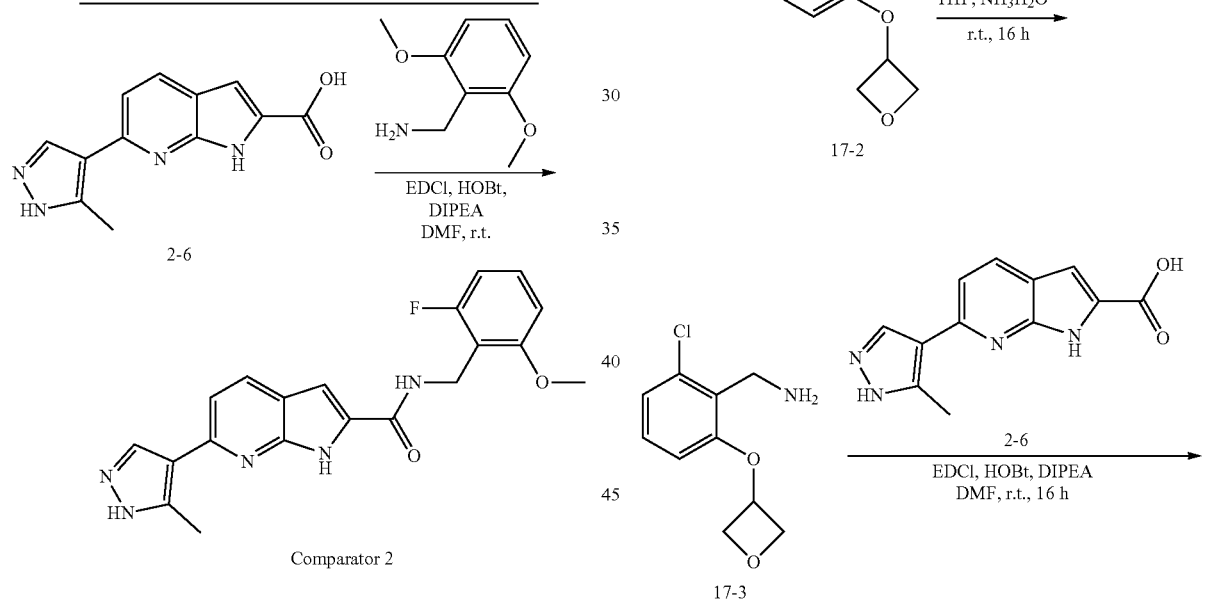

Comparator 2

To a solution of 2-6 (70.0 mg, 0.289 mmol) in N,N-dimethylformamide (3.00 mL), (2-fluoro-6-methoxyphenyl)methanamine (53.8 mg, 0.347 mmol), N-(3-(dimethylamino)propyl) propionamide dihydrochloride (83.2 mg, 0.434 mmol), 1-hydroxybenzotriazole (58.6 mg, 0.434 mmol) and N,N-diisopropylethylamine (187 mg, 1.45 mmol) was added. The reaction mixture was stirred at 25° C. for 18 hours. Then water (6 mL) was added to the reaction mixture. And the reaction mixture was extracted with ethyl acetate (30 mL×3), the organic phase was combined and washed with saturated sodium chloride solution (10 mL), then dried with sodium sulfate, and filtered. The filtrate was concentrated. The residue was purified with prep-HPLC to give N-(2-fluoro-6-methoxybenzyl)-6-(5-methyl-1H-pyrazol-4-yl)-1H-pyrrolo[2,3-b]pyridine-2-carboxamide (Comparator 2) (28.8 mg, 26.4%) as a white solid. LCMS: ESI (M+H)$^+$ 379.9, retention time 1.56 min, purity 98.7% at 254 nm. $^1$H NMR (500 MHz, DMSO) δ 12.68 (s, 1H), 11.81 (s,

2-Chloro-6-(oxetan-3-yloxy)benzonitrile (17-2)

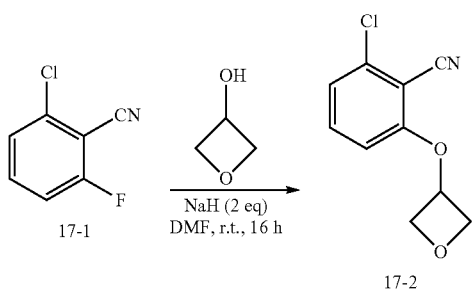

N-(2-chloro-6-(oxetan-3-yloxy)benzyl)-6-(5-methyl-1H-pyrazol-4-yl)-1H-pyrrolo[2,3-b]pyridine-2-carboxamide (Comparator 3)

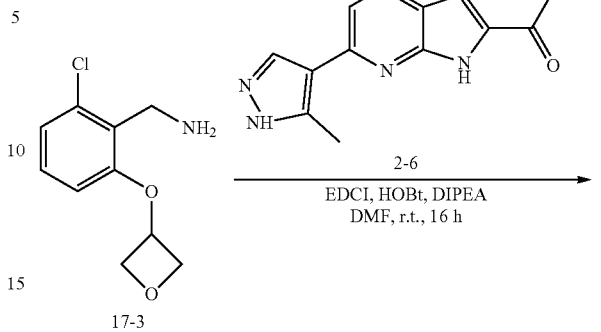

To a solution of oxetan-3-ol (1.05 g, 0.0142 mol) in N,N-dimethylformamide (10 mL) was added NaH (0.62 g, 0.0258 mol). The reaction mixture was stirred at room temperature for 1 hour. Then 2-chloro-6-fluorobenzonitrile (17-1) (2 g, 0.0129 mol) was added to the reaction. The reaction mixture was stirred at room temperature for 16 hours. Then the reaction mixture was extracted with dichloromethane (50 mL×3) and washed with water (50 mL), the organic layers were concentrated and purified by flash column chromatography (ethyl acetate in petroleum ether 0-10%) to afford 2-chloro-6-(oxetan-3-yloxy) benzonitrile (17-2) (1.2 g, 44%). LCMS: LC retention time 1.58 min. MS (ESI) m/z 209.9 [M+H]+.

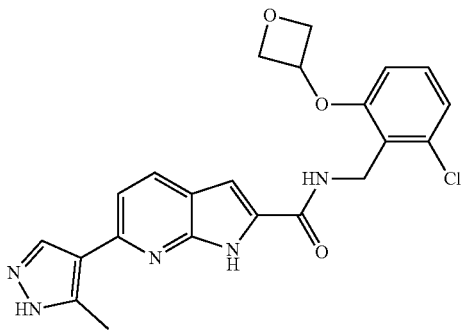

(2-Chloro-6-(oxetan-3-yloxy)phenyl)methanamine (17-3)

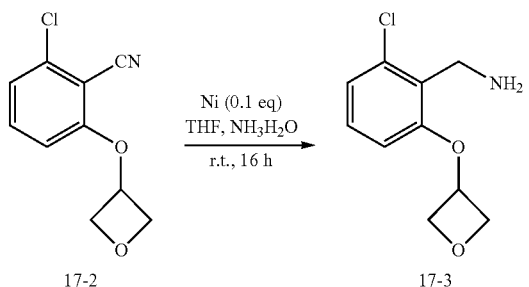

The reaction mixture of 2-chloro-6-(oxetan-3-yloxy)benzonitrile (17-2) (1.2 g, 5.7 mmol), NH$_3$·H$_2$O (2 mL) and Raney Ni (0.03 g, 0.57 mmol) in tetrahydrofuran (50 mL) was stirred at room temperature for 16 hours under H$_2$. The reaction mixture was filtered and concentrated in vacuo, then purified by flash column chromatography (ethyl acetate in petroleum ether 0-60%) to afford (2-chloro-6-(oxetan-3-yloxy)phenyl)methanamine (17-3) (0.28 g, 23%). LCMS: LC retention time 1.33 min. MS (ESI) m/z: 213.9 [M+H]+. $^1$H NMR (500 MHz, DMSO-d$_6$) δ 7.19-7.16 (m, 1H), 7.05 (d, J=8 Hz, 1H), 6.59 (d, J=8 Hz, 1H), 5.33-5.29 (m, 1H), 4.94-4.91 (m, 2H), 4.59-4.57 (m, 2H), 3.83 (s, 2H) ppm.

To a solution of (2-chloro-6-(oxetan-3-yloxy)phenyl)methanamine (17-3) (0.07 g, 0.33 mmol) in N,N-dimethylformamide (2 mL) was added 2-6 (0.07 g, 0.29 mmol), 1-hydroxybenzotriazole (0.058 g, 0.435 mmol), 1-ethyl-3-(3-dimethylaminopropyl)carbodiimide hydrochloride (67 mg, 0.435 mmol) and N,N-diisopropylethylamine (0.012 g, 0.87 mmol). The reaction mixture was stirred at room temperature for 16 hours. The reaction was extracted with dichloromethane (20 mL×3) and washed with water (20 mL). The organic layers were combined, concentrated and then purified by prep-HPLC to afford N-(2-chloro-6-(oxetan-3-yloxy)benzyl)-6-(5-methyl-1H-pyrazol-4-yl)-1H-pyrrolo[2,3-b]pyridine-2-carboxamide (Comparator 3) (0.0258 g, 18%) as a white solid. LCMS: LC retention time 1.54 min. MS (ESI) m/z: 437.8 [M+H]+, purity:100% (254 nm) $^1$H NMR (400 MHz, DMSO) δ 11.83 (s, 1H), 8.35 (s, 1H), 7.99 (s, 1H), 7.97 (d, J=6 Hz, 1H), 7.39 (d, J=8 Hz, 1H), 7.30-7.28 (m, 1H), 7.14 (d, J=8.4 Hz, 1H), 7.09 (s, 1H), 6.68 (d, J=8 Hz, 1H), 5.36-5.34 (m, 1H), 4.90-4.88 (m 2H), 4.69 (s, 2H), 4.60-4.57 (m, 2H), 2.58 (s, 3H).

Example 18: Synthesis of 6-(5-Methyl-1H-pyrazol-4-yl)-N-(2-(oxetan-3-yloxy)benzyl)-1H-pyrrolo[2,3-b]pyridine-2-carboxamide (Comparator 4, see generally WO 2011/050245)

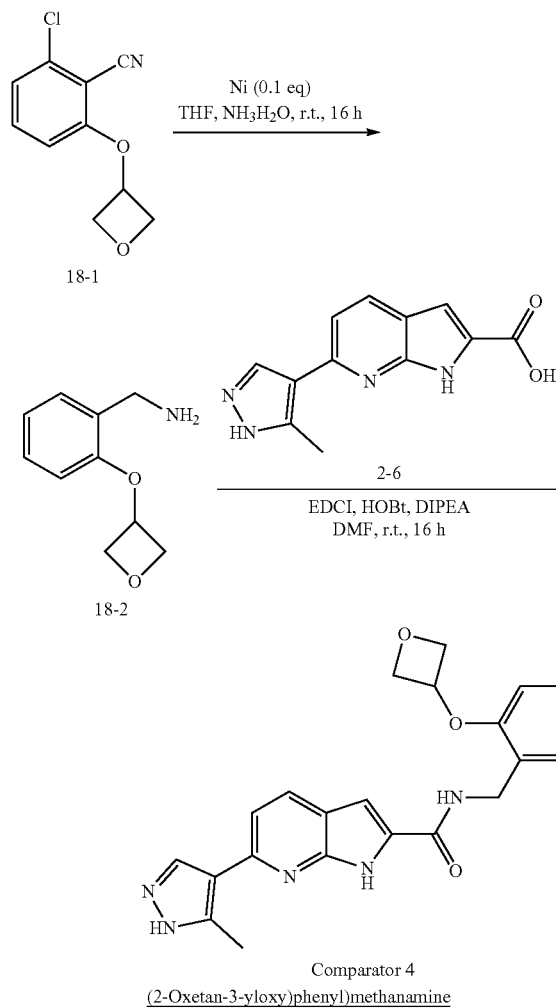

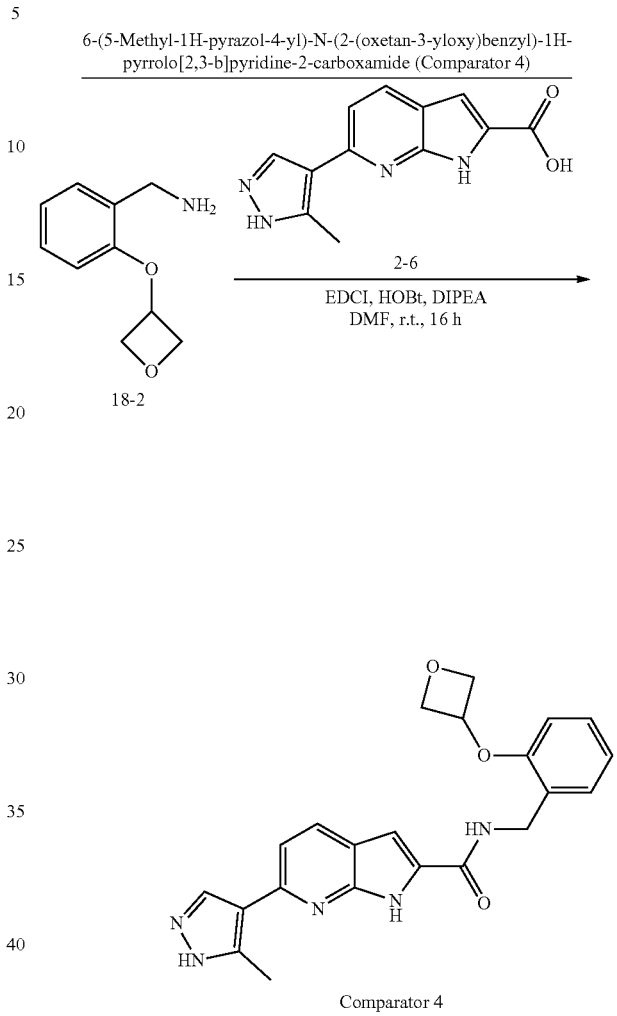

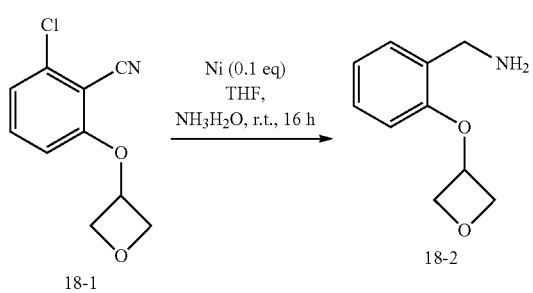

The reaction mixture of 2-chloro-6-(oxetan-3-yloxy)benzonitrile (18-1) (1.2 g, 5.7 mmol), NH$_3$·H$_2$O (2 mL) and Raney Ni (0.03 g, 0.57 mmol) in tetrahydrofuran (50 mL) was stirred at room temperature for 16 hours under H$_2$. The reaction mixture was filtered and concentrated in vacuo, then purified by flash chromatography (ethyl acetate in petroleum ether 0-60%) to afford (2-(oxetan-3-yloxy)phenyl)methanamine (18-2) (0.18 g, 15%). LCMS:LC retention time 0.55 min. MS (ESI) m/z: 180.1 [M+H]$^+$, purity: 100% (254 nm) $^1$H NMR (500 MHz, DMSO-d$_6$) δ 7.37 (d, J=6.5 Hz, 1H), 7.14 (m, 1H), 6.94 (m, 1H), 6.54 (d, J=8 Hz, 1H), 5.28-5.26 (m, 1H), 4.94-4.91 (m, 2H), 4.57-4.54 (m, 2H), 3.72 (s, 2H).

To a solution of 2-(oxetan-3-yloxy)phenyl)methanamine (18-2) (0.06 g, 0.33 mmol) in N,N-dimethylformamide (2 mL) was added 6-(5.-methyl-1H-pyrazol-4-yl)-1H-pyrrolo[2,3-b]pyridine-2-carboxylic acid (2-6) (0.07 g, 0.29 mmol), 1-hydroxybenzotriazole (0.058 g, 0.435 mmol), 1-ethyl-3-(3-dimethylaminopropyl)carbodiimide hydrochloride (0.067 g, 0.435 mmol) and N,N-diisopropyl ethylamine (0.012 g, 0.87 mmol). The reaction mixture was stirred at room temperature for 16 hours. The reaction was extracted with dichloromethane (20 mL×3) and washed with water (20 mL), concentrated and purified by prep-HPLC to afford 6-(5-methyl-1H-pyrazol-4-yl)-N-(2-(oxetan-3-yloxy)benzyl)-1H-pyrrolo[2,3-b]pyridine-2-carboxamide (Comparator 4) (38.7 mg, 31.5%) as a white solid. LCMS: LC retention time 1.52 min. MS (ESI) m/z: 403.9 [M+H]$^+$, purity: 100% (254 nm). $^1$H NMR (400 MHz, DMSO-d$_6$) δ 11.91 (s, 1H), 8.78 (s, 1H), 8.03 (d, J=8 Hz, 1H), 7.40 (d, J=8 Hz, 1H), 7.29 (d, J=1.2 Hz, 1H), 7.14 (d, J=1.2 Hz, 1H), 6.96 (s, 1H), 6.63 (d, J=7.6 Hz, 1H), 5.35-5.34 (m, 1H), 4.95 (m, 2H), 4.62-4.59 (m, 2H), 4.55 (d, J=6 Hz, 2H), 2.60 (s, 3H).

117

Example 19: Synthesis of N-(4-cyano-5-ethoxy-2-fluorobenzyl)-6-(5-methyl-1H-pyrazol-4-yl)-1H-pyrrolo[2,3-b]pyridine-2-carboxamide (Comparator 5, see generally WO 2011/050245)

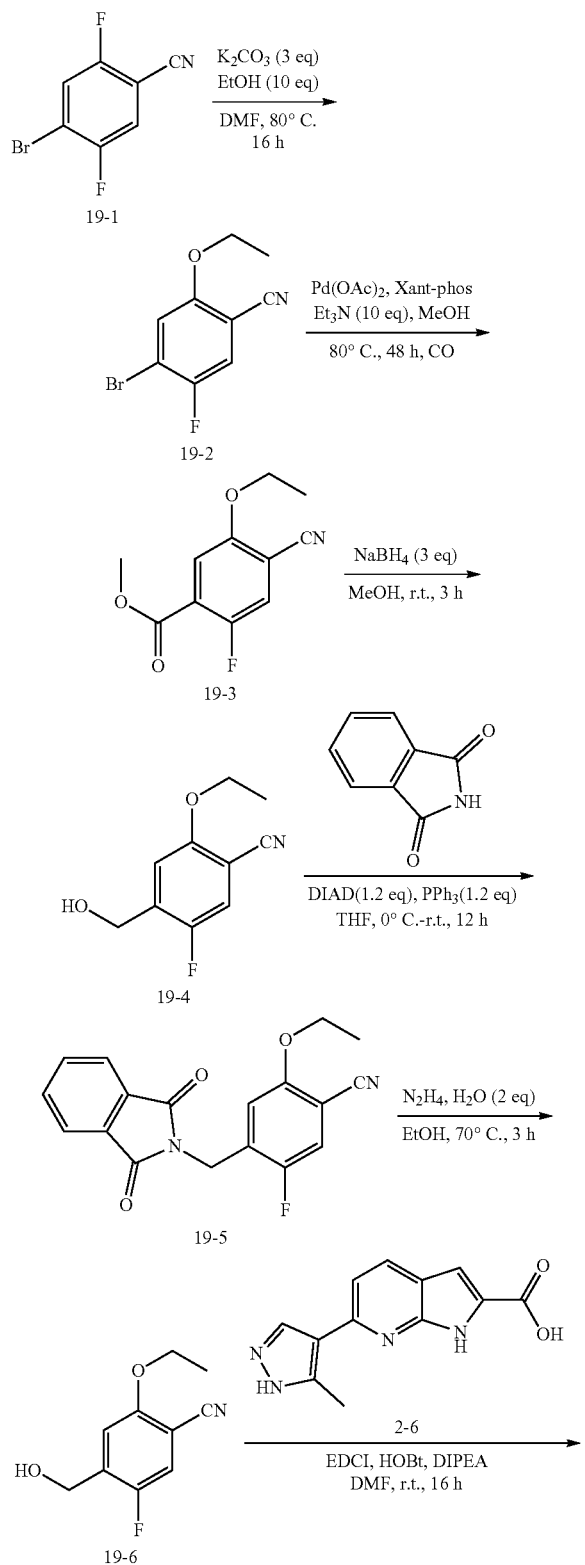

118

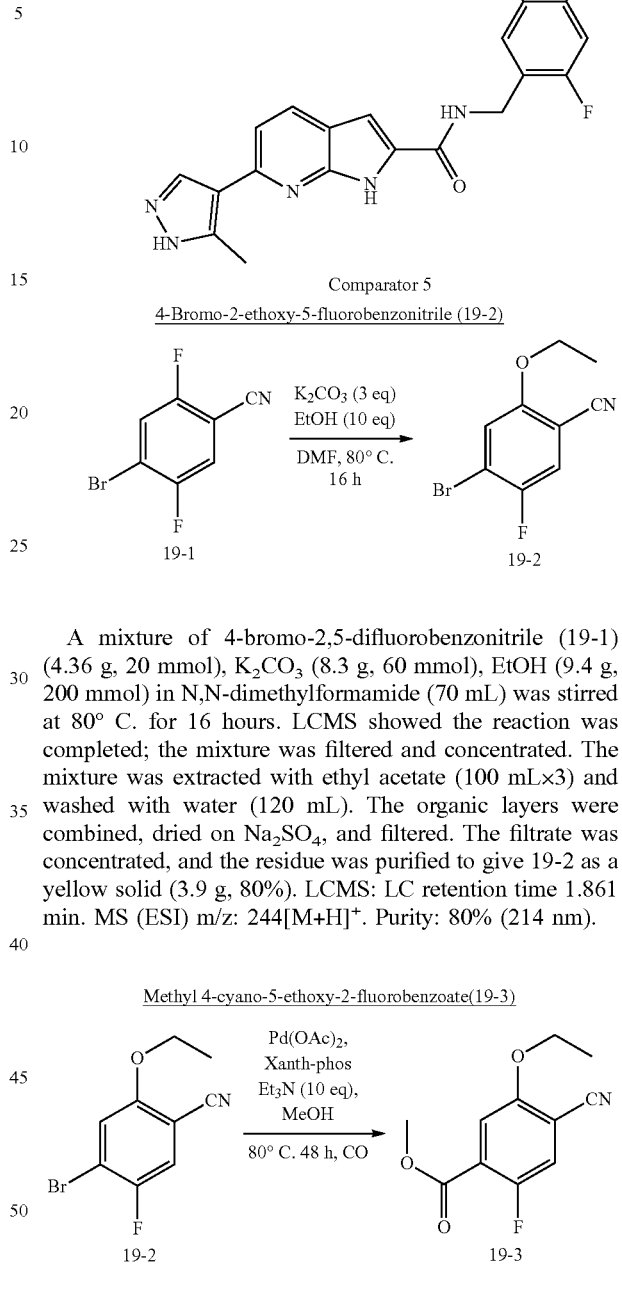

Comparator 5

4-Bromo-2-ethoxy-5-fluorobenzonitrile (19-2)

A mixture of 4-bromo-2,5-difluorobenzonitrile (19-1) (4.36 g, 20 mmol), $K_2CO_3$ (8.3 g, 60 mmol), EtOH (9.4 g, 200 mmol) in N,N-dimethylformamide (70 mL) was stirred at 80° C. for 16 hours. LCMS showed the reaction was completed; the mixture was filtered and concentrated. The mixture was extracted with ethyl acetate (100 mL×3) and washed with water (120 mL). The organic layers were combined, dried on $Na_2SO_4$, and filtered. The filtrate was concentrated, and the residue was purified to give 19-2 as a yellow solid (3.9 g, 80%). LCMS: LC retention time 1.861 min. MS (ESI) m/z: 244[M+H]$^+$. Purity: 80% (214 nm).

Methyl 4-cyano-5-ethoxy-2-fluorobenzoate(19-3)

A mixture of 4-bromo-2-ethoxy-5-fluorobenzonitrile (19-2) (1 g, 4.1 mmol), Pd(OAc)$_2$ (50 mg, catalyst), 4,5-bis (diphenylphosphino)-9,9-dimethylxanthene (100 mg, catalyst), Et$_3$N (4.1 g, 41 mmol) in methanol (20 mL) was stirred at 80° C. for 48 hours under carbon monoxide gas. LCMS showed the reaction was completed, then the mixture was concentrated and diluted with H$_2$O (60 mL) and extracted with ethyl acetate (30 mL×3). The organic layers were combined and washed with water (60 mL), followed by drying on Na$_2$SO$_4$, and filtered. The filtrate was concentrated; the residue was purified by SGC to give 19-3 as a yellow solid (0.73 g, 80%). LCMS: LC retention time 1.761 min. MS (ESI) m/z: 224 [M+H]$^+$. Purity: 100% (214 nm).

2-Ethoxy-5-fluoro-4-(hydroxymethyl)benzonitrile (19-4)

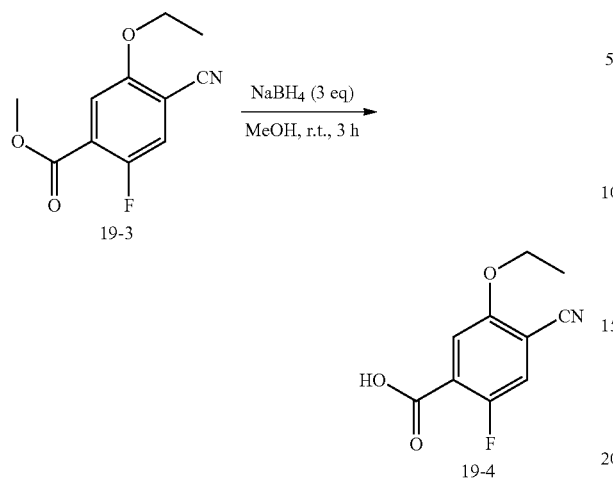

To a mixture of methyl 4-cyano-5-ethoxy-2-fluorobenzoate (19-3) (730 mg, 3.3 mmol) in methanol (20 mL) was added NaBH$_4$ (371 mg, 9.9 mmol) at 0° C. After addition, the mixture was stirred at room temperature for 3 hours. LCMS showed the reaction was completed, the mixture was concentrated the residue was purified by SGC to give 19-4 as a yellow solid (0.60 g, 94%). LCMS: LC retention time 1.58 min. MS (ESI) m/z: 196 [M+H]$^+$. Purity: 95% (214 nm).

2-Ethoxy-5-fluoro-4-(hydroxymethyl)benzonitrile (19-5)

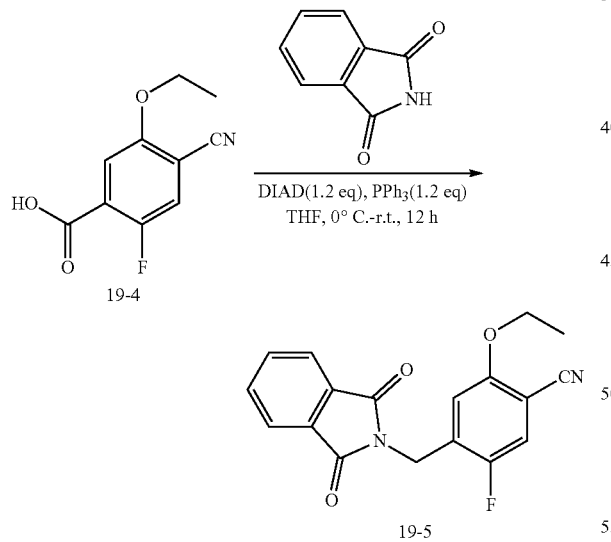

To a mixture of 2-ethoxy-5-fluoro-4-(hydroxymethyl)benzonitrile (19-4) (600 mg, 3.1 mmol), isoindoline-1,3-dione (456 mg, 3.1 mmol), PPh$_3$ (975 mg, 3.72 mmol) in tetrahydrofuran (20 mL) was added DIAD (750 mg, 3.72 mmol) at 0° C. under argon atmosphere. After addition, the mixture was stirred at room temperature for 12 hours. LCMS showed the reaction was completed; the mixture was diluted with ethyl acetate (80 mL) and washed with water (50 mL). The organic layers were combined, dried on Na$_2$SO$_4$, and filtered. The filtrate was concentrated, and the residue was purified by SGC to give 19-5 as a yellow solid (0.8 g, 80%). LCMS: LC retention time 1.842 min. MS (ESI) m/z: 325 [M+H]$^+$. Purity: 75% (214 nm).

4-(Aminomethyl)-2-ethoxy-5-fluorobenzonitrile (19-6)

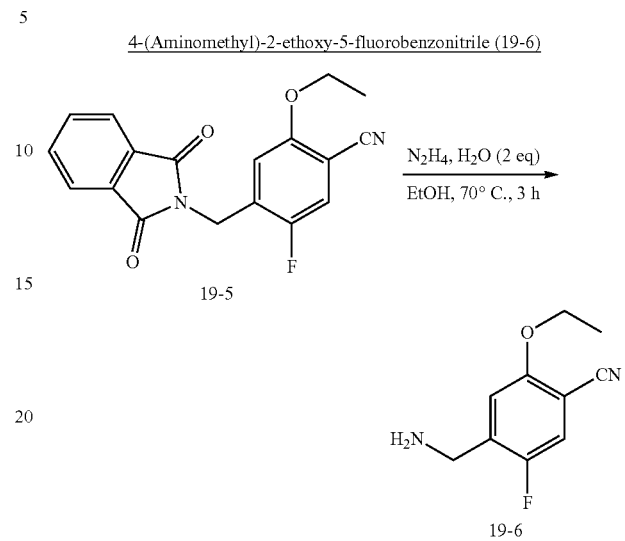

A mixture of 4-((1,3-dioxoisoindolin-2-yl)methyl)-2-ethoxy-5-fluorobenzonitrile (19-5) (0.8 g, 2.46 mmol), N$_2$H$_4$·H$_2$O (200 mg, 5 mmol) in ethanol (12 mL) was stirred at 70° C. for 3 hours. LCMS showed the reaction was completed, the mixture was concentrated, and the residue was purified by prep-HPLC to give 19-6 as a white solid (300 mg, 63%). LCMS: LC retention time 1.04 min. MS (ESI) m/z: 195 [M+H]$^+$. Purity: 95% (214 nm).

N-(4-cyano-5-ethoxy-2-fluorobenzyl)-6-(5-methyl-1H-pyrazol-4-yl)-1H-pyrrolo[2,3-b]pyridine-2-carboxamide (Comparator 5)

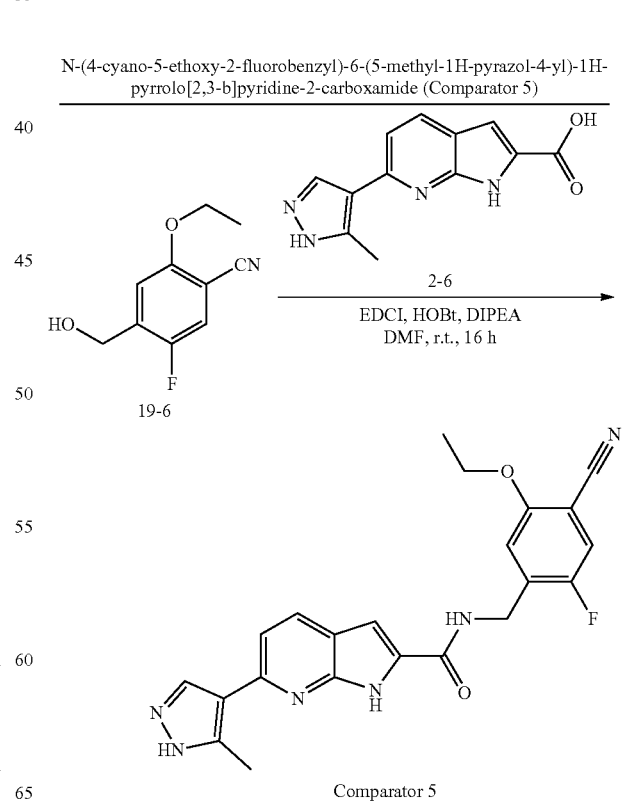

Comparator 5

A mixture of 4-(aminomethyl)-2-ethoxy-5-fluorobenzonitrile (19-6) (56 mg, 0.29 mmol), 6-(5-methyl-1H-pyrazol-4-yl)-1H-pyrrolo[2,3-b]pyridine-2-carboxylic acid (2-6) (70 mg, 0.29 mmol), EDCI (84 mg, 0.44 mmol), HOBt (54 mg, 0.44 mmol), DIPEA (187 mg, 1.5 mmol) in N,N-dimethylformamide (2 mL) was stirred at room temperature for 12 hours. LCMS showed the reaction was completed; the reaction was extracted with dichloromethane (20 mL×3) and washed with water (20 mL), concentrated, and purified by prep-HPLC to give Comparator 5 as a white solid (33 mg, 27%). LCMS: LC retention time 1.523 min. MS (ESI) m/z: 419 [M+H]$^+$. Purity: 100% (214 nm). $^1$H NMR (500 MHz, DMSO-d6) δ 12.70 (s, 1H), 11.90 (s, 1H), 8.99 (t, J=6.0 Hz, 1H), 8.03 (d, J=8.5 Hz, 2H), 7.77 (d, J=9.0 Hz, 1H), 7.40 (d, J=8.5 Hz, 1H), 7.25 (d, J=6.0 Hz, 1H), 7.13 (d, J=2.0 Hz, 1H), 4.58 (d, J=5.5 Hz, 2H), 4.14 (q, J=7.0 Hz, 2H), 2.59 (s, 3H), 1.34 (t, J=7.0 Hz, 3H) ppm.

Example 20: Synthesis of N-(3-methoxybenzyl)-6-(1H-pyrazol-4-yl)-1H-pyrrolo[2,3-b]pyridine-2-carboxamide (Comparator 6, see WO 2011/050245)

A solution of 6-chloro-1H-pyrrolo[2,3-b]pyridine-2-carboxylic acid (1 g, 5.087 mmol, 1 equiv) in N,N-dimethylformamide (9 mL) was treated with HATU (2.90 g, 7.630 mmol, 1.5 equiv) for half an hour at room temperature followed by the addition of 1-(3-methoxyphenyl)methanamine (1.05 g, 7.630 mmol, 1.5 equiv) and triethylamine (1.03 g, 10.174 mmol, 2 equiv) at 0° C. The resulting mixture was stirred for one hour at room temperature. The reaction was monitored by LCMS. The resulting mixture was concentrated under reduced pressure. The residue was purified by silica gel column chromatography, eluted with dichloromethane/methanol (0-10%) to give the crude product. The crude was purified by trituration with H$_2$O (10 mL) to afford 6-chloro-N-[(3-methoxyphenyl)methyl]-1H-pyrrolo[2,3-b]pyridine-2-carboxamide (20-1) (420 mg, 26.15%) as a yellow solid. LC-MS (ESI, m/z): 316 [M+H]$^+$. $^1$H NMR (400 MHz, DMSO-d$_6$) δ 12.40 (s, 1H), 9.12 (t, J=6.0 Hz, 1H), 8.15 (d, J=8.3 Hz, 1H), 7.26 (t, J=8.1 Hz, 1H), 7.22 (d, J=2.1 Hz, 1H), 7.18 (d, J=8.2 Hz, 1H), 6.94-6.89 (m, 2H), 6.83 (dd, J=9.0, 2.4 Hz, 1H), 4.49 (d, J=6.0 Hz, 2H), 3.74 (s, 3H).

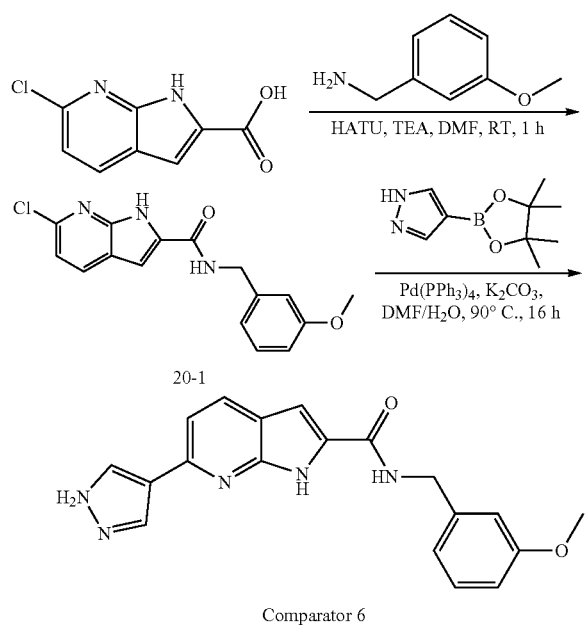

Comparator 6
6-chloro-N-(3-methoxybenzyl)-1H-pyrrolo[2,3-b]pyridine-2-carboxamide (20-1)

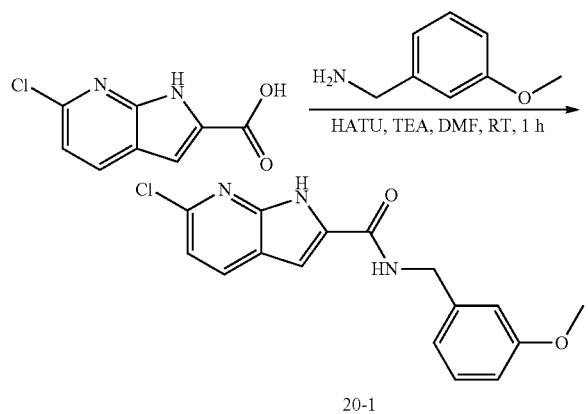

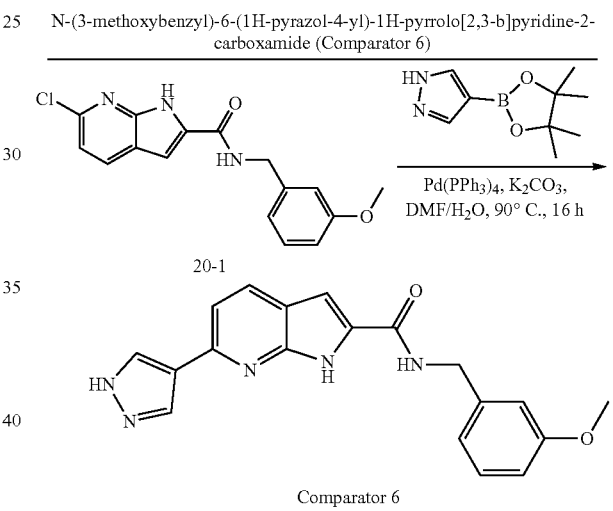

N-(3-methoxybenzyl)-6-(1H-pyrazol-4-yl)-1H-pyrrolo[2,3-b]pyridine-2-carboxamide (Comparator 6)

To a stirred mixture of 6-chloro-N-[(3-methoxyphenyl)methyl]-1H-pyrrolo[2,3-b]pyridine-2-carboxamide (20-1) (400 mg, 1.267 mmol, 1 equiv) and 4-(4,4,5,5-tetramethyl-1,3,2-dioxaborolan-2-yl)-1H-pyrazole (737.42 mg, 3.801 mmol, 3 equiv) in N,N-dimethylformamide/H$_2$O (4 mL/0.8 mL) were added Pd(PPh$_3$)$_4$ (146.39 mg, 0.127 mmol, 0.1 equiv) and K$_2$CO$_3$ (350.15 mg, 2.534 mmol, 2 equiv) at room temperature under nitrogen atmosphere. The resulting mixture was stirred for 16 hours at 90° C. under nitrogen atmosphere. The reaction was monitored by LCMS. The resulting mixture was concentrated under reduced pressure. The residue was purified by silica gel column chromatography, eluted with dichloromethane/methanol (0-10%) to give the crude product. The crude was purified by trituration with methanol (10 mL) to afford N-[(3-methoxyphenyl)methyl]-6-(1H-pyrazol-4-yl)-1H-pyrrolo[2,3-b]pyridine-2-carboxamide (Comparator 6) (186.2 mg, 42.14%) as a white solid which was contaminated with about 2% methanol residue. LC-MS (ESI, m/z): 348 [M+H]$^+$. $^1$H NMR (400 MHz, DMSO-d$_6$) δ 13.02 (s, 1H), 11.94 (s, 1H), 8.92 (t, J=6.0 Hz, 1H), 8.30 (s, 1H), 8.06 (s, 1H), 8.03 (d, J=8.2 Hz, 1H), 7.48 (d, J=8.3 Hz, 1H), 7.26 (t, J=8.1 Hz, 1H), 7.12 (d, J=2.1 Hz, 1H), 6.95-6.89 (m, 2H), 6.85-6.79 (m, 1H), 4.48 (d, J=5.9 Hz, 2H), 3.74 (s, 3H).

Example 21: Synthesis of N-(3,4-difluorobenzyl)-6-(1H-pyrazol-4-yl)-1H-indole-3-carboxamide (Comparator 7, see WO 2011/050245)

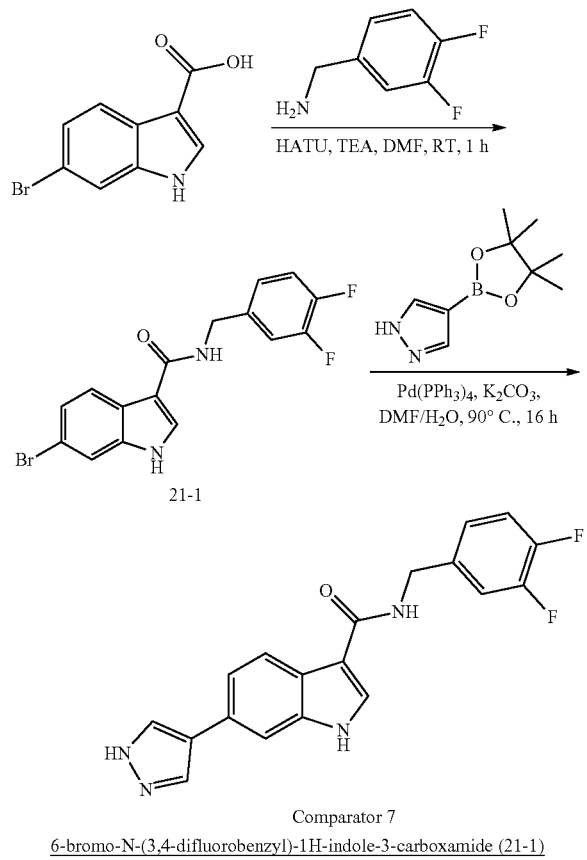

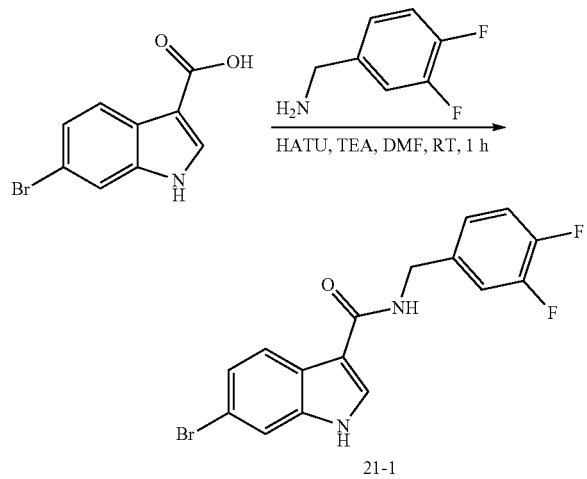

A solution of 6-bromo-1H-indole-3-carboxylic acid (1 g, 4.166 mmol, 1 equiv) in N,N-dimethylformamide (9 mL) was treated with HATU (2.38 g, 6.249 mmol, 1.5 equiv) for 30 minutes at room temperature followed by the addition of 1-(3,4-difluorophenyl)methanamine (0.89 g, 6.249 mmol, 1.5 equiv) and triethylamine (1.26 g, 12.498 mmol, 3 equiv) at 0° C. The resulting mixture was stirred for 1 hour at room temperature. The reaction was monitored by LCMS. The reaction mixture was concentrated under vacuum. The residue was purified by silica gel column chromatography, eluted with dichloromethane/methanol (0-10%) to give crude product. The crude was further purified by trituration with H$_2$O (10 mL) to afford 6-bromo-N-[(3,4-difluorophenyl)methyl]-1H-indole-3-carboxamide (400 mg, 26.29%) as a yellow solid. LC-MS (ESI, m/z): 365, 367 [M+H]$^+$. $^1$H NMR (400 MHz, DMSO-d$_6$) δ 11.69 (s, 1H), 8.56 (t, J=6.0 Hz, 1H), 8.11-8.06 (m, 2H), 7.64 (s, 1H), 7.50-7.31 (m, 2H), 7.24 (dd, J=8.6, 1.8 Hz, 1H), 7.22-7.15 (m, 1H), 4.45 (d, J=6.0 Hz, 2H).

N-(3,4-difluorobenzyl)-6-(1H-pyrazol-4-yl)-1H-indole-3-carboxamide (Comparator 7)

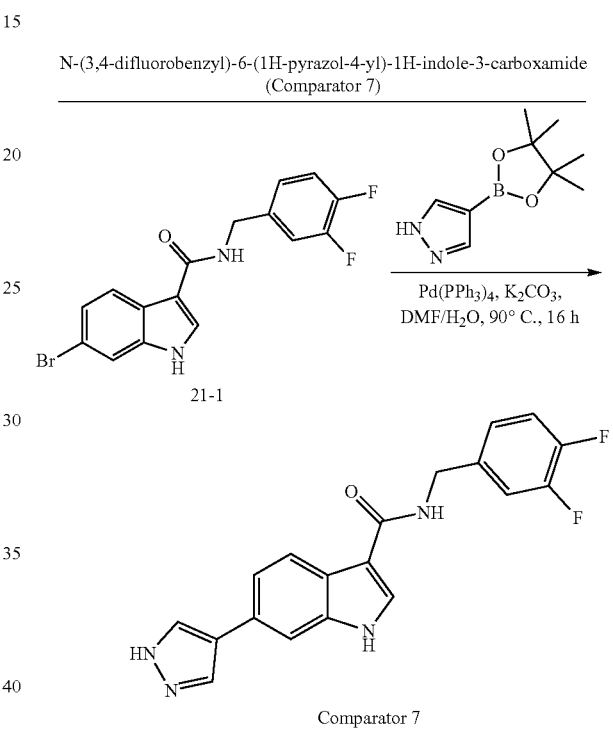

To a stirred mixture of 6-bromo-N-[(3,4-difluorophenyl)methyl]-1H-indole-3-carboxamide (370 mg, 1.013 mmol, 1 equiv) and 4-(4,4,5,5-tetramethyl-1,3,2-dioxaborolan-2-yl)-1H-pyrazole (589.81 mg, 3.039 mmol, 3 equiv) in N,N-dimethylformamide/H$_2$O (4 mL/0.8 mL) was added Pd(PPh$_3$)$_4$(117.08 mg, 0.101 mmol, 0.1 equiv) and K$_2$CO$_3$ (280.06 mg, 2.026 mmol, 2 equiv) at room temperature under nitrogen atmosphere. The resulting mixture was stirred for 16 hours at 90° C. under nitrogen atmosphere. The reaction was monitored by LCMS. The resulting mixture was concentrated under reduced pressure. The residue was purified by silica gel column chromatography, eluted with dichloromethane/methanol (0-10%) to give crude product. The crude was further purified by trituration with methanol (10 mL) to afford N-[(3,4-difluorophenyl)methyl]-6-(1H-pyrazol-4-yl)-1H-indole-3-carboxamide (236.4 mg, 65.42%) as a white solid. LC-MS (ESI, m/z): 353 [M+H]$^+$. $^1$H NMR (400 MHz, DMSO-d$_6$) δ 12.86 (s, 1H), 11.52 (d, J=3.0 Hz, 1H), 8.48 (t, J=6.1 Hz, 1H), 8.23-7.85 (m, 4H), 7.60 (d, J=1.5 Hz, 1H), 7.46-7.33 (m, 3H), 7.26-7.13 (m, 1H), 4.46 (d, J=6.0 Hz, 2H).

Example 22: Synthesis of 6-(1H-pyrazol-4-yl)-N-(pyridin-4-ylmethyl)-1H-pyrrolo[2,3-b]pyridine-3-carboxamide (Comparator 8, see WO 2011/050245)

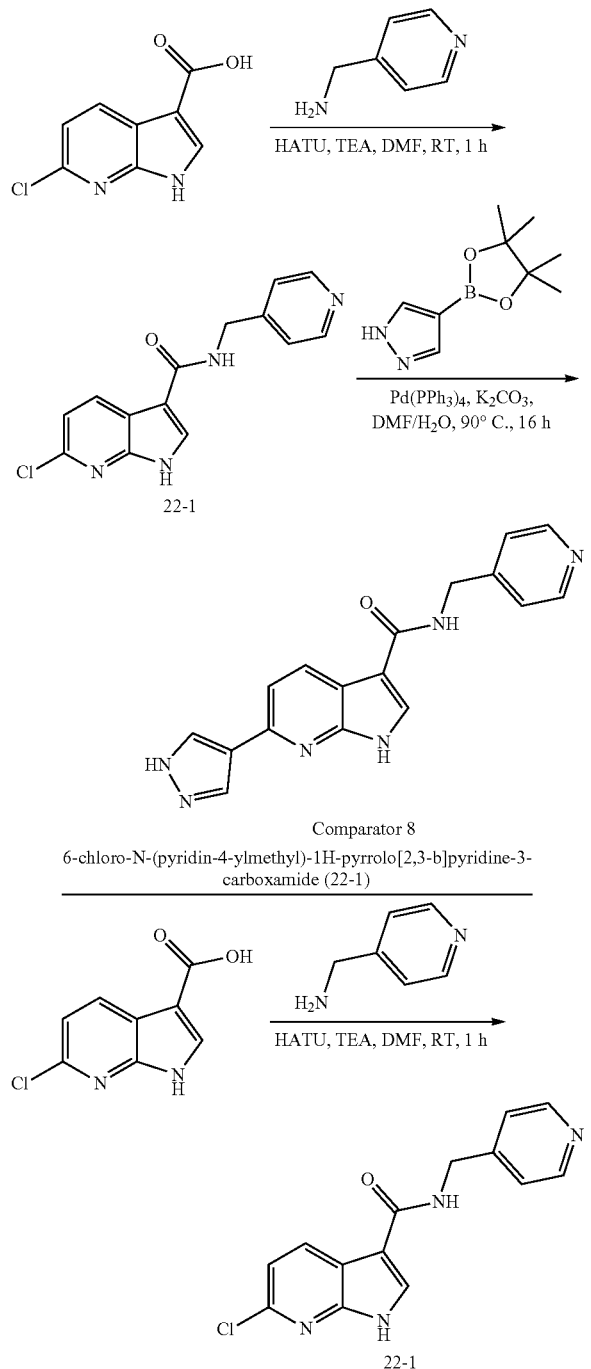

Comparator 8
6-chloro-N-(pyridin-4-ylmethyl)-1H-pyrrolo[2,3-b]pyridine-3-carboxamide (22-1)

A solution of 6-chloro-1H-pyrrolo[2,3-b]pyridine-3-carboxylic acid (1 g, 5.087 mmol, 1 equiv) in N,N-dimethylformamide (10 mL) was treated with HATU (2.90 g, 7.630 mmol, 1.5 equiv) for 30 minutes at room temperature followed by the addition of 4-pyridinemethanamine (0.83 g, 7.630 mmol, 1.5 equiv) and triethylamine (1.03 g, 10.174 mmol, 2 equiv) at 0° C. The resulting mixture was stirred for one hour at room temperature. The resulting mixture was concentrated under reduced pressure. The residue was purified by silica gel column chromatography, eluted with dichloromethane/methanol (0-10%) to give crude product. The crude was purified by trituration with water (15 mL) to afford 6-chloro-N-(pyridin-4-ylmethyl)-1H-pyrrolo[2,3-b]pyridine-3-carboxamide (22-1) (430 mg, 29.48%) as a yellow solid. LC-MS (ESI, m/z): 287 [M+H]$^+$. $^1$H NMR (400 MHz, DMSO-$d_6$) δ 12.36 (s, 1H), 8.75 (t, J=6.1 Hz, 1H), 8.54-8.49 (m, 2H), 8.46 (d, J=8.2 Hz, 1H), 8.25 (s, 1H), 7.33 (d, J=5.0 Hz, 2H), 7.26 (d, J=8.2 Hz, 1H), 4.51 (d, J=5.9 Hz, 2H).

6-(1H-pyrazol-4-yl)-N-(pyridin-4-ylmethyl)-1H-pyrrolo[2,3-b]pyridine-3-carboxamide (Comparator 8)

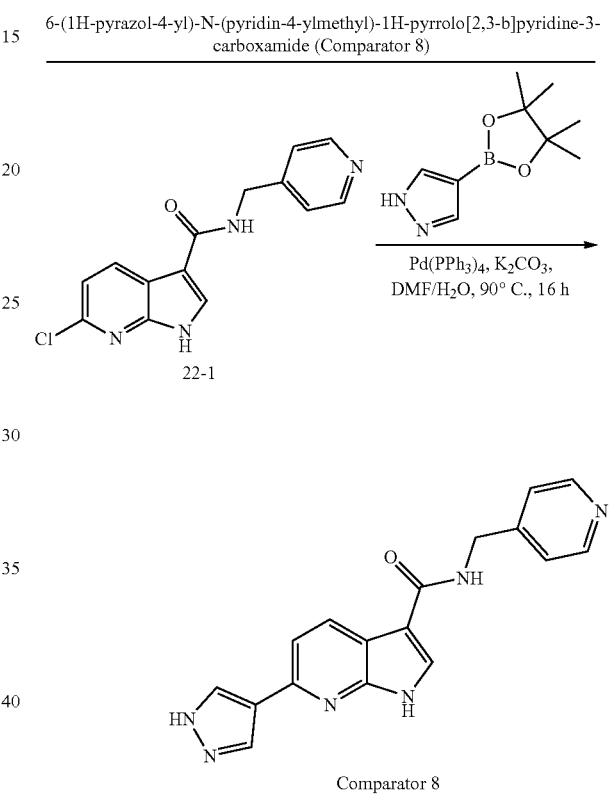

Comparator 8

To a stirred of 6-chloro-N-(pyridin-4-ylmethyl)-1H-pyrrolo[2,3-b]pyridine-3-carboxamide (400 mg, 1.395 mmol, 1 equiv) and 4-(4,4,5,5-tetramethyl-1,3,2-dioxaborolan-2-yl)-1H-pyrazole (812.11 mg, 4.185 mmol, 3 equiv) in N,N-dimethylformamide/H$_2$O (4 mL/0.8 mL) were added K$_2$CO$_3$ (385.62 mg, 2.790 mmol, 2 equiv) and Pd(PPh$_3$)$_4$(161.22 mg, 0.140 mmol, 0.1 equiv) at room temperature under nitrogen atmosphere. The resulting mixture was stirred for 16 hours at 90° C. under nitrogen atmosphere. The reaction was monitored by LCMS. The resulting mixture was concentrated under reduced pressure. The residue was purified by silica gel column chromatography, eluted with dichloromethane/methanol (10%-30%) to give crude product. The crude was further purified by trituration with acetonitrile (10 mL) to afford 6-(1H-pyrazol-4-yl)-N-(pyridin-4-ylmethyl)-1H-pyrrolo[2,3-b]pyridine-3-carboxamide (220.0 mg, 49.54%) as a white solid. LC-MS (ESI, m/z): 319 [M+H]$^+$. $^1$H NMR (400 MHz, DMSO-$d_6$) δ 12.99 (s, 1H), 12.06 (d, J=2.9 Hz, 1H), 8.65 (t, J=6.0 Hz, 1H), 8.56-8.47 (m, 2H), 8.47-8.00 (m, 4H), 7.54 (d, J=8.3 Hz, 1H), 7.40-7.27 (m, 2H), 4.51 (d, J=5.9 Hz, 2H).

Example 23: Exemplary Compounds of the Present Invention

TABLE 1A

| Cmpd # | Structure |
| --- | --- |
| 1 | 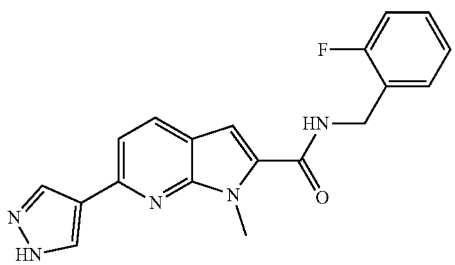 |
| 2 | 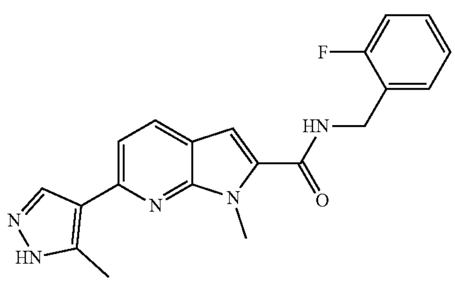 |
| 3 | 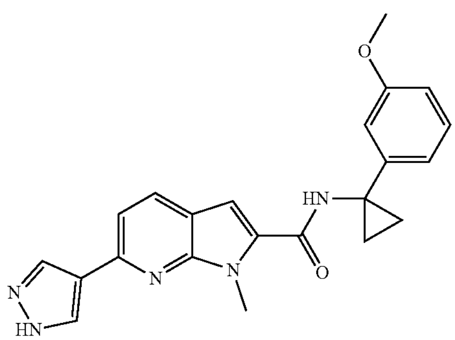 |
| 4 | 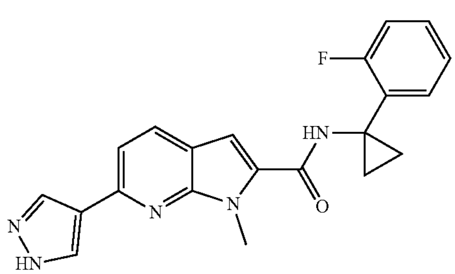 |
| 5 | 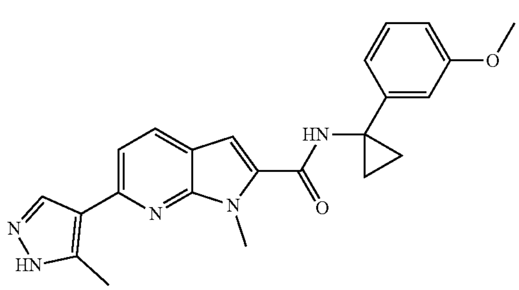 |

TABLE 1A-continued
| Cmpd # | Structure |
|---|---|
| 6 | 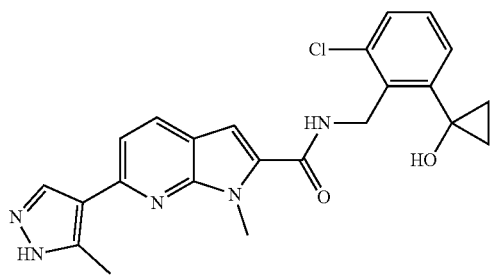 |
| 7 | 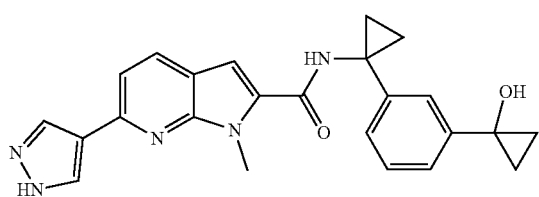 |
| 8 | 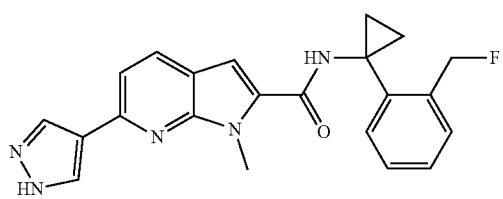 |
| 9 | 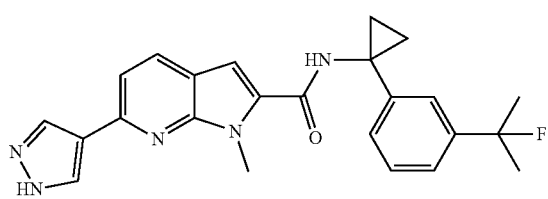 [SMILES: Cn1c(C(=O)NC2(c3cccc(C(C)(C)F)c3)CC2)cc2ccc(-c3cn[nH]c3)nc21] |
| 10 | 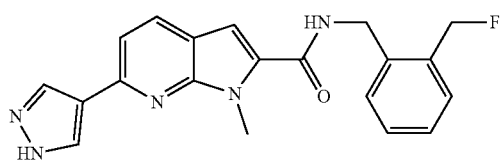 |
| 11 | 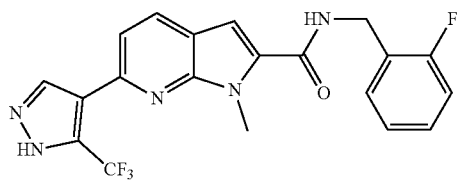 |
| 12 | 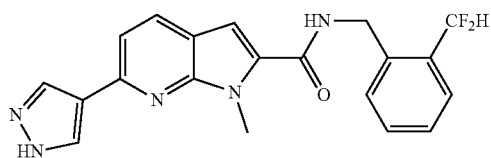 [SMILES: Cn1c(C(=O)NCc2ccccc2C(F)F)cc2ccc(-c3cn[nH]c3)nc21] |
| 13 | 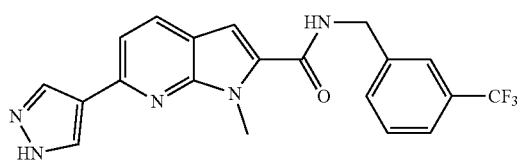 |

TABLE 1A-continued
| Cmpd # | Structure |
|---|---|
| 14 | 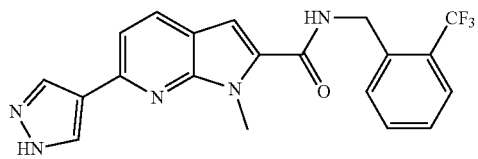 |
TABLE 1B
Comparators:
| Cmpd # | Structure |
|---|---|
Comparator 1
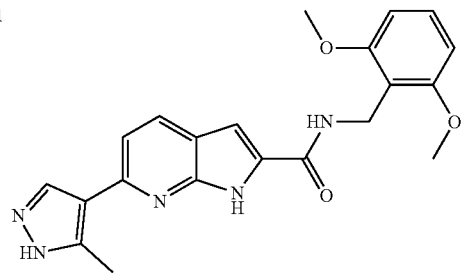
Comparator 2
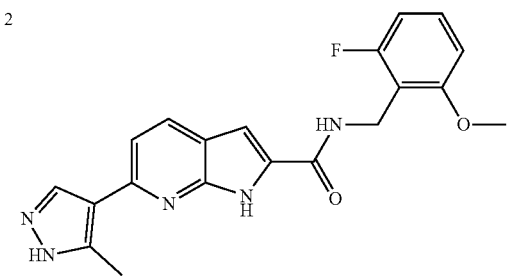
Comparator 3
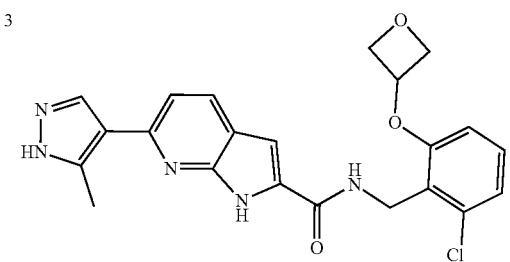
Comparator 4
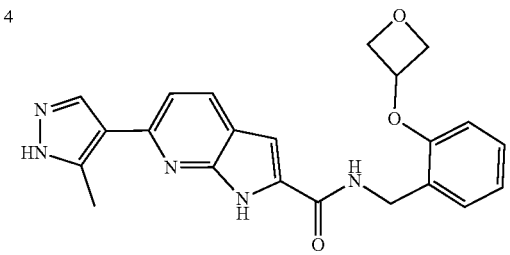

TABLE 1B-continued

Comparators:

| Cmpd # | Structure |
|---|---|
| Comparator 5 | 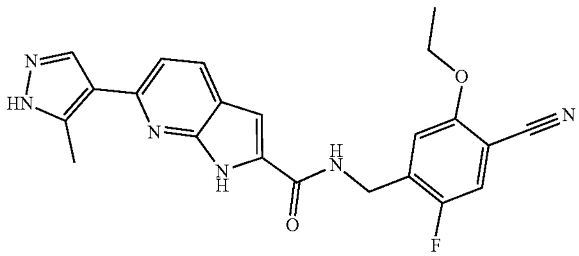 [SMILES: CCOc1cc(CNC(=O)c2cc3ccc(-c4cn[nH]c4C)nc3[nH]2)c(F)cc1C#N] |
| Comparator 6 | 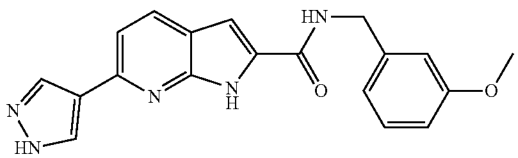 |
| Comparator 7 | 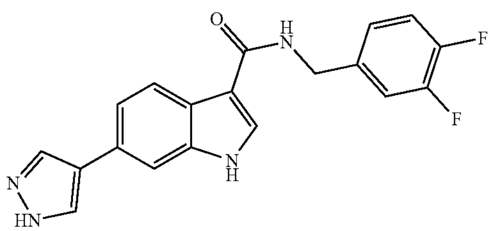 |
| Comparator 8 | 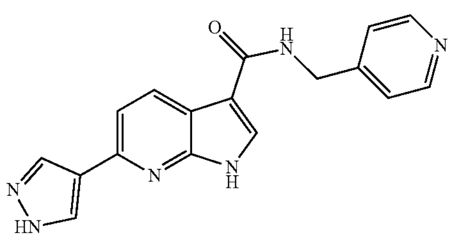 [SMILES: O=C(NCc1ccncc1)c1c[nH]c2nc(-c3cn[nH]c3)ccc12] |

Example 24: ROCK1, ROCK2, PRKX, and PKA Inhibition Assay

Compounds as a powder were dissolved in dimethyl sulfoxide to make a 10 mM stock. Compounds were tested in 10-dose $IC_{50}$ triplicate mode with a 3-fold serial dilution starting at 1 µM. The control compound, staurosporine, was tested in 10-dose $IC_{50}$ mode with 4-fold serial dilution starting at 20 µM. The HotSpot kit employing $^{33}$P-ATP was used with reactions conducted at 10 M ATP for each tested enzyme. The percent activity relative to DMSO controls for each concentration was then fitted to a curve using GraphPad Prism to determine the $IC_{50}$. Curve fits were performed where the enzyme activities at the highest concentration of compounds were less than 65%. An $IC_{50}$ value less than 50.8 µM or higher than 1 M is estimated based on the best curve fitting available. The resulting data for the tested compounds is shown in Table 2A and Table 2B below. The data for Compound 1 in Table 2B is the geometric mean of the $IC_{50}$ data from multiple enzyme inhibition experiments. Each experiment was run in the same lab with this procedure.

TABLE 2A $IC_{50}$ Values of Representative Compounds of the Present Invention

| Compound | ROCK1 $IC_{50}$ (nM) | ROCK2 $IC_{50}$ (nM) |
|---|---|---|
| Compound 1 | 16.4 | 2.3 |
| Compound 2 | 61.0 | 6.0 |
| Compound 3 | 21.2 | 0.8 |

TABLE 2A-continued

IC$_{50}$ Values of Representative Compounds of the Present Invention

| Compound | ROCK1 IC$_{50}$ (nM) | ROCK2 IC$_{50}$ (nM) |
|---|---|---|
| Compound 4 | 37.4 | 10.5 |
| Compound 5 | 18.5 | 3.6 |
| Compound 6 | 35.6 | 10.1 |
| Fasudil | 367 | 164 |
| Comparator 1 | >1000 | >1000 |
| Comparator 2 | >1000 | 279.0 |
| Comparator 3 | >1000 | 587.0 |
| Comparator 4 | >1000 | 282.0 |
| Comparator 5 | >1000 | >1000 |
| Staurosporine | 0.627 | 0.884 |

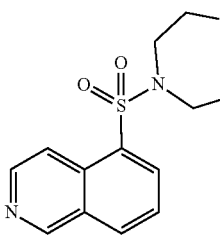

TABLE 2B

IC$_{50}$ Values of Representative Compounds of the Present Invention

| Compound | ROCK1 IC$_{50}$ (nM) | ROCK2 IC$_{50}$ (nM) | PRKX IC$_{50}$ (nM) | PKA IC$_{50}$ (nM) |
|---|---|---|---|---|
| Compound 1 | 30.3 | 2.7 | 31.4 | 237.7 |
| Compound 2 | | 7.8 | | 63.3 |
| Compound 3 | | | 396 | 830 |
| Compound 4 | | 6.6 | | 9.9 |
| Compound 5 | | | 614 | 414 |
| Compound 6 | | 32.3 | | 103 |
| Compound 7 | | 357 | 28.2 | 104 |
| Compound 9 | | >820 | | >10000 |
| Compound 10 | 45.1 | 6.9 | 27.3 | 133 |
| Compound 11 | >1000 | 1370 | | |
| Compound 12 | 47.1 | 8.3 | | |
| Compound 13 | 414 | 53.3 | | |
| Compound 14 | 440 | 70 | | |
| Comparator 1 | | | 3400 | >10000 |
| Comparator 2 | | | 73 | 523 |
| Comparator 3 | | | 376 | 1400 |
| Comparator 4 | | | 62 | 190 |
| Comparator 5 | | | 1560 | 7970 |
| Comparator 6 | 10.2 | 0.96 | 165.2 | 46.2 |
| Comparator 7 | 56.1 | 7.4 | 222.2 | 618.5 |
| Comparator 8 | >1000 | 628.0 | >1000 | >1000 |
| Staurosporine | | | | 0.678 |

Example 25: MDCK-MDR1 Efflux Assay

Experimental Procedure 1:

MDCK-MDR1 cells grown in tissue culture flasks were trypsinized, suspended in medium, and the suspensions were applied to wells of a Millipore 96 well plate. The cells were allowed to grow and differentiate for five days, feeding at 2-day intervals.

For Apical to Basolateral (A-B) permeability, the test article was added to the apical (A) side and amount of permeation was determined on the basolateral (B) side; for Basolateral to Apical (B-A) permeability, the test article was added to the B side and the amount of permeation was determined on the A side. The A-side buffer contained 100 µM lucifer yellow dye, in Transport Buffer (1.98 g/L glucose in 10 mM HEPES, 1× Hank's Balanced Salt Solution) pH 7.4, and the B-side buffer was Transport Buffer at pH 7.4. MDCK-MDR1 cells were incubated with test articles in these buffers for 2 hours, and at the end of the assay, donor and receiver side solution samples were collected, quenched by 100% methanol containing an internal standard and centrifuged at 5000 rpm for 10 minutes at 4° C. Following centrifugation, the supernatant for donor and receiver side samples were analyzed by LC-MS/MS.

Data Analysis:

Data was expressed as permeability (Papp): $P_{app}=(dQ/dt)/(C_0A)$ where dQ/dt is rate of permeation, Co is initial concentration of test article, and A is the area of monolayer.

In bidirectional permeability studies, the Efflux Ratio ($R_e$) was calculated:

$R_e = [P_{app}(B \rightarrow A)]/[P_{app}(A \rightarrow B)]$ $R_e$ >2 indicates a potential substrate for P-gp efflux transporters.

Detailed data are shown in Table 3A.

TABLE 3A

Efflux Ratios of Representative Compounds

| Compound | Efflux Ratio MDCK-MDR1 |
|---|---|
| Compound 1 | 1.46 |
| Compound 2 | 15.9 |
| Compound 3 | 8.44 |
| Compound 4 | 1.83 |
| Compound 5 | 85.4 |
| Compound 6 | 133 |
| Compound 10 | 2.34 |
| Fasudil | 45.1 |
| Comparator 1 | 59.1 |
| Comparator 2 | 39.4 |
| Comparator 3 | 256 |
| Comparator 4 | 178 |
| Comparator 5 | 258 |
| Digoxin | 28.35 |
| Metoprolol | 0.99 |

Experimental Procedure 2:

1. Preparation of MDCKII-MDR1 Cells

Cell culture medium (50 µL and 25 mL) was added to each well of the Transwell insert and reservoir, respectively. And then the HTS Transwell plates were incubated at 37° C., 5% CO$_2$ for one hour before cell seeding. Afterwards, MDCKII-MDR1 cells were diluted to 1.56×10$^6$ cells/mL with culture medium and 50 µL of cell suspension were dispensed into the filter well of the 96-well HTS Transwell plate. Cells were cultivated for 4-8 days in a cell culture incubator at 37° C., 5% CO$_2$, 95% relative humidity. Cell culture medium was replaced every other day, beginning no later than 24 hours after initial plating.

2. Preparation of Stock Solutions

Stock solutions (10 mM) of test compounds were prepared in DMSO. The stock solutions of positive controls were prepared in DMSO at the concentration of 10 mM. Metoprolol, Digoxin, and Fasudil were used as control compounds in this assay.

3. Assessment of Cell Monolayer Integrity

Medium was removed from the reservoir and each Transwell insert and replaced with prewarmed fresh culture medium. Then transepithelial electrical resistance (TEER)

across the monolayer is measured using Millicell Epithelial Volt-Ohm measuring system (Millipore, USA). The plates were returned to the incubator once the measurement was done.

The TEER value was calculated according to the following equation:

TEER measurement (ohms)×Area of membrane (cm$^2$)=TEER value (ohm·cm$^2$)

TEER value should be greater than 42 ohm·cm$^2$, which indicates the well-qualified MDCKII-MDR1 monolayer.

4. Assay Procedures

The MDCKII-MDR1 plate was removed from the incubator and washed twice with pre-warmed HBSS (10 mM HEPES, pH 7.4), and then incubated at 37° C. for 30 minutes. The stock solutions of the control compounds and test compounds were diluted in DMSO to get 200 µM solutions and then diluted with HBSS (10 mM HEPES, pH 7.4) to get 1 µM working solutions. The final concentration of DMSO in the incubation system is 0.5%.

To determine the rate of drug transport in the apical to basolateral direction. 125 µL of the working solution was added to the Transwell insert (apical compartment), and 50 µL of sample was transferred immediately from the apical compartment to 200 µL of acetonitrile containing IS (100 nM alprazolam, 200 nM caffeine, 200 nM labetalol and 100 nM tolbutamide) in a new 96-well plate as the initial donor sample (A-B). The sample was vortexed at 1000 rpm for 10 minutes. The wells in the receiver plate (basolateral compartment) were filled with 235 µL of transport buffer.

To determine the rate of drug transport in the basolateral to apical direction. 285 µL of the working solution was added to the receiver plate wells (basolateral compartment), and 50 µL of sample was transferred immediately from the basolateral compartment to 200 µL of acetonitrile containing IS (100 nM alprazolam, 200 nM caffeine, 200 nM labetalol and 100 nM tolbutamide) in a new 96-well plate as the initial donor sample (B-A). The sample was vortexed at 1000 rpm for 10 minutes. The Transwell insert (apical compartment) was filled with 75 µL of transport buffer. The apical to basolateral direction and the basolateral to apical direction were done at the same time.

Then, the plates were incubated at 37° C. for 2 hours. At the end of the incubation, 50 µL of samples from donor sides (apical compartment for Ap→Bl flux, and basolateral compartment for Bl→Ap) and receiver sides (basolateral compartment for Ap→Bl flux, and apical compartment for Bl→Ap) were transferred to wells of a new 96-well plate, followed by the addition of 4 volume of acetonitrile containing IS (100 nM alprazolam, 200 nM caffeine, 200 nM labetalol and 100 nM tolbutamide). Samples were vortexed for 10 minutes and then centrifuged at 3220 g for 40 minutes. An aliquot of 100 µL of the supernatant was mixed with an appropriate volume of ultra-pure water before LC-MS/MS analysis.

To determine the Lucifer Yellow leakage after 2-hour transport period, the stock solution of Lucifer Yellow was prepared in DMSO and diluted with HBSS (10 mM HEPES, pH 7.4) to reach the final concentration of 100 µM. Then, 100 µL of the Lucifer Yellow solution was added to each Transwell insert (apical compartment), followed by filling the wells in the receiver plate (basolateral compartment) with 300 µL of HBSS (10 mM HEPES, pH 7.4). The plates were incubated at 37° C. for 30 minutes. Then, 80 µL samples were removed directly from the apical and basolateral wells (using the basolateral access holes) and transferred to wells of new 96 wells plates. The Lucifer Yellow fluorescence was used to monitor monolayer integrity and its signal was measured in a fluorescence plate reader at 480 nM excitation and 530 nM emission.

Detailed data are shown in Table 3B.

TABLE 3B

Efflux Ratios of Representative Compounds

| Compound | Efflux Ratio MDCK-MDR1 |
|---|---|
| Compound 1 | 0.8 |
| Compound 2 | 1.34 |
| Compound 3 | 1.08 |
| Compound 4 | 0.893 |
| Compound 7 | 4.55 |
| Compound 9 | 1.65 |
| Compound 10 | 0.961 |
| Compound 11 | 4.77 |
| Compound 12 | 0.98 |
| Compound 13 | 0.75 |
| Compound 14 | 0.93 |
| Comparator 6 | 2.62 |
| Comparator 7 | 4.95 |
| Comparator 8 | 3.82 |

Example 26: hERG $K_d$

Compounds were dissolved in DMSO to a stock concentration of 10 mM and tested in 10-dose IC$_{50}$ mode, in triplicate, with a 3-fold serial dilution starting at 100 µM. Control compound E-4031 was tested in 10-dose IC$_{50}$ mode with 3-fold serial dilution starting at 1 µM. The assay is based on the competition of fluorescently labeled Tracer binding to the membrane preparation containing 1× Predictor™ hERG Membrane with 1 nM Predictor™ hERG Tracer Red in a buffer with the composition of 25 mM Hepes, pH 7.5, 15 mM KCl, 1 mM MgCl$_2$, 0.05% PF-127, and 1% DMSO.

Compounds in DMSO were added into the membrane mixture by using sonication, the tracer was added and gently mixed in the dark. The fluorescence was measured after 4 hours incubation at room temperature. The measurement parameters are as follows: Ex=531 nm FP and Em=595 nm P and S.

Curve fits were performed by GraphPad Prism software when the activities at the highest concentration of compounds were less than 65%. The background was established by the average FP signal in the presence of 10 µM E-4031. The data is provided in Table 4 below.

TABLE 4 hERG Activity

| Compound | hERG $K_d$ (nM) |
|---|---|
| Compound 1 | >100,000 |
| Compound 3 | 89,000 |
| E-4031 | 33.3 |

Example 27: Mouse, Human and Rat Liver Microsomes

The master solution was prepared according to Table 5 and using the correct species' microsomes.

TABLE 5

Preparation of master solution

| Reagent | Stock Concentration | Volume | Final Concentration |
|---|---|---|---|
| Phosphate buffer | 100 mM | 216.25 µL | 100 mM |
| Microsomes | 20 mg/mL | 6.25 µL | 0.5 mg/mL |

Two separate experiments were performed as follows. a) Cofactors (NADPH): 25 µL of 10 mM NADPH were added to the incubations. The final concentration of microsomes and NADPH was 0.5 mg/mL and 1 mM, respectively. b) Without Cofactors (NADPH): 25 µL of 100 mM Phosphate buffer was added to the incubations. The final concentration of microsomes was 0.5 mg/mL. The mixture was pre-warmed at 37° C. for 10 minutes.

The reaction was started with the addition of 2.5 µL of 100 µM control compound or test compound solutions. Verapamil was used as positive control in this study. The final concentration of test compound or control compound was 1 M. The incubation solution was incubated in water batch at 37° C.

Four Aliquots of 30 µL were taken from the reaction solution at 0.5, 5, 15, 30 and 60 minutes. The reaction was stopped by the addition of 5 volumes of cold acetonitrile with IS (100 nM alprazolam, 200 nM caffeine and 100 nM tolbutamide). Samples were centrifuged at 3220 g for 40 minutes. Aliquot of 100 µL of the supernatant was mixed with 100 µL of ultra-pure $H_2O$ and then used for LC-MS/MS analysis. All calculations were carried out using Microsoft Excel. Peak areas were determined from extracted ion chromatograms. The slope value, k, was determined by linear regression of the natural logarithm of the remaining percentage of the parent drug vs. incubation time curve. The in vitro half-life (in vitro $t_{1/2}$) was determined from the slope value: in vitro $t_{1/2}$=−(0.693/k)

Conversion of the in vitro $t_{1/2}$(min) into the in vitro intrinsic clearance (in vitro $C_{Lint}$, in µL/min/mg protein) was done using the following equation (mean of duplicate determinations):

$$\text{in vitro } C_{Lint} = \frac{0.693}{t1/2} * \left(\frac{\text{volume of incubation (µL)}}{\text{amount of proteins (mg)}}\right)$$

The resulting data is shown in Table 6 below.

TABLE 6

Mouse, Rat, and Human Live Microsome Data

| Compound | Mouse Liver Microsomes $T_{1/2}$ (min) | Rat Liver Microsomes $T_{1/2}$ (min) | Human Liver Microsomes $T_{1/2}$ (min) |
|---|---|---|---|
| Compound 1 | 2.88 | 6.10 | 46.0 |
| Compound 2 | 4.81 | 10.13 | 49.0 |
| Compound 3 | 3.26 | 6.90 | 21.4 |
| Compound 4 | 9.22 | 7.97 | 88.3 |
| Compound 7 | 5.27 | 9.45 | 28.4 |
| Compound 9 | 5.98 | 9.92 | 19.2 |
| Compound 10 | 3.31 | 6.5 | 1.19 |
| Compound 11 | 91.5 | 74.4 | ∞ |
| Compound 12 | 5.75 | 10.5 | 69.4 |
| Compound 13 | 11.2 | 23.6 | >293 |
| Compound 14 | 11.6 | 22.8 | 209 |
| Comparator 6 | 3.34 | 5.60 | 61.4 |
| Comparator 7 | 4.91 | 7.14 | 61.1 |
| Comparator 8 | 3.47 | 6.76 | 69.4 |
| Verapamil | 6.23 | 2.66 | 3.45 |

Example 28: Kinetic Solubility

The stock solutions of test compounds and control compound progesterone were prepared in DMSO at the concentrations of 10 mM. 15 µL of stock solution (10 mM) of each sample was placed in order into their proper 96-well rack. 485 µL of PBS pH 7.4 was added into each vial of the cap-less solubility sample plate. The assay was performed in duplicate. One stir stick was added to each vial and sealed using a molded PTFE/Silicone plug. Then the solubility sample plate was transferred to the Eppendorf Thermomixer Comfort plate shaker and shook at 25° C. at 1100 rpm for 2 hours. After completion of the 2 hours, plugs were removed and the stir sticks were removed using a big magnet, the samples from the Solubility Sample plate were transferred into the filter plate. All the samples were filtered using the Vacuum Manifold. Aliquot of 5 µL DMSO were taken from the filtrate followed by addition of 490 µL of a mixture of $H_2O$ and acetonitrile containing internal standard (1:1). Ultrapure water was used to dilute the diluent according to the peak shape. The dilution factor was changed according to the solubility values and the LC-MS signal response.

From the 10 mM DMSO STD plate, 6 µL was transferred into the remaining empty plate, and then 194 µL of DMSO was added to that plate to have a STD concentration of 300 µM. From the 300 µM DMSO STD plate, 5 µL DMSO STD and 5 µL PBS pH 7.4 were transferred into the remaining empty plate, and then 490 µL of a mixture of $H_2O$ and acetonitrile containing internal standard (1:1) was added to that plate to have a final STD concentration of 3 µM. A certain proportion of ultrapure water was used to dilute the diluent according to the peak shape. The concentrations of the standard samples were changed according to the LC-MS signal response. The plate was placed into the well plate autosampler. The samples were evaluated by LC-MS/MS analysis.

All calculations were carried out using Microsoft Excel. The filtrate was analyzed and quantified against a standard of known concentration using LC coupled with mass spectral peak identification and quantitation. Solubility values of the test compound and control compound were calculated as follows:

$$[\text{Sample}] = \frac{\text{Area ratio}_{Sample} \times INJ\ VOL\ STD \times DF_{Sample} \times [STD]}{\text{Area ratio } STD \times INJ\ VOL_{Sample}}$$

The resulting data is shown in Table 7 below.

TABLE 7

Kinetic Solubility of Representative Compounds

| Compound | Kinetic Solubility PBS pH 7.4 (μM) |
|---|---|
| Compound 1 | 0.64 |
| Compound 2 | 3.83 |
| Compound 3 | 1.4 |
| Compound 4 | 59.4 |
| Compound 7 | 1.52 |
| Compound 9 | <0.002 |
| Compound 10 | 2.85 |
| Compound 11 | 0.28 |
| Compound 12 | 0.92 |
| Compound 13 | 0.036 |
| Compound 14 | 0.062 |
| Comparator 6 | 4.02 |
| Comparator 7 | 1.15 |
| Comparator 8 | 8.92 |
| Progesterone | 13.32 |

Example 29: 24 Hour Mouse Pharmacokinetic Summary

The following method evaluated the pharmacokinetics of repeat-dosing of compound at 20 mg/kg via oral administration in B6SJLF1/J mice over 24 hours.

TABLE 8

Animal Specifications

| | |
|---|---|
| Species: | Mouse |
| Strain: | B6SJLF1/J |
| Age Range: | 5-6 weeks |
| Weight Range: | 20-25 g |
| Source: | The Jackson Laboratory |
| Gender: | 72 male/24 female |
| Surgical Model: | NA |
| Total number of animals: | 96 |

TABLE 9

Husbandry Information

| | |
|---|---|
| Feed: | Envigo Rodent #2016 Diet (Pellets) |
| Water: | Automatic municipal water, particulate and charcoal filtered or water bottles (as needed) |
| Bedding: | Corncob |
| Housing: | Group housed, with no more than 5 per cage |
| Temperature Range: | 18 to 26° C. (69 to 75° F.) |
| Humidity Range: | 30 to 70% |
| Light Cycle: | 12-hour light/12-hour dark, interrupted as necessary for study-related events |

Feed and water were provided ad libitum, unless otherwise noted. The feed was analyzed by the manufacturer for concentrations of specified heavy metals, aflatoxin, chlorinated hydrocarbons, and organophosphates. The bedding was analyzed by the manufacturer for acceptable levels of heavy metals, aflatoxins, bacteria, yeasts, molds, and organophosphates prior to certification. No contaminants were known to be present in the feed, water, or bedding at levels that might have interfered with achieving the objectives of the study.

TABLE 10

Study Design

| Group | No. of Animals | Sex | Route of Administration | Dose (mg/kg) | Volume (mL/kg) | Conc. (mg/mL) | Test Article |
|---|---|---|---|---|---|---|---|
| 1 | 12 | M | IV | 3 | 10 | 0.3 | Compound 1 |
| 2 | 12 | M | PO | 10 | 10 | 1 | Compound 1 |
| 3 | 12 | M | PO | 100 | $10^D$ | $10^D$ | Compound 1 |
| 4 | 12 | F | PO | 10 | 10 | 1 | Compound 1 |
| 5 | 12 | M | IV | 3 | $10^D$ | $0.3^D$ | Compound 3 |
| 6 | 12 | M | PO | 10 | 10 | 1 | Compound 3 |
| 7 | 12 | M | PO | 100 | 10 | 10 | Compound 3 |
| 8 | 12 | F | PO | 10 | 10 | 1 | Compound 3 |

$D$ = See Table 11 below for adjustments to Study Design dosing regimen.

TABLE 11

Dose Formulations

| Group | Route of Admin. | Vehicle | Dose (mg/kg) | Volume (mL/kg) | Conc. (mg/mL) | Test Article |
|---|---|---|---|---|---|---|
| 1 | IV | 5% NMP, 5% Kolliphor HS-15, 30% PEG-400, Saline | 3 | 10 | 0.3 | Compound 1 |
| 2 | PO | DMSO, 0.5% methylcellulose | 10 | 10 | 1 | Compound 1 |
| 3 | PO | DMSO, 0.5% methylcellulose | 100 | $20^A$ | $5^A$ | Compound 1 |
| 4 | PO | DMSO, 0.5% methylcellulose | 10 | 10 | 1 | Compound 1 |
| 5 | IV | 5% NMP, 5% Kolliphor EL, 30% PEG-400, Saline | 3 | $5^B$ | $0.6^B$ | Compound 3 |
| 6 | PO | DMSO, 0.5% methylcellulose | 10 | 10 | 1 | Compound 3 |

TABLE 11-continued

| | | Dose Formulations | | | | |
|---|---|---|---|---|---|---|
| Group | Route of Admin. | Vehicle | Dose (mg/kg) | Volume (mL/kg) | Conc. (mg/mL) | Test Article |
| 7 | PO | DMSO, Saline[C] | 100 | 10 | 10 | Compound 3 |
| 8 | PO | DMSO, 0.5% methylcellulose | 10 | 10 | 1 | Compound 3 |

[A]=Solution concentration was adjusted from 10 mg/mL (specified in the Protocol) to 5 mg/mL due to the viscosity of the 10 mg/mL solution. The higher concentration solution was gel-like and could not be drawn into a syringe. The dose volume was doubled to compensate for the lowered concentration. Full dosing was completed in two parts with an approximate 1-2-minute rest between.
[B]=Solution concentration was adjusted from 0.3 mg/mL (specified in the Protocol) to 0.6 mg/mL due to the resultant volume of the IV injection. NIH Guidelines for Rodent Injection Routes and Volumes specifies that maximum volume for mouse lateral tail vein injection should be <0.2 mL. The dose volume was halved to compensate for the increased concentration.
[C]=Due to viscosity issues experienced with Group 3, the vehicle component for this solution was changed from 0.5% methylcellulose to saline. This change allowed for dosing concentration and volume to be completed as specified in the protocol.

PO Administrations:
  Groups 2, 3, 4, 6, and 8: Test article was dissolved in a minimal amount of DMSO (Groups 2, 4, 6, 8: 40-50 µL, Group 3: 100 µL), 0.5% methylcellulose was added to final volume, then solution was sonicated for 2 minutes.
  Group 7: Test article was dissolved in 100 µL DMSO, saline was added to final volume, then solution was sonicated for 2 minutes.
IV Administrations:
  Group 1 and 5: Test article was dissolved in NMP (N-methylpyrrolidone) corresponding to a final concentration of 5% NMP, Solutol HS-15 was added corresponding to a final concentration of 5% Solutol HS-15, PEG-400 was added corresponding to a final concentration of 30% PEG-400, then solution was diluted to final volume with saline.
Dose Administration
  Groups 1, 5: The test article was administered as a single dose via slow bolus intravenous administration into a lateral tail vein, with a 27G needle.
  Groups 2, 4, 6, 7, 8: The test article was administered as a single dose directly to the stomach by oral gavage.
  Group 3: The test article was administered as a single dose in two parts with an approximate 1-2-minute rest between due to volume administered.
Sampling
  Blood and cerebrospinal fluid (CSF) samples were collected as shown in Table 12.

TABLE 12

| | Sample Collection | | | | |
|---|---|---|---|---|---|
| | | Sample timepoints (h) Animal # | | | |
| Group | Sample Collected | 1-3 | 4-6 | 7-9 | 10-12 |
| 1-8 | Blood: Tail nick | 0.5 | 2 | NA | 8 |
| 1-8 | Blood: Cardiac Stick/CSF | 1 | 4 | 12 | 24 |

Approximately 150 µL of blood was collected by tail nick or the first time point and then the maximal volume by cardiac stick for the second, terminal time point in each mouse. The plasma was spun and separated within 30 minutes of collection and stored frozen at −20° C. until shipment.

Prior to the terminal blood collection, CSF was collected. The animal was fully anesthetized with a cocktail of ketamine/xylazine, and CSF was collected by gaining access to the cisterna magna by cutting through the skin at the back of the neck and skull, separation of the muscles at the back of the neck and insertion of a pulled beveled glass microneedle. The glass microneedle was attached via polyethylene tubing to a syringe positioned in a foot pedal actuated syringe pump. The syringe provided a controlled vacuum for removal of CSF. Approximately 5-12 µL of CSF was collected from the anesthetized mouse prior to cardiac stick for the plasma sample. The resulting data is shown in Tables 13, 14, 15, 16 and 17 below.

TABLE 13

Mouse Pharmacokinetics Summary for Compound 1

| G# | Route | Sex | $T_{max}$ (h) | $T_{1/2}$ (h) | $T_{last}$ (h) | $C_{max}$ (ng/mL) | $AUC_{0-t}$ (h * ng/mL) | $AUC_{0-\infty}$ (h * ng/mL) | $AUC_{0-t}/D$ (h * ng/mL)/ (mg/kg) |
|---|---|---|---|---|---|---|---|---|---|
| 1 | IV 3 mg/kg | M | NA | 0.987 | 8 | 12200 | 10100 | 10200 | 3380 |
| 2 | PO 10 mg/kg | M | 1 | 2.72 | 12 | 1040 | 5350 | 5750 | 535 |
| 3 | PO 100 mg/kg | M | 8 | 4.47 | 24 | 4070 | 44100 | 46000 | 441 |

TABLE 13-continued

Mouse Pharmacokinetics Summary for Compound 1

| G# | Route | Sex | $T_{max}$ (h) | $T_{1/2}$ (h) | $T_{last}$ (h) | $C_{max}$ (ng/mL) | $AUC_{0-t}$ (h * ng/mL) | $AUC_{0-\infty}$ (h * ng/mL) | $AUC_{0-t}/D$ (h * ng/mL)/ (mg/kg) |
|---|---|---|---|---|---|---|---|---|---|
| 4 | PO 10 mg/kg | F | 1 | NR | 24 | 1110 | 5670 | NR | 567 |
| Bioavailability R (Male/Female) | | | | | | | 0.937 | 0.944 | 0.169 |

NA = not applicable; NR = not reportable due to $R^2$ value < 0.8

TABLE 14

Mouse Pharmacokinetics Summary for Compound 1 Continued

| | | | Ratio to 10 mg/kg Dose Level | | |
|---|---|---|---|---|---|
| G# | Route | Sex | $C_{max}$ (ng/mL) | $AUC_{0-t}$ (h * ng/mL) | $AUC_{0-\infty}$ (h * ng/mL) |
| 3 | PO 100 mg/kg | M | 3.91 | 8.24 | 8.00 |

TABLE 15

Mouse Pharmacokinetics Summary for Compound 3

| G# | Route | Sex | $T_{max}$ (h) | $T_{1/2}$ (h) | $T_{last}$ (h) | $C_{max}$ (ng/mL) | $AUC_{0-t}$ (h * ng/mL) | $AUC_{0-\infty}$ (h * ng/mL) | Vd | $AUC_{0-t}/D$ (h * ng/mL)/ (mg/kg) |
|---|---|---|---|---|---|---|---|---|---|---|
| 1 | IV 3 mg/kg | M | NA | 4.71 | 24 | 7020 | 2800 | 2800 | 0.428 | 932 |
| 2 | PO 10 mg/kg | M | 1 | 4.91 | 24 | 148 | 668 | 679 | | 66.8 |
| 3 | PO 100 mg/kg | M | 4 | 3.33 | 24 | 137 | 1520 | 1540 | | 15.2 |
| 4 | PO 10 mg/kg | F | 1 | 4.01 | 24 | 91.8 | 444 | 452 | | 44.4 |
| Bioavailability R (Male/Female) | | | | | | 1.61 | 1.50 | 0.0728 1.50 | | 1.50 |

TABLE 16

Mouse Pharmacokinetics Summary for Compound 3 Continued

| | | | Ratio to 10 mg/kg Dose Level | | |
|---|---|---|---|---|---|
| G# | Route | Sex | $C_{max}$ (ng/mL) | $AUC_{0-t}$ (h * ng/mL) | $AUC_{0-\infty}$ (h * ng/mL) |
| 3 | PO 100 mg/kg | M | 0.926 | 2.28 | 2.27 |

TABLE 17

| Animal Specifications | |
|---|---|
| Species: | Mouse |
| Strain: | B6SJLF1/J |
| Age Range: | 7-8 weeks |
| Weight Range: | 22-27 g |
| Source: | The Jackson Laboratory |
| Gender: | 76 Male |
| Surgical Model: | NA |
| Total number of animals: | 80 |

Example 30: Seven Day Mouse Pharmacokinetic Summary

The following method evaluated the pharmacokinetics of repeat-dosing of Compound 1 at 20 mg/kg via oral administration in B6SJLF1/J mice over 7 days. Parameters evaluated included mortality, cage-side observations, physical examinations, and body weights over a 7-day period. Blood and cerebrospinal fluid (CSF) samples were collected at identified timepoints and plasma and CSF samples were submitted to KCAS Bioanalytical Service for analysis.

Animals were weighed upon arrival and acclimated to laboratory conditions for at least 24 hours prior to the first dose. During that time, animals were identified by an indelible marker according to Xyzagen's procedure that was recorded and used throughout the study. Before the start of the in-life phase, each animal was physically examined and weighed prior to test article administration.

TABLE 18

| | Husbandry Information |
|---|---|
| Feed: | Envigo Rodent #2016 Diet (Pellets) |
| Water: | Automatic municipal water, particulate and charcoal filtered or water bottles (as needed) |
| Bedding: | Corncob |
| Housing: | Group housed, with no more than 5 per cage |
| Temperature Range: | 18 to 26° C. (69 to 75° F.) |
| Humidity Range: | 30 to 70% |
| Light Cycle: | 12-hour light/12-hour dark, interrupted as necessary for study-related events |

Feed and water were provided ad libitum, unless otherwise noted. The feed was analyzed by the manufacturer for concentrations of specified heavy metals, aflatoxin, chlorinated hydrocarbons, and organophosphates. The bedding was analyzed by the manufacturer for acceptable levels of heavy metals, aflatoxins, bacteria, yeasts, molds, and organophosphates prior to certification. No contaminants were known to be present in the feed, water, or bedding at levels that might have interfered with achieving the objectives of the study.

TABLE 19

Study Design

| G# | No. of Animals | Sex | Route of Admin. | Dosing Period | Dose (mg/kg) | Vol. (mL/kg) | Conc. (mg/mL) | Test Article |
|---|---|---|---|---|---|---|---|---|
| 1 | 6 | M | PO | QD × 1 day | 20 | 10 | 2 | Compound 1 |
| 2 | 35 | M | PO | QD × 7 days | 20 | 10 | 2 | Compound 1 |
| 3 | 35 | M | PO | QD × 7 days | 0 | 10 | 0 | Vehicle |

All mice in groups 2 & 3 were dosed on Day 1, and remaining mice were dosed daily thereafter.
QD = once daily Dose Formulations and Administration On day of dosing, Compound 1 was dissolved in a minimum of DMSO (50 µL per 3.0 mg of Compound 1), then mixed with vehicle, 0.5% (w/v) methyl cellulose in water. The resulting formulation was vortexed and sonicated for 3-5 minutes to ensure homogeneity. The daily formulations were also vortexed throughout the day's dosing procedure.

TABLE 20

Formulations

| | Day 1 | Day 2 | Day 3 | Day 4 | Day 5 | Day 6 | Day 7 |
|---|---|---|---|---|---|---|---|
| Drug Soln. Required (mL) | 2.27 | 3.26 | 5.78 | 5.82 | 5.94 | 6.09 | 5.16 |
| Drug Soln. Mixed (mL) | 3.00 | 6.00 | 9.00 | 9.00 | 9.00 | 9.00 | 9.00 |
| Compound 1 (mg) | 6.1 | 12.0 | 18.1 | 18.1 | 17.9 | 18.0 | 18.2* |
| DMSO (mL) | 50 | 100 | 150 | 150 | 150 | 150 | 150 |
| Sonication (min) | 3 | 3 | 3 | 4 | 3 | 4 | 5 |
| Vehicle Soln. Mixed (mL) | 3.00 | 6.00 | 9.00 | 9.00 | 9.00 | 9.00 | 9.00 |
| DMSO (mL) | 50 | 10 | 150 | 150 | 150 | 150 | 150 |

Additional Information: Day 7-Drug solution separated more readily than previous days.

Soln. = solution, min = minute, *= 9.0 mg second lot of Compound 1 + 9.2 mg first lot of Compound 1

Animals were dosed once daily, by oral gavage at the dose volume specified. Dose volumes were based on the most recently recorded body weight.

TABLE 21

Sampling
Blood and CSF samples were collected as outlined below in the following tables.
Animals Sampled for Each Time Point

| Group | Sample Collected | Day 1 | Day 2 | Day 3 | Day 4 | Day 5 | Day 6 | Day 7 |
|---|---|---|---|---|---|---|---|---|
| | | | | Animal ID Numbers | | | | |
| 1 | CSF, Plasma | 1-6* | | | | | | |
| 2 | CSF, Plasma | | | | | | | 31-35 |
| 2 | Plasma | 1-5 | 6-10 | 11-15 | 16-20 | 21-25 | 26-30 | |
| 3 | Plasma | 1-5 | 6-10 | 11-15 | 16-20 | 21-25 | 26-30 | 31-35 |

Additional Information: Plasma timepoints are 1 h pre-dose and 1 h post-dose
*= collection at 1 h post-dose, h = hour

TABLE 22

Sample Timepoints-Groups 2 and 3

| Animal | Day 1 | Day 2 | | Day 3 | | Day 4 | | Day 5 | | Day 6 | | Day 7 | |
|---|---|---|---|---|---|---|---|---|---|---|---|---|---|
| | 1 h post-dose | 1 h pre-dose | 1 h post-dose | 1 h pre-dose | 1 h post-dose | 1 h pre-dose | 1 h post-dose | 1 h pre-dose | 1 h post-dose | 1 h pre-dose | 1 h post-dose | 1 h pre-dose | 1 h post-dose |
| 1 | T | | | | | | | | | | | | |
| 2 | T | | | | | | | | | | | | |
| 3 | T | | | | | | | | | | | | |
| 4 | T | | | | | | | | | | | | |
| 5 | T | | | | | | | | | | | | |
| 6 | | X | T | | | | | | | | | | |
| 7 | | X | T | | | | | | | | | | |
| 8 | | X | T | | | | | | | | | | |
| 9 | | X | T | | | | | | | | | | |
| 10 | | X | T | | | | | | | | | | |
| 11 | | | | X | T | | | | | | | | |
| 12 | | | | X | T | | | | | | | | |
| 13 | | | | X | T | | | | | | | | |
| 14 | | | | X | T | | | | | | | | |
| 15 | | | | X | T | | | | | | | | |
| 16 | | | | | | X | T | | | | | | |
| 17 | | | | | | X | T | | | | | | |
| 00 | | | | | | X | T | | | | | | |
| 19 | | | | | | X | T | | | | | | |
| 20 | | | | | | X | T | | | | | | |
| 21 | | | | | | | | X | T | | | | |
| 22 | | | | | | | | X | T | | | | |
| 23 | | | | | | | | X | T | | | | |
| 24 | | | | | | | | X | T | | | | |
| 25 | | | | | | | | X | T | | | | |
| 26 | | | | | | | | | | X | T | | |
| 27 | | | | | | | | | | X | T | | |
| 28 | | | | | | | | | | X | T | | |
| 29 | | | | | | | | | | X | T | | |
| 30 | | | | | | | | | | X | T | | |
| 31 | | | | | | | | | | | | X | T |
| 32 | | | | | | | | | | | | X | T |
| 33 | | | | | | | | | | | | X | T |
| 34 | | | | | | | | | | | | X | T |
| 35 | | | | | | | | | | | | X | T |

Additional Information: h = hour, X = tail nick blood collection, T = terminal cardiac stick blood collection Blood was collected via tai nick at the time points defined above. Total volume or pre-dose timepoints 100-150 µl, then the maximal volume by cardiac stick was collected for the final timepoint post-dose. Blood was collected in K₂EDTA tubes and kept on wet ice until processing. The blood was be spun and plasma separated within 30 minutes of collection.

Prior to the terminal blood collection for groups 1 and 2 (animals 31-35), CSF was collected. The animal was fully anesthetized with a cocktail of ketamine/xylazine, and CSF was collected by gaining access to the cisterna magna by cutting through the skin at the back of the neck and skull, separation of the muscles at the back of the neck and insertion of a pulled beveled glass microneedle. The glass microneedle was attached via polyethylene tubing to a syringe positioned in a foot pedal actuated syringe pump. The syringe provided a controlled vacuum for removal of CSF. Approximately 5-12 µL of CSF was collected from the anesthetized mouse prior to cardiac stick for the plasma sample.

Plasma and CSF samples were stored at −20° C. In the study of 20 mg/kg, PO, QD no animals died or had adverse events. There was no accumulation and average CSF levels were 183 ng/ml and 105 ng/ml one hour after dosing at day 1 and day 7, respectively. Plasma dosing was found to be below the detection limit in 24 hours.

Example 31: 24 Hour Rat Pharmacokinetic Summary

Following similar techniques to those described in Example 30 a pharmacokinetic (PK) study was conducted on rats.

Male Sprague-dawley rats averaging 7-9 weeks of age and approximately 200-300 g weight were separated into groups of three. The rats were then administered a test article at a dose of 3 mg/kg by IV or a dose of 10 mg/kg orally. The intravenously administered test articles were formulated with 20% DMA, 20% PEG400, and 20% Kolliphor HS 15, in saline and the orally administered test articles were formulated in a 100 DMSO and 0.5% methylcellulose in aqueous solution. The solutions were prepared at a concentration of 1.5 mg/mL for intravenous 1 administration and 1 mg/mL for oral administration. Blood samples were taken at 0.25, 0.5, 1, 2, 4, 8, 12 and 24 hours.

The resulting data is provided in the following tables.

TABLE 23

Rat Pharmacokinetics Summary for Compound 1

| G# | Route | Sex | $T_{max}$ (h) | $T_{1/2}$ (h) | $T_{last}$ (h) | $C_{max}$ (ng/mL) | $AUC_{0-t}$ (h * ng/mL) | $AUC_{0-\infty}$ (h * ng/mL) | Vss | $AUC_{0-t}/D$ (h * ng/mL)/ (mg/kg) |
|---|---|---|---|---|---|---|---|---|---|---|
| 1 | IV 3 mg/kg | M | NA | 5.33 | 24 | 5537 | 4623 | 4650 | 1.20 | 1541 |
| 2 | PO 10 mg/kg | M | 2.67 | 3.67 | 24 | 409 | 2609 | 2664 | — | 261 |
| Bioavailability | | | | | | | | 0.172 | | |

TABLE 24

Rat Pharmacokinetics Summary for Compound 2

| G# | Route | Sex | $T_{max}$ (h) | $T_{1/2}$ (h) | $T_{last}$ (h) | $C_{max}$ (ng/mL) | $AUC_{0-t}$ (h * ng/mL) | $AUC_{0-\infty}$ (h * ng/mL) | Vss | $AUC_{0-t}/D$ (h * ng/mL)/ (mg/kg) |
|---|---|---|---|---|---|---|---|---|---|---|
| 1 | IV 3 mg/kg | M | NA | 1.28 | 12 | 5538 | 5718 | 5721 | 0.492 | 1906 |
| 2 | PO 10 mg/kg | M | 2.00 | 1.00 | 12 | 3163 | 13171 | 13182 | — | 1317 |
| Bioavailability | | | | | | | | 0.691 | | |

TABLE 25

Rat Pharmacokinetics Summary for Compound 3

| G# | Route | Sex | $T_{max}$ (h) | $T_{1/2}$ (h) | $T_{last}$ (h) | $C_{max}$ (ng/mL) | $AUC_{0-t}$ (h * ng/mL) | $AUC_{0-\infty}$ (h * ng/mL) | Vss | $AUC_{0-t}/D$ (h * ng/mL)/ (mg/kg) |
|---|---|---|---|---|---|---|---|---|---|---|
| 1 | IV 3 mg/kg | M | NA | 1.18 | 12 | 4387 | 4150 | 4155 | 0.641 | 1383 |
| 2 | PO 10 mg/kg | M | 2.67 | 5.03 | 24 | 154 | 1069 | 1241 | — | 107 |
| Bioavailability | | | | | | | | 0.078 | | |

TABLE 26

Rat Pharmacokinetics Summary for Compound 4

| G# | Route | Sex | $T_{max}$ (h) | $T_{1/2}$ (h) | $T_{last}$ (h) | $C_{max}$ (ng/mL) | $AUC_{0-t}$ (h * ng/mL) | $AUC_{0-\infty}$ (h * ng/mL) | Vss | $AUC_{0-t}/D$ (h * ng/mL)/ (mg/kg) |
|---|---|---|---|---|---|---|---|---|---|---|
| 1 | IV 3 mg/kg | M | NA | 0.449 | 4 | 5445 | 1872 | 1874 | 0.534 | 624 |
| 2 | PO 10 mg/kg | M | 0.5 | 2.05 | 12 | 281 | 578 | 582 | — | 57.8 |
| Bioavailability | | | | | | | | 0.093 | | |

TABLE 27

Rat Pharmacokinetics Summary for Compound 10

| G# | Route | Sex | $T_{1/2}$ (h) | $C_{max}$ (ng/mL) | $AUC_{0-t}$ (h * ng/mL) | Vss |
|---|---|---|---|---|---|---|
| 1 | IV 3 mg/kg | M | 0.23 | 7790 | 1240 | 0.39 |
| 2 | PO 10 mg/kg | M | 1.67 | 214 | 370 | — |
| Bioavailability | | | | | 0.089 | |

TABLE 28

Rat Pharmacokinetics Summary for Comparator 6

| G# | Route | Sex | $T_{max}$ (h) | $T_{1/2}$ (h) | $T_{last}$ (h) | $C_{max}$ (ng/mL) | $AUC_{0-t}$ (h * ng/mL) | $AUC_{0-\infty}$ (h * ng/mL) | Vss | $AUC_{0-t}/D$ (h * ng/mL)/ (mg/kg) |
|---|---|---|---|---|---|---|---|---|---|---|
| 1 | IV 3 mg/kg | M | NA | 3.51 | 24 | 10295 | 24240 | 24358 | 0.404 | 8080 |
| 2 | PO 10 mg/kg | M | 3.33 | 3.05 | 24 | 7083 | 60164 | 60623 | — | 6016 |
| Bioavailability | | | | | | | | 0.75 | | |

TABLE 29

Rat Pharmacokinetics Summary for Comparator 7

| G# | Route | Sex | $T_{max}$ (h) | $T_{1/2}$ (h) | $T_{last}$ (h) | $C_{max}$ (ng/mL) | $AUC_{0-t}$ (h * ng/mL) | $AUC_{0-\infty}$ (h * ng/mL) | Vss | $AUC_{0-t}/D$ (h * ng/mL)/ (mg/kg) |
|---|---|---|---|---|---|---|---|---|---|---|
| 1 | IV 3 mg/kg | M | NA | 2.75 | 12 | 10459 | 6256 | 6263 | 0.512 | 2085 |
| 2 | PO 10 mg/kg | M | 2.00 | 2.68 | 12 | 344 | 1687 | 1705 | — | 169 |
| Bioavailability | | | | | | | | 0.082 | | |

TABLE 30

Rat Pharmacokinetics Summary for Comparator 8

| G# | Route | Sex | $T_{max}$ (h) | $T_{1/2}$ (h) | $T_{last}$ (h) | $C_{max}$ (ng/mL) | $AUC_{0-t}$ (h * ng/mL) | $AUC_{0-\infty}$ (h * ng/mL) | Vss | $AUC_{0-t}/D$ (h * ng/mL)/ (mg/kg) |
|---|---|---|---|---|---|---|---|---|---|---|
| 1 | IV 3 mg/kg | M | NA | 1.30 | 8 | 4939 | 1517 | 1522 | 1.26 | 506 |
| 2 | PO 10 mg/kg | M | 1.42 | 3.47 | 12 | 22.4 | 98 | 106 | — | 9.8 |
| Bioavailability | | | | | | | | 0.021 | | |

All publications and patent applications cited in this specification are herein incorporated by reference as if each individual publication or patent application were specifically and individually indicated to be incorporated by reference.

Although the foregoing invention has been described in some detail by way of illustration and example for the purposes of clarity of understanding, it will be readily apparent to one of ordinary skill in the art in light of the teaching of this invention that certain changes and modification may be made thereto without departing from the spirit or scope of the invention as defined in the appended claims. Additionally, those skilled in the art will recognize, or be able to ascertain using no more than routine experimentation, many equivalents to the specific embodiments and methods described herein. Such equivalents are intended to be encompassed by the scope of the present application.

I claim:

1. A compound of structure:

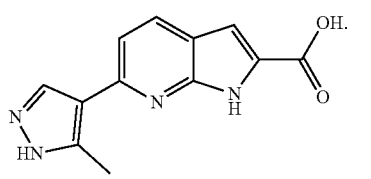

* * * * *